United States Patent
Kamal et al.

(10) Patent No.: US 10,246,411 B2
(45) Date of Patent: Apr. 2, 2019

(54) (Z)-3,4,5-TRIMETHOXYSTYRYLBENZENES-ULFONAMIDES AS POTENTIAL ANTICANCER AGENTS

(71) Applicant: COUNCIL OF SCIENTIFIC & INDUSTRIAL RESEARCH, New Delhi (IN)

(72) Inventors: Ahmed Kamal, Hyderabad (IN); Mahesh Rasala, Hyderabad (IN); Challa Ratna Reddy, Hyderabad (IN); Gajjela Bharath Kumar, Hyderabad (IN); Visweswara Sastry, Hyderabad (IN); Anver Basha Shaik, Hyderabad (IN); Vangala Santhosh Reedy, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/523,205

(22) PCT Filed: Oct. 27, 2015

(86) PCT No.: PCT/IN2015/050148
§ 371 (c)(1),
(2) Date: Apr. 28, 2017

(87) PCT Pub. No.: WO2016/067311
PCT Pub. Date: May 6, 2016

(65) Prior Publication Data
US 2017/0327462 A1 Nov. 16, 2017

(30) Foreign Application Priority Data
Oct. 29, 2014 (IN) .......................... 3076/DEL/2014

(51) Int. Cl.
C07C 311/21 (2006.01)
C07C 311/29 (2006.01)
C07C 311/44 (2006.01)

(52) U.S. Cl.
CPC .......... C07C 311/44 (2013.01); C07C 311/21 (2013.01); C07C 311/29 (2013.01)

(58) Field of Classification Search
None
See application file for complete search history.

(56) References Cited

FOREIGN PATENT DOCUMENTS

WO 2010046926 A2 4/2010

OTHER PUBLICATIONS

Dumontet ("Microtuble-binding agents: a dynamic field of cancer therapeutics", Nat. Rev. Drug Discov. 2010, 9, 790-803).*

Sigma Aldrich ("Authenticated Cancer Cell Lines" downloaded from < https://www.sigmaaldrich.com/europe/life-science-offers/cell-cycle/sigma-ecacc-cell/cancer-cell-lines.html#Cervical> on Dec. 1, 2017, p. 1-21).*
NIH ("Cell Lines in the In Vitro Screen" downloaded from < https://dtp.cancer.gov/discovery_development/nci-60/cell_list.htm> on Dec. 1, 2017, p. 1-3).*
Jang ("Metal-Free C—H Amination for Indole Synthesis", Org. Lett. 16, Jul. 1, 2014, p. 3720-3723, including SI, p. S1-S151).*
Tokimizu ("Gold-Catalyzed Cascade Cyclization of (Azido)ynamides: An Efficient Strategy for the Construction of Indoloquinolines" Organic Letters, 16, May 29, 2014, p. 3138-3141, including SI, p. S1-S80).*
Monk ("Design, synthesis, and biological evaluation of combretastatin nitrogen-containing derivatives as inhibitors of tubulin assembly and vascular disrupting agents" Bioorganic and Medicinal Chemistry 14 (2006), p. 3231-3244).*
Chang ("2-Amino and 2'-Aminocombretastatin Derivatives as Potent Antimitotic Agents" J. Med. Chem. 2006, 49, p. 6412-6415).*
Kim ("Structure-Activity Relationships of Benzimidazoles and Related Heterocycles as Topoisomerase I Poisons" Bioorganic and Medicinal Chemistry, 1996, 4, p. 621-630).*
ACS ("What is Non-Small Cell Lung Cancer", downloaded from https://www.cancer.org/cancer/non-small-cell-lung-cancer/about/what-is-non-small-cell-lung-cancer.html on May 30, 2018, last updated Feb. 8, 2016, p. 1-5) (Year: 2018).*
International Search Report and Written Opinion prepared for PCT/IN2015/050148, dated Mar. 17, 2016, 9 pages.
Monk, K. et al., "Design, synthesis, and biological evaluation of combretastatin nitrogen-containing derivatives as inhibitors of tubulin assembly and vascular disrupting agents," Bioorganic & Medicinal Chemistry, 2006, 14, 3231-3244.
Pinney, K. et al., "Synthesis and biological evaluation of aryl azide derivatives of combretastatin a-4 as molecular probes for tubulin," Bioorganic & Medicinal Chemistry, 2000, 8, 2417-2425.

* cited by examiner

*Primary Examiner* — Amy C Bonaparte
(74) *Attorney, Agent, or Firm* — Barnes & Thornburg LLP

(57) ABSTRACT

This present invention relates to (Z)-3,4,5-Trimethoxystyrylbenzenesulfonamides of general formula A. The invention also provides the synthesis of (Z)-3,4,5-trimethoxystyrylbenzenesulfonamides useful as potential antitumor agents against human cancer cell lines and a process for the preparation thereof.

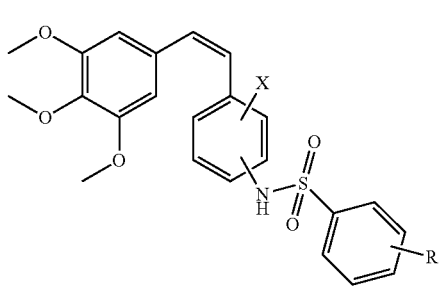

5 Claims, No Drawings

(Z)-3,4,5-TRIMETHOXYSTYRYLBENZENES-ULFONAMIDES AS POTENTIAL ANTICANCER AGENTS

FIELD OF THE INVENTION

This patent application is a U.S. National Phase of International Patent Application No. PCT/IN2015/050148 filed 27 Oct. 2017, which claims the benefit of priority to Indian Patent Application 3076/DEL/2014, entitled "(Z)-3,4,5-TRIMETHOXYSTYRYLBENZENESULFONAMIDES AS POTENTIAL ANTICANCER AGENTS," filed Oct. 29, 2014, the contents of which are incorporated herein by reference in their entirety.

BACKGROUND AND PRIOR ART SEARCH OF THE INVENTION

Microtubules are protein polymers that are involved in many physiological processes, especially mitosis and cell division, and are formed by α-tubulin and β-tubulin heterodimers. Microtubules are essential for maintaining cell shape and polarity, the intracellular transport of vesicles and organelles. During eukaryotic cell division, microtubules form mitotic spindles, which align replicated chromosomes to the equatorial plane and mediate the subsequent segregation of chromosomes to the two daughter cells [K. H. Downing, E. Nogales, Curr. Opin. Cell Biol. 1998, 10, 16-22]. These drugs interfere with the polymerization depolymerization properties of microtubules to prevent cell cycle progression, inducing the cells to undergo programmed cell death. Due to this microtubules are potential targets for the development of chemotherapeutic drugs which target rapidly dividing cancer cells [S. Honore, E. Pasquier, D. Braguer, Cell Mol. Life Sci. 2005, 62, 3039-3056]. Combretastatin A-4 (CA-4) S1 is a natural cis-stilbene that was isolated by Pettit co workers in 1989 from the South African willow tree Combretumcaffrum. Because of its structural simplicity and strong anticancer properties, CA-4 is presently one of the most promising target to develop new potential drugs for cancer. CA-4 has been found to be a potent inhibitor of tubulin polymerization, as it binds to the colchicine binding site and exerts significant cytotoxicity toward a wide range of human cancer cell lines, including multidrug-resistant cancer cells G. R. Pettit, M. R. Rhodes, D. L. Herald, E. Hamel, J. M. Schmidt, R. K. Pettit, J. Med. Chem. 2005, 48, 4087-4099]. Recently it has been reported that a new class of combretastatins such as (Z)-5-(3,5-dimethoxystyryl)-2-methoxyaniline S3 exhibit potential cell proliferation against CA-4 resistant cell lines (BMEC and HT-29) and also explained that in these (Z)-5-(3,5-dimethoxystyryl)-2-methoxyaniline inhibited tubulin polymerization five times stronger than CA-4 by binding at colchicine binding site. (Simoni D, Romagnoli R, Baruchello R, Rondanin R, Grisolia G, Eleopra M, Rizzi M, Tolomeo M, Giannini G, Alloatti D, Castorina M, Marcellini M, Pisano C, Novel A-ring and B-ring modified combretastatin A-4 (CA-4) analogues endowed with interesting cytotoxic activity, *J. Med. Chem.* 2008, 51, (19), 6211-6215). E7010 (N-[2-[(4-hydroxyphenyl)amino]-3-pyridinyl]-4-methoxybenzenesulfonamide) S4 an orally active sulfonamide antitumor agent that is currently in a Phase I clinical trial, showed rather consistent growth-inhibitory activities against a panel of different human tumor cell lines. It also showed a dose-dependent inhibition of tubulin polymerization, which correlated well with the cell growth-inhibitory activity. 14C-labeled E7010 bound to purified tubulin, and this binding was inhibited by colchicine but not by VCR. However, its binding properties were different from those of colchicine, as well as those of VCR. E7010 was active against two kinds of VCR-resistant P388 cell lines, one of which showed multidrug resistance due to the overexpression of P-glycoprotein (resistant to Taxol), and the other did not show multidrug resistance (sensitive to Taxol). Furthermore, E7010 is a tubulin-binding agent that has a wider antitumor spectrum than VCR and has different properties from those of VCR or Taxol [Yoshino, Hiroshi; Ueda, Norihiro; Niijima, Jun; Sugumi, Hiroyuki; et al. J. Med. Chem. 1992, (35), 2496-2497].

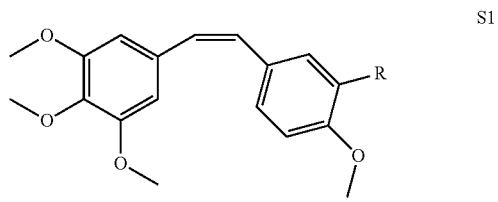

R = OH (CA4)
R = OPO₃Na₂ (CA4P)
R = NHSer, NH₂·HCl (AVE8062)

S1

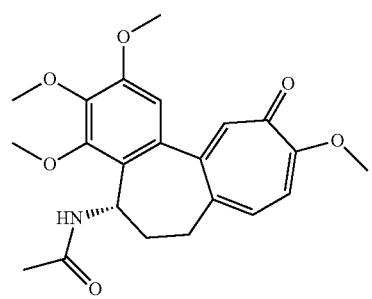

S2

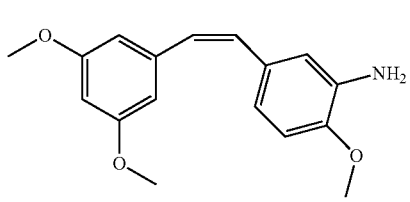

S3

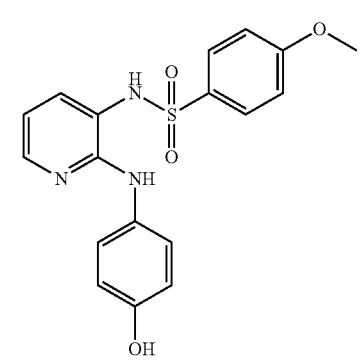

S4

In continuation of these efforts and our interest in the structural modifications of the combretastatin A4 and E7010, we describe here in an efficient access to the construction of some new (Z)-3,4,5-trimethoxystyryl benzene sulfonamides with improved cytotoxic activity in certain cell lines.

OBJECTIVES OF THE INVENTION

The main objective of the present invention to provide (Z)-3,4,5-trimethoxystyryl benzene sulfonamides useful as potential anticancer agents.

Yet another objective of the present invention is to provide a process for the preparation of (Z)-3,4,5-trimethoxystyryl benzene sulfonamides.

Further objective of the present invention is to provide (Z)-3,4,5-trimethoxystyryl benzene sulfonamides of general formula A as promising tubulin polymerization inhibitors.

SUMMARY OF THE INVENTION

Accordingly, the present invention provides a(Z)-3,4,5-trimethoxystyrylbenzene sulfonamides of general formulae A

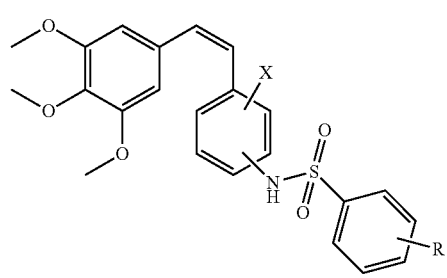

A wherein, X=H, F, OCH$_3$, OH; R=H, Cl, F, OCH$_3$, NH$_2$, NO$_2$, OH

In an embodiment of the present invention (Z)-3,4,5-trimethoxystyryl benzene sulfonamides of general formulae A is represented by the compounds of general formulae 9a-9y, 10a-10y, 11a-11y, 12a-12y, 13a-13y, 14a-14y, 15a-15y, 16a-16y, 17a-17y, 18a-18y, 19a-19y, 20a-20y, 21a-21y, 22a-22y and 23a-23y.

9a-9y

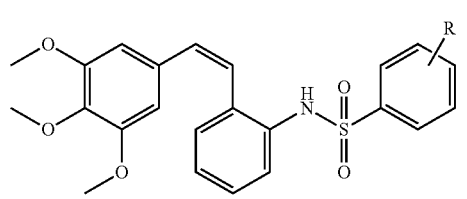

10a-10y

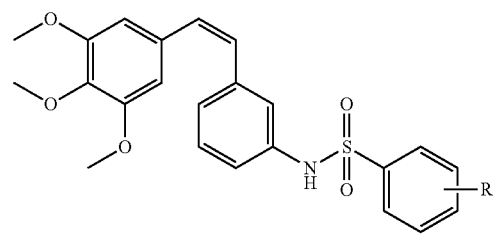

11a-11y

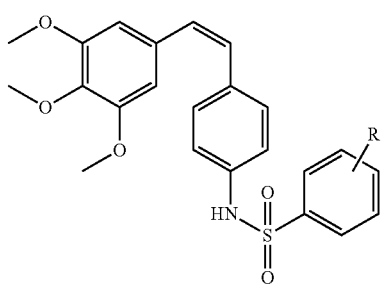

12a-12y

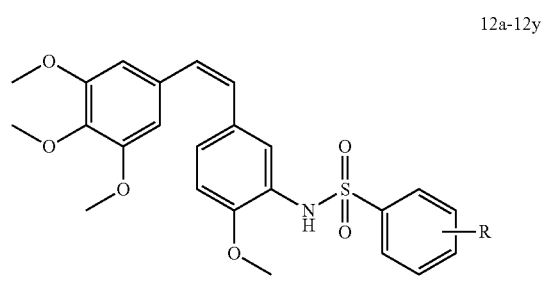

13a-13y

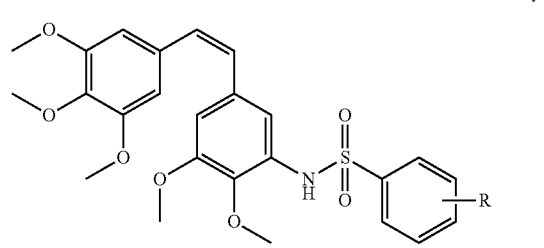

14a-14y

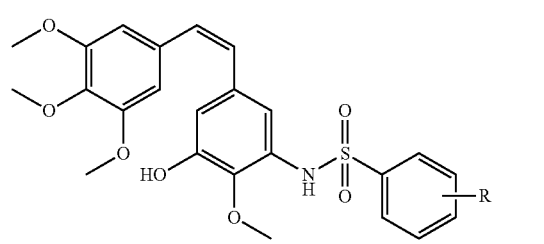

15a-15y

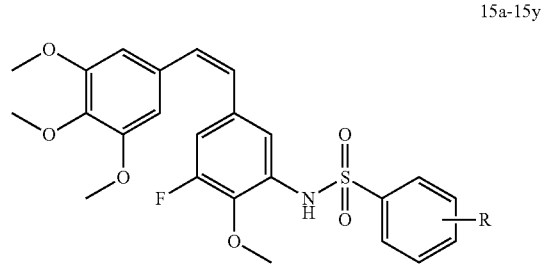

16a-16y

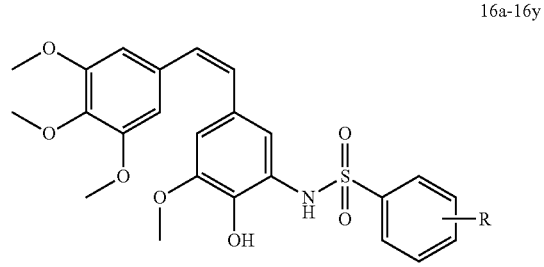

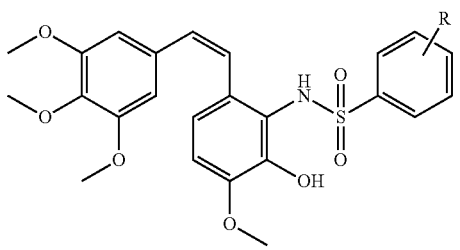

17a-17y

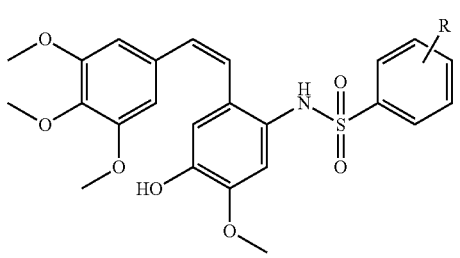

18a-18y

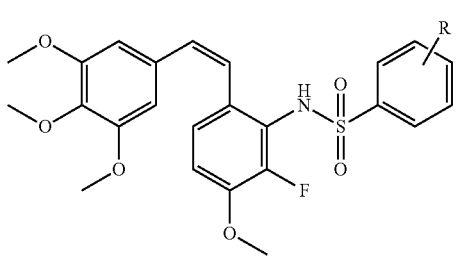

19a-19y

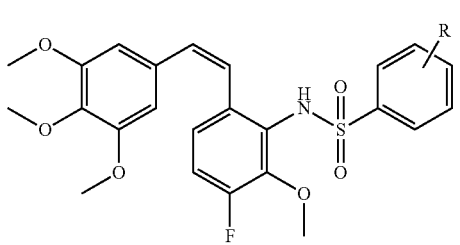

20a-20y

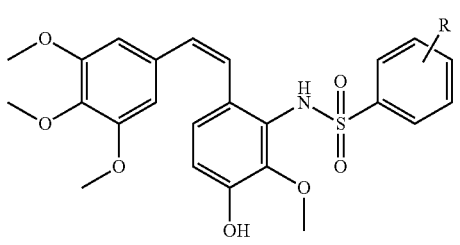

21a-21y

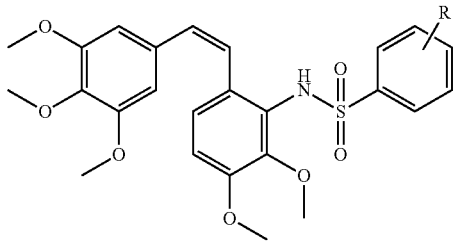

22a-22y

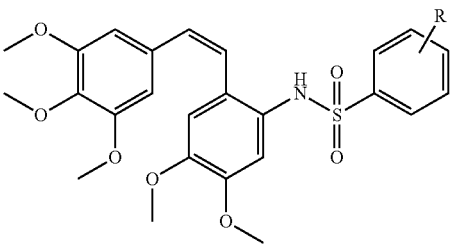

23a-23y wherein R=H, Cl, F, OCH$_3$, NH$_2$, NO$_2$, OH.

In yet another embodiment the (Z)-trimethoxystyryl)phenyl)benzenesulfonamide are represented by the following compounds:
(Z)-4-methoxy-N-(2-(3,4,5-trimethoxystyryl)phenyl)benzenesulfonamide (9a)
(Z)-3,4-dimethoxy-N-(2-(3,4,5-trimethoxystyryl)phenyl)benzenesulfonamide (9b)
(Z)-4-chloro-N-(2-(3,4,5-trimethoxystyryl)phenyl)benzenesulfonamide (9c)
(Z)-3-chloro-N-(2-(3,4,5-trimethoxystyryl)phenyl)benzenesulfonamide (9d)
(Z)-3,4-dichloro-N-(2-(3,4,5-trimethoxystyryl)phenyl)benzenesulfonamide (9e)
(Z)-4-fluoro-N-(2-(3,4,5-trimethoxystyryl)phenyl)benzenesulfonamide (9f)
(Z)-4-tert-butyl-N-(2-(3,4,5-trimethoxystyryl)phenyl)benzenesulfonamide (9g)
(Z)-4-nitro-N-(2-(3,4,5-trimethoxystyryl)phenyl)benzenesulfonamide (9h)
(Z)-4-amino-N-(2-(3,4,5-trimethoxystyryl)phenyl)benzenesulfonamide (9i)
(Z)-3-(trifluoromethyl)-N-(2-(3,4,5-trimethoxystyryl)phenyl)benzenesulfonamide (9J)
(Z)-3-(trifluoromethoxy)-N-(2-(3,4,5-trimethoxystyryl)phenyl)benzenesulfonamide (9k)
(Z)-4-(trifluoromethyl)-N-(2-(3,4,5-trimethoxystyryl)phenyl)benzenesulfonamide (9l)
(Z)-4-(trifluoromethoxy)-N-(2-(3,4,5-trimethoxystyryl)phenyl)benzenesulfonamide (9m)
(Z)-3-nitro-N-(2-(3,4,5-trimethoxystyryl)phenyl)benzenesulfonamide (9n)
(Z)-3-amino-N-(2-(3,4,5-trimethoxystyryl)phenyl)benzenesulfonamide (9o)
(Z)-3-fluoro-N-(2-(3,4,5-trimethoxystyryl)phenyl)benzenesulfonamide (9p)
(Z)-3-tert-butyl-N-(2-(3,4,5-trimethoxystyryl)phenyl)benzenesulfonamide (9q)
(Z)-3-fluoro-4-methoxy-N-(2-(3,4,5-trimethoxystyryl)phenyl)benzenesulfonamide (9r)
(Z)-3-hydroxy-4-methoxy-N-(2-(3,4,5-trimethoxystyryl)phenyl)benzenesulfonamide (9s)
(Z)-4-methoxy-3-nitro-N-(2-(3,4,5-trimethoxystyryl)phenyl)benzenesulfonamide (9t)
(Z)-3,4,5-trimethoxy-N-(2-(3,4,5-trimethoxystyryl)phenyl)benzenesulfonamide (9u)
(Z)-4-methyl-N-(2-(3,4,5-trimethoxystyryl)phenyl)benzenesulfonamide (9v)
(Z)-4-hydroxy-N-(2-(3,4,5-trimethoxystyryl)phenyl)benzenesulfonamide (9w)
(Z)-3,4-difluoro-N-(2-(3,4,5-trimethoxystyryl)phenyl)benzenesulfonamide (9x)
(Z)-3-chloro-4-methoxy-N-(2-(3,4,5-trimethoxystyryl)phenyl)benzenesulfonamide (9y)

(Z)-4-methoxy-N-(3-(3,4,5-trimethoxystyryl)phenyl)benzenesulfonamide (10a)
(Z)-3,4-dimethoxy-N-(3-(3,4,5-trimethoxystyryl)phenyl)benzenesulfonamide (10b)
(Z)-4-chloro-N-(3-(3,4,5-trimethoxystyryl)phenyl)benzenesulfonamide (10c)
(Z)-3-chloro-N-(3-(3,4,5-trimethoxystyryl)phenyl)benzenesulfonamide (10d)
(Z)-3,4-dichloro-N-(3-(3,4,5-trimethoxystyryl)phenyl)benzenesulfonamide (10e)
(Z)-4-fluoro-N-(3-(3,4,5-trimethoxystyryl)phenyl)benzenesulfonamide (10f)
(Z)-4-tert-butyl-N-(3-(3,4,5-trimethoxystyryl)phenyl)benzenesulfonamide (10g)
(Z)-4-nitro-N-(3-(3,4,5-trimethoxystyryl)phenyl)benzenesulfonamide (10h)
(Z)-4-amino-N-(3-(3,4,5-trimethoxystyryl)phenyl)benzenesulfonamide (10i)
(Z)-3-(trifluoromethyl)-N-(3-(3,4,5-trimethoxystyryl)phenyl)benzenesulfonamide (10j)
(Z)-3-(trifluoromethoxy)-N-(3-(3,4,5-trimethoxystyryl)phenyl)benzenesulfonamide (10k)
(Z)-4-(trifluoromethyl)-N-(3-(3,4,5-trimethoxystyryl)phenyl)benzenesulfonamide (10l)
(Z)-4-(trifluoromethoxy)-N-(3-(3,4,5-trimethoxystyryl)phenyl)benzenesulfonamide (10m)
(Z)-3-nitro-N-(3-(3,4,5-trimethoxystyryl)phenyl)benzenesulfonamide (10n)
(Z)-3-amino-N-(3-(3,4,5-trimethoxystyryl)phenyl)benzenesulfonamide (10o)
(Z)-3-fluoro-N-(3-(3,4,5-trimethoxystyryl)phenyl)benzenesulfonamide (10p)
(Z)-3-tert-butyl-N-(3-(3,4,5-trimethoxystyryl)phenyl)benzenesulfonamide (10q)
(Z)-3-fluoro-4-methoxy-N-(3-(3,4,5-trimethoxystyryl)phenyl)benzenesulfonamide (10r)
(Z)-3-hydroxy-4-methoxy-N-(3-(3,4,5-trimethoxystyryl)phenyl)benzenesulfonamide (10s)
(Z)-4-methoxy-3-nitro-N-(3-(3,4,5-trimethoxystyryl)phenyl)benzenesulfonamide (10t)
(Z)-3-amino-4-methoxy-N-(3-(3,4,5-trimethoxystyryl)phenyl)benzenesulfonamide (10u)
(Z)-3,4,5-trimethoxy-N-(3-(3,4,5-trimethoxystyryl)phenyl)benzenesulfonamide (10v)
(Z)-4-methyl-N-(3-(3,4,5-trimethoxystyryl)phenyl)benzenesulfonamide (10w)
(Z)-3,4-difluoro-N-(3-(3,4,5-trimethoxystyryl)phenyl)benzenesulfonamide (10x)
(Z)-3-chloro-4-methoxy-N-(3-(3,4,5-trimethoxystyryl)phenyl)benzenesulfonamide (10y)
(Z)-4-methoxy-N-(4-(3,4,5-trimethoxystyryl)phenyl)benzenesulfonamide (11a)
(Z)-3,4-dimethoxy-N-(4-(3,4,5-trimethoxystyryl)phenyl)benzenesulfonamide (11b)
(Z)-4-chloro-N-(4-(3,4,5-trimethoxystyryl)phenyl)benzenesulfonamide (11c)
(Z)-3-chloro-N-(4-(3,4,5-trimethoxystyryl)phenyl)benzenesulfonamide (11d)
(Z)-3,4-dichloro-N-(4-(3,4,5-trimethoxystyryl)phenyl)benzenesulfonamide (11e)
(Z)-4-fluoro-N-(4-(3,4,5-trimethoxystyryl)phenyl)benzenesulfonamide (11f)
(Z)-4-tert-butyl-N-(4-(3,4,5-trimethoxystyryl)phenyl)benzenesulfonamide (11g)
(Z)-4-nitro-N-(4-(3,4,5-trimethoxystyryl)phenyl)benzenesulfonamide (11h)
(Z)-4-amino-N-(4-(3,4,5-trimethoxystyryl)phenyl)benzenesulfonamide (11i)
(Z)-3-(trifluoromethyl)-N-(4-(3,4,5-trimethoxystyryl)phenyl)benzenesulfonamide (11j)
(Z)-3-(trifluoromethoxy)-N-(4-(3,4,5-trimethoxystyryl)phenyl)benzenesulfonamide (11k)
(Z)-4-(trifluoromethyl)-N-(4-(3,4,5-trimethoxystyryl)phenyl)benzenesulfonamide (11l)
(Z)-4-(trifluoromethoxy)-N-(4-(3,4,5-trimethoxystyryl)phenyl)benzenesulfonamide (11m)
(Z)-3-nitro-N-(4-(3,4,5-trimethoxystyryl)phenyl)benzenesulfonamide (11n)
(Z)-3-amino-N-(4-(3,4,5-trimethoxystyryl)phenyl)benzenesulfonamide (11o)
(Z)-3-fluoro-N-(4-(3,4,5-trimethoxystyryl)phenyl)benzenesulfonamide (11p)
(Z)-3-tert-butyl-N-(4-(3,4,5-trimethoxystyryl)phenyl)benzenesulfonamide (11q)
(Z)-3-fluoro-4-methoxy-N-(4-(3,4,5-trimethoxystyryl)phenyl)benzenesulfonamide (11r)
(Z)-3-hydroxy-4-methoxy-N-(4-(3,4,5-trimethoxystyryl)phenyl)benzenesulfonamide (11s)
(Z)-4-methoxy-3-nitro-N-(4-(3,4,5-trimethoxystyryl)phenyl)benzenesulfonamide (11t)
(Z)-3-amino-4-methoxy-N-(4-(3,4,5-trimethoxystyryl)phenyl)benzenesulfonamide (11u)
(Z)-3,4,5-trimethoxy-N-(4-(3,4,5-trimethoxystyryl)phenyl)benzenesulfonamide (11v)
(Z)-4-methyl-N-(4-(3,4,5-trimethoxystyryl)phenyl)benzenesulfonamide (11w)
(Z)-3,4-difluoro-N-(4-(3,4,5-trimethoxystyryl)phenyl)benzenesulfonamide (11x)
(Z)-3-chloro-4-methoxy-N-(4-(3,4,5-trimethoxystyryl)phenyl)benzenesulfonamide (11y)
(Z)-4-methoxy-N-(2-methoxy-5-(3,4,5-trimethoxystyryl)phenyl)benzenesulfonamide (12a)
(Z)-3,4-dimethoxy-N-(2-methoxy-5-(3,4,5-trimethoxystyryl)phenyl)benzenesulfonamide (12b)
(Z)-4-chloro-N-(2-methoxy-5-(3,4,5-trimethoxystyryl)phenyl)benzenesulfonamide (12c)
(Z)-3-chloro-N-(2-methoxy-5-(3,4,5-trimethoxystyryl)phenyl)benzenesulfonamide (12d)
(Z)-3,4-dichloro-N-(2-methoxy-5-(3,4,5-trimethoxystyryl)phenyl)benzenesulfonamide (12e)
(Z)-4-fluoro-N-(2-methoxy-5-(3,4,5-trimethoxystyryl)phenyl)benzenesulfonamide (12f)
(Z)-4-tert-butyl-N-(2-methoxy-5-(3,4,5-trimethoxystyryl)phenyl)benzenesulfonamide (12g)
(Z)—N-(2-methoxy-5-(3,4,5-trimethoxystyryl)phenyl)-4-nitrobenzenesulfonamide (12h)
(Z)-4-amino-N-(2-methoxy-5-(3,4,5-trimethoxystyryl)phenyl)benzenesulfonamide (12i)
(Z)—N-(2-methoxy-5-(3,4,5-trimethoxystyryl)phenyl)-3-(trifluoromethyl)benzenesulfonamide (12j)
(Z)—N-(2-methoxy-5-(3,4,5-trimethoxystyryl)phenyl)-3-(trifluoromethoxy) benzenesulfonamide (12k)
(Z)—N-(2-methoxy-5-(3,4,5-trimethoxystyryl)phenyl)-4-(trifluoromethyl)benzenesulfonamide (12l)
(Z)—N-(2-methoxy-5-(3,4,5-trimethoxystyryl)phenyl)-4-(trifluoromethoxy)benzenesulfonamide (12m)
(Z)—N-(2-methoxy-5-(3,4,5-trimethoxystyryl)phenyl)-3-nitrobenzenesulfonamide (12n)
(Z)-3-amino-N-(2-methoxy-5-(3,4,5-trimethoxystyryl)phenyl)benzenesulfonamide (12o)
(Z)-3-fluoro-N-(2-methoxy-5-(3,4,5-trimethoxystyryl)phenyl)benzenesulfonamide (12p)

(Z)-3-tert-butyl-N-(2-methoxy-5-(3,4,5-trimethoxystyryl) phenyl)benzenesulfonamide (12q)

(Z)-3-fluoro-4-methoxy-N-(2-methoxy-5-(3,4,5-trimethoxystyryl)phenyl)benzenesulfonamide (12r)

(Z)-3-hydroxy-4-methoxy-N-(2-methoxy-5-(3,4,5-trimethoxystyryl)phenyl)benzenesulfonamide (12s)

(Z)-4-methoxy-N-(2-methoxy-5-(3,4,5-trimethoxystyryl) phenyl)-3-nitrobenzenesulfonamide (12t)

(Z)-3-amino-4-methoxy-N-(2-methoxy-5-(3,4,5-trimethoxystyryl)phenyl)benzenesulfonamide (12u)

(Z)-3,4,5-trimethoxy-N-(2-methoxy-5-(3,4,5-trimethoxystyryl)phenyl)benzenesulfonamide (12v)

(Z)—N-(2-methoxy-5-(3,4,5-trimethoxystyryl)phenyl)-4-methylbenzenesulfonamide (12w)

(Z)-3,4-difluoro-N-(2-methoxy-5-(3,4,5-trimethoxystyryl) phenyl)benzenesulfonamide (12x)

(Z)-3-chloro-4-methoxy-N-(2-methoxy-5-(3,4,5-trimethoxystyryl)phenyl)benzenesulfonamide (12y)

(Z)—N-(2,3-dimethoxy-5-(3,4,5-trimethoxystyryl)phenyl)-4-methoxybenzenesulfonamide (13a)

(Z)—N-(2,3-dimethoxy-5-(3,4,5-trimethoxystyryl)phenyl)-3,4-dimethoxybenzenesulfonamide (13b)

(Z)-4-chloro-N-(2,3-dimethoxy-5-(3,4,5-trimethoxystyryl) phenyl)benzenesulfonamide (13c)

(Z)-3-chloro-N-(2,3-dimethoxy-5-(3,4,5-trimethoxystyryl) phenyl)benzenesulfonamide (13d)

(Z)-3,4-dichloro-N-(2,3-dimethoxy-5-(3,4,5-trimethoxystyryl)phenyl)benzenesulfonamide (13e)

(Z)—N-(2,3-dimethoxy-5-(3,4,5-trimethoxystyryl)phenyl)-4-fluorobenzenesulfonamide (13l)

(Z)-4-tert-butyl-N-(2,3-dimethoxy-5-(3,4,5-trimethoxystyryl)phenyl)benzenesulfonamide (13g)

(Z)—N-(2,3-dimethoxy-5-(3,4,5-trimethoxystyryl)phenyl)-4-nitrobenzenesulfonamide (13h)

(Z)-4-amino-N-(2,3-dimethoxy-5-(3,4,5-trimethoxystyryl) phenyl)benzenesulfonamide (13i)

(Z)—N-(2,3-dimethoxy-5-(3,4,5-trimethoxystyryl)phenyl)-3-(trifluoromethyl)benzenesulfonamide (13j)

(Z)—N-(2,3-dimethoxy-5-(3,4,5-trimethoxystyryl)phenyl)-3(trifluoromethoxy) benzenesulfonamide (13k)

(Z)—N-(2,3-dimethoxy-5-(3,4,5-trimethoxystyryl)phenyl)-4-(trifluoromethyl) benzenesulfonamide (13l)

(Z)—N-(2,3-dimethoxy-5-(3,4,5-trimethoxystyryl)phenyl)-4-(trifluoromethoxy)Benzenesulfonamide (13m)

(Z)—N-(2,3-dimethoxy-5-(3,4,5-trimethoxystyryl)phenyl)-3-nitrobenzenesulfonamide (13n)

(Z)-3-amino-N-(2,3-dimethoxy-5-(3,4,5-trimethoxystyryl) phenyl)benzenesulfonamide (13o)

(Z)—N-(2,3-dimethoxy-5-(3,4,5-trimethoxystyryl)phenyl)-3-fluorobenzenesulfonamide (13p)

(Z)-3-tert-butyl-N-(2,3-dimethoxy-5-(3,4,5-trimethoxystyryl)phenyl)benzenesulfonamide (13q)

(Z)—N-(2,3-dimethoxy-5-(3,4,5-trimethoxystyryl)phenyl)-3-fluoro-4-methoxyBenzenesulfonamide (13r)

(Z)—N-(2,3-dimethoxy-5-(3,4,5-trimethoxystyryl)phenyl)-3-hydroxy-4-methoxy Benzenesulfonamide (13s)

(Z)—N-(2,3-dimethoxy-5-(3,4,5-trimethoxystyryl)phenyl)-4-methoxy-3-nitro Benzenesulfonamide (13t)

(Z)-3-amino-N-(2,3-dimethoxy-5-(3,4,5-trimethoxystyryl) phenyl)-4-methoxyBenzenesulfonamide (13u)

(Z)—N-(2,3-dimethoxy-5-(3,4,5-trimethoxystyryl)phenyl)-3,4,5-trimethoxyBenzenesulfonamide (13v)

(Z)—N-(2,3-dimethoxy-5-(3,4,5-trimethoxystyryl)phenyl)-4-methyl benzene sulfonamide (13w)

(Z)—N-(2,3-dimethoxy-5-(3,4,5-trimethoxystyryl)phenyl)-3,4-difluoro Benzenesulfonamide (13x)

(Z)-3-chloro-N-(2,3-dimethoxy-5-(3,4,5-trimethoxystyryl) phenyl)-4-methoxybenzene sulfonamide (13y)

(Z)—N-(3-hydroxy-2-methoxy-5-(3,4,5-trimethoxystyryl) phenyl)-4-methoxy benzene sulfonamide (14a)

(Z)—N-(3-hydroxy-2-methoxy-5-(3,4,5-trimethoxystyryl) phenyl)-3,4-dimethoxybenzenesulfonamide (14b)

(Z)-4-chloro-N-(3-hydroxy-2-methoxy-5-(3,4,5-trimethoxystyryl)phenyl)benzenesulfonamide (14c)

(Z)-3-chloro-N-(3-hydroxy-2-methoxy-5-(3,4,5-trimethoxystyryl) phenyl)benzenesulfonamide (14d)

(Z)-3,4-dichloro-N-(3-hydroxy-2-methoxy-5-(3,4,5-trimethoxystyryl)phenyl)benzenesulfonamide (14e)

(Z)-4-fluoro-N-(3-hydroxy-2-methoxy-5-(3,4,5-trimethoxystyryl)phenyl)benzenesulfonamide (14f)

(Z)-4-tert-butyl-N-(3-hydroxy-2-methoxy-5-(3,4,5-trimethoxystyryl)phenyl)benzenesulfonamide (14g)

(Z)—N-(3-hydroxy-2-methoxy-5-(3,4,5-trimethoxystyryl) phenyl)-4-nitrobenzenesulfonamide (14h)

(Z)-4-amino-N-(3-hydroxy-2-methoxy-5-(3,4,5-trimethoxystyryl)phenyl)benzenesulfonamide (14i)

(Z)—N-(3-hydroxy-2-methoxy-5-(3,4,5-trimethoxystyryl) phenyl)-3-(trifluoromethyl)benzenesulfonamide (14j)

(Z)—N-(3-hydroxy-2-methoxy-5-(3,4,5-trimethoxystyryl) phenyl)-3-(trifluoromethoxy)benzenesulfonamide (14k)

(Z)—N-(3-hydroxy-2-methoxy-5-(3,4,5-trimethoxystyryl) phenyl)-4-(trifluoromethyl)benzenesulfonamide (14l)

(Z)—N-(3-hydroxy-2-methoxy-5-(3,4,5-trimethoxystyryl) phenyl)-4-(trifluoromethoxy)benzenesulfonamide (14m)

(Z)—N-(3-hydroxy-2-methoxy-5-(3,4,5-trimethoxystyryl) phenyl)-3-nitrobenzenesulfonamide (14n)

(Z)-3-amino-N-(3-hydroxy-2-methoxy-5-(3,4,5-trimethoxystyryl)phenyl)benzenesulfonamide (14o)

(Z)-3-fluoro-N-(3-hydroxy-2-methoxy-5-(3,4,5-trimethoxystyryl)phenyl)benzenesulfonamide (14p)

(Z)-3-tert-butyl-N-(3-hydroxy-2-methoxy-5-(3,4,5-trimethoxystyryl)phenyl)benzenesulfonamide (14q)

(Z)-3-fluoro-N-(3-hydroxy-2-methoxy-5-(3,4,5-trimethoxystyryl)phenyl)-4-methoxybenzenesulfonamide (14r)

(Z)-3-hydroxy-N-(3-hydroxy-2-methoxy-5-(3,4,5-trimethoxystyryl)phenyl)-4-ethoxybenzenesulfonamide (14s)

(Z)—N-(3-hydroxy-2-methoxy-5-(3,4,5-trimethoxystyryl) phenyl)-4-methoxy-3-nitrobenzenesulfonamide (14t)

(Z)-3-amino-N-(3-hydroxy-2-methoxy-5-(3,4,5-trimethoxystyryl)phenyl)-4-ethoxybenzenesulfonamide (14u)

(Z)—N-(3-hydroxy-2-methoxy-5-(3,4,5-trimethoxystyryl) phenyl)-3,4,5-trimethoxybenzenesulfonamide (14v)

(Z)—N-(3-hydroxy-2-methoxy-5-(3,4,5-trimethoxystyryl) phenyl)-4-methylbenzenesulfonamide (14w)

(Z)-3,4-difluoro-N-(3-hydroxy-2-methoxy-5-(3,4,5-trimethoxystyryl)phenyl)benzenesulfonamide (14x)

(Z)-3-chloro-N-(3-hydroxy-2-methoxy-5-(3,4,5-trimethoxystyryl)phenyl)-4-methoxybenzenesulfonamide (14y)

(Z)—N-(3-fluoro-2-methoxy-5-(3,4,5-trimethoxystyryl) phenyl)-4-methoxybenzenesulfonamide (15a)

(Z)—N-(3-fluoro-2-methoxy-5-(3,4,5-trimethoxystyryl) phenyl)-3,4-dimethoxybenzenesulfonamide (15b)

(Z)-4-chloro-N-(3-fluoro-2-methoxy-5-(3,4,5-trimethoxystyryl)phenyl)benzenesulfonamide (15c)

(Z)-3-chloro-N-(3-fluoro-2-methoxy-5-(3,4,5-trimethoxystyryl)phenyl)benzenesulfonamide (15d)

(Z)-3,4-dichloro-N-(3-fluoro-2-methoxy-5-(3,4,5-trimethoxystyryl)phenyl)benzenesulfonamide (15e)

(Z)-4-fluoro-N-(3-fluoro-2-methoxy-5-(3,4,5-trimethoxystyryl)phenyl)benzenesulfonamide (15f)

(Z)-4-tert-butyl-N-(3-fluoro-2-methoxy-5-(3,4,5-trimethoxystyryl)phenyl)benzenesulfonamide (15g)

(Z)—N-(3-fluoro-2-methoxy-5-(3,4,5-trimethoxystyryl)phenyl)-4-nitrobenzenesulfonamide (15h)
(Z)-4-amino-N-(3-fluoro-2-methoxy-5-(3,4,5-trimethoxystyryl)phenyl)benzenesulfonamide (15i)
(Z)—N-(3-fluoro-2-methoxy-5-(3,4,5-trimethoxystyryl)phenyl)-3-(trifluoromethyl)benzenesulfonamide (15j)
(Z)—N-(3-fluoro-2-methoxy-5-(3,4,5-trimethoxystyryl)phenyl)-3-(trifluoromethoxy)benzenesulfonamide (15k)
(Z)—N-(3-fluoro-2-methoxy-5-(3,4,5-trimethoxystyryl)phenyl)-4-(trifluoromethyl)benzenesulfonamide (15l)
(Z)—N-(3-fluoro-2-methoxy-5-(3,4,5-trimethoxystyryl)phenyl)-4-(trifluoromethoxy)benzenesulfonamide (15m)
(Z)—N-(3-fluoro-2-methoxy-5-(3,4,5-trimethoxystyryl)phenyl)-3-nitrobenzenesulfonamide (15n)
(Z)-3-amino-N-(3-fluoro-2-methoxy-5-(3,4,5-trimethoxystyryl)phenyl)benzenesulfonamide (15o)
(Z)-3-fluoro-N-(3-fluoro-2-methoxy-5-(3,4,5-trimethoxystyryl)phenyl)benzenesulfonamide (15p)
(Z)-3-tert-butyl-N-(3-fluoro-2-methoxy-5-(3,4,5-trimethoxystyryl)phenyl)benzenesulfonamide (15q)
(Z)-3-fluoro-N-(3-fluoro-2-methoxy-5-(3,4,5-trimethoxystyryl)phenyl)-4-methoxybenzenesulfonamide (15r)
(Z)—N-(3-fluoro-2-methoxy-5-(3,4,5-trimethoxystyryl)phenyl)-3-hydroxy-4-methoxybenzenesulfonamide (15s)
(Z)—N-(3-fluoro-2-methoxy-5-(3,4,5-trimethoxystyryl)phenyl)-4-methoxy-3-nitrobenzenesulfonamide (15t)
(Z)-3-amino-N-(3-fluoro-2-methoxy-5-(3,4,5-trimethoxystyryl)phenyl)-4-methoxybenzenesulfonamide (15u)
(Z)—N-(3-fluoro-2-methoxy-5-(3,4,5-trimethoxystyryl)phenyl)-3,4,5-trimethoxybenzenesulfonamide (15v)
(Z)—N-(3-fluoro-2-methoxy-5-(3,4,5-trimethoxystyryl)phenyl)-4-methyl benzenesulfonamide (15w)
(Z)-3,4-difluoro-N-(3-fluoro-2-methoxy-5-(3,4,5-trimethoxystyryl)phenyl)benzenesulfonamide (15x)
(Z)-3-chloro-N-(3-fluoro-2-methoxy-5-(3,4,5-trimethoxystyryl)phenyl)-4-methoxybenzenesulfonamide (15y)
(Z)—N-(2-hydroxy-3-methoxy-5-(3,4,5-trimethoxystyryl)phenyl)-4-methoxybenzenesulfonamide (16a)
(Z)—N-(2-hydroxy-3-methoxy-5-(3,4,5-trimethoxystyryl)phenyl)-3,4-dimethoxybenzenesulfonamide (16b)
(Z)-4-chloro-N-(2-hydroxy-3-methoxy-5-(3,4,5-trimethoxystyryl)phenyl)benzenesulfonamide (16c)
(Z)-3-chloro-N-(2-hydroxy-3-methoxy-5-(3,4,5-trimethoxystyryl)phenyl)Benzenesulfonamide (16d)
(Z)-3,4-dichloro-N-(2-hydroxy-3-methoxy-5-(3,4,5-trimethoxystyryl)phenyl)benzenesulfonamide (16e)
(Z)-4-fluoro-N-(2-hydroxy-3-methoxy-5-(3,4,5-trimethoxystyryl)phenyl)benzenesulfonamide (16f)
(Z)-4-tert-butyl-N-(2-hydroxy-3-methoxy-5-(3,4,5-trimethoxystyryl)phenyl)benzenesulfonamide (16g)
(Z)—N-(2-hydroxy-3-methoxy-5-(3,4,5-trimethoxystyryl)phenyl)-4-nitrobenzenesulfonamide (16h)
(Z)-4-amino-N-(2-hydroxy-3-methoxy-5-(3,4,5-trimethoxystyryl)phenyl)benzenesulfonamide (16I)
(Z)—N-(2-hydroxy-3-methoxy-5-(3,4,5-trimethoxystyryl)phenyl)-3-(trifluoromethyl)benzenesulfonamide (16j)
(Z)—N-(2-hydroxy-3-methoxy-5-(3,4,5-trimethoxystyryl)phenyl)-3-(trifluoromethoxy)benzenesulfonamide (16k)
(Z)—N-(2-hydroxy-3-methoxy-5-(3,4,5-trimethoxystyryl)phenyl)-4-(trifluoromethyl)benzenesulfonamide (16l)
(Z)—N-(2-hydroxy-3-methoxy-5-(3,4,5-trimethoxystyryl)phenyl)-4-(trifluoromethoxy) benzenesulfonamide (16m)
(Z)—N-(2-hydroxy-3-methoxy-5-(3,4,5-trimethoxystyryl)phenyl)-3-nitrobenzenesulfonamide (16n)
(Z)-3-amino-N-(2-hydroxy-3-methoxy-5-(3,4,5-trimethoxystyryl)phenyl) benzenesulfonamide (16o)
(Z)-3-fluoro-N-(2-hydroxy-3-methoxy-5-(3,4,5-trimethoxystyryl)phenyl)benzenesulfonamide (16p)
(Z)-3-tert-butyl-N-(2-hydroxy-3-methoxy-5-(3,4,5-trimethoxystyryl)phenyl)benzenesulfonamide (16q)
(Z)-3-fluoro-N-(2-hydroxy-3-methoxy-5-(3,4,5-trimethoxystyryl)phenyl)-4-methoxybenzenesulfonamide (16r)
(Z)-3-hydroxy-N-(2-hydroxy-3-methoxy-5-(3,4,5-trimethoxystyryl)phenyl)-4-methoxybenzenesulfonamide (16s)
(Z)—N-(2-hydroxy-3-methoxy-5-(3,4,5-trimethoxystyryl)phenyl)-4-methoxy-3-nitrobenzenesulfonamide (16t)
(Z)-3-amino-N-(2-hydroxy-3-methoxy-5-(3,4,5-trimethoxystyryl)phenyl)-4-methoxybenzenesulfonamide (16u)
(Z)—N-(2-hydroxy-3-methoxy-5-(3,4,5-trimethoxystyryl)phenyl)-3,4,5-trimethoxybenzenesulfonamide (16v)
(Z)—N-(2-hydroxy-3-methoxy-5-(3,4,5-trimethoxystyryl)phenyl)-4-methylbenzenesulfonamide (16w)
(Z)-3,4-difluoro-N-(2-hydroxy-3-methoxy-5-(3,4,5-trimethoxystyryl)phenyl)benzenesulfonamide (16x)
(Z)-3-chloro-N-(2-hydroxy-3-methoxy-5-(3,4,5-trimethoxystyryl)phenyl)-4-methoxybenzenesulfonamide (16y)
(Z)—N-(2-hydroxy-3-methoxy-6-(3,4,5-trimethoxystyryl)phenyl)-4-methoxybenzenesulfonamide (17a)
(Z)—N-(2-hydroxy-3-methoxy-6-(3,4,5-trimethoxystyryl)phenyl)-3,4-dimethoxybenzenesulfonamide (17b)
(Z)-4-chloro-N-(2-hydroxy-3-methoxy-6-(3,4,5-trimethoxystyryl)phenyl)benzenesulfonamide (17c)
(Z)-3-chloro-N-(2-hydroxy-3-methoxy-6-(3,4,5-trimethoxystyryl)phenyl)benzenesulfonamide (17d)
(Z)-3,4-dichloro-N-(2-hydroxy-3-methoxy-6-(3,4,5-trimethoxystyryl)phenyl)benzenesulfonamide (17e)
(Z)-4-fluoro-N-(2-hydroxy-3-methoxy-6-(3,4,5-trimethoxystyryl)phenyl)benzenesulfonamide (17f)
(Z)-4-tert-butyl-N-(2-hydroxy-3-methoxy-6-(3,4,5-trimethoxystyryl)phenyl)benzenesulfonamide (17g)
(Z)—N-(2-hydroxy-3-methoxy-6-(3,4,5-trimethoxystyryl)phenyl)-4-nitrobenzenesulfonamide (17h)
(Z)—N-(2-hydroxy-3-methoxy-6-(3,4,5-trimethoxystyryl)phenyl)-3-(trifluoromethyl)benzenesulfonamide (17i)
(Z)—N-(2-hydroxy-3-methoxy-6-(3,4,5-trimethoxystyryl)phenyl)-3-(trifluoromethoxy)benzenesulfonamide (17j)
(Z)—N-(2-hydroxy-3-methoxy-6-(3,4,5-trimethoxystyryl)phenyl)-3-(trifluoromethoxy)benzenesulfonamide (17k)
(Z)—N-(2-hydroxy-3-methoxy-6-(3,4,5-trimethoxystyryl)phenyl)-4-(trifluoromethyl)benzenesulfonamide (17l)
(Z)—N-(2-hydroxy-3-methoxy-6-(3,4,5-trimethoxystyryl)phenyl)-4-(trifluoromethoxy)benzenesulfonamide (17m)
(Z)—N-(2-hydroxy-3-methoxy-6-(3,4,5-trimethoxystyryl)phenyl)-3-nitrobenzenesulfonamide (17n)
(Z)-3-amino-N-(2-hydroxy-3-methoxy-6-(3,4,5-trimethoxystyryl)phenyl)benzenesulfonamide (17o)
(Z)-3-fluoro-N-(2-hydroxy-3-methoxy-6-(3,4,5-trimethoxystyryl)phenyl)benzenesulfonamide (17p)
(Z)-3-tert-butyl-N-(2-hydroxy-3-methoxy-6-(3,4,5-trimethoxystyryl)phenyl)benzenesulfonamide (17q)
(Z)-3-fluoro-N-(2-hydroxy-3-methoxy-6-(3,4,5-trimethoxystyryl)phenyl)-4-methoxybenzenesulfonamide (17r)
(Z)-3-hydroxy-N-(2-hydroxy-3-methoxy-6-(3,4,5-trimethoxystyryl)phenyl)-4-methoxybenzenesulfonamide (17s)
(Z)—N-(2-hydroxy-3-methoxy-6-(3,4,5-trimethoxystyryl)phenyl)-4-methoxy-3-nitrobenzenesulfonamide (17t)
(Z)—N-(2-hydroxy-3-methoxy-6-(3,4,5-trimethoxystyryl)phenyl)-3,4,5-trimethoxybenzenesulfonamide (17u)
(Z)—N-(2-hydroxy-3-methoxy-6-(3,4,5-trimethoxystyryl)phenyl)-4-methylbenzenesulfonamide (17v)

(Z)-4-hydroxy-N-(2-hydroxy-3-methoxy-6-(3,4,5-trimethoxystyryl)phenyl)benzenesulfonamide (17w)
(Z)-3,4-difluoro-N-(2-hydroxy-3-methoxy-6-(3,4,5-trimethoxystyryl)phenyl)benzenesulfonamide (17x)
(Z)-3-chloro-N-(2-hydroxy-3-methoxy-6-(3,4,5-trimethoxystyryl)phenyl)-4-methoxybenzenesulfonamide (17y)
(Z)—N-(4-hydroxy-5-methoxy-2-(3,4,5-trimethoxystyryl)phenyl)-4-methoxybenzenesulfonamide (18a)
(Z)—N-(4-hydroxy-5-methoxy-2-(3,4,5-trimethoxystyryl)phenyl)-3,4-dimethoxybenzenesulfonamide (18b)
(Z)-4-chloro-N-(4-hydroxy-5-methoxy-2-(3,4,5-trimethoxystyryl)phenyl)benzenesulfonamide (18c)
(Z)-3-chloro-N-(4-hydroxy-5-methoxy-2-(3,4,5-trimethoxystyryl)phenyl)benzenesulfonamide (18d)
(Z)-3,4-dichloro-N-(4-hydroxy-5-methoxy-2-(3,4,5-trimethoxystyryl)phenyl)benzenesulfonamide (18e)
(Z)-4-fluoro-N-(4-hydroxy-5-methoxy-2-(3,4,5-trimethoxystyryl)phenyl)benzenesulfonamide (18f)
(Z)-4-tert-butyl-N-(4-hydroxy-5-methoxy-2-(3,4,5-trimethoxystyryl)phenyl)benzenesulfonamide (18g)
(Z)—N-(4-hydroxy-5-methoxy-2-(3,4,5-trimethoxystyryl)phenyl)-4-nitrobenzenesulfonamide (18h)
(Z)-4-amino-N-(4-hydroxy-5-methoxy-2-(3,4,5-trimethoxystyryl)phenyl)benzenesulfonamide (18i)
(Z)—N-(4-hydroxy-5-methoxy-2-(3,4,5-trimethoxystyryl)phenyl)-3-(trifluoromethyl)benzenesulfonamide (18j)
(Z)—N-(4-hydroxy-5-methoxy-2-(3,4,5-trimethoxystyryl)phenyl)-4-(trifluoromethyl)benzenesulfonamide (18k)
(Z)—N-(4-hydroxy-5-methoxy-2-(3,4,5-trimethoxystyryl)phenyl)-4-(trifluoromethyl)benzenesulfonamide (18l)
(Z)—N-(4-hydroxy-5-methoxy-2-(3,4,5-trimethoxystyryl)phenyl)-4-(trifluoromethoxy)benzenesulfonamide (18m)
(Z)—N-(4-hydroxy-5-methoxy-2-(3,4,5-trimethoxystyryl)phenyl)-3-nitrobenzenesulfonamide (18n)
(Z)-3-amino-N-(4-hydroxy-5-methoxy-2-(3,4,5-trimethoxystyryl)phenyl)benzenesulfonamide (18o)
(Z)-3-fluoro-N-(4-hydroxy-5-methoxy-2-(3,4,5-trimethoxystyryl)phenyl)benzenesulfonamide (18p)
(Z)-3-tert-butyl-N-(4-hydroxy-5-methoxy-2-(3,4,5-trimethoxystyryl)phenyl)benzenesulfonamide (18q)
(Z)-3-fluoro-N-(4-hydroxy-5-methoxy-2-(3,4,5-trimethoxystyryl)phenyl)-4-methoxybenzenesulfonamide (18r)
(Z)-3-hydroxy-N-(4-hydroxy-5-methoxy-2-(3,4,5-trimethoxystyryl)phenyl)-4-methoxybenzenesulfonamide (18s)
(Z)—N-(4-hydroxy-5-methoxy-2-(3,4,5-trimethoxystyryl)phenyl)-4-methoxy-3-nitrobenzenesulfonamide (18t)
(Z)—N-(4-hydroxy-5-methoxy-2-(3,4,5-trimethoxystyryl)phenyl)-3,4,5-trimethoxybenzenesulfonamide (18u)
(Z)—N-(4-hydroxy-5-methoxy-2-(3,4,5-trimethoxystyryl)phenyl)-4-methylbenzenesulfonamide (18v)
(Z)-4-hydroxy-N-(4-hydroxy-5-methoxy-2-(3,4,5-trimethoxystyryl)phenyl)benzenesulfonamide (18w)
(Z)-3,4-difluoro-N-(4-hydroxy-5-methoxy-2-(3,4,5-trimethoxystyryl)phenyl)benzenesulfonamide (18x)
(Z)-3-chloro-N-(4-hydroxy-5-methoxy-2-(3,4,5-trimethoxystyryl)phenyl)-4-methoxybenzenesulfonamide (18y)
(Z)—N-(2-fluoro-3-methoxy-6-(3,4,5-trimethoxystyryl)phenyl)-4-methoxybenzenesulfonamide (19a)
(Z)—N-(2-fluoro-3-methoxy-6-(3,4,5-trimethoxystyryl)phenyl)-3,4-dimethoxybenzenesulfonamide (19b)
(Z)-4-chloro-N-(2-fluoro-3-methoxy-6-(3,4,5-trimethoxystyryl)phenyl)benzenesulfonamide (19c)
(Z)-3-chloro-N-(2-fluoro-3-methoxy-6-(3,4,5-trimethoxystyryl)phenyl)benzenesulfonamide (19d)
(Z)-3,4-dichloro-N-(2-fluoro-3-methoxy-6-(3,4,5-trimethoxystyryl)phenyl)benzenesulfonamide (19e)
(Z)-4-fluoro-N-(2-fluoro-3-methoxy-6-(3,4,5-trimethoxystyryl)phenyl)benzenesulfonamide (19f)
(Z)-4-tert-butyl-N-(2-fluoro-3-methoxy-6-(3,4,5-trimethoxystyryl)phenyl)benzenesulfonamide (19g)
(Z)—N-(2-fluoro-3-methoxy-6-(3,4,5-trimethoxystyryl)phenyl)-4-nitrobenzenesulfonamide (19h)
(Z)-4-amino-N-(2-fluoro-3-methoxy-6-(3,4,5-trimethoxystyryl)phenyl)benzenesulfonamide (19i)
(Z)—N-(2-fluoro-3-methoxy-6-(3,4,5-trimethoxystyryl)phenyl)-3-(trifluoromethyl)benzenesulfonamide (19j)
(Z)—N-(2-fluoro-3-methoxy-6-(3,4,5-trimethoxystyryl)phenyl)-3-(trifluoromethoxy) benzenesulfonamide (19k)
(Z)—N-(2-fluoro-3-methoxy-6-(3,4,5-trimethoxystyryl)phenyl)-4-(trifluoromethyl)benzenesulfonamide (19l)
(Z)—N-(2-fluoro-3-methoxy-6-(3,4,5-trimethoxystyryl)phenyl)-4-(trifluoromethoxy)benzenesulfonamide (19m)
(Z)—N-(2-fluoro-3-methoxy-6-(3,4,5-trimethoxystyryl)phenyl)-3-nitrobenzenesulfonamide (19n)
(Z)-3-amino-N-(2-fluoro-3-methoxy-6-(3,4,5-trimethoxystyryl)phenyl)benzenesulfonamide (19o)
(Z)-3-fluoro-N-(2-fluoro-3-methoxy-6-(3,4,5-trimethoxystyryl)phenyl)benzenesulfonamide (19p)
(Z)-3-tert-butyl-N-(2-fluoro-3-methoxy-6-(3,4,5-trimethoxystyryl)phenyl)benzenesulfonamide (19q)
(Z)-3-fluoro-N-(2-fluoro-3-methoxy-6-(3,4,5-trimethoxystyryl)phenyl)-4-methoxybenzenesulfonamide (19r)
(Z)—N-(2-fluoro-3-methoxy-6-(3,4,5-trimethoxystyryl)phenyl)-3-hydroxy-4-methoxybenzenesulfonamide (19s)
(Z)—N-(2-fluoro-3-methoxy-6-(3,4,5-trimethoxystyryl)phenyl)-4-methoxy-3-nitrobenzenesulfonamide (19t)
(Z)—N-(2-fluoro-3-methoxy-6-(3,4,5-trimethoxystyryl)phenyl)-3,4,5-trimethoxybenzenesulfonamide (19u)
(Z)—N-(2-fluoro-3-methoxy-6-(3,4,5-trimethoxystyryl)phenyl)-4-methylbenzenesulfonamide (19v)
(Z)—N-(2-fluoro-3-methoxy-6-(3,4,5-trimethoxystyryl)phenyl)-4-hydroxybenzenesulfonamide (19w)
(Z)-3,4-difluoro-N-(2-fluoro-3-methoxy-6-(3,4,5-trimethoxystyryl)phenyl)benzenesulfonamide (19x)
(Z)-3-chloro-N-(2-fluoro-3-methoxy-6-(3,4,5-trimethoxystyryl)phenyl)-4-methoxybenzenesulfonamide (19y)
(Z)—N-(3-fluoro-2-methoxy-6-(3,4,5-trimethoxystyryl)phenyl)-4-methoxybenzenesulfonamide (20a)
(Z)—N-(3-fluoro-2-methoxy-6-(3,4,5-trimethoxystyryl)phenyl)-3,4-dimethoxybenzenesulfonamide (20b)
(Z)-4-chloro-N-(3-fluoro-2-methoxy-6-(3,4,5-trimethoxystyryl)phenyl)benzenesulfonamide (20c)
(Z)-3-chloro-N-(3-fluoro-2-methoxy-6-(3,4,5-trimethoxystyryl)phenyl)benzenesulfonamide (20d)
(Z)-3,4-dichloro-N-(3-fluoro-2-methoxy-6-(3,4,5-trimethoxystyryl)phenyl) benzenesulfonamide (20e)
(Z)-4-fluoro-N-(3-fluoro-2-methoxy-6-(3,4,5-trimethoxystyryl)phenyl)benzenesulfonamide (20f)
(Z)-4-tert-butyl-N-(3-fluoro-2-methoxy-6-(3,4,5-trimethoxystyryl)phenyl)benzenesulfonamide (20g)
(Z)—N-(3-fluoro-2-methoxy-6-(3,4,5-trimethoxystyryl)phenyl)-4-nitrobenzenesulfonamide (20h)
(Z)-4-amino-N-(3-fluoro-2-methoxy-6-(3,4,5-trimethoxystyryl)phenyl)benzenesulfonamide (20i)
(Z)—N-(3-fluoro-2-methoxy-6-(3,4,5-trimethoxystyryl)phenyl)-3-(trifluoromethyl)benzenesulfonamide (20j)
(Z)—N-(3-fluoro-2-methoxy-6-(3,4,5-trimethoxystyryl)phenyl)-3-(trifluoromethoxy)benzenesulfonamide (20k))
(Z)—N-(3-fluoro-2-methoxy-6-(3,4,5-trimethoxystyryl)phenyl)-4-(trifluoromethyl)benzenesulfonamide (20l)
(Z)—N-(3-fluoro-2-methoxy-6-(3,4,5-trimethoxystyryl)phenyl)-4-(trifluoromethoxy)benzenesulfonamide (20m)

(Z)—N-(3-fluoro-2-methoxy-6-(3,4,5-trimethoxystyryl) phenyl)-3-nitrobenzenesulfonamide (20n)
(Z)-3-amino-N-(3-fluoro-2-methoxy-6-(3,4,5-trimethoxystyryl)phenyl)benzenesulfonamide (20o)
(Z)-3-fluoro-N-(3-fluoro-2-methoxy-6-(3,4,5-trimethoxystyryl)phenyl)benzenesulfonamide (20p)
(Z)-3-tert-butyl-N-(3-fluoro-2-methoxy-6-(3,4,5-trimethoxystyryl)phenyl)benzenesulfonamide (20q)
(Z)-3-fluoro-N-(3-fluoro-2-methoxy-6-(3,4,5-trimethoxystyryl)phenyl)-4-methoxybenzenesulfonamide (20r)
(Z)—N-(3-fluoro-2-methoxy-6-(3,4,5-trimethoxystyryl) phenyl)-3-hydroxy-4-methoxybenzenesulfonamide (20s)
(Z)—N-(3-fluoro-2-methoxy-6-(3,4,5-trimethoxystyryl) phenyl)-4-methoxy-3-nitrobenzenesulfonamide (20t)
(Z)—N-(3-fluoro-2-methoxy-6-(3,4,5-trimethoxystyryl) phenyl)-3,4,5-trimethoxybenzenesulfonamide (20u)
(Z)—N-(3-fluoro-2-methoxy-6-(3,4,5-trimethoxystyryl) phenyl)-4-methylbenzenesulfonamide (20v)
(Z)—N-(3-fluoro-2-methoxy-6-(3,4,5-trimethoxystyryl) phenyl)-4-hydroxybenzenesulfonamide (20w)
(Z)-3,4-difluoro-N-(3-fluoro-2-methoxy-6-(3,4,5-trimethoxystyryl)phenyl)benzenesulfonamide (20x)
(Z)-3-chloro-N-(3-fluoro-2-methoxy-6-(3,4,5-trimethoxystyryl)phenyl)-4-methoxybenzenesulfonamide (20y)
(Z)—N-(3-hydroxy-2-methoxy-6-(3,4,5-trimethoxystyryl) phenyl)-4-methoxybenzenesulfonamide (21a)
(Z)—N-(3-hydroxy-2-methoxy-6-(3,4,5-trimethoxystyryl) phenyl)-3,4-dimethoxybenzenesulfonamide (21b)
(Z)-4-chloro-N-(3-hydroxy-2-methoxy-6-(3,4,5-trimethoxystyryl)phenyl)benzenesulfonamide (21c)
(Z)-3-chloro-N-(3-hydroxy-2-methoxy-6-(3,4,5-trimethoxystyryl)phenyl)benzenesulfonamide (21d)
(Z)-3,4-dichloro-N-(3-hydroxy-2-methoxy-6-(3,4,5-trimethoxystyryl)phenyl)benzenesulfonamide (21e)
(Z)-4-fluoro-N-(3-hydroxy-2-methoxy-6-(3,4,5-trimethoxystyryl)phenyl)benzenesulfonamide (21f)
(Z)-4-tert-butyl-N-(3-hydroxy-2-methoxy-6-(3,4,5-trimethoxystyryl)phenyl)benzenesulfonamide (21g)
(Z)—N-(3-hydroxy-2-methoxy-6-(3,4,5-trimethoxystyryl) phenyl)-4-nitrobenzenesulfonamide (21h)
(Z)-4-amino-N-(3-hydroxy-2-methoxy-6-(3,4,5-trimethoxystyryl)phenyl)benzenesulfonamide (21i)
(Z)—N-(3-hydroxy-2-methoxy-6-(3,4,5-trimethoxystyryl) phenyl)-3-(trifluoromethyl)benzenesulfonamide (21j)
(Z)—N-(3-hydroxy-2-methoxy-6-(3,4,5-trimethoxystyryl) phenyl)-3-(trifluoromethoxy)benzenesulfonamide (21k)
(Z)—N-(3-hydroxy-2-methoxy-6-(3,4,5-trimethoxystyryl) phenyl)-4-(trifluoromethyl)benzenesulfonamide (21l)
(Z)—N-(3-hydroxy-2-methoxy-6-(3,4,5-trimethoxystyryl) phenyl)-4-(trifluoromethoxy)benzenesulfonamide (21m)
(Z)—N-(3-hydroxy-2-methoxy-6-(3,4,5-trimethoxystyryl) phenyl)-3-nitrobenzenesulfonamide (21n)
(Z)-3-amino-N-(3-hydroxy-2-methoxy-6-(3,4,5-trimethoxystyryl)phenyl)benzenesulfonamide (21o)
(Z)-3-fluoro-N-(3-hydroxy-2-methoxy-6-(3,4,5-trimethoxystyryl)phenyl)benzenesulfonamide (21p)
(Z)-3-tert-butyl-N-(3-hydroxy-2-methoxy-6-(3,4,5-trimethoxystyryl)phenyl)benzenesulfonamide (21q)
(Z)-3-fluoro-N-(3-hydroxy-2-methoxy-6-(3,4,5-trimethoxystyryl)phenyl)-4-methoxybenzenesulfonamide (21r)
(Z)-3-hydroxy-N-(3-hydroxy-2-methoxy-6-(3,4,5-trimethoxystyryl)phenyl)-4-methoxybenzenesulfonamide (21s)
(Z)—N-(3-hydroxy-2-methoxy-6-(3,4,5-trimethoxystyryl) phenyl)-4-methoxy-3-nitrobenzenesulfonamide (21t)
(Z)—N-(3-hydroxy-2-methoxy-6-(3,4,5-trimethoxystyryl) phenyl)-3,4,5-trimethoxybenzenesulfonamide (21u)
(Z)—N-(3-hydroxy-2-methoxy-6-(3,4,5-trimethoxystyryl) phenyl)-4-methylbenzenesulfonamide (21v)
(Z)-4-hydroxy-N-(3-hydroxy-2-methoxy-6-(3,4,5-trimethoxystyryl)phenyl)benzenesulfonamide (21w)
(Z)-3,4-difluoro-N-(3-hydroxy-2-methoxy-6-(3,4,5-trimethoxystyryl)phenyl)benzenesulfonamide (21x)
(Z)-3-chloro-N-(3-hydroxy-2-methoxy-6-(3,4,5-trimethoxystyryl)phenyl)-4-methoxybenzenesulfonamide (21y)
(Z)—N-(2,3-dimethoxy-6-(3,4,5-trimethoxystyryl)phenyl)-4-methoxybenzenesulfonamide (22a)
(Z)—N-(2,3-dimethoxy-6-(3,4,5-trimethoxystyryl)phenyl)-3,4-dimethoxybenzenesulfonamide (22b)
(Z)-4-chloro-N-(2,3-dimethoxy-6-(3,4,5-trimethoxystyryl) phenyl)benzenesulfonamide (22c)
(Z)-3-chloro-N-(2,3-dimethoxy-6-(3,4,5-trimethoxystyryl) phenyl)benzenesulfonamide (22d)
(Z)-3,4-dichloro-N-(2,3-dimethoxy-6-(3,4,5-trimethoxystyryl)phenyl)benzenesulfonamide (22e)
(Z)—N-(2,3-dimethoxy-6-(3,4,5-trimethoxystyryl)phenyl)-4-fluorobenzenesulfonamide (22f)
(Z)-4-tert-butyl-N-(2,3-dimethoxy-6-(3,4,5-trimethoxystyryl)phenyl)benzenesulfonamide (22g)
(Z)—N-(2,3-dimethoxy-6-(3,4,5-trimethoxystyryl)phenyl)-4-nitrobenzenesulfonamide (22h)
(Z)-4-amino-N-(2,3-dimethoxy-6-(3,4,5-trimethoxystyryl) phenyl)benzenesulfonamide (22I)
(Z)—N-(2,3-dimethoxy-6-(3,4,5-trimethoxystyryl)phenyl)-3-(trifluoromethyl)benzenesulfonamide (22j)
(Z)—N-(2,3-dimethoxy-6-(3,4,5-trimethoxystyryl)phenyl)-3-(trifluoromethoxy)benzenesulfonamide (22k)
(Z)—N-(2,3-dimethoxy-6-(3,4,5-trimethoxystyryl)phenyl)-4-(trifluoromethyl)benzenesulfonamide (22l)
(Z)—N-(2,3-dimethoxy-6-(3,4,5-trimethoxystyryl)phenyl)-4-(trifluoromethoxy)benzenesulfonamide (22m)
(Z)—N-(2,3-dimethoxy-6-(3,4,5-trimethoxystyryl)phenyl)-3-nitrobenzenesulfonamide (22n)
(Z)-3-amino-N-(2,3-dimethoxy-6-(3,4,5-trimethoxystyryl) phenyl)benzenesulfonamide (22o)
(Z)—N-(2,3-dimethoxy-6-(3,4,5-trimethoxystyryl)phenyl)-3-fluorobenzenesulfonamide (22p)
(Z)-3-tert-butyl-N-(2,3-dimethoxy-6-(3,4,5-trimethoxystyryl)phenyl)benzenesulfonamide (22q)
(Z)—N-(2,3-dimethoxy-6-(3,4,5-trimethoxystyryl)phenyl)-3-fluoro-4-methoxybenzenesulfonamide (22r)
(Z)—N-(2,3-dimethoxy-6-(3,4,5-trimethoxystyryl)phenyl)-3-hydroxy-4-methoxybenzenesulfonamide (22s)
(Z)—N-(2,3-dimethoxy-6-(3,4,5-trimethoxystyryl)phenyl)-4-methoxy-3-nitrobenzenesulfonamide (22t)
(Z)—N-(2,3-dimethoxy-6-(3,4,5-trimethoxystyryl)phenyl)-3,4,5-trimethoxybenzenesulfonamide (22u)
(Z)—N-(2,3-dimethoxy-6-(3,4,5-trimethoxystyryl)phenyl)-4-methylbenzenesulfonamide (22v)
(Z)—N-(2,3-dimethoxy-6-(3,4,5-trimethoxystyryl)phenyl)-4-hydroxybenzenesulfonamide (22w)
(Z)—N-(2,3-dimethoxy-6-(3,4,5-trimethoxystyryl)phenyl)-3,4-difluorobenzenesulfonamide (22x)
(Z)-3-chloro-N-(2,3-dimethoxy-6-(3,4,5-trimethoxystyryl) phenyl)-4-methoxybenzenesulfonamide (22y)
(Z)—N-(4,5-dimethoxy-2-(3,4,5-trimethoxystyryl)phenyl)-4-methoxybenzenesulfonamide (23a)
(Z)—N-(4,5-dimethoxy-2-(3,4,5-trimethoxystyryl)phenyl)-3,4-dimethoxybenzenesulfonamide (23b)
(Z)-4-chloro-N-(4,5-dimethoxy-2-(3,4,5-trimethoxystyryl) phenyl)benzenesulfonamide (23c)
(Z)-3-chloro-N-(4,5-dimethoxy-2-(3,4,5-trimethoxystyryl) phenyl)benzenesulfonamide (23d)

(Z)-3,4-dichloro-N-(4,5-dimethoxy-2-(3,4,5-trimethoxystyryl)phenyl)benzenesulfonamide (23e)
(Z)—N-(4,5-dimethoxy-2-(3,4,5-trimethoxystyryl)phenyl)-4-fluorobenzenesulfonamide (23f)
(Z)-4-tert-butyl-N-(4,5-dimethoxy-2-(3,4,5-trimethoxystyryl)phenyl)benzenesulfonamide (23g)
(Z)—N-(4,5-dimethoxy-2-(3,4,5-trimethoxystyryl)phenyl)-4-nitrobenzenesulfonamide (23h)
(Z)-4-amino-N-(4,5-dimethoxy-2-(3,4,5-trimethoxystyryl)phenyl)benzenesulfonamide (23i)
(Z)—N-(4,5-dimethoxy-2-(3,4,5-trimethoxystyryl)phenyl)-3-(trifluoromethyl)benzenesulfonamide (23j)
(Z)—N-(4,5-dimethoxy-2-(3,4,5-trimethoxystyryl)phenyl)-3-(trifluoromethoxy)benzenesulfonamide (23k)
(Z)—N-(4,5-dimethoxy-2-(3,4,5-trimethoxystyryl)phenyl)-4-(trifluoromethyl)benzenesulfonamide (23l)
(Z)—N-(4,5-dimethoxy-2-(3,4,5-trimethoxystyryl)phenyl)-4-(trifluoromethoxy)benzenesulfonamide (23m)
(Z)—N-(4,5-dimethoxy-2-(3,4,5-trimethoxystyryl)phenyl)-3-nitrobenzenesulfonamide (23n)
(Z)-3-amino-N-(4,5-dimethoxy-2-(3,4,5-trimethoxystyryl)phenyl)benzenesulfonamide (23o)
(Z)—N-(4,5-dimethoxy-2-(3,4,5-trimethoxystyryl)phenyl)-3-fluorobenzenesulfonamide (23p)
(Z)-3-tert-butyl-N-(4,5-dimethoxy-2-(3,4,5-trimethoxystyryl)phenyl)benzenesulfonamide (23q)
(Z)—N-(4,5-dimethoxy-2-(3,4,5-trimethoxystyryl)phenyl)-3-fluoro-4-methoxybenzenesulfonamide (23r)
(Z)—N-(4,5-dimethoxy-2-(3,4,5-trimethoxystyryl)phenyl)-3-hydroxy-4-methoxybenzenesulfonamide (23s)
(Z)—N-(4,5-dimethoxy-2-(3,4,5-trimethoxystyryl)phenyl)-4-methoxy-3-nitrobenzenesulfonamide (23t)
(Z)—N-(4,5-dimethoxy-2-(3,4,5-trimethoxystyryl)phenyl)-3,4,5-trimethoxybenzenesulfonamide (23u)
(Z)—N-(4,5-dimethoxy-2-(3,4,5-trimethoxystyryl)phenyl)-4-methylbenzenesulfonamide (23v)
(Z)—N-(4,5-dimethoxy-2-(3,4,5-trimethoxystyryl)phenyl)-4-hydroxybenzenesulfonamide (23w)
(Z)—N-(4,5-dimethoxy-2-(3,4,5-trimethoxystyryl)phenyl)-3,4-difluorobenzenesulfonamide (23x), and
(Z)-3-chloro-N-(4,5-dimethoxy-2-(3,4,5-trimethoxystyryl)phenyl)-4-methoxybenzenesulfonamide (23y).

The present invention further provides a process for preparation of (Z)-3,4,5-trimethoxystyryl benzene sulfonamides of formula 9a-9y, 10a-10y, 11a-11y, 12a-12y, 13a-13y, 14a-14y, 15a-15y, 16a-16y, 17a-17y, 18a-18y, 19a-19y, 20a-20y, 21a-21y, 22a-22y and 23a-23y

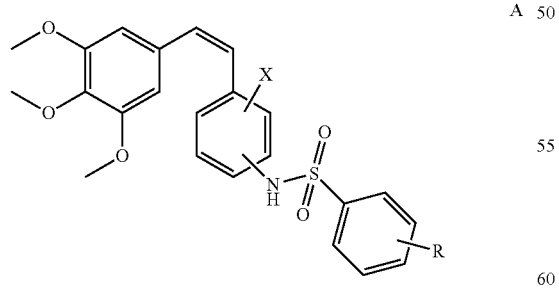

A comprising the steps of reacting (Z)-3-(3,4,5-trimethoxystyryl)aniline of formula 7(a-o) with benzenesulfonylchlorides of formulae (a-y) to produce following the compounds (9a-9y to 23a-23y) in solvent pyridine at 0° C. to room temperature for a period of about 2-3 h. After quenching with 2N HCl and addition of appropriate amount of ethyl acetate to the reaction mixture is then extracted the organic layer dried over under reduced pressure resulted to obtain crude products. These crude products were purified by column chromatography using ethyl acetate and hexane solvent system to produce the desired products of formulae 9a-9y, 10a-10y, 11a-11y, 12a-12y, 13a-13y, 14a-14y, 15a-15y, 16a-16y, 17a-17y, 18a-18y, 19a-19y, 20a-20y, 21a-21y, 22a-22y and 23a-23y respectively wherein, X=H, F, OCH$_3$, OH; R=H, Cl, F, OCH$_3$, NH$_2$, NO$_2$, OH

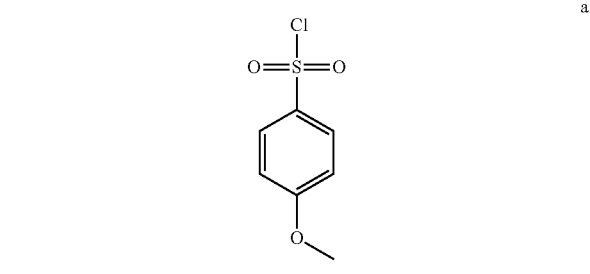

a

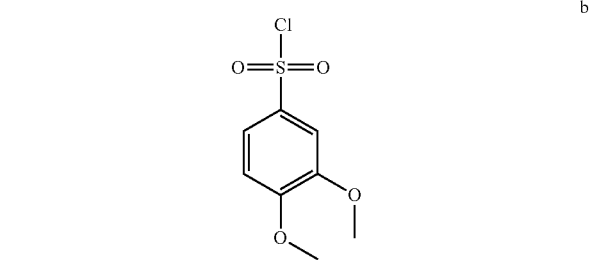

b

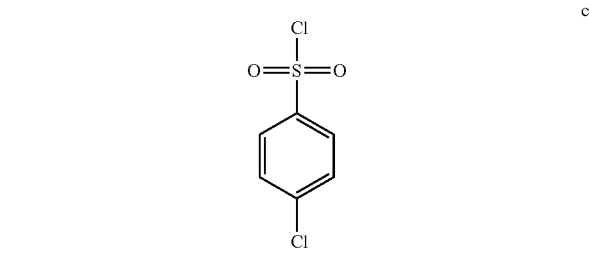

c

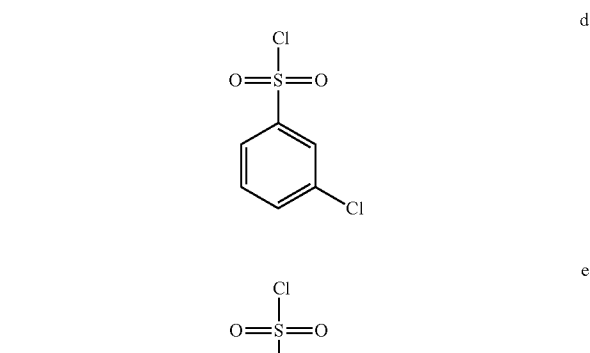

d e

-continued
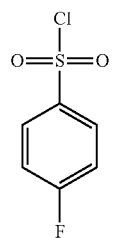
f
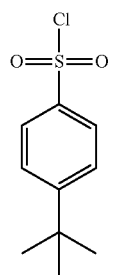
g
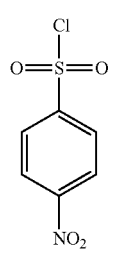
h
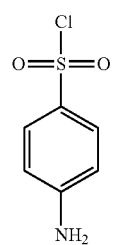
i
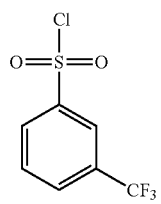
j
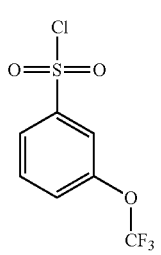
k
-continued
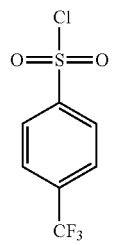
l
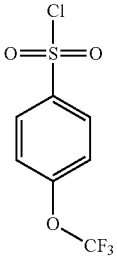
m
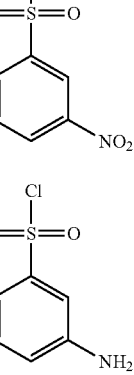
n
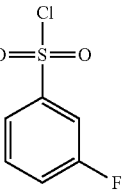
o
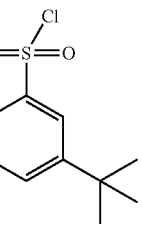
p
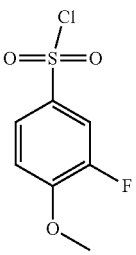
q
r s 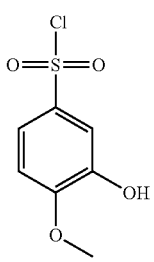

t 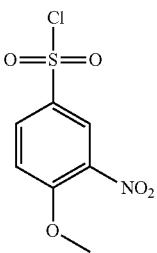

u 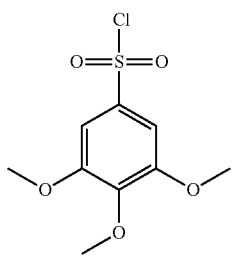

v 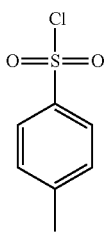

w 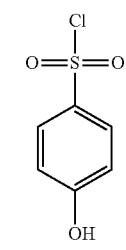

x 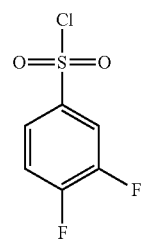

y 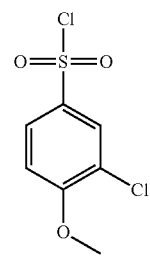

In an embodiment of the invention wherein the compound of general formula A are useful as antitumor agents.

In another embodiment of the invention wherein the compound of general formula A have antitumour activity against cell lines selected from the group of non-small cell lung cancer, colon cancer, cervical carcinoma and breast cancer)

In another embodiment, the present invention provides the process for preparation of compounds of general formulae A

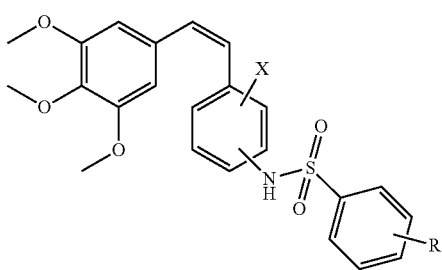
A wherein the said process comprising;

a) reacting (Z)-3-(3,4,5 trimethoxystyryl)aniline of formula 7(a-o)

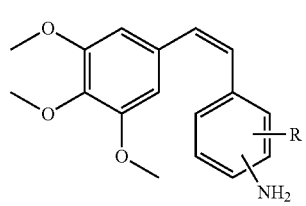
7(a-o)

wherein R=H, OMe, OH, Cl, F.

with a compound selected from a group consisting of formulae a, b, c, d, f, g, h, I, j, k, l, m, n, o, p, q, r, s, t, u, v, w, x and y.

a 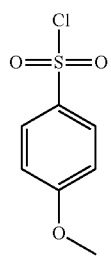

23
-continued
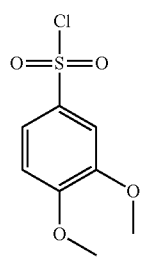 b
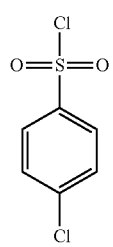 c
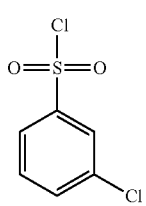 d
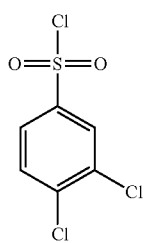 e
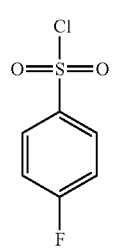 f
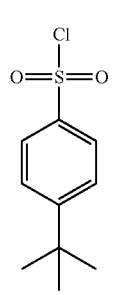 g
24
-continued
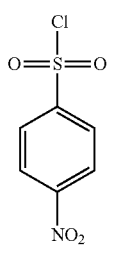 h
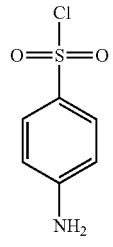 i
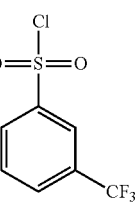 j
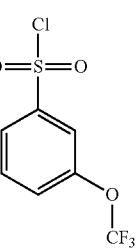 k
l
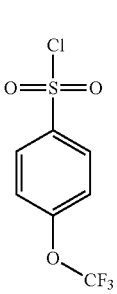 m n 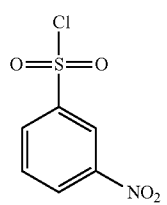

o 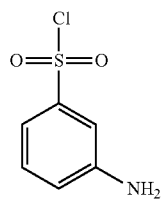

p 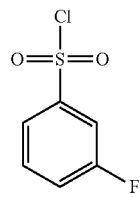

q 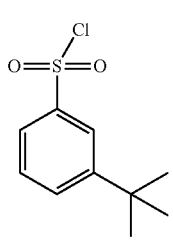

r 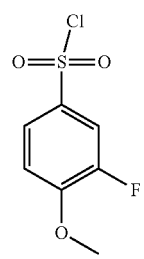

s 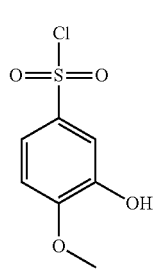

t 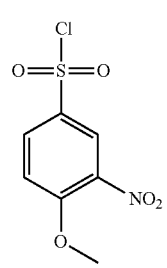

u 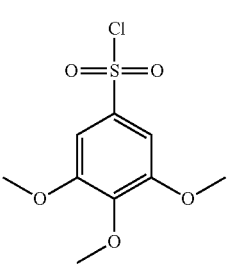

v 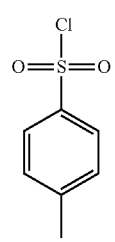

w 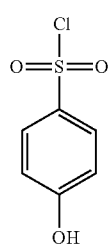

x 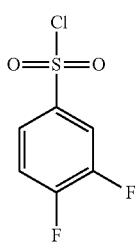

y 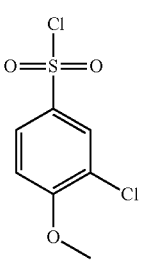

in pyridine at a temperature ranging between 0 to 33° C. for a period of about 2-3 h to obtain a reaction mixture, (b) adding HCl and appropriate amount of ethyl acetate to the reaction mixture to obtain an organic layer;

(c) extracting the organic layer followed by drying under reduced pressure to obtain crude products, (d) purifying the crude product by column chromatography using ethyl acetate and hexane solvent system to obtain the desired products of formulae 9a-9y, 10a-10y, 11a-11y, 12a-12y, 13a-13y, 14a-14y, 15a-15y, 16a-16y, 17a-17y, 18a-18y, 19a-19y, 20a-20y, 21a-21y, 22a-22y and 23a-y.

DETAILED DESCRIPTION OF THE INVENTION

The precursors (Z)-3-(3,4,5-trimethoxystyryl)aniline of formula 7(a-o) have been prepared using literature method (Keith A. Monk, a Rogelio Siles, a Mallinath B. Hadimani, a Benon E. ugabe, a J. Freeland Ackley, a Scott W. Studerus, a Klaus Edvardsen, b Mary Lynn Trawick, a Charles M. Garner, a Monte R. Rhodes, c George R. Pettit c and Kevin G. Pinney a,*, Bioorganic & Medicinal Chemistry 14 (2006) 3231-3244). The crucial intermediates for the preparation of precursors (Z)-3-(3,4,5-trimethoxystyryl)aniline formula 7(a-o) are (Z)-1,2,3-trimethoxy-5-(3-nitrostyryl)benzene 6(a-o) have been prepared using literature methods (Kevin G. Pinney, a,* Maria P. Mejia, a Victor M. Villalobos, a Brent E. Rosenquist, a George R. Pettit, b Pascal Verdier-Pinard c and Ernest Hamel c, Bioorganic & Medicinal Chemistry 8 (2000) 2417±2425).

These new 3,4,5-trimethoxystyrylaryl sulfonamide derivatives have shown promising anticancer activity in various cancer cell lines. The molecules synthesized are of immense biological significance. This resulted in design and synthesis of new congeners as illustrated in scheme 1 which comprise: The reaction between (Z)-3-(3,4,5-trimethoxystyryl)aniline of formula 7(a-o) and the benzene sulfonyl chlorides compounds of formulae a to y for the compounds (9a-9y to 23a-23y).

1. Stirring the amines at 0° C. and add benzenesulfonyl-chlorides slowly to the reaction mixture, maintain for 2-3 h at room temperature to obtain the compounds (9a-y to 23a-23y) respectively.
2. Synthesis of (Z)-3,4,5-trimethoxystyryl benzenesulfonamides.
3. Purified by the column chromatography using different solvents like ethyl acetate and hexane
4. The final step has been carried out by the (Z)-3-(3,4,5-trimethoxystyryl)aniline of formula 7(a-o) and substituted benzene sulfonyl chlorides in pyridine at 0° C. The compounds of formulae a to y for the compounds (9a-9y to 23a-23y)

The key intermediates 3-substituted (Z)-3-(3,4,5-trimethoxystyryl)aniline 7(a-o) are prepared in five sequential steps. 3,4,5-Trimethoxybenzaldehyde (1) reduces with sodium borohydride in methanol gives (3,4,5-trimethoxyphenyl)methanol (2). This was further reacted with PBr$_3$ in CH$_2$Cl$_2$ to produce 5-(bromomethyl)-1,2,3-trimethoxybenzene (3), then this was further reacted with triphenylphosphine in toluene to give 3,4,5-trimethoxybenzyltriphenylphosphonium bromide (4) in good yields. The obtained witting salt was reacted with substituted benzaldehydes (5a-5o) in presence of NaH in CH$_2$Cl$_2$ to produce (Z)-1,2,3-trimethoxy-5-(substituted-nitrostyryl)benzene 6(a-o) and (E)-1,2,3-trimethoxy-5-(substituted-nitrostyryl)benzene in (1:1)% of yield. Z)-1,2,3-trimethoxy-5-(substituted nitrostyryl)benzene reduced with Zn ammoniumformate in methanol produced (Z)-3-(3,4,5-trimethoxystyryl)aniline.

Scheme 1

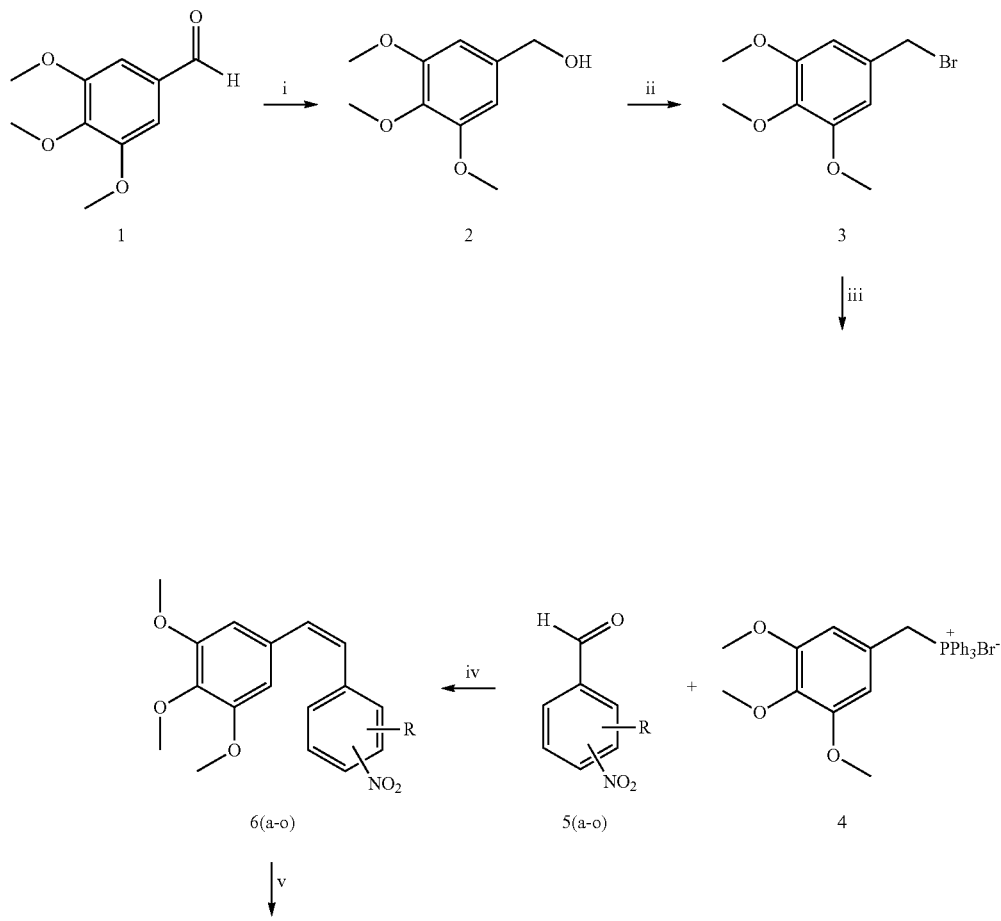

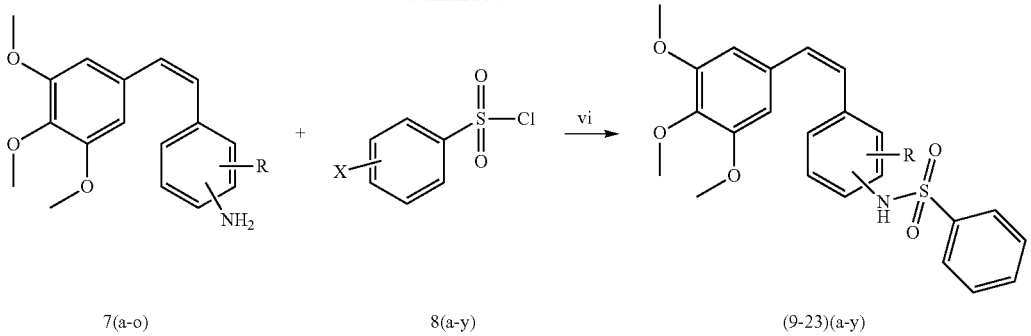

7(a-o)  8(a-y)  (9-23)(a-y)

Reagents and conditions: (i) NaBH$_4$, MeOH, 3 h, 15-20° C. (95%) (ii) PBr$_3$, CH$_2$Cl$_2$, 2 h, 15-20° C. (90%) (iii) PPh$_3$, toluene, 12 h, 80° C. (80%) (iv) NaH, CH$_2$Cl$_2$, 18 h, 15-20° C. (65%) (v) Zn, HCOONH$_4$, 3 h, 30-40° C., 70%; (vi) Pyridine, 0° C.-RT, 2 h (90%).

The present invention relates to the compounds, synthesis and biological evaluation of novel (Z)-3,4,5-trimethoxystyryl benzene sulfonamide derivatives of general formula A as potential anticancer agents and a process for the preparation thereof

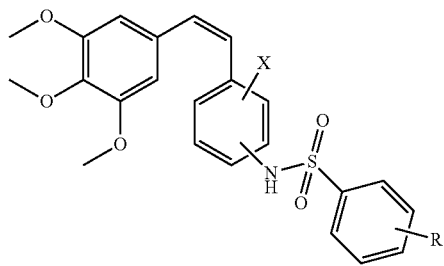

A wherein, X=H, F, OCH$_3$, NH$_2$, OH; R=H, Cl, F, OCH$_3$, NH$_2$, NO$_2$, OH

More particularly the present invention relates to the following compounds:
(Z)-4-methoxy-N-(2-(3,4,5-trimethoxystyryl)phenyl)benzenesulfonamide (9a)
(Z)-3,4-dimethoxy-N-(2-(3,4,5-trimethoxystyryl)phenyl)benzenesulfonamide (9b)
(Z)-4-chloro-N-(2-(3,4,5-trimethoxystyryl)phenyl)benzenesulfonamide (9c)
(Z)-3-chloro-N-(2-(3,4,5-trimethoxystyryl)phenyl)benzenesulfonamide (9d)
(Z)-3,4-dichloro-N-(2-(3,4,5-trimethoxystyryl)phenyl)benzenesulfonamide (9e)
(Z)-4-fluoro-N-(2-(3,4,5-trimethoxystyryl)phenyl)benzenesulfonamide (9f)
(Z)-4-tert-butyl-N-(2-(3,4,5-trimethoxystyryl)phenyl)benzenesulfonamide (9g)
(Z)-4-nitro-N-(2-(3,4,5-trimethoxystyryl)phenyl)benzenesulfonamide (9h)
(Z)-4-amino-N-(2-(3,4,5-trimethoxystyryl)phenyl)benzenesulfonamide (9i)
(Z)-3-(trifluoromethyl)-N-(2-(3,4,5-trimethoxystyryl)phenyl)benzenesulfonamide (9J)
(Z)-3-(trifluoromethoxy)-N-(2-(3,4,5-trimethoxystyryl)phenyl)benzenesulfonamide (9k)
(Z)-4-(trifluoromethyl)-N-(2-(3,4,5-trimethoxystyryl)phenyl)benzenesulfonamide (9l)
(Z)-4-(trifluoromethoxy)-N-(2-(3,4,5-trimethoxystyryl)phenyl)benzenesulfonamide (9m)
(Z)-3-nitro-N-(2-(3,4,5-trimethoxystyryl)phenyl)benzenesulfonamide (9n)
(Z)-3-amino-N-(2-(3,4,5-trimethoxystyryl)phenyl)benzenesulfonamide (9o)
(Z)-3-fluoro-N-(2-(3,4,5-trimethoxystyryl)phenyl)benzenesulfonamide (9p)
(Z)-3-tert-butyl-N-(2-(3,4,5-trimethoxystyryl)phenyl)benzenesulfonamide (9q)
(Z)-3-fluoro-4-methoxy-N-(2-(3,4,5-trimethoxystyryl)phenyl)benzenesulfonamide (9r)
(Z)-3-hydroxy-4-methoxy-N-(2-(3,4,5-trimethoxystyryl)phenyl)benzenesulfonamide (9s)
(Z)-4-methoxy-3-nitro-N-(2-(3,4,5-trimethoxystyryl)phenyl)benzenesulfonamide (9t)
(Z)-3,4,5-trimethoxy-N-(2-(3,4,5-trimethoxystyryl)phenyl)benzenesulfonamide (9u)
(Z)-4-methyl-N-(2-(3,4,5-trimethoxystyryl)phenyl)benzenesulfonamide (9v)
(Z)-4-hydroxy-N-(2-(3,4,5-trimethoxystyryl)phenyl)benzenesulfonamide (9w)
(Z)-3,4-difluoro-N-(2-(3,4,5-trimethoxystyryl)phenyl)benzenesulfonamide (9x)
(Z)-3-chloro-4-methoxy-N-(2-(3,4,5-trimethoxystyryl)phenyl)benzenesulfonamide (9y)
(Z)-4-methoxy-N-(3-(3,4,5-trimethoxystyryl)phenyl)benzenesulfonamide (10a)
(Z)-3,4-dimethoxy-N-(3-(3,4,5-trimethoxystyryl)phenyl)benzenesulfonamide (10b)
(Z)-4-chloro-N-(3-(3,4,5-trimethoxystyryl)phenyl)benzenesulfonamide (10c)
(Z)-3-chloro-N-(3-(3,4,5-trimethoxystyryl)phenyl)benzenesulfonamide (10d)
(Z)-3,4-dichloro-N-(3-(3,4,5-trimethoxystyryl)phenyl)benzenesulfonamide (10e)
(Z)-4-fluoro-N-(3-(3,4,5-trimethoxystyryl)phenyl)benzenesulfonamide (10f)
(Z)-4-tert-butyl-N-(3-(3,4,5-trimethoxystyryl)phenyl)benzenesulfonamide (10g)
(Z)-4-nitro-N-(3-(3,4,5-trimethoxystyryl)phenyl)benzenesulfonamide (10h)
(Z)-4-amino-N-(3-(3,4,5-trimethoxystyryl)phenyl)benzenesulfonamide (10i)
(Z)-3-(trifluoromethyl)-N-(3-(3,4,5-trimethoxystyryl)phenyl)benzenesulfonamide (10j)
(Z)-3-(trifluoromethoxy)-N-(3-(3,4,5-trimethoxystyryl)phenyl)benzenesulfonamide (10k)

(Z)-4-(trifluoromethyl)-N-(3-(3,4,5-trimethoxystyryl)phenyl)benzenesulfonamide (10l)
(Z)-4-(trifluoromethoxy)-N-(3-(3,4,5-trimethoxystyryl)phenyl)benzenesulfonamide (10m)
(Z)-3-nitro-N-(3-(3,4,5-trimethoxystyryl)phenyl)benzenesulfonamide (10n)
(Z)-3-amino-N-(3-(3,4,5-trimethoxystyryl)phenyl)benzenesulfonamide (10o)
(Z)-3-fluoro-N-(3-(3,4,5-trimethoxystyryl)phenyl)benzenesulfonamide (10p)
(Z)-3-tert-butyl-N-(3-(3,4,5-trimethoxystyryl)phenyl)benzenesulfonamide (10q)
(Z)-3-fluoro-4-methoxy-N-(3-(3,4,5-trimethoxystyryl)phenyl)benzenesulfonamide (10r)
(Z)-3-hydroxy-4-methoxy-N-(3-(3,4,5-trimethoxystyryl)phenyl)benzenesulfonamide (10s)
(Z)-4-methoxy-3-nitro-N-(3-(3,4,5-trimethoxystyryl)phenyl)benzenesulfonamide (10t)
(Z)-3-amino-4-methoxy-N-(3-(3,4,5-trimethoxystyryl)phenyl)benzenesulfonamide (10u)
(Z)-3,4,5-trimethoxy-N-(3-(3,4,5-trimethoxystyryl)phenyl)benzenesulfonamide (10v)
(Z)-4-methyl-N-(3-(3,4,5-trimethoxystyryl)phenyl)benzenesulfonamide (10w)
(Z)-3,4-difluoro-N-(3-(3,4,5-trimethoxystyryl)phenyl)benzenesulfonamide (10x)
(Z)-3-chloro-4-methoxy-N-(3-(3,4,5-trimethoxystyryl)phenyl)benzenesulfonamide (10y)
(Z)-4-methoxy-N-(4-(3,4,5-trimethoxystyryl)phenyl)benzenesulfonamide (11a)
(Z)-3,4-dimethoxy-N-(4-(3,4,5-trimethoxystyryl)phenyl)benzenesulfonamide (11b)
(Z)-4-chloro-N-(4-(3,4,5-trimethoxystyryl)phenyl)benzenesulfonamide (11c)
(Z)-3-chloro-N-(4-(3,4,5-trimethoxystyryl)phenyl)benzenesulfonamide (11d)
(Z)-3,4-dichloro-N-(4-(3,4,5-trimethoxystyryl)phenyl)benzenesulfonamide (11e)
(Z)-4-fluoro-N-(4-(3,4,5-trimethoxystyryl)phenyl)benzenesulfonamide (11f)
(Z)-4-tert-butyl-N-(4-(3,4,5-trimethoxystyryl)phenyl)benzenesulfonamide (11g)
(Z)-4-nitro-N-(4-(3,4,5-trimethoxystyryl)phenyl)benzenesulfonamide (11h)
(Z)-4-amino-N-(4-(3,4,5-trimethoxystyryl)phenyl)benzenesulfonamide (11i)
(Z)-3-(trifluoromethyl)-N-(4-(3,4,5-trimethoxystyryl)phenyl)benzenesulfonamide (11j)
(Z)-3-(trifluoromethoxy)-N-(4-(3,4,5-trimethoxystyryl)phenyl)benzenesulfonamide (11k)
(Z)-4-(trifluoromethyl)-N-(4-(3,4,5-trimethoxystyryl)phenyl)benzenesulfonamide (11l)
(Z)-4-(trifluoromethoxy)-N-(4-(3,4,5-trimethoxystyryl)phenyl)benzenesulfonamide (11m)
(Z)-3-nitro-N-(4-(3,4,5-trimethoxystyryl)phenyl)benzenesulfonamide (11n)
(Z)-3-amino-N-(4-(3,4,5-trimethoxystyryl)phenyl)benzenesulfonamide (11o)
(Z)-3-fluoro-N-(4-(3,4,5-trimethoxystyryl)phenyl)benzenesulfonamide (11p)
(Z)-3-tert-butyl-N-(4-(3,4,5-trimethoxystyryl)phenyl)benzenesulfonamide (11q)
(Z)-3-fluoro-4-methoxy-N-(4-(3,4,5-trimethoxystyryl)phenyl)benzenesulfonamide (11r)
(Z)-3-hydroxy-4-methoxy-N-(4-(3,4,5-trimethoxystyryl)phenyl)benzenesulfonamide (11s)
(Z)-4-methoxy-3-nitro-N-(4-(3,4,5-trimethoxystyryl)phenyl)benzenesulfonamide (11t)
(Z)-3-amino-4-methoxy-N-(4-(3,4,5-trimethoxystyryl)phenyl)benzenesulfonamide (11u)
(Z)-3,4,5-trimethoxy-N-(4-(3,4,5-trimethoxystyryl)phenyl)benzenesulfonamide (11v)
(Z)-4-methyl-N-(4-(3,4,5-trimethoxystyryl)phenyl)benzenesulfonamide (11w)
(Z)-3,4-difluoro-N-(4-(3,4,5-trimethoxystyryl)phenyl)benzenesulfonamide (11x)
(Z)-3-chloro-4-methoxy-N-(4-(3,4,5-trimethoxystyryl)phenyl)benzenesulfonamide (11y)
(Z)-4-methoxy-N-(2-methoxy-5-(3,4,5-trimethoxystyryl)phenyl)benzenesulfonamide (12a)
(Z)-3,4-dimethoxy-N-(2-methoxy-5-(3,4,5-trimethoxystyryl)phenyl)benzenesulfonamide (12b)
(Z)-4-chloro-N-(2-methoxy-5-(3,4,5-trimethoxystyryl)phenyl)benzenesulfonamide (12c)
(Z)-3-chloro-N-(2-methoxy-5-(3,4,5-trimethoxystyryl)phenyl)benzenesulfonamide (12d)
(Z)-3,4-dichloro-N-(2-methoxy-5-(3,4,5-trimethoxystyryl)phenyl)benzenesulfonamide (12e)
(Z)-4-fluoro-N-(2-methoxy-5-(3,4,5-trimethoxystyryl)phenyl)benzenesulfonamide (12f)
(Z)-4-tert-butyl-N-(2-methoxy-5-(3,4,5-trimethoxystyryl)phenyl)benzenesulfonamide (12g)
(Z)—N-(2-methoxy-5-(3,4,5-trimethoxystyryl)phenyl)-4-nitrobenzenesulfonamide (12h)
(Z)-4-amino-N-(2-methoxy-5-(3,4,5-trimethoxystyryl)phenyl)benzenesulfonamide (12i)
(Z)—N-(2-methoxy-5-(3,4,5-trimethoxystyryl)phenyl)-3-(trifluoromethyl)benzenesulfonamide (12j)
(Z)—N-(2-methoxy-5-(3,4,5-trimethoxystyryl)phenyl)-3-(trifluoromethoxy) benzenesulfonamide (12k)
(Z)—N-(2-methoxy-5-(3,4,5-trimethoxystyryl)phenyl)-4-(trifluoromethyl)benzenesulfonamide (12l)
(Z)—N-(2-methoxy-5-(3,4,5-trimethoxystyryl)phenyl)-4-(trifluoromethoxy)benzenesulfonamide (12m)
(Z)—N-(2-methoxy-5-(3,4,5-trimethoxystyryl)phenyl)-3-nitrobenzenesulfonamide (12n)
(Z)-3-amino-N-(2-methoxy-5-(3,4,5-trimethoxystyryl)phenyl)benzenesulfonamide (12o)
(Z)-3-fluoro-N-(2-methoxy-5-(3,4,5-trimethoxystyryl)phenyl)benzenesulfonamide (12p)
(Z)-3-tert-butyl-N-(2-methoxy-5-(3,4,5-trimethoxystyryl)phenyl)benzenesulfonamide (12q)
(Z)-3-fluoro-4-methoxy-N-(2-methoxy-5-(3,4,5-trimethoxystyryl)phenyl)benzenesulfonamide (12r)
(Z)-3-hydroxy-4-methoxy-N-(2-methoxy-5-(3,4,5-trimethoxystyryl)phenyl)benzenesulfonamide (12s)
(Z)-4-methoxy-N-(2-methoxy-5-(3,4,5-trimethoxystyryl)phenyl)-3-nitrobenzenesulfonamide (12t)
(Z)-3-amino-4-methoxy-N-(2-methoxy-5-(3,4,5-trimethoxystyryl)phenyl)benzenesulfonamide (12u)
(Z)-3,4,5-trimethoxy-N-(2-methoxy-5-(3,4,5-trimethoxystyryl)phenyl)benzenesulfonamide (12v)
(Z)—N-(2-methoxy-5-(3,4,5-trimethoxystyryl)phenyl)-4-methylbenzenesulfonamide (12w)
(Z)-3,4-difluoro-N-(2-methoxy-5-(3,4,5-trimethoxystyryl)phenyl)benzenesulfonamide (12x)
(Z)-3-chloro-4-methoxy-N-(2-methoxy-5-(3,4,5-trimethoxystyryl)phenyl)benzenesulfonamide (12y)
(Z)—N-(2,3-dimethoxy-5-(3,4,5-trimethoxystyryl)phenyl)-4-methoxybenzenesulfonamide (13a)
(Z)—N-(2,3-dimethoxy-5-(3,4,5-trimethoxystyryl)phenyl)-3,4-dimethoxybenzenesulfonamide (13b)

(Z)-4-chloro-N-(2,3-dimethoxy-5-(3,4,5-trimethoxystyryl)phenyl)benzenesulfonamide (13c)
(Z)-3-chloro-N-(2,3-dimethoxy-5-(3,4,5-trimethoxystyryl)phenyl)benzenesulfonamide (13d)
(Z)-3,4-dichloro-N-(2,3-dimethoxy-5-(3,4,5-trimethoxystyryl)phenyl)benzenesulfonamide (13e)
(Z)—N-(2,3-dimethoxy-5-(3,4,5-trimethoxystyryl)phenyl)-4-fluorobenzenesulfonamide (13f)
(Z)-4-tert-butyl-N-(2,3-dimethoxy-5-(3,4,5-trimethoxystyryl)phenyl)benzenesulfonamide (13g)
(Z)—N-(2,3-dimethoxy-5-(3,4,5-trimethoxystyryl)phenyl)-4-nitrobenzenesulfonamide (13h)
(Z)-4-amino-N-(2,3-dimethoxy-5-(3,4,5-trimethoxystyryl)phenyl)benzenesulfonamide (13i)
(Z)—N-(2,3-dimethoxy-5-(3,4,5-trimethoxystyryl)phenyl)-3-(trifluoromethyl)benzenesulfonamide (13j)
(Z)—N-(2,3-dimethoxy-5-(3,4,5-trimethoxystyryl)phenyl)-3(trifluoromethoxy) benzenesulfonamide (13k)
(Z)—N-(2,3-dimethoxy-5-(3,4,5-trimethoxystyryl)phenyl)-4-(trifluoromethyl) benzenesulfonamide (13l)
(Z)—N-(2,3-dimethoxy-5-(3,4,5-trimethoxystyryl)phenyl)-4-(trifluoromethoxy)Benzenesulfonamide (13m)
(Z)—N-(2,3-dimethoxy-5-(3,4,5-trimethoxystyryl)phenyl)-3-nitrobenzenesulfonamide (13n)
(Z)-3-amino-N-(2,3-dimethoxy-5-(3,4,5-trimethoxystyryl)phenyl)benzenesulfonamide (13o)
(Z)—N-(2,3-dimethoxy-5-(3,4,5-trimethoxystyryl)phenyl)-3-fluorobenzenesulfonamide (13p)
(Z)-3-tert-butyl-N-(2,3-dimethoxy-5-(3,4,5-trimethoxystyryl)phenyl)benzenesulfonamide (13q)
(Z)—N-(2,3-dimethoxy-5-(3,4,5-trimethoxystyryl)phenyl)-3-fluoro-4-methoxyBenzenesulfonamide (13r)
(Z)—N-(2,3-dimethoxy-5-(3,4,5-trimethoxystyryl)phenyl)-3-hydroxy-4-methoxy Benzenesulfonamide (13s)
(Z)—N-(2,3-dimethoxy-5-(3,4,5-trimethoxystyryl)phenyl)-4-methoxy-3-nitro Benzenesulfonamide (13t)
(Z)-3-amino-N-(2,3-dimethoxy-5-(3,4,5-trimethoxystyryl)phenyl)-4-methoxyBenzenesulfonamide (13u)
(Z)—N-(2,3-dimethoxy-5-(3,4,5-trimethoxystyryl)phenyl)-3,4,5-trimethoxyBenzenesulfonamide (13v)
(Z)—N-(2,3-dimethoxy-5-(3,4,5-trimethoxystyryl)phenyl)-4-methyl benzene sulfonamide (13w)
(Z)—N-(2,3-dimethoxy-5-(3,4,5-trimethoxystyryl)phenyl)-3,4-difluoro Benzenesulfonamide (13x)
(Z)-3-chloro-N-(2,3-dimethoxy-5-(3,4,5-trimethoxystyryl)phenyl)-4-methoxybenzene sulfonamide (13y)
(Z)—N-(3-hydroxy-2-methoxy-5-(3,4,5-trimethoxystyryl)phenyl)-4-methoxy benzene sulfonamide (14a)
(Z)—N-(3-hydroxy-2-methoxy-5-(3,4,5-trimethoxystyryl)phenyl)-3,4-dimethoxybenzenesulfonamide (14b)
(Z)-4-chloro-N-(3-hydroxy-2-methoxy-5-(3,4,5-trimethoxystyryl)phenyl)benzenesulfonamide (14c)
(Z)-3-chloro-N-(3-hydroxy-2-methoxy-5-(3,4,5-trimethoxystyryl) phenyl)benzenesulfonamide (14d)
(Z)-3,4-dichloro-N-(3-hydroxy-2-methoxy-5-(3,4,5-trimethoxystyryl)phenyl)benzenesulfonamide (14e)
(Z)-4-fluoro-N-(3-hydroxy-2-methoxy-5-(3,4,5-trimethoxystyryl)phenyl)benzenesulfonamide (14f)
(Z)-4-tert-butyl-N-(3-hydroxy-2-methoxy-5-(3,4,5-trimethoxystyryl)phenyl)benzenesulfonamide (14g)
(Z)—N-(3-hydroxy-2-methoxy-5-(3,4,5-trimethoxystyryl)phenyl)-4-nitrobenzenesulfonamide (14h)
(Z)-4-amino-N-(3-hydroxy-2-methoxy-5-(3,4,5-trimethoxystyryl)phenyl)benzenesulfonamide (14i)
(Z)—N-(3-hydroxy-2-methoxy-5-(3,4,5-trimethoxystyryl)phenyl)-3-(trifluoromethyl)benzenesulfonamide (14j)
(Z)—N-(3-hydroxy-2-methoxy-5-(3,4,5-trimethoxystyryl)phenyl)-3-(trifluoromethoxy)benzenesulfonamide (14k)
(Z)—N-(3-hydroxy-2-methoxy-5-(3,4,5-trimethoxystyryl)phenyl)-4-(trifluoromethyl)benzenesulfonamide (14l)
(Z)—N-(3-hydroxy-2-methoxy-5-(3,4,5-trimethoxystyryl)phenyl)-4-(trifluoromethoxy)benzenesulfonamide (14m)
(Z)—N-(3-hydroxy-2-methoxy-5-(3,4,5-trimethoxystyryl)phenyl)-3-nitrobenzenesulfonamide (14n)
(Z)-3-amino-N-(3-hydroxy-2-methoxy-5-(3,4,5-trimethoxystyryl)phenyl)benzenesulfonamide (14o)
(Z)-3-fluoro-N-(3-hydroxy-2-methoxy-5-(3,4,5-trimethoxystyryl)phenyl)benzenesulfonamide (14p)
(Z)-3-tert-butyl-N-(3-hydroxy-2-methoxy-5-(3,4,5-trimethoxystyryl)phenyl)benzenesulfonamide (14q)
(Z)-3-fluoro-N-(3-hydroxy-2-methoxy-5-(3,4,5-trimethoxystyryl)phenyl)-4-methoxybenzenesulfonamide (14r)
(Z)-3-hydroxy-N-(3-hydroxy-2-methoxy-5-(3,4,5-trimethoxystyryl)phenyl)-4-ethoxybenzenesulfonamide (14s)
(Z)—N-(3-hydroxy-2-methoxy-5-(3,4,5-trimethoxystyryl)phenyl)-4-methoxy-3-nitrobenzenesulfonamide (14t)
(Z)-3-amino-N-(3-hydroxy-2-methoxy-5-(3,4,5-trimethoxystyryl)phenyl)-4-ethoxybenzenesulfonamide (14u)
(Z)—N-(3-hydroxy-2-methoxy-5-(3,4,5-trimethoxystyryl)phenyl)-3,4,5-trimethoxybenzenesulfonamide (14v)
(Z)—N-(3-hydroxy-2-methoxy-5-(3,4,5-trimethoxystyryl)phenyl)-4-methylbenzenesulfonamide (14w)
(Z)-3,4-difluoro-N-(3-hydroxy-2-methoxy-5-(3,4,5-trimethoxystyryl)phenyl)benzenesulfonamide (14x)
(Z)-3-chloro-N-(3-hydroxy-2-methoxy-5-(3,4,5-trimethoxystyryl)phenyl)-4-methoxybenzenesulfonamide (14y)
(Z)—N-(3-fluoro-2-methoxy-5-(3,4,5-trimethoxystyryl)phenyl)-4-methoxybenzenesulfonamide (15a)
(Z)—N-(3-fluoro-2-methoxy-5-(3,4,5-trimethoxystyryl)phenyl)-3,4-dimethoxybenzenesulfonamide (15b)
(Z)-4-chloro-N-(3-fluoro-2-methoxy-5-(3,4,5-trimethoxystyryl)phenyl)benzenesulfonamide (15c)
(Z)-3-chloro-N-(3-fluoro-2-methoxy-5-(3,4,5-trimethoxystyryl)phenyl)benzenesulfonamide (15d)
(Z)-3,4-dichloro-N-(3-fluoro-2-methoxy-5-(3,4,5-trimethoxystyryl)phenyl)benzenesulfonamide (15e)
(Z)-4-fluoro-N-(3-fluoro-2-methoxy-5-(3,4,5-trimethoxystyryl)phenyl)benzenesulfonamide (15f)
(Z)-4-tert-butyl-N-(3-fluoro-2-methoxy-5-(3,4,5-trimethoxystyryl)phenyl)benzenesulfonamide (15g)
(Z)—N-(3-fluoro-2-methoxy-5-(3,4,5-trimethoxystyryl)phenyl)-4-nitrobenzenesulfonamide (15h)
(Z)-4-amino-N-(3-fluoro-2-methoxy-5-(3,4,5-trimethoxystyryl)phenyl)benzenesulfonamide (15i)
(Z)—N-(3-fluoro-2-methoxy-5-(3,4,5-trimethoxystyryl)phenyl)-3-(trifluoromethyl)benzenesulfonamide (15j)
(Z)—N-(3-fluoro-2-methoxy-5-(3,4,5-trimethoxystyryl)phenyl)-3-(trifluoromethoxy)benzenesulfonamide (15k)
(Z)—N-(3-fluoro-2-methoxy-5-(3,4,5-trimethoxystyryl)phenyl)-4-(trifluoromethyl)benzenesulfonamide (15l)
(Z)—N-(3-fluoro-2-methoxy-5-(3,4,5-trimethoxystyryl)phenyl)-4-(trifluoromethoxy)benzenesulfonamide (15m)
(Z)—N-(3-fluoro-2-methoxy-5-(3,4,5-trimethoxystyryl)phenyl)-3-nitrobenzenesulfonamide (15n)
(Z)-3-amino-N-(3-fluoro-2-methoxy-5-(3,4,5-trimethoxystyryl)phenyl)benzenesulfonamide (15o)
(Z)-3-fluoro-N-(3-fluoro-2-methoxy-5-(3,4,5-trimethoxystyryl)phenyl)benzenesulfonamide (15p)
(Z)-3-tert-butyl-N-(3-fluoro-2-methoxy-5-(3,4,5-trimethoxystyryl)phenyl)benzenesulfonamide (15q)
(Z)-3-fluoro-N-(3-fluoro-2-methoxy-5-(3,4,5-trimethoxystyryl)phenyl)-4-methoxybenzenesulfonamide (15r)

(Z)—N-(3-fluoro-2-methoxy-5-(3,4,5-trimethoxystyryl)phenyl)-3-hydroxy-4-methoxybenzenesulfonamide (15s)
(Z)—N-(3-fluoro-2-methoxy-5-(3,4,5-trimethoxystyryl)phenyl)-4-methoxy-3-nitrobenzenesulfonamide (15t)
(Z)-3-amino-N-(3-fluoro-2-methoxy-5-(3,4,5-trimethoxystyryl)phenyl)-4-methoxybenzenesulfonamide (15u)
(Z)—N-(3-fluoro-2-methoxy-5-(3,4,5-trimethoxystyryl)phenyl)-3,4,5-trimethoxybenzenesulfonamide (15v)
(Z)—N-(3-fluoro-2-methoxy-5-(3,4,5-trimethoxystyryl)phenyl)-4-methyl benzenesulfonamide (15w)
(Z)-3,4-difluoro-N-(3-fluoro-2-methoxy-5-(3,4,5-trimethoxystyryl)phenyl)benzenesulfonamide (15x)
(Z)-3-chloro-N-(3-fluoro-2-methoxy-5-(3,4,5-trimethoxystyryl)phenyl)-4-methoxybenzenesulfonamide (15y)
(Z)—N-(2-hydroxy-3-methoxy-5-(3,4,5-trimethoxystyryl)phenyl)-4-methoxybenzenesulfonamide (16a)
(Z)—N-(2-hydroxy-3-methoxy-5-(3,4,5-trimethoxystyryl)phenyl)-3,4-dimethoxybenzenesulfonamide (16b)
(Z)-4-chloro-N-(2-hydroxy-3-methoxy-5-(3,4,5-trimethoxystyryl)phenyl)benzenesulfonamide (16c)
(Z)-3-chloro-N-(2-hydroxy-3-methoxy-5-(3,4,5-trimethoxystyryl)phenyl)Benzenesulfonamide (16d)
(Z)-3,4-dichloro-N-(2-hydroxy-3-methoxy-5-(3,4,5-trimethoxystyryl)phenyl)benzenesulfonamide (16e)
(Z)-4-fluoro-N-(2-hydroxy-3-methoxy-5-(3,4,5-trimethoxystyryl)phenyl)benzenesulfonamide (16f)
(Z)-4-tert-butyl-N-(2-hydroxy-3-methoxy-5-(3,4,5-trimethoxystyryl)phenyl)benzenesulfonamide (16g)
(Z)—N-(2-hydroxy-3-methoxy-5-(3,4,5-trimethoxystyryl)phenyl)-4-nitrobenzenesulfonamide (16h)
(Z)-4-amino-N-(2-hydroxy-3-methoxy-5-(3,4,5-trimethoxystyryl)phenyl)benzenesulfonamide (16i)
(Z)—N-(2-hydroxy-3-methoxy-5-(3,4,5-trimethoxystyryl)phenyl)-3-(trifluoromethyl)benzenesulfonamide (16j)
(Z)—N-(2-hydroxy-3-methoxy-5-(3,4,5-trimethoxystyryl)phenyl)-3-(trifluoromethoxy)benzenesulfonamide (16k)
(Z)—N-(2-hydroxy-3-methoxy-5-(3,4,5-trimethoxystyryl)phenyl)-4-(trifluoromethyl)benzenesulfonamide (16l)
(Z)—N-(2-hydroxy-3-methoxy-5-(3,4,5-trimethoxystyryl)phenyl)-4-(trifluoromethoxy) benzenesulfonamide (16m)
(Z)—N-(2-hydroxy-3-methoxy-5-(3,4,5-trimethoxystyryl)phenyl)-3-nitrobenzenesulfonamide (16n)
(Z)-3-amino-N-(2-hydroxy-3-methoxy-5-(3,4,5-trimethoxystyryl)phenyl) benzenesulfonamide (16o)
(Z)-3-fluoro-N-(2-hydroxy-3-methoxy-5-(3,4,5-trimethoxystyryl)phenyl)benzenesulfonamide (16p)
(Z)-3-tert-butyl-N-(2-hydroxy-3-methoxy-5-(3,4,5-trimethoxystyryl)phenyl)benzenesulfonamide (16q)
(Z)-3-fluoro-N-(2-hydroxy-3-methoxy-5-(3,4,5-trimethoxystyryl)phenyl)-4-methoxybenzenesulfonamide (16r)
(Z)-3-hydroxy-N-(2-hydroxy-3-methoxy-5-(3,4,5-trimethoxystyryl)phenyl)-4-methoxybenzenesulfonamide (16s)
(Z)—N-(2-hydroxy-3-methoxy-5-(3,4,5-trimethoxystyryl)phenyl)-4-methoxy-3-nitrobenzenesulfonamide (16t)
(Z)-3-amino-N-(2-hydroxy-3-methoxy-5-(3,4,5-trimethoxystyryl)phenyl)-4-methoxybenzenesulfonamide (16u)
(Z)—N-(2-hydroxy-3-methoxy-5-(3,4,5-trimethoxystyryl)phenyl)-3,4,5-trimethoxybenzenesulfonamide (16v)
(Z)—N-(2-hydroxy-3-methoxy-5-(3,4,5-trimethoxystyryl)phenyl)-4-methylbenzenesulfonamide (16w)
(Z)-3,4-difluoro-N-(2-hydroxy-3-methoxy-5-(3,4,5-trimethoxystyryl)phenyl)benzenesulfonamide (16x)
(Z)-3-chloro-N-(2-hydroxy-3-methoxy-5-(3,4,5-trimethoxystyryl)phenyl)-4-methoxybenzenesulfonamide (16y)
(Z)—N-(2-hydroxy-3-methoxy-6-(3,4,5-trimethoxystyryl)phenyl)-4-methoxybenzenesulfonamide (17a)
(Z)—N-(2-hydroxy-3-methoxy-6-(3,4,5-trimethoxystyryl)phenyl)-3,4-dimethoxybenzenesulfonamide (17b)
(Z)-4-chloro-N-(2-hydroxy-3-methoxy-6-(3,4,5-trimethoxystyryl)phenyl)benzenesulfonamide (17c)
(Z)-3-chloro-N-(2-hydroxy-3-methoxy-6-(3,4,5-trimethoxystyryl)phenyl)benzenesulfonamide (17d)
(Z)-3,4-dichloro-N-(2-hydroxy-3-methoxy-6-(3,4,5-trimethoxystyryl)phenyl)benzenesulfonamide (17e)
(Z)-4-fluoro-N-(2-hydroxy-3-methoxy-6-(3,4,5-trimethoxystyryl)phenyl)benzenesulfonamide (17f)
(Z)-4-tert-butyl-N-(2-hydroxy-3-methoxy-6-(3,4,5-trimethoxystyryl)phenyl)benzenesulfonamide (17g)
(Z)—N-(2-hydroxy-3-methoxy-6-(3,4,5-trimethoxystyryl)phenyl)-4-nitrobenzenesulfonamide (17h)
(Z)—N-(2-hydroxy-3-methoxy-6-(3,4,5-trimethoxystyryl)phenyl)-3-(trifluoromethyl)benzenesulfonamide (17i)
(Z)—N-(2-hydroxy-3-methoxy-6-(3,4,5-trimethoxystyryl)phenyl)-3-(trifluoromethoxy)benzenesulfonamide (17j)
(Z)—N-(2-hydroxy-3-methoxy-6-(3,4,5-trimethoxystyryl)phenyl)-3-(trifluoromethoxy)benzenesulfonamide (17k)
(Z)—N-(2-hydroxy-3-methoxy-6-(3,4,5-trimethoxystyryl)phenyl)-4-(trifluoromethyl)benzenesulfonamide (17l)
(Z)—N-(2-hydroxy-3-methoxy-6-(3,4,5-trimethoxystyryl)phenyl)-4-(trifluoromethoxy)benzenesulfonamide (17m)
(Z)—N-(2-hydroxy-3-methoxy-6-(3,4,5-trimethoxystyryl)phenyl)-3-nitrobenzenesulfonamide (17n)
(Z)-3-amino-N-(2-hydroxy-3-methoxy-6-(3,4,5-trimethoxystyryl)phenyl)benzenesulfonamide (17o)
(Z)-3-fluoro-N-(2-hydroxy-3-methoxy-6-(3,4,5-trimethoxystyryl)phenyl)benzenesulfonamide (17p)
(Z)-3-tert-butyl-N-(2-hydroxy-3-methoxy-6-(3,4,5-trimethoxystyryl)phenyl)benzenesulfonamide (17q)
(Z)-3-fluoro-N-(2-hydroxy-3-methoxy-6-(3,4,5-trimethoxystyryl)phenyl)-4-methoxybenzenesulfonamide (17r)
(Z)-3-hydroxy-N-(2-hydroxy-3-methoxy-6-(3,4,5-trimethoxystyryl)phenyl)-4-methoxybenzenesulfonamide (17s)
(Z)—N-(2-hydroxy-3-methoxy-6-(3,4,5-trimethoxystyryl)phenyl)-4-methoxy-3-nitrobenzenesulfonamide (17t)
(Z)—N-(2-hydroxy-3-methoxy-6-(3,4,5-trimethoxystyryl)phenyl)-3,4,5-trimethoxybenzenesulfonamide (17u)
(Z)—N-(2-hydroxy-3-methoxy-6-(3,4,5-trimethoxystyryl)phenyl)-4-methylbenzenesulfonamide (17v)
(Z)-4-hydroxy-N-(2-hydroxy-3-methoxy-6-(3,4,5-trimethoxystyryl)phenyl)benzenesulfonamide (17w)
(Z)-3,4-difluoro-N-(2-hydroxy-3-methoxy-6-(3,4,5-trimethoxystyryl)phenyl)benzenesulfonamide (17x)
(Z)-3-chloro-N-(2-hydroxy-3-methoxy-6-(3,4,5-trimethoxystyryl)phenyl)-4-methoxybenzenesulfonamide (17y)
(Z)—N-(4-hydroxy-5-methoxy-2-(3,4,5-trimethoxystyryl)phenyl)-4-methoxybenzenesulfonamide (18a)
(Z)—N-(4-hydroxy-5-methoxy-2-(3,4,5-trimethoxystyryl)phenyl)-3,4-dimethoxybenzenesulfonamide (18b)
(Z)-4-chloro-N-(4-hydroxy-5-methoxy-2-(3,4,5-trimethoxystyryl)phenyl)benzenesulfonamide (18c)
(Z)-3-chloro-N-(4-hydroxy-5-methoxy-2-(3,4,5-trimethoxystyryl)phenyl)benzenesulfonamide (18d)
(Z)-3,4-dichloro-N-(4-hydroxy-5-methoxy-2-(3,4,5-trimethoxystyryl)phenyl)benzenesulfonamide (18e)
(Z)-4-fluoro-N-(4-hydroxy-5-methoxy-2-(3,4,5-trimethoxystyryl)phenyl)benzenesulfonamide (18f)
(Z)-4-tert-butyl-N-(4-hydroxy-5-methoxy-2-(3,4,5-trimethoxystyryl)phenyl)benzenesulfonamide (18g)
(Z)—N-(4-hydroxy-5-methoxy-2-(3,4,5-trimethoxystyryl)phenyl)-4-nitrobenzenesulfonamide (18h)
(Z)-4-amino-N-(4-hydroxy-5-methoxy-2-(3,4,5-trimethoxystyryl)phenyl)benzenesulfonamide (18i)

(Z)—N-(4-hydroxy-5-methoxy-2-(3,4,5-trimethoxystyryl)phenyl)-3-(trifluoromethyl)benzenesulfonamide (18j)
(Z)—N-(4-hydroxy-5-methoxy-2-(3,4,5-trimethoxystyryl)phenyl)-4-(trifluoromethyl)benzenesulfonamide (18k)
(Z)—N-(4-hydroxy-5-methoxy-2-(3,4,5-trimethoxystyryl)phenyl)-4-(trifluoromethyl)benzenesulfonamide (18l)
(Z)—N-(4-hydroxy-5-methoxy-2-(3,4,5-trimethoxystyryl)phenyl)-4-(trifluoromethoxy)benzenesulfonamide (18m)
(Z)—N-(4-hydroxy-5-methoxy-2-(3,4,5-trimethoxystyryl)phenyl)-3-nitrobenzenesulfonamide (18n)
(Z)-3-amino-N-(4-hydroxy-5-methoxy-2-(3,4,5-trimethoxystyryl)phenyl)benzenesulfonamide (18o)
(Z)-3-fluoro-N-(4-hydroxy-5-methoxy-2-(3,4,5-trimethoxystyryl)phenyl)benzenesulfonamide (18p)
(Z)-3-tert-butyl-N-(4-hydroxy-5-methoxy-2-(3,4,5-trimethoxystyryl)phenyl)benzenesulfonamide (18q)
(Z)-3-fluoro-N-(4-hydroxy-5-methoxy-2-(3,4,5-trimethoxystyryl)phenyl)-4-methoxybenzenesulfonamide (18r)
(Z)-3-hydroxy-N-(4-hydroxy-5-methoxy-2-(3,4,5-trimethoxystyryl)phenyl)-4-methoxybenzenesulfonamide (18s)
(Z)—N-(4-hydroxy-5-methoxy-2-(3,4,5-trimethoxystyryl)phenyl)-4-methoxy-3-nitrobenzenesulfonamide (18t)
(Z)—N-(4-hydroxy-5-methoxy-2-(3,4,5-trimethoxystyryl)phenyl)-3,4,5-trimethoxybenzenesulfonamide (18u)
(Z)—N-(4-hydroxy-5-methoxy-2-(3,4,5-trimethoxystyryl)phenyl)-4-methylbenzenesulfonamide (18v)
(Z)-4-hydroxy-N-(4-hydroxy-5-methoxy-2-(3,4,5-trimethoxystyryl)phenyl)benzenesulfonamide (18w)
(Z)-3,4-difluoro-N-(4-hydroxy-5-methoxy-2-(3,4,5-trimethoxystyryl)phenyl)benzenesulfonamide (18x)
(Z)-3-chloro-N-(4-hydroxy-5-methoxy-2-(3,4,5-trimethoxystyryl)phenyl)-4-methoxybenzenesulfonamide (18y)
(Z)—N-(2-fluoro-3-methoxy-6-(3,4,5-trimethoxystyryl)phenyl)-4-methoxybenzenesulfonamide (19a)
(Z)—N-(2-fluoro-3-methoxy-6-(3,4,5-trimethoxystyryl)phenyl)-3,4-dimethoxybenzenesulfonamide (19b)
(Z)-4-chloro-N-(2-fluoro-3-methoxy-6-(3,4,5-trimethoxystyryl)phenyl)benzenesulfonamide (19c)
(Z)-3-chloro-N-(2-fluoro-3-methoxy-6-(3,4,5-trimethoxystyryl)phenyl)benzenesulfonamide (19d)
(Z)-3,4-dichloro-N-(2-fluoro-3-methoxy-6-(3,4,5-trimethoxystyryl)phenyl)benzenesulfonamide (19e)
(Z)-4-fluoro-N-(2-fluoro-3-methoxy-6-(3,4,5-trimethoxystyryl)phenyl)benzenesulfonamide (19f)
(Z)-4-tert-butyl-N-(2-fluoro-3-methoxy-6-(3,4,5-trimethoxystyryl)phenyl)benzenesulfonamide (19g)
(Z)—N-(2-fluoro-3-methoxy-6-(3,4,5-trimethoxystyryl)phenyl)-4-nitrobenzenesulfonamide (19h)
(Z)-4-amino-N-(2-fluoro-3-methoxy-6-(3,4,5-trimethoxystyryl)phenyl)benzenesulfonamide (19i)
(Z)—N-(2-fluoro-3-methoxy-6-(3,4,5-trimethoxystyryl)phenyl)-3-(trifluoromethyl)benzenesulfonamide (19j)
(Z)—N-(2-fluoro-3-methoxy-6-(3,4,5-trimethoxystyryl)phenyl)-3-(trifluoromethoxy) benzenesulfonamide (19k)
(Z)—N-(2-fluoro-3-methoxy-6-(3,4,5-trimethoxystyryl)phenyl)-4-(trifluoromethyl)benzenesulfonamide (19l)
(Z)—N-(2-fluoro-3-methoxy-6-(3,4,5-trimethoxystyryl)phenyl)-4-(trifluoromethoxy)benzenesulfonamide (19m)
(Z)—N-(2-fluoro-3-methoxy-6-(3,4,5-trimethoxystyryl)phenyl)-3-nitrobenzenesulfonamide (19n)
(Z)-3-amino-N-(2-fluoro-3-methoxy-6-(3,4,5-trimethoxystyryl)phenyl)benzenesulfonamide (19o)
(Z)-3-fluoro-N-(2-fluoro-3-methoxy-6-(3,4,5-trimethoxystyryl)phenyl)benzenesulfonamide (19p)
(Z)-3-tert-butyl-N-(2-fluoro-3-methoxy-6-(3,4,5-trimethoxystyryl)phenyl)benzenesulfonamide (19q)
(Z)-3-fluoro-N-(2-fluoro-3-methoxy-6-(3,4,5-trimethoxystyryl)phenyl)-4-methoxybenzenesulfonamide (19r)
(Z)—N-(2-fluoro-3-methoxy-6-(3,4,5-trimethoxystyryl)phenyl)-3-hydroxy-4-methoxybenzenesulfonamide (19s)
(Z)—N-(2-fluoro-3-methoxy-6-(3,4,5-trimethoxystyryl)phenyl)-4-methoxy-3-nitrobenzenesulfonamide (19t)
(Z)—N-(2-fluoro-3-methoxy-6-(3,4,5-trimethoxystyryl)phenyl)-3,4,5-trimethoxybenzenesulfonamide (19u)
(Z)—N-(2-fluoro-3-methoxy-6-(3,4,5-trimethoxystyryl)phenyl)-4-methylbenzenesulfonamide (19v)
(Z)—N-(2-fluoro-3-methoxy-6-(3,4,5-trimethoxystyryl)phenyl)-4-hydroxybenzenesulfonamide (19w)
(Z)-3,4-difluoro-N-(2-fluoro-3-methoxy-6-(3,4,5-trimethoxystyryl)phenyl)benzenesulfonamide (19x)
(Z)-3-chloro-N-(2-fluoro-3-methoxy-6-(3,4,5-trimethoxystyryl)phenyl)-4-methoxybenzenesulfonamide (19y)
(Z)—N-(3-fluoro-2-methoxy-6-(3,4,5-trimethoxystyryl)phenyl)-4-methoxybenzenesulfonamide (20a)
(Z)—N-(3-fluoro-2-methoxy-6-(3,4,5-trimethoxystyryl)phenyl)-3,4-dimethoxybenzenesulfonamide (20b)
(Z)-4-chloro-N-(3-fluoro-2-methoxy-6-(3,4,5-trimethoxystyryl)phenyl)benzenesulfonamide (20c)
(Z)-3-chloro-N-(3-fluoro-2-methoxy-6-(3,4,5-trimethoxystyryl)phenyl)benzenesulfonamide (20d)
(Z)-3,4-dichloro-N-(3-fluoro-2-methoxy-6-(3,4,5-trimethoxystyryl)phenyl) benzenesulfonamide (20e)
(Z)-4-fluoro-N-(3-fluoro-2-methoxy-6-(3,4,5-trimethoxystyryl)phenyl)benzenesulfonamide (20f)
(Z)-4-tert-butyl-N-(3-fluoro-2-methoxy-6-(3,4,5-trimethoxystyryl)phenyl)benzenesulfonamide (20g)
(Z)—N-(3-fluoro-2-methoxy-6-(3,4,5-trimethoxystyryl)phenyl)-4-nitrobenzenesulfonamide (20h)
(Z)-4-amino-N-(3-fluoro-2-methoxy-6-(3,4,5-trimethoxystyryl)phenyl)benzenesulfonamide (20i)
(Z)—N-(3-fluoro-2-methoxy-6-(3,4,5-trimethoxystyryl)phenyl)-3-(trifluoromethyl)benzenesulfonamide (20j)
(Z)—N-(3-fluoro-2-methoxy-6-(3,4,5-trimethoxystyryl)phenyl)-3-(trifluoromethoxy)benzenesulfonamide (20k)
(Z)—N-(3-fluoro-2-methoxy-6-(3,4,5-trimethoxystyryl)phenyl)-4-(trifluoromethyl)benzenesulfonamide (20l)
(Z)—N-(3-fluoro-2-methoxy-6-(3,4,5-trimethoxystyryl)phenyl)-4-(trifluoromethoxy)benzenesulfonamide (20m)
(Z)—N-(3-fluoro-2-methoxy-6-(3,4,5-trimethoxystyryl)phenyl)-3-nitrobenzenesulfonamide (20n)
(Z)-3-amino-N-(3-fluoro-2-methoxy-6-(3,4,5-trimethoxystyryl)phenyl)benzenesulfonamide (20o)
(Z)-3-fluoro-N-(3-fluoro-2-methoxy-6-(3,4,5-trimethoxystyryl)phenyl)benzenesulfonamide (20p)
(Z)-3-tert-butyl-N-(3-fluoro-2-methoxy-6-(3,4,5-trimethoxystyryl)phenyl)benzenesulfonamide (20q)
(Z)-3-fluoro-N-(3-fluoro-2-methoxy-6-(3,4,5-trimethoxystyryl)phenyl)-4-methoxybenzenesulfonamide (20r)
(Z)—N-(3-fluoro-2-methoxy-6-(3,4,5-trimethoxystyryl)phenyl)-3-hydroxy-4-methoxybenzenesulfonamide (20s)
(Z)—N-(3-fluoro-2-methoxy-6-(3,4,5-trimethoxystyryl)phenyl)-4-methoxy-3-nitrobenzenesulfonamide (20t)
(Z)—N-(3-fluoro-2-methoxy-6-(3,4,5-trimethoxystyryl)phenyl)-3,4,5-trimethoxybenzenesulfonamide (20u)
(Z)—N-(3-fluoro-2-methoxy-6-(3,4,5-trimethoxystyryl)phenyl)-4-methylbenzenesulfonamide (20v)
(Z)—N-(3-fluoro-2-methoxy-6-(3,4,5-trimethoxystyryl)phenyl)-4-hydroxybenzenesulfonamide (20w)
(Z)-3,4-difluoro-N-(3-fluoro-2-methoxy-6-(3,4,5-trimethoxystyryl)phenyl)benzenesulfonamide (20x)
(Z)-3-chloro-N-(3-fluoro-2-methoxy-6-(3,4,5-trimethoxystyryl)phenyl)-4-methoxybenzenesulfonamide (20y)

(Z)—N-(3-hydroxy-2-methoxy-6-(3,4,5-trimethoxystyryl)phenyl)-4-methoxybenzenesulfonamide (21a)
(Z)—N-(3-hydroxy-2-methoxy-6-(3,4,5-trimethoxystyryl)phenyl)-3,4-dimethoxybenzenesulfonamide (21b)
(Z)-4-chloro-N-(3-hydroxy-2-methoxy-6-(3,4,5-trimethoxystyryl)phenyl)benzenesulfonamide (21c)
(Z)-3-chloro-N-(3-hydroxy-2-methoxy-6-(3,4,5-trimethoxystyryl)phenyl)benzenesulfonamide (21d)
(Z)-3,4-dichloro-N-(3-hydroxy-2-methoxy-6-(3,4,5-trimethoxystyryl)phenyl)benzenesulfonamide (21e)
(Z)-4-fluoro-N-(3-hydroxy-2-methoxy-6-(3,4,5-trimethoxystyryl)phenyl)benzenesulfonamide (21f)
(Z)-4-tert-butyl-N-(3-hydroxy-2-methoxy-6-(3,4,5-trimethoxystyryl)phenyl)benzenesulfonamide (21g)
(Z)—N-(3-hydroxy-2-methoxy-6-(3,4,5-trimethoxystyryl)phenyl)-4-nitrobenzenesulfonamide (21h)
(Z)-4-amino-N-(3-hydroxy-2-methoxy-6-(3,4,5-trimethoxystyryl)phenyl)benzenesulfonamide (21h)
(Z)—N-(3-hydroxy-2-methoxy-6-(3,4,5-trimethoxystyryl)phenyl)-3-(trifluoromethyl)benzenesulfonamide (21j)
(Z)—N-(3-hydroxy-2-methoxy-6-(3,4,5-trimethoxystyryl)phenyl)-3-(trifluoromethoxy)benzenesulfonamide (21k)
(Z)—N-(3-hydroxy-2-methoxy-6-(3,4,5-trimethoxystyryl)phenyl)-4-(trifluoromethyl)benzenesulfonamide (21l)
(Z)—N-(3-hydroxy-2-methoxy-6-(3,4,5-trimethoxystyryl)phenyl)-4-(trifluoromethoxy)benzenesulfonamide (21m)
(Z)—N-(3-hydroxy-2-methoxy-6-(3,4,5-trimethoxystyryl)phenyl)-3-nitrobenzenesulfonamide (21n)
(Z)-3-amino-N-(3-hydroxy-2-methoxy-6-(3,4,5-trimethoxystyryl)phenyl)benzenesulfonamide (21o)
(Z)-3-fluoro-N-(3-hydroxy-2-methoxy-6-(3,4,5-trimethoxystyryl)phenyl)benzenesulfonamide (21p)
(Z)-3-tert-butyl-N-(3-hydroxy-2-methoxy-6-(3,4,5-trimethoxystyryl)phenyl)benzenesulfonamide (21q)
(Z)-3-fluoro-N-(3-hydroxy-2-methoxy-6-(3,4,5-trimethoxystyryl)phenyl)-4-methoxybenzenesulfonamide (21r)
(Z)-3-hydroxy-N-(3-hydroxy-2-methoxy-6-(3,4,5-trimethoxystyryl)phenyl)-4-methoxybenzenesulfonamide (21s)
(Z)—N-(3-hydroxy-2-methoxy-6-(3,4,5-trimethoxystyryl)phenyl)-4-methoxy-3-nitrobenzenesulfonamide (21t)
(Z)—N-(3-hydroxy-2-methoxy-6-(3,4,5-trimethoxystyryl)phenyl)-3,4,5-trimethoxybenzenesulfonamide (21u)
(Z)—N-(3-hydroxy-2-methoxy-6-(3,4,5-trimethoxystyryl)phenyl)-4-methylbenzenesulfonamide (21v)
(Z)-4-hydroxy-N-(3-hydroxy-2-methoxy-6-(3,4,5-trimethoxystyryl)phenyl)benzenesulfonamide (21w)
(Z)-3,4-difluoro-N-(3-hydroxy-2-methoxy-6-(3,4,5-trimethoxystyryl)phenyl)benzenesulfonamide (21x)
(Z)-3-chloro-N-(3-hydroxy-2-methoxy-6-(3,4,5-trimethoxystyryl)phenyl)-4-methoxybenzenesulfonamide (21y)
(Z)—N-(2,3-dimethoxy-6-(3,4,5-trimethoxystyryl)phenyl)-4-methoxybenzenesulfonamide (22a)
(Z)—N-(2,3-dimethoxy-6-(3,4,5-trimethoxystyryl)phenyl)-3,4-dimethoxybenzenesulfonamide (22b)
(Z)-4-chloro-N-(2,3-dimethoxy-6-(3,4,5-trimethoxystyryl)phenyl)benzenesulfonamide (22c)
(Z)-3-chloro-N-(2,3-dimethoxy-6-(3,4,5-trimethoxystyryl)phenyl)benzenesulfonamide (22d)
(Z)-3,4-dichloro-N-(2,3-dimethoxy-6-(3,4,5-trimethoxystyryl)phenyl)benzenesulfonamide (22e)
(Z)—N-(2,3-dimethoxy-6-(3,4,5-trimethoxystyryl)phenyl)-4-fluorobenzenesulfonamide (22f)
(Z)-4-tert-butyl-N-(2,3-dimethoxy-6-(3,4,5-trimethoxystyryl)phenyl)benzenesulfonamide (22g)
(Z)—N-(2,3-dimethoxy-6-(3,4,5-trimethoxystyryl)phenyl)-4-nitrobenzenesulfonamide (22h)
(Z)-4-amino-N-(2,3-dimethoxy-6-(3,4,5-trimethoxystyryl)phenyl)benzenesulfonamide (22i)
(Z)—N-(2,3-dimethoxy-6-(3,4,5-trimethoxystyryl)phenyl)-3-(trifluoromethyl)benzenesulfonamide (22j)
(Z)—N-(2,3-dimethoxy-6-(3,4,5-trimethoxystyryl)phenyl)-3-(trifluoromethoxy)benzenesulfonamide (22k)
(Z)—N-(2,3-dimethoxy-6-(3,4,5-trimethoxystyryl)phenyl)-4-(trifluoromethyl)benzenesulfonamide (22l)
(Z)—N-(2,3-dimethoxy-6-(3,4,5-trimethoxystyryl)phenyl)-4-(trifluoromethoxy)benzenesulfonamide (22m)
(Z)—N-(2,3-dimethoxy-6-(3,4,5-trimethoxystyryl)phenyl)-3-nitrobenzenesulfonamide (22n)
(Z)-3-amino-N-(2,3-dimethoxy-6-(3,4,5-trimethoxystyryl)phenyl)benzenesulfonamide (22o)
(Z)—N-(2,3-dimethoxy-6-(3,4,5-trimethoxystyryl)phenyl)-3-fluorobenzenesulfonamide (22p)
(Z)-3-tert-butyl-N-(2,3-dimethoxy-6-(3,4,5-trimethoxystyryl)phenyl)benzenesulfonamide (22q)
(Z)—N-(2,3-dimethoxy-6-(3,4,5-trimethoxystyryl)phenyl)-3-fluoro-4-methoxybenzenesulfonamide (22r)
(Z)—N-(2,3-dimethoxy-6-(3,4,5-trimethoxystyryl)phenyl)-3-hydroxy-4-methoxybenzenesulfonamide (22s)
(Z)—N-(2,3-dimethoxy-6-(3,4,5-trimethoxystyryl)phenyl)-4-methoxy-3-nitrobenzenesulfonamide (22t)
(Z)—N-(2,3-dimethoxy-6-(3,4,5-trimethoxystyryl)phenyl)-3,4,5-trimethoxybenzenesulfonamide (22u)
(Z)—N-(2,3-dimethoxy-6-(3,4,5-trimethoxystyryl)phenyl)-4-methylbenzenesulfonamide (22v)
(Z)—N-(2,3-dimethoxy-6-(3,4,5-trimethoxystyryl)phenyl)-4-hydroxybenzenesulfonamide (22w)
(Z)—N-(2,3-dimethoxy-6-(3,4,5-trimethoxystyryl)phenyl)-3,4-difluorobenzenesulfonamide (22x)
(Z)-3-chloro-N-(2,3-dimethoxy-6-(3,4,5-trimethoxystyryl)phenyl)-4-methoxybenzenesulfonamide (22y)
(Z)—N-(4,5-dimethoxy-2-(3,4,5-trimethoxystyryl)phenyl)-4-methoxybenzenesulfonamide (23a)
(Z)—N-(4,5-dimethoxy-2-(3,4,5-trimethoxystyryl)phenyl)-3,4-dimethoxybenzenesulfonamide (23b)
(Z)-4-chloro-N-(4,5-dimethoxy-2-(3,4,5-trimethoxystyryl)phenyl)benzenesulfonamide (23c)
(Z)-3-chloro-N-(4,5-dimethoxy-2-(3,4,5-trimethoxystyryl)phenyl)benzenesulfonamide (23d)
(Z)-3,4-dichloro-N-(4,5-dimethoxy-2-(3,4,5-trimethoxystyryl)phenyl)benzenesulfonamide (23e)
(Z)—N-(4,5-dimethoxy-2-(3,4,5-trimethoxystyryl)phenyl)-4-fluorobenzenesulfonamide (23f)
(Z)-4-tert-butyl-N-(4,5-dimethoxy-2-(3,4,5-trimethoxystyryl)phenyl)benzenesulfonamide (23g)
(Z)—N-(4,5-dimethoxy-2-(3,4,5-trimethoxystyryl)phenyl)-4-nitrobenzenesulfonamide (23h)
(Z)-4-amino-N-(4,5-dimethoxy-2-(3,4,5-trimethoxystyryl)phenyl)benzenesulfonamide (23i)
(Z)—N-(4,5-dimethoxy-2-(3,4,5-trimethoxystyryl)phenyl)-3-(trifluoromethyl)benzenesulfonamide (23j)
(Z)—N-(4,5-dimethoxy-2-(3,4,5-trimethoxystyryl)phenyl)-3-(trifluoromethoxy)benzenesulfonamide (23k)
(Z)—N-(4,5-dimethoxy-2-(3,4,5-trimethoxystyryl)phenyl)-4-(trifluoromethyl)benzenesulfonamide (23l)
(Z)—N-(4,5-dimethoxy-2-(3,4,5-trimethoxystyryl)phenyl)-4-(trifluoromethoxy)benzenesulfonamide (23m)
(Z)—N-(4,5-dimethoxy-2-(3,4,5-trimethoxystyryl)phenyl)-3-nitrobenzenesulfonamide (23n)
(Z)-3-amino-N-(4,5-dimethoxy-2-(3,4,5-trimethoxystyryl)phenyl)benzenesulfonamide (23o)
(Z)—N-(4,5-dimethoxy-2-(3,4,5-trimethoxystyryl)phenyl)-3-fluorobenzenesulfonamide (23p)

(Z)-3-tert-butyl-N-(4,5-dimethoxy-2-(3,4,5-trimethoxystyryl)phenyl)benzenesulfonamide (23q)

(Z)—N-(4,5-dimethoxy-2-(3,4,5-trimethoxystyryl)phenyl)-3-fluoro-4-methoxybenzenesulfonamide (23r)

(Z)—N-(4,5-dimethoxy-2-(3,4,5-trimethoxystyryl)phenyl)-3-hydroxy-4-methoxybenzenesulfonamide (23s)

(Z)—N-(4,5-dimethoxy-2-(3,4,5-trimethoxystyryl)phenyl)-4-methoxy-3-nitrobenzenesulfonamide (23t)

(Z)—N-(4,5-dimethoxy-2-(3,4,5-trimethoxystyryl)phenyl)-3,4,5-trimethoxybenzenesulfonamide (23u)

(Z)—N-(4,5-dimethoxy-2-(3,4,5-trimethoxystyryl)phenyl)-4-methylbenzenesulfonamide (23v)

(Z)—N-(4,5-dimethoxy-2-(3,4,5-trimethoxystyryl)phenyl)-4-hydroxybenzenesulfonamide (23w)

(Z)—N-(4,5-dimethoxy-2-(3,4,5-trimethoxystyryl)phenyl)-3,4-difluorobenzenesulfonamide (23x), and (Z)-3-chloro-N-(4,5-dimethoxy-2-(3,4,5-trimethoxystyryl)phenyl)-4-methoxybenzenesulfonamide (23y).

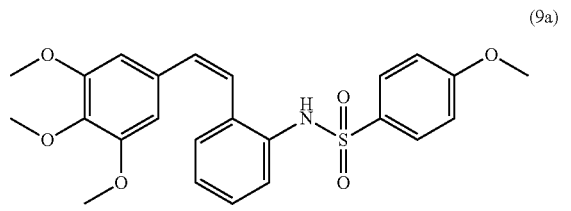
(9a)

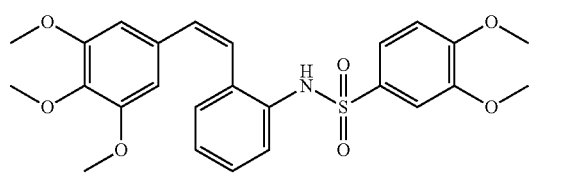
(9b)

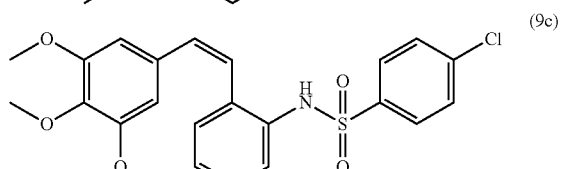
(9c)

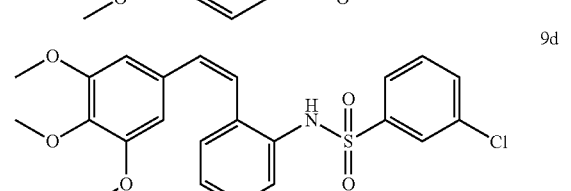
(9d)

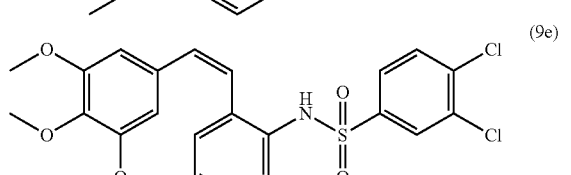
(9e)

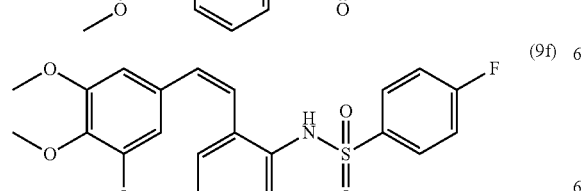
(9f)

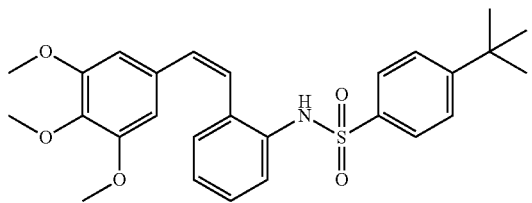
(9g)

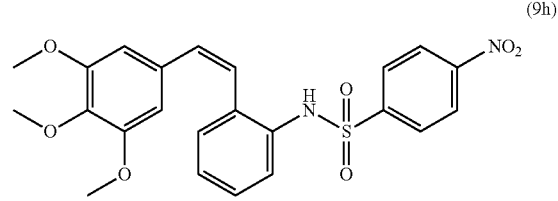
(9h)

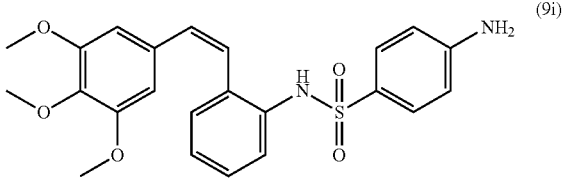
(9i)

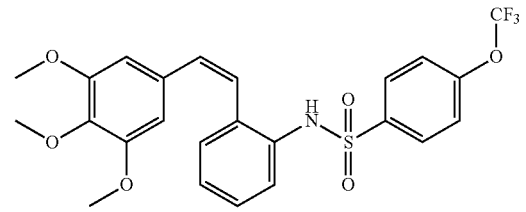
(9m)

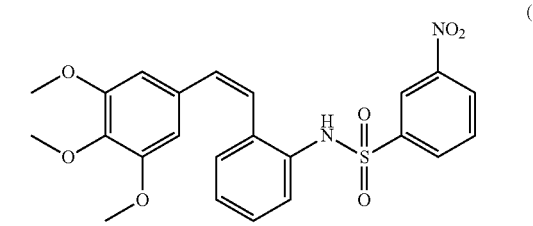
(9n)

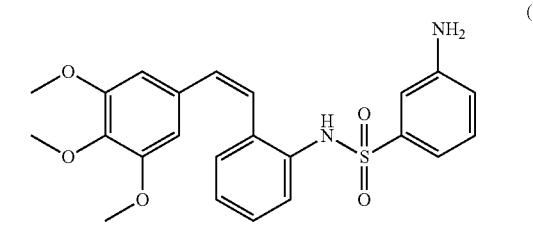
(9o)

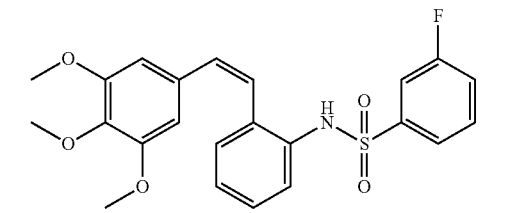
(9p)

(9q) 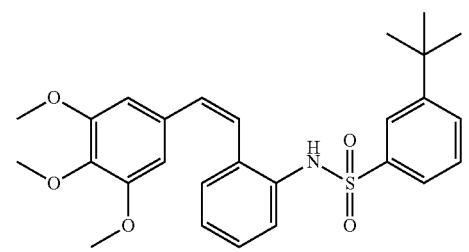
(9r) 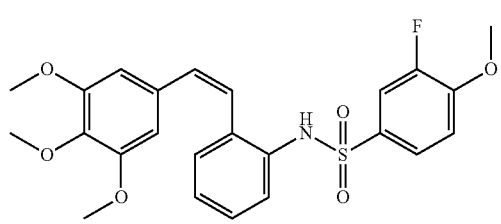
(9s) 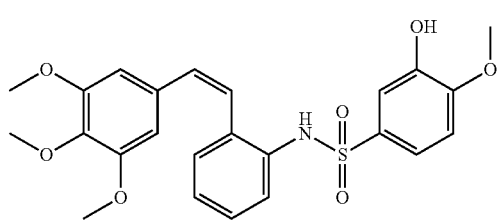
(9t) 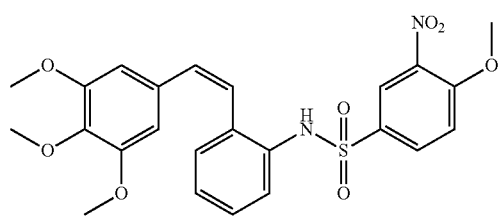
(9u) 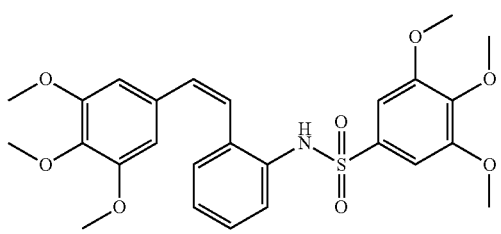
(9v) 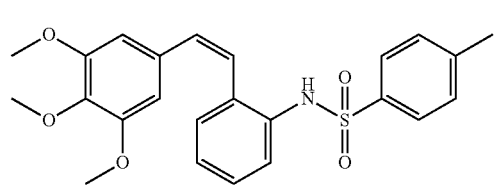
(9w) 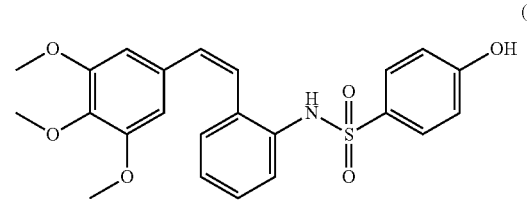
(9x) 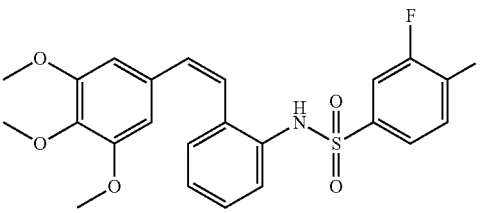
(9Y) 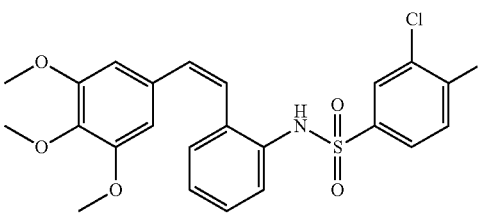
(10a) 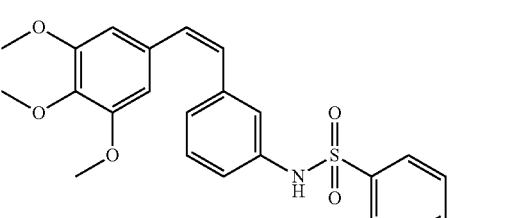
(10b) 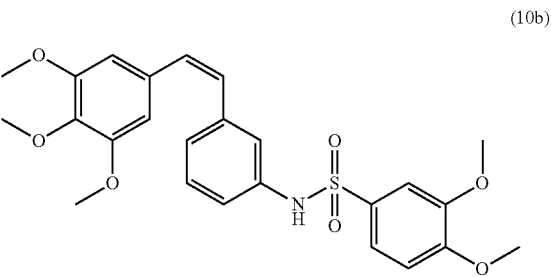
(10c) 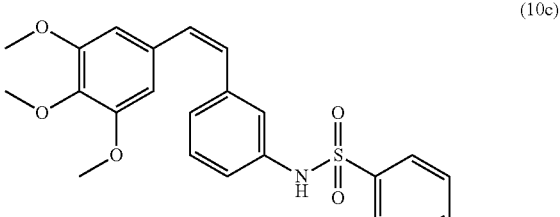
(10d) 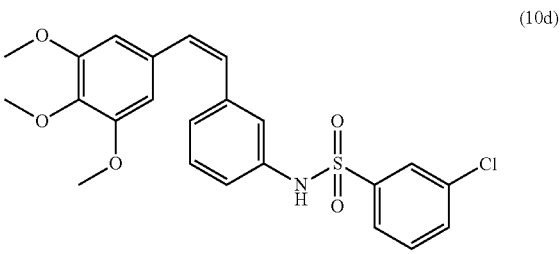

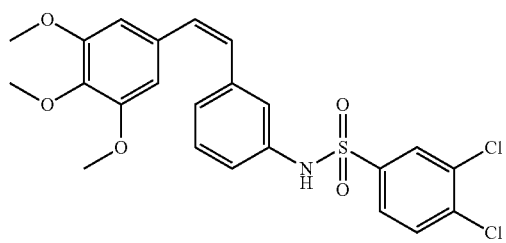
(10e)
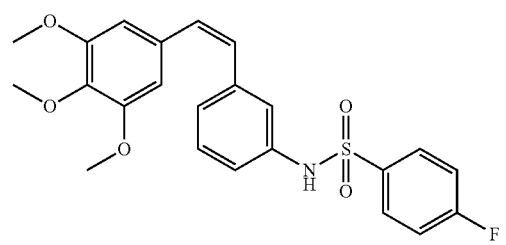
(10f)
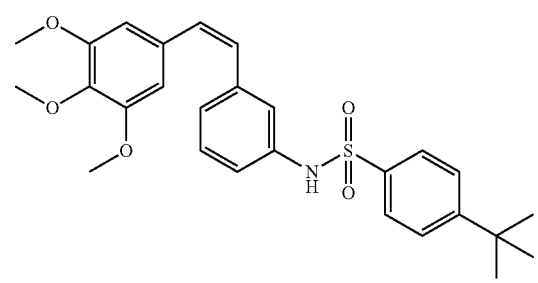
(10g)
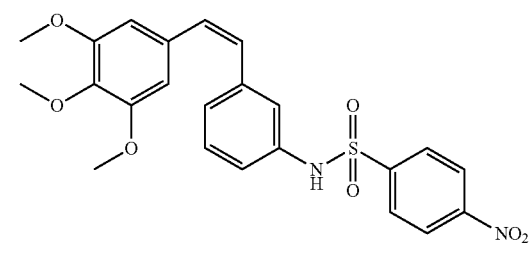
(10h)
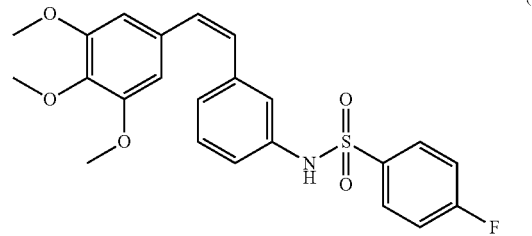
(10f)
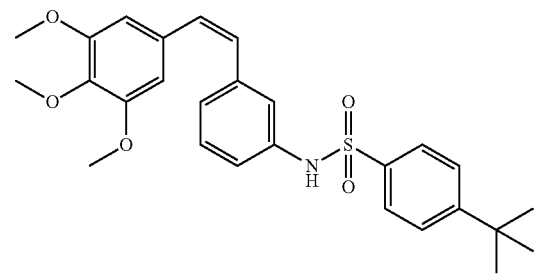
(10g)
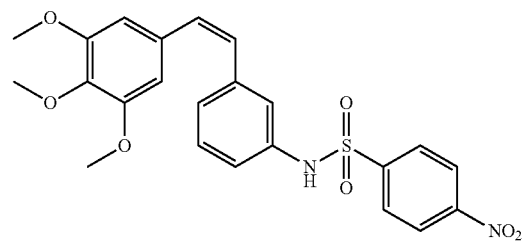
(10h)
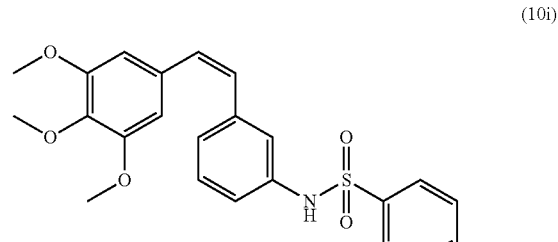
(10i)
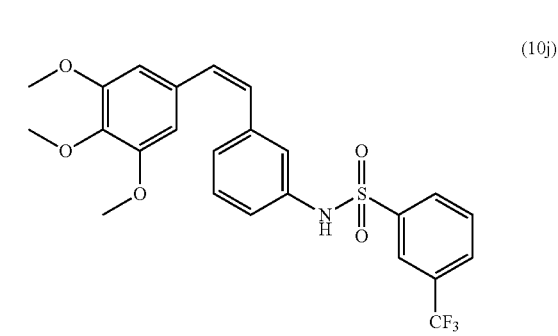
(10j)
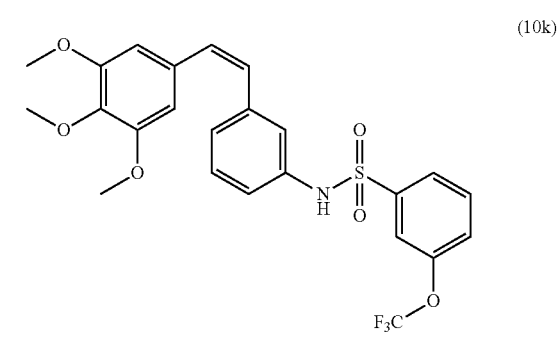
(10k)
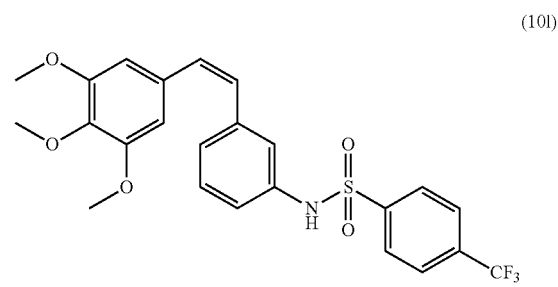
(10l)

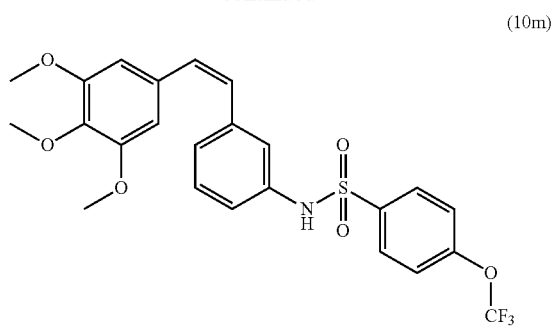
(10m)
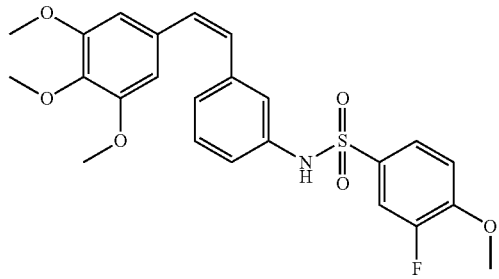
(10r)
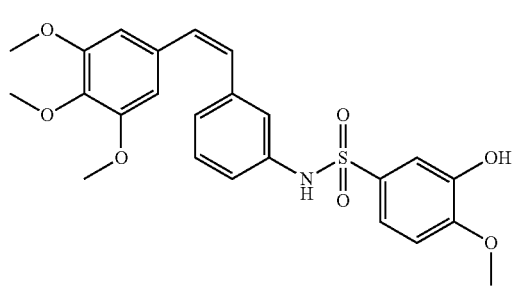
(10s)
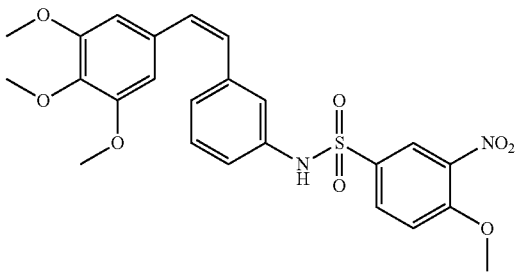
(10t)
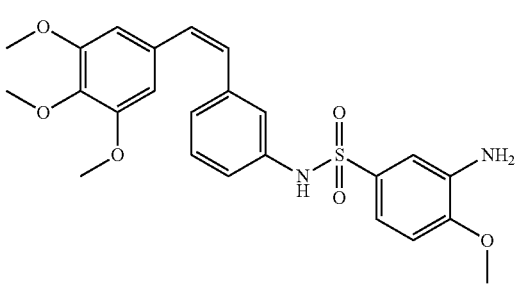
(10u)
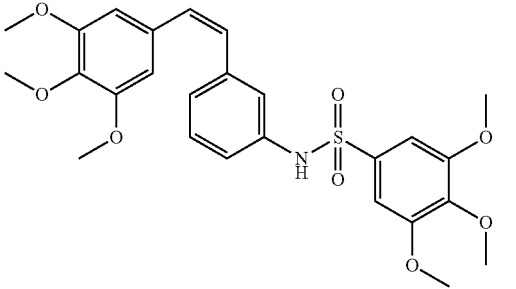
(10v)

(10w)
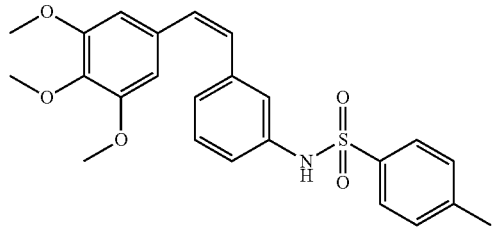
(10x)
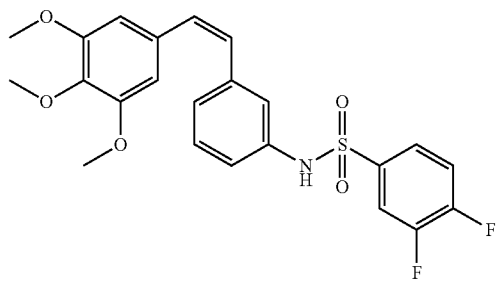
(10y)
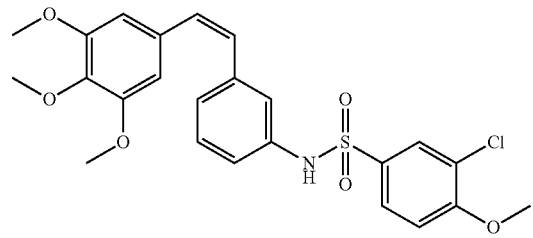
(11a)
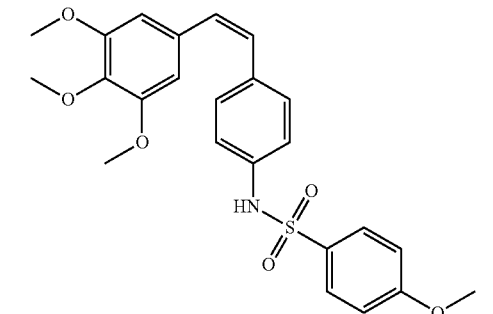
(11b)
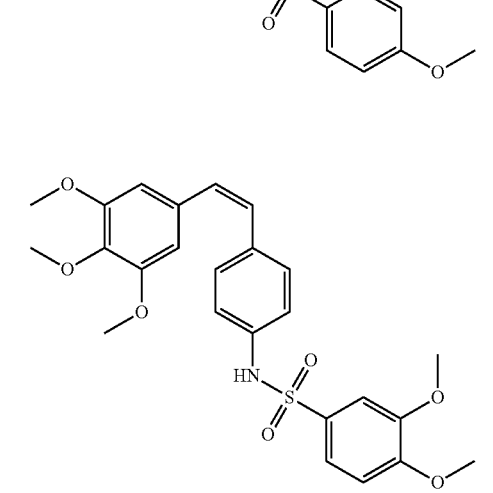
(11c)
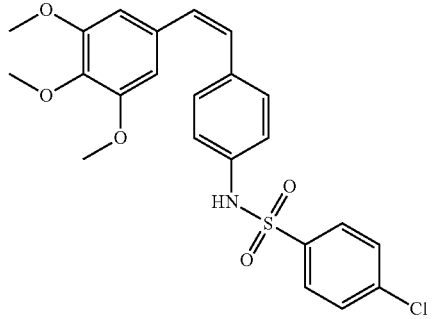
(11d)
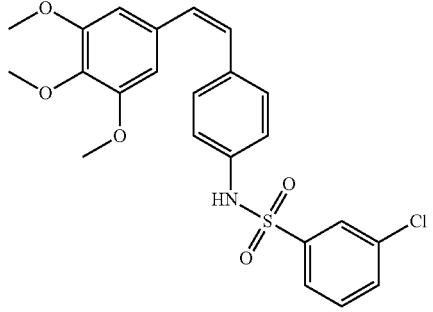
(11e)
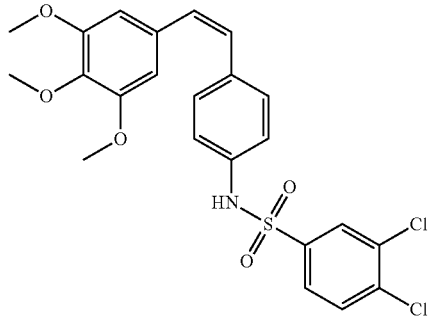
(11f)
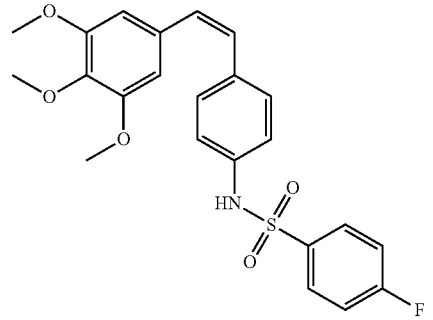

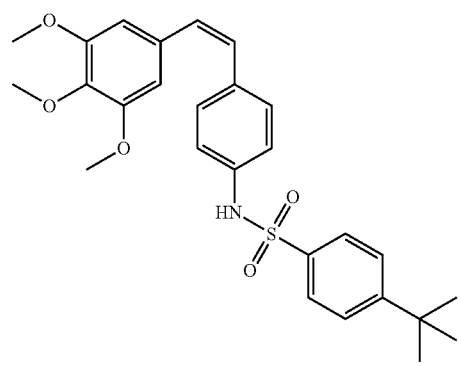
(11g)
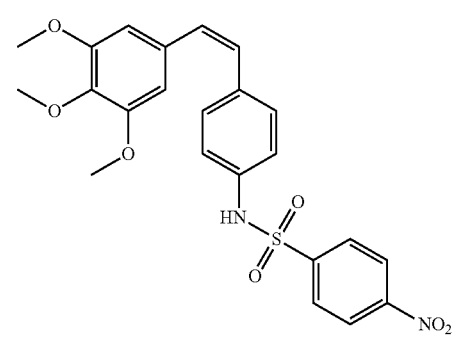
(11h)
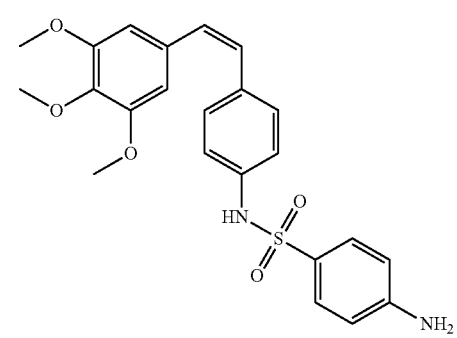
(11i)
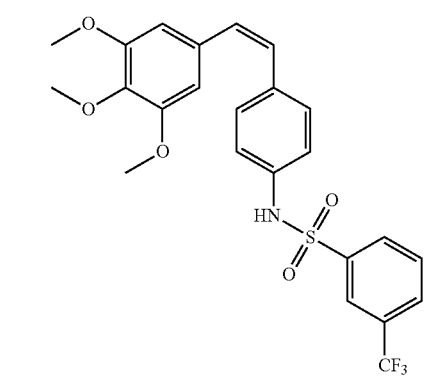
(11j)
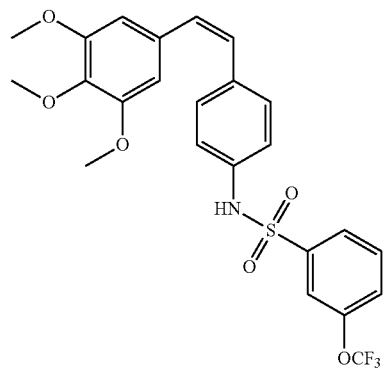
(11k)
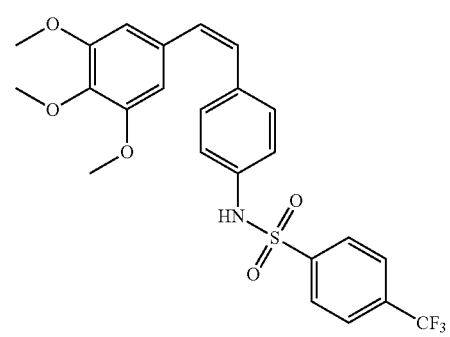
(11l)
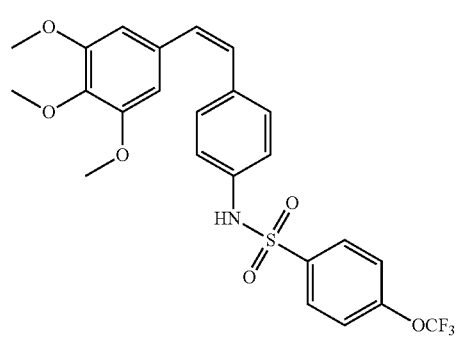
(11m)
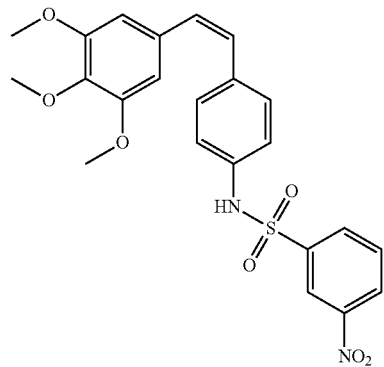
(11n)

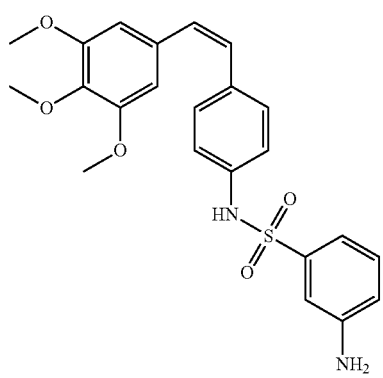
(11o)
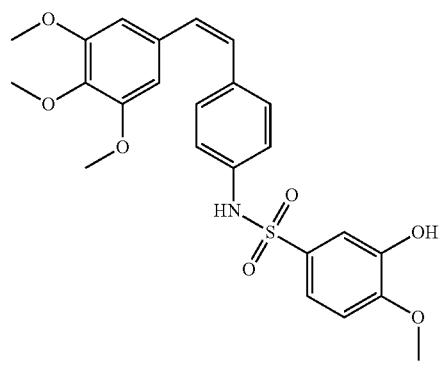
(11s)
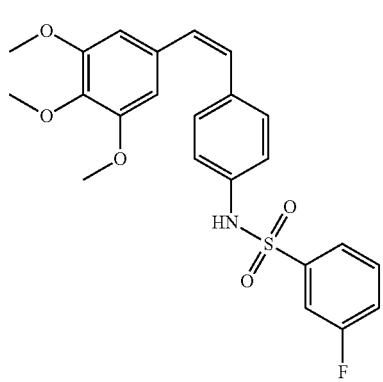
(11p)
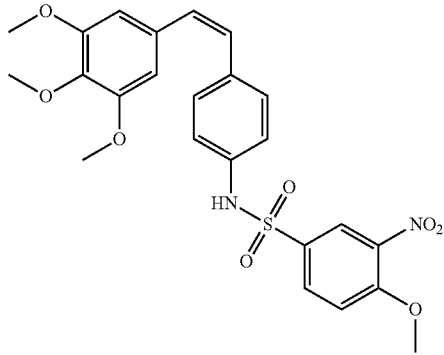
(11t)
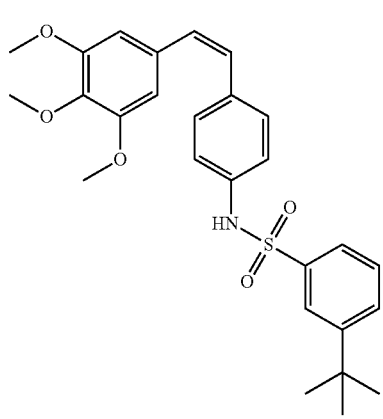
(11q)
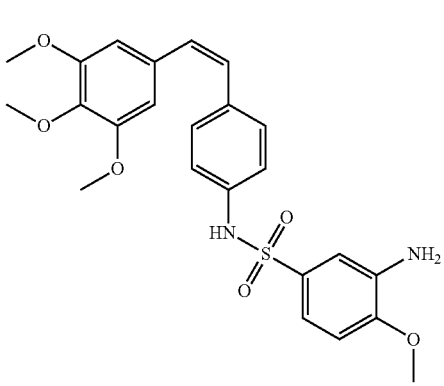
(11u)
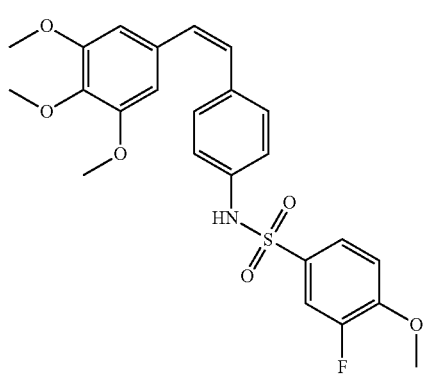
(11r)
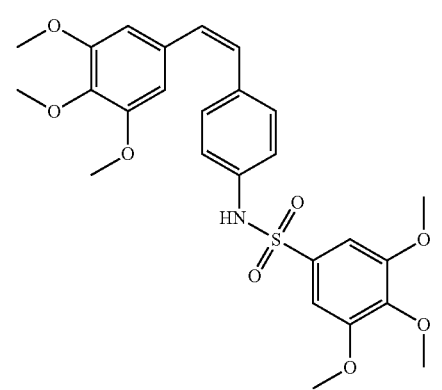
(11v)

(11w)
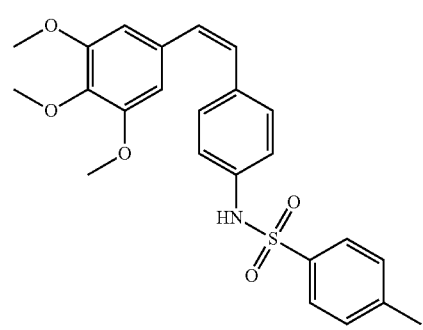
(11x)
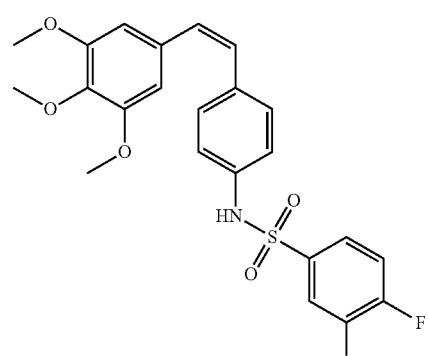
(11y)
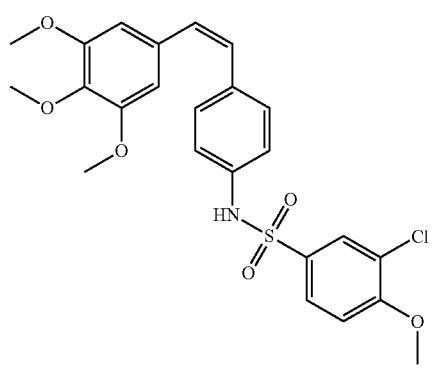
(12a)
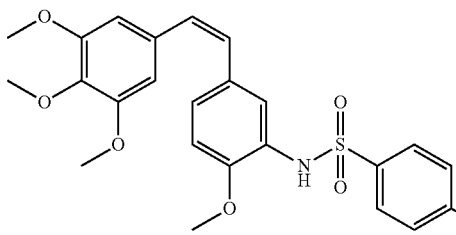
(12b)
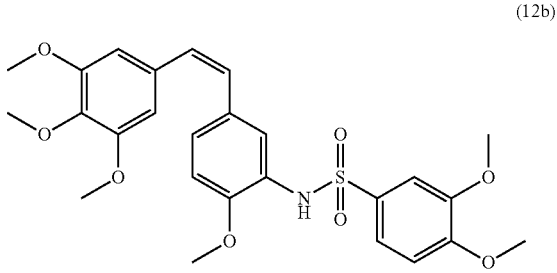
(12c)
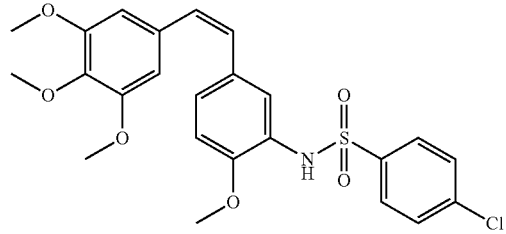
(12d)
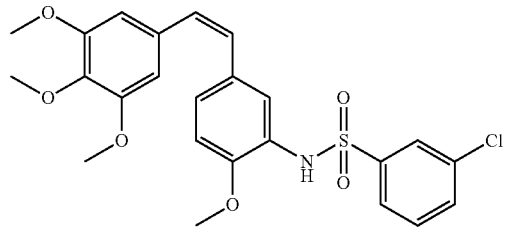
(12e)
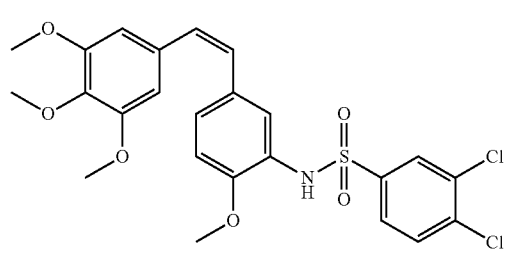
(12f)
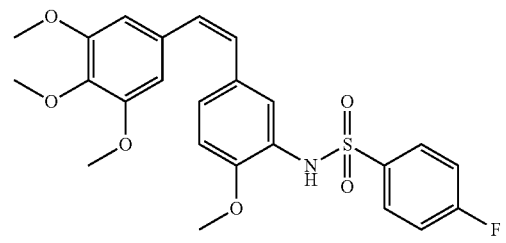
(12g)
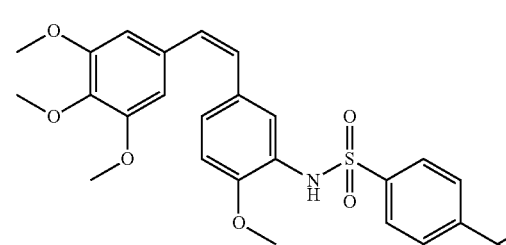
(12h)
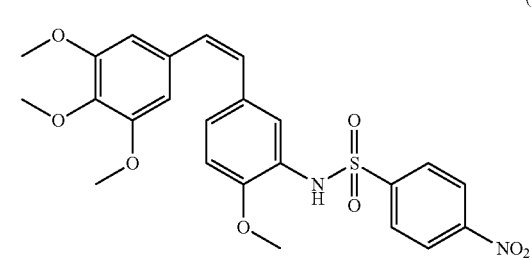

(12i)
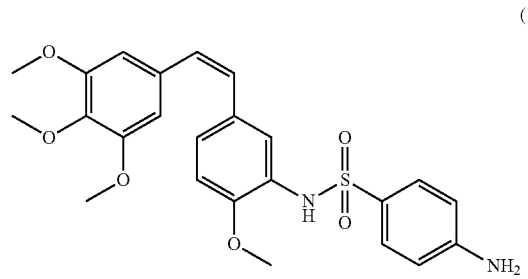
(12j)
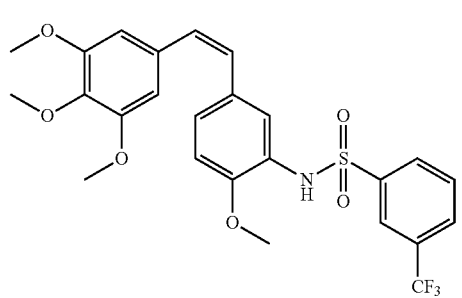
(12k)
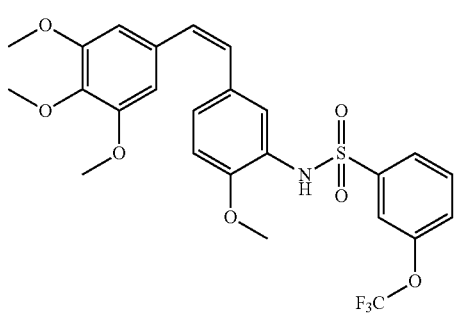
(12l)
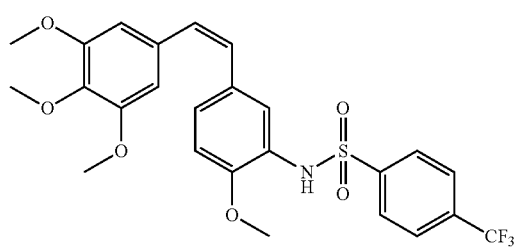
(12m)
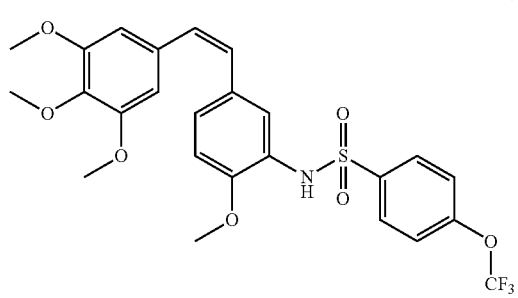
(12n)
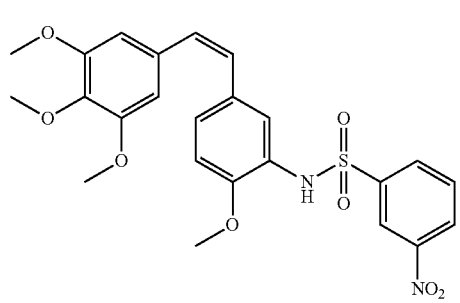
(12o)
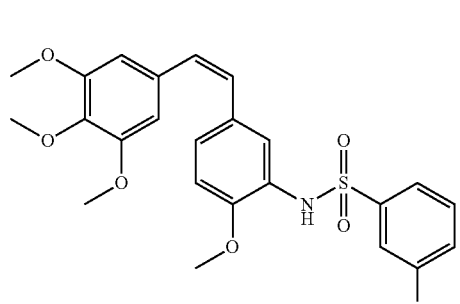
(12p)
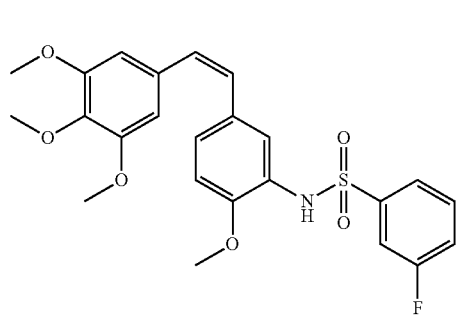
(12q)
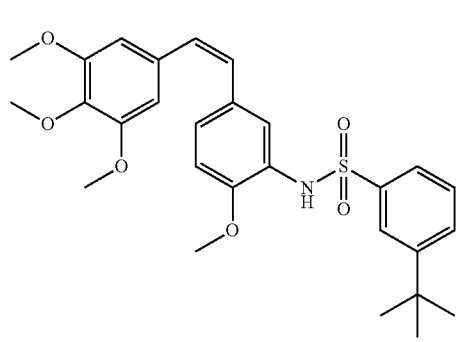
(12r)
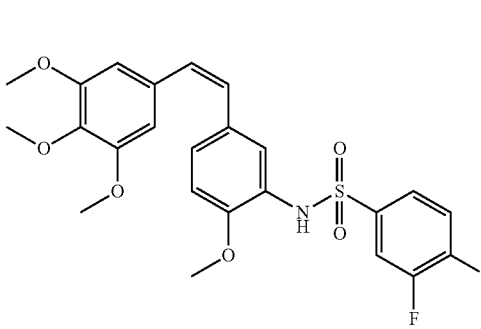

(12s)
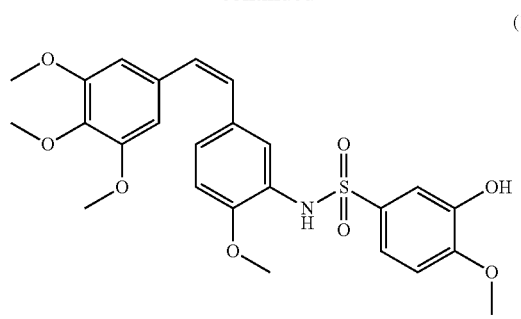
(12t)
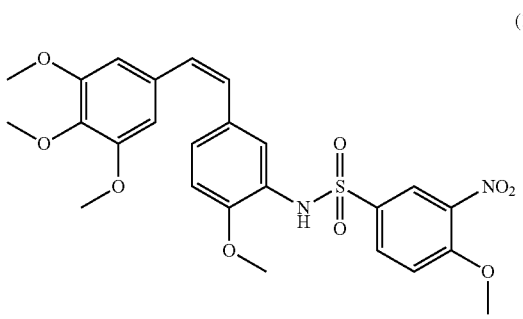
(12u)
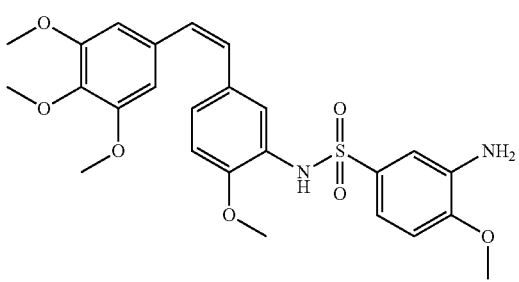
(12v)
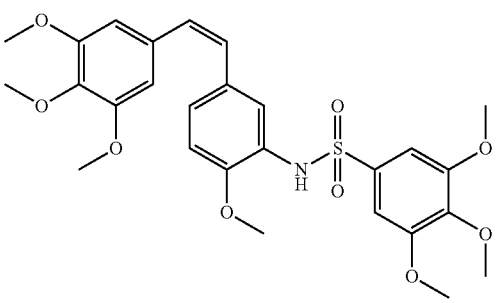
(12w)
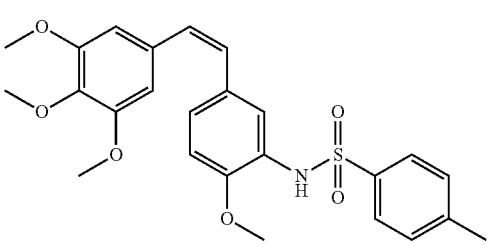
(12x)
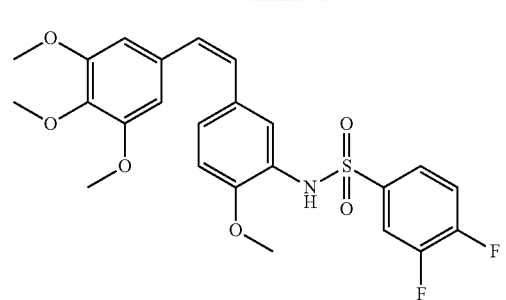
(12y)
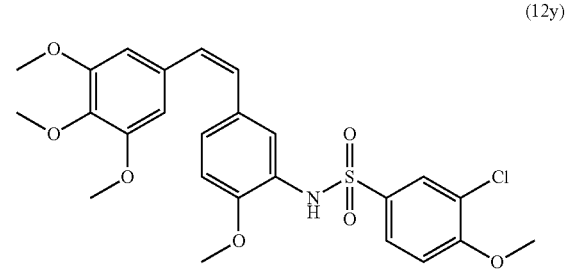
(13a)
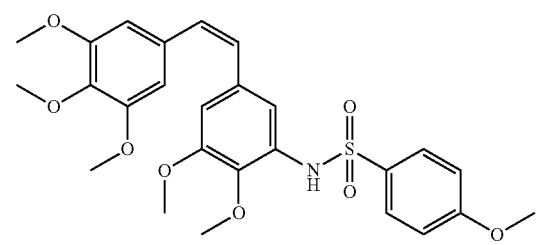
(13b)
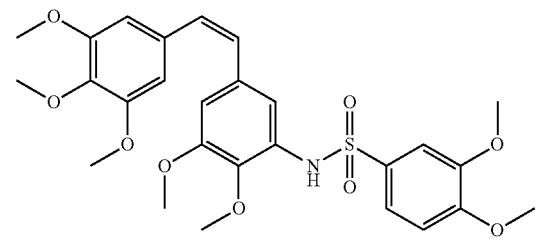
(13c)
(13d)
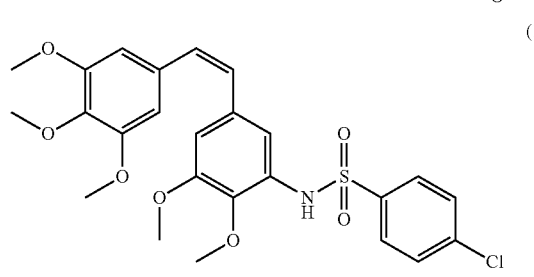

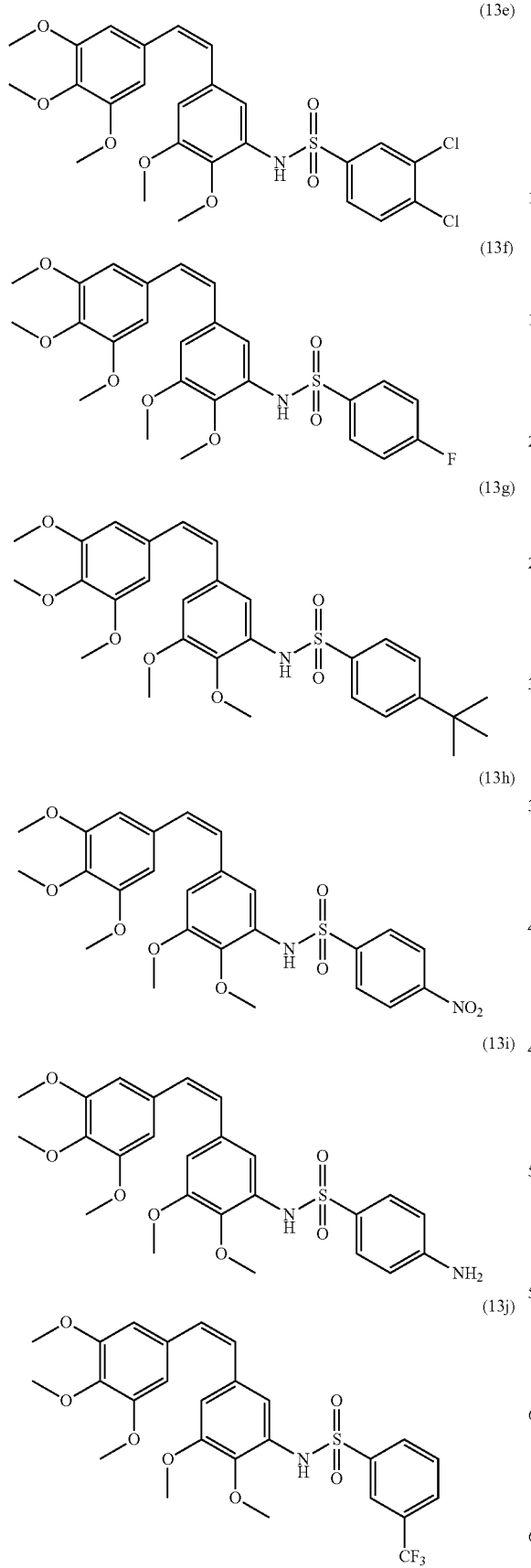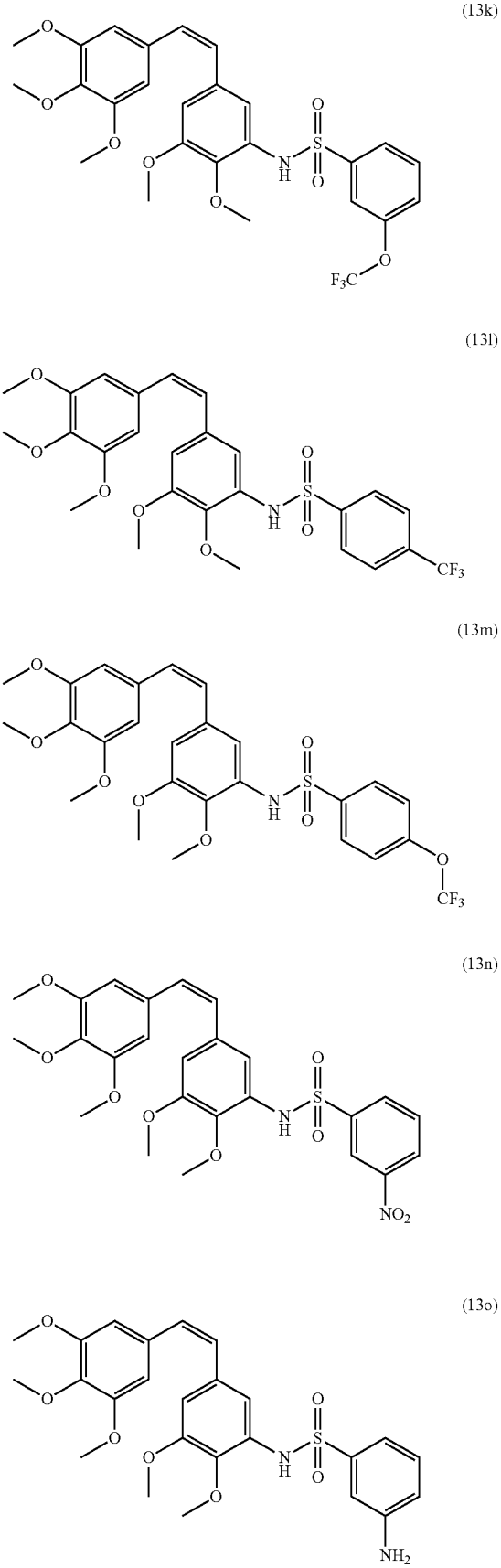

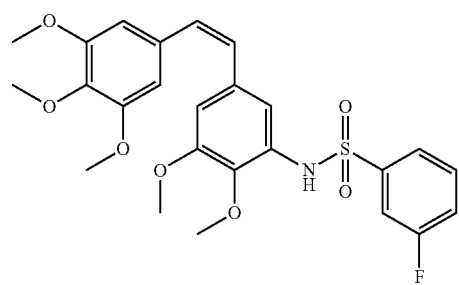
(13p)
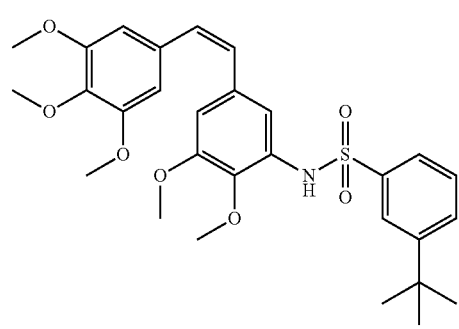
(13q)
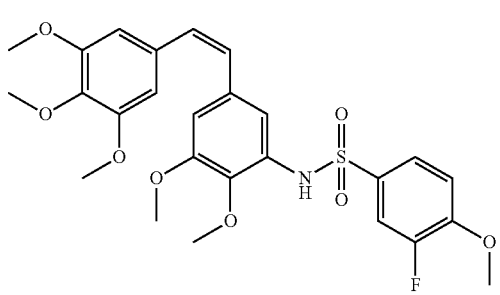
(13r)
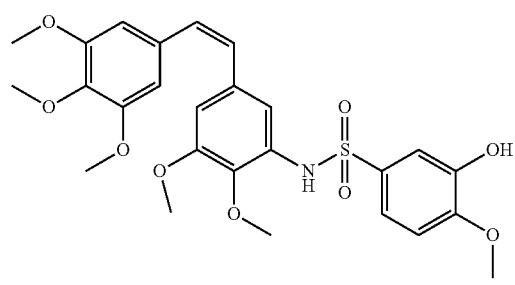
(13s)
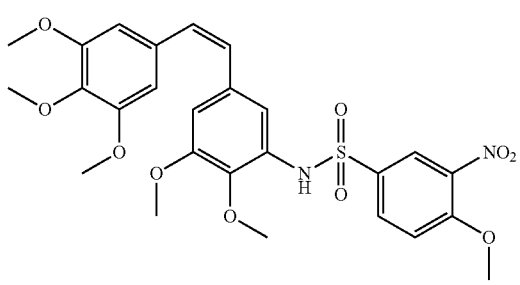
(13t)
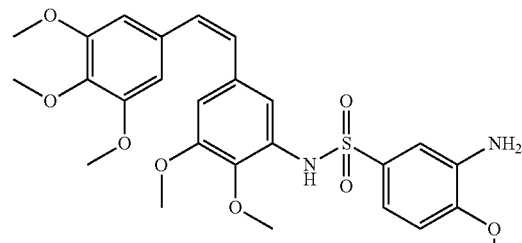
(13u)
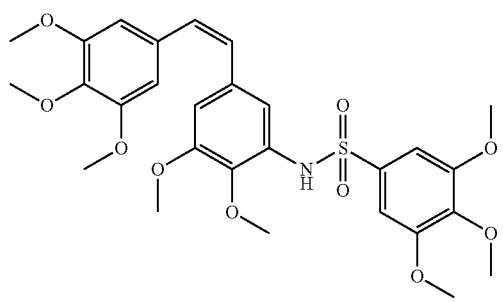
(13v)
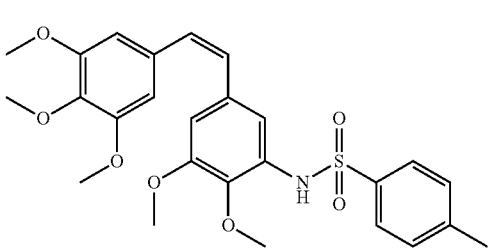
(13w)
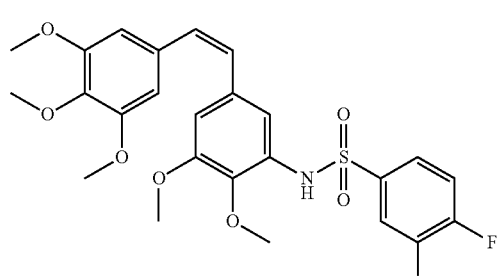
(13x)
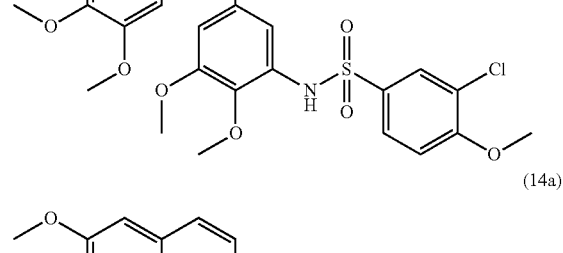
(13y)
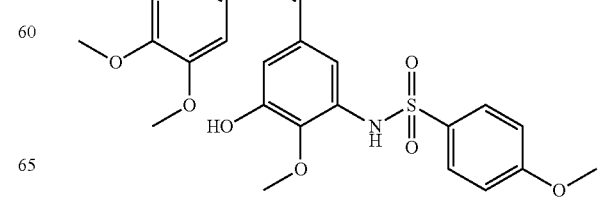
(14a)

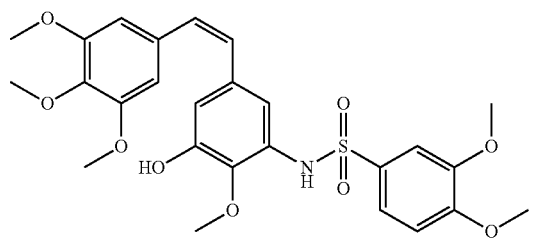
(14b)
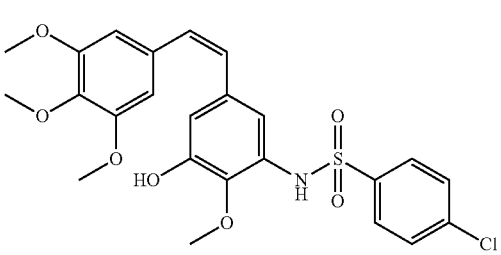
(14c)
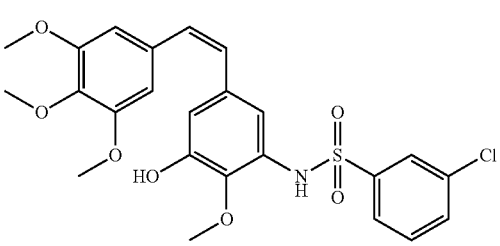
(14d)
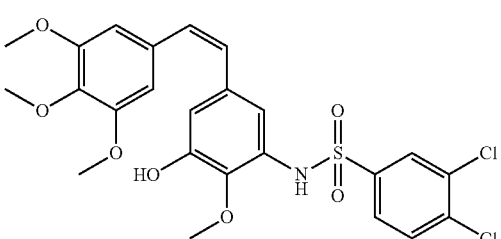
(14e)
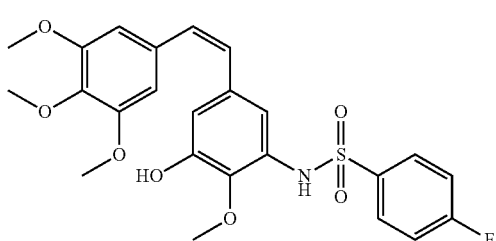
(14f)
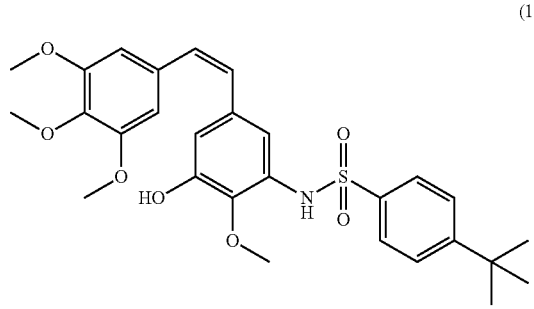
(14g)
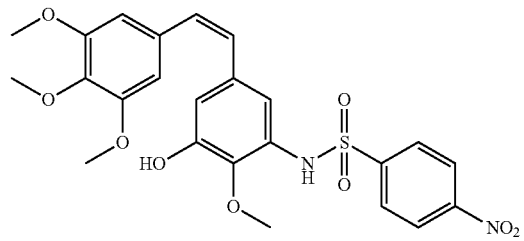
(14h)
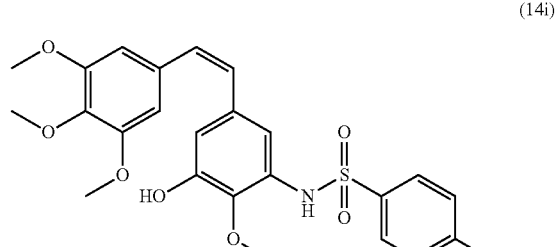
(14i)
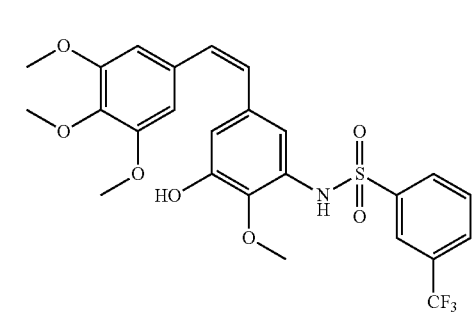
(14j)
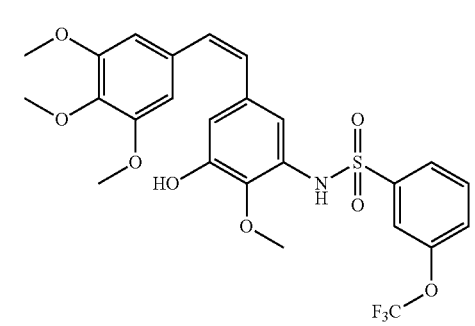
(14k)
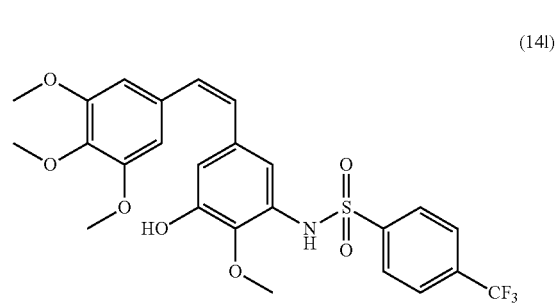
(14l)

(14m)
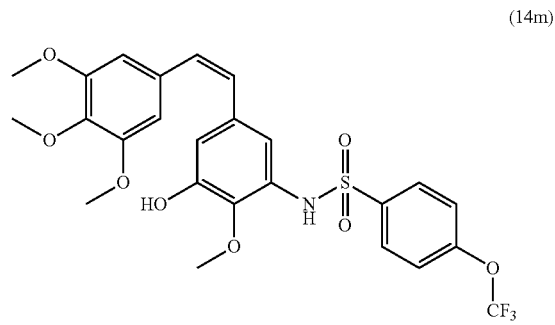
(14n)
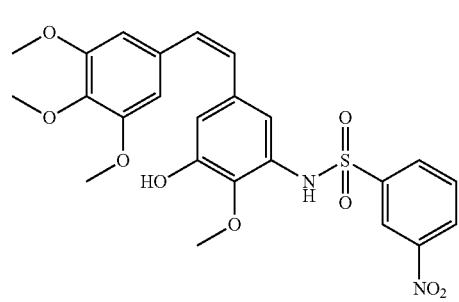
(14o)
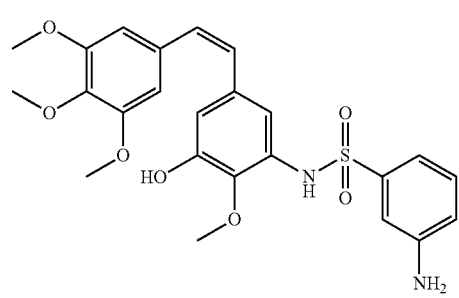
(14p)
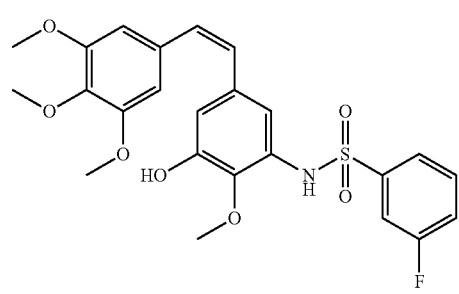
(14q)
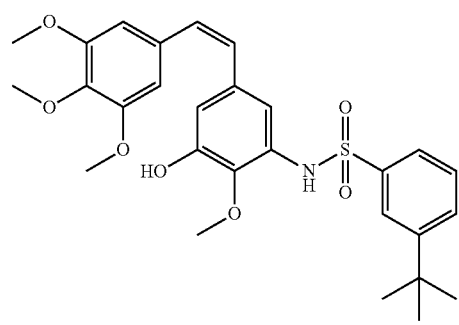
(14r)
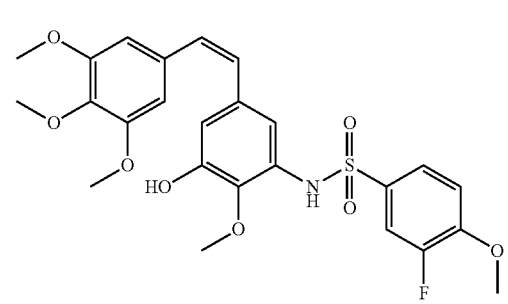
(14s)
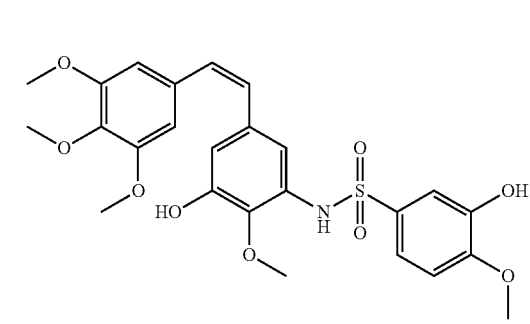
(14t)
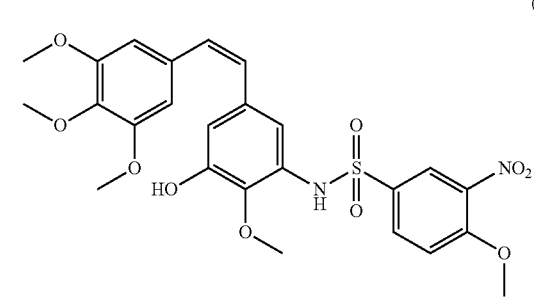
(14u)
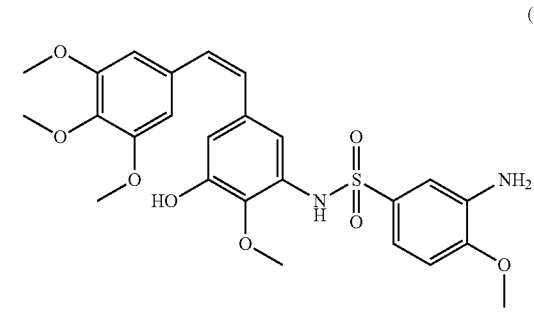
(14v)
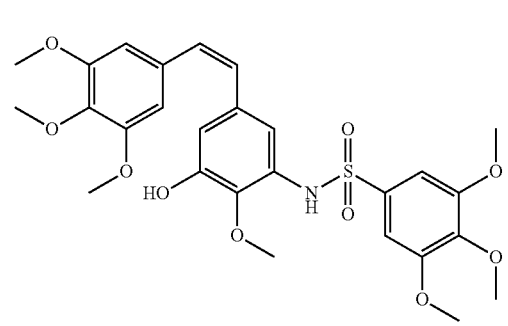

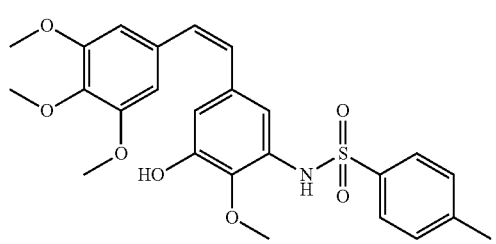
(14w)
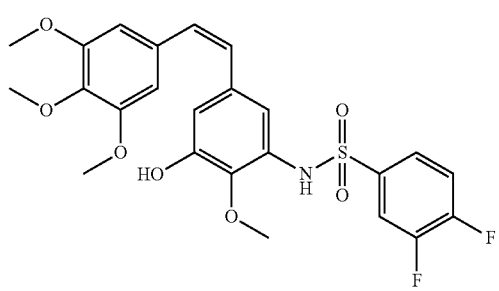
(14x)
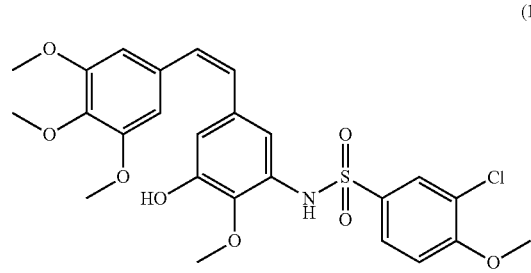
(14y)
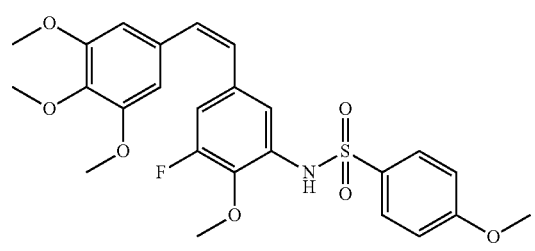
(15a)
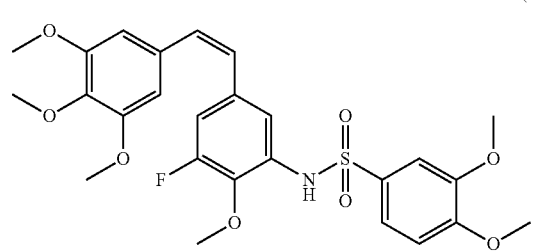
(15b)
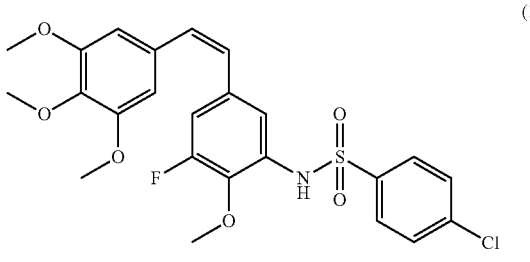
(15c)
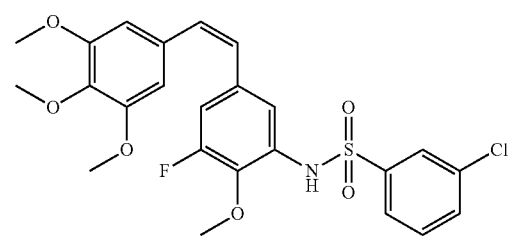
(15d)
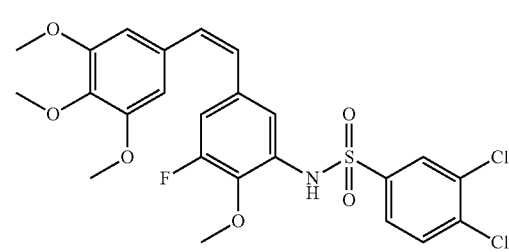
(15e)
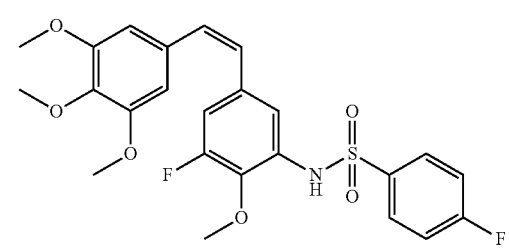
(15f)
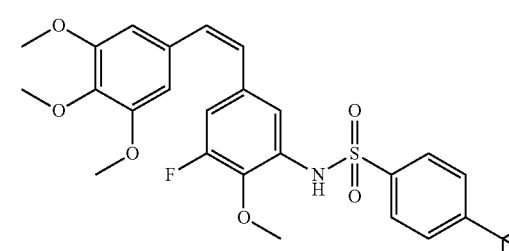
(15g)
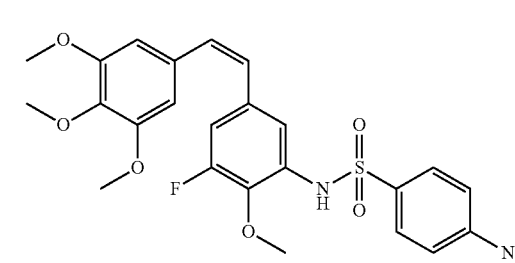
(15h)
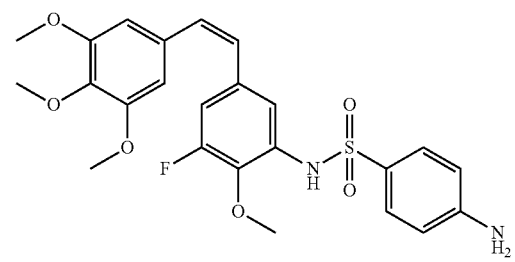
(15i)

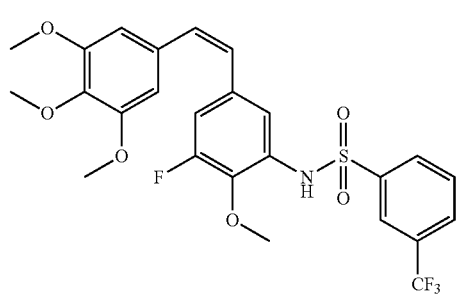
(15j)
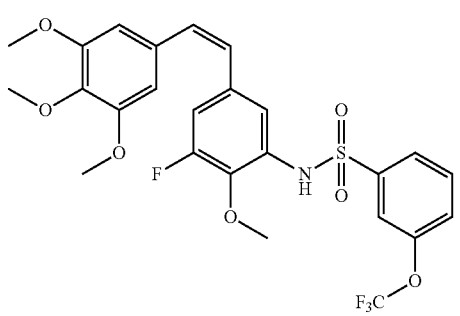
(15k)
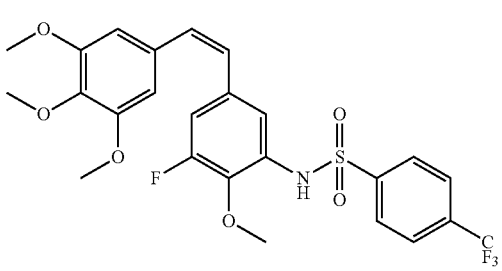
(15l)
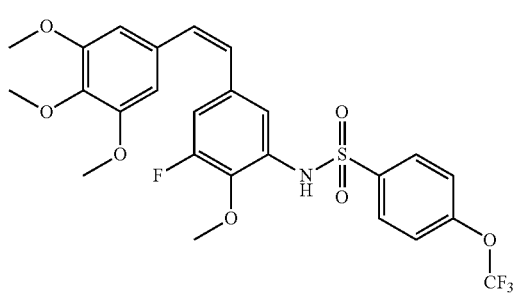
(15m)
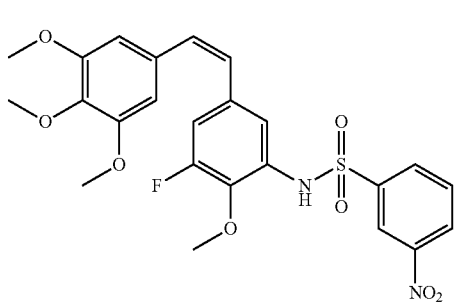
(15n)
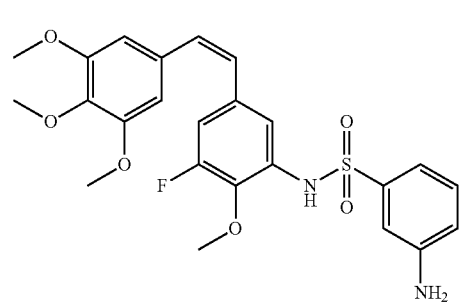
(15o)
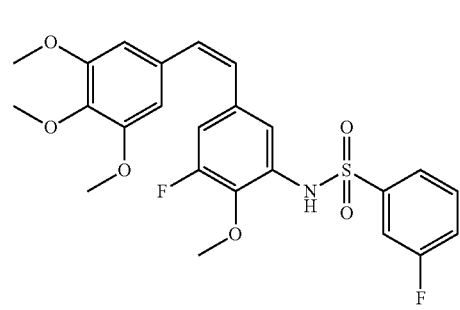
(15p)
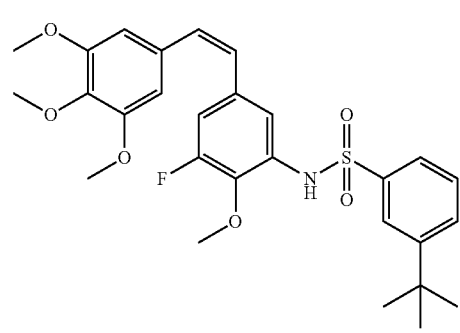
(15q)
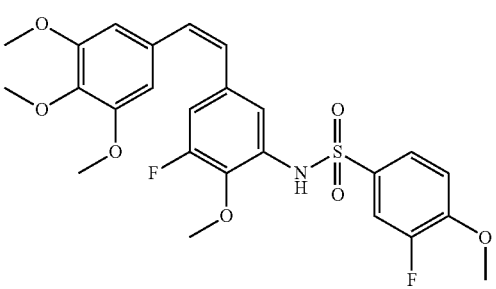
(15r)
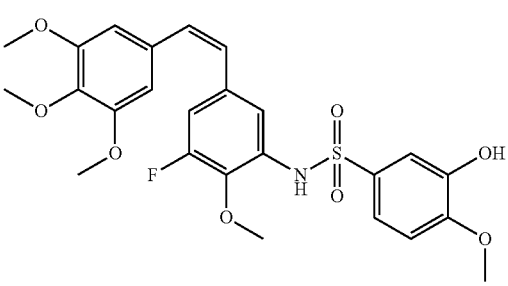
(15s)

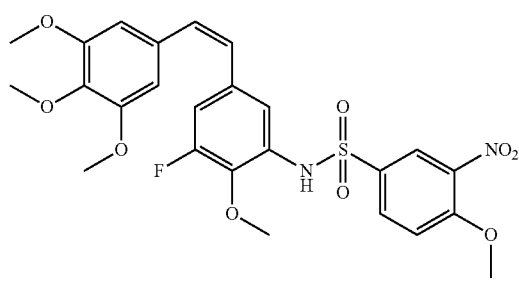
(15t)
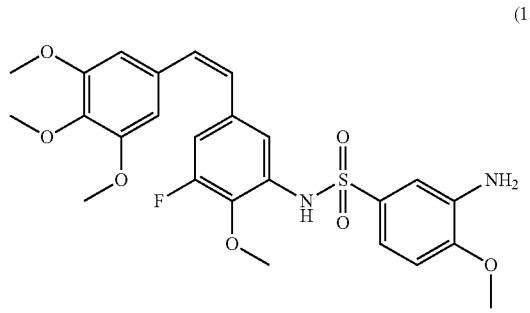
(15u)
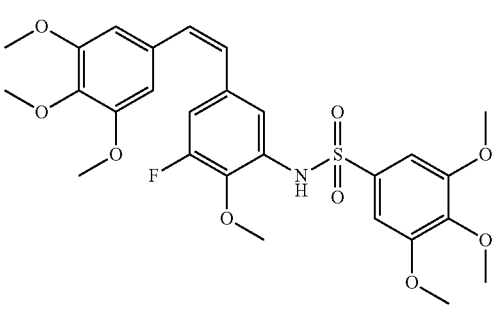
(15v)
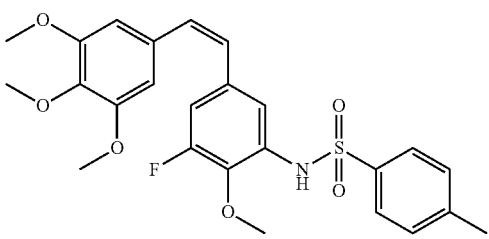
(15w)
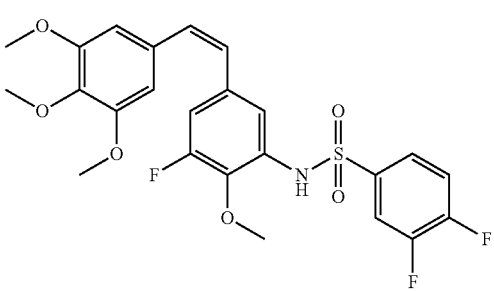
(15x)
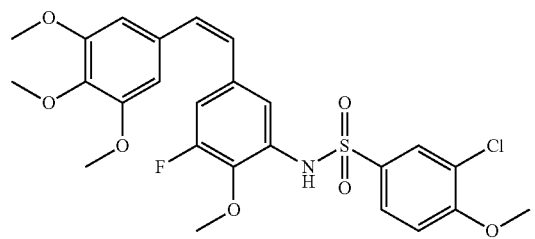
(15y)
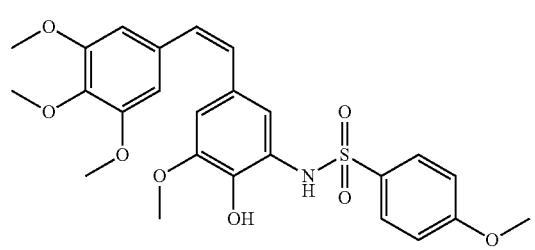
(16a)
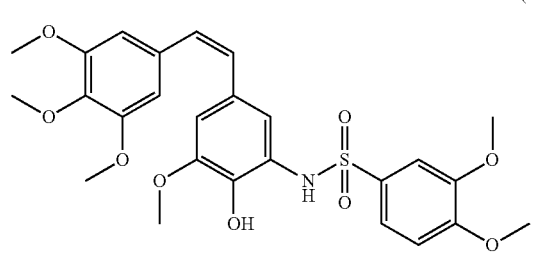
(16b)
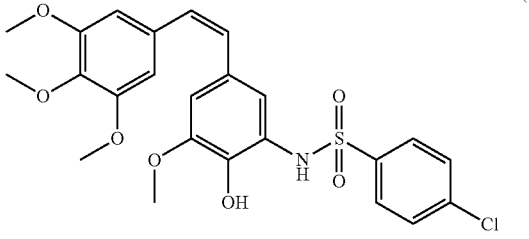
(16c)
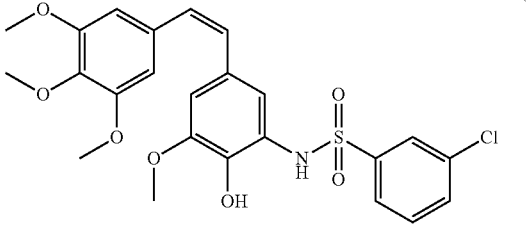
(16d)
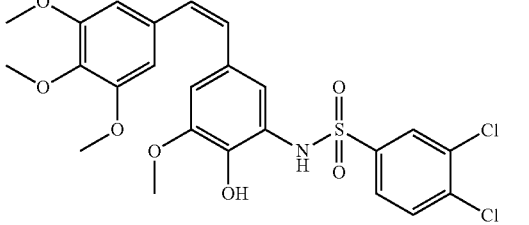
(16e)

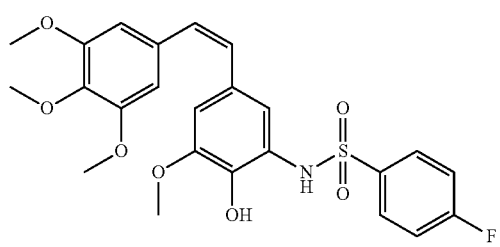
(16f)
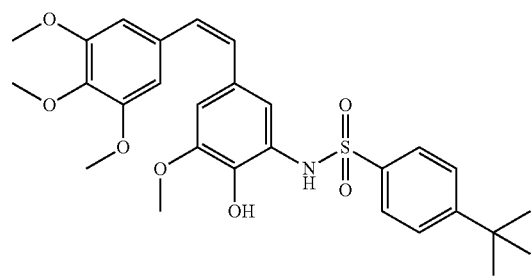
(16g)
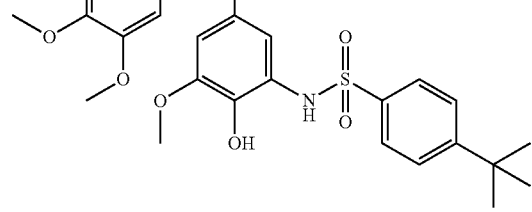
(16h)
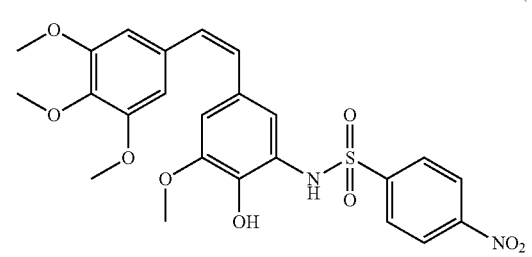
(16i)
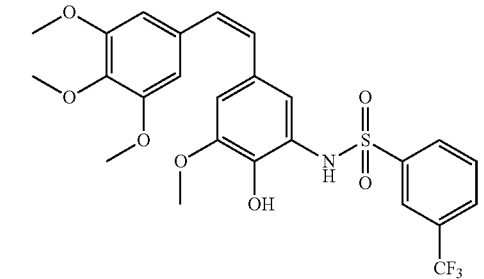
(16j)
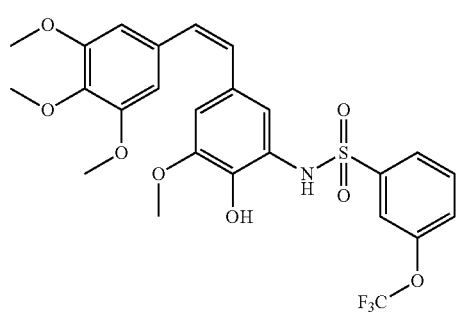
(16k)
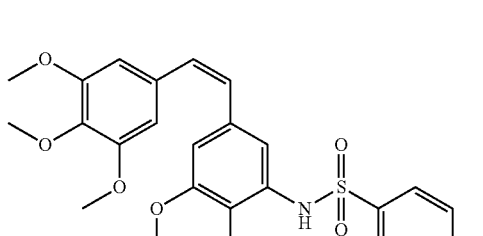
(16l)
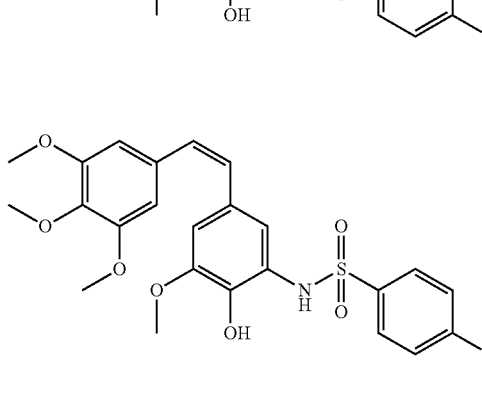
(16m)
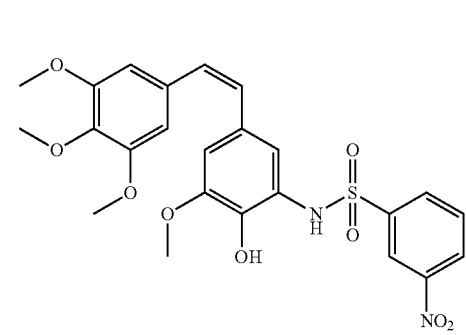
(16n)
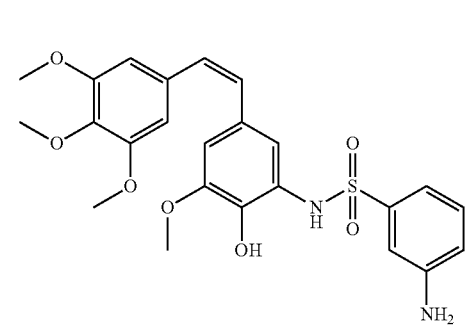
(16o)

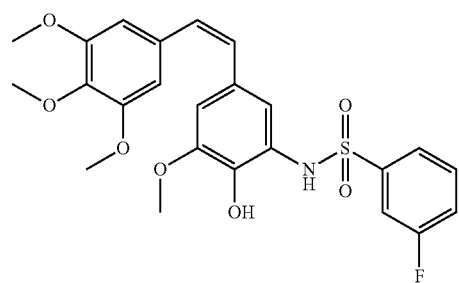
(16p)
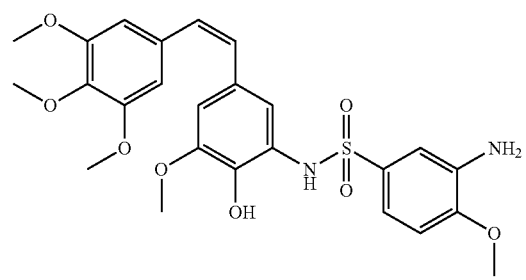
(16u)
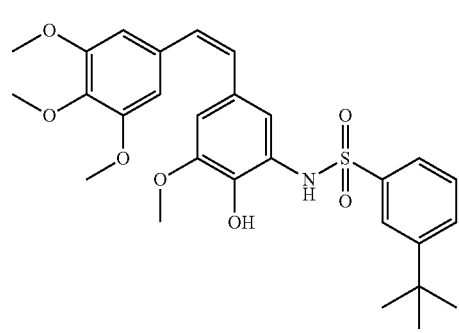
(16q)
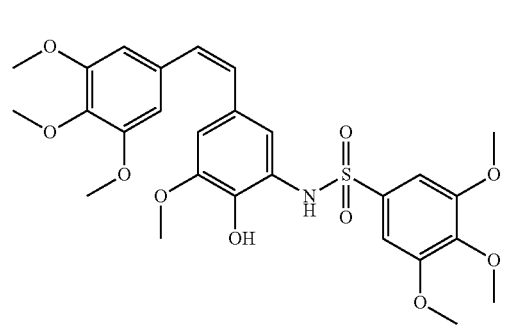
(16v)
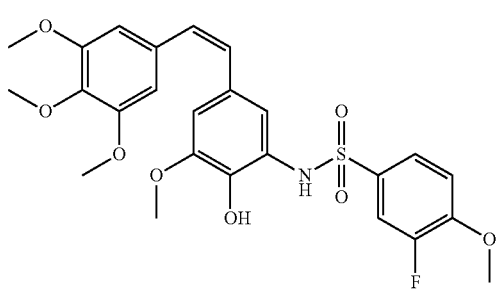
(16r)
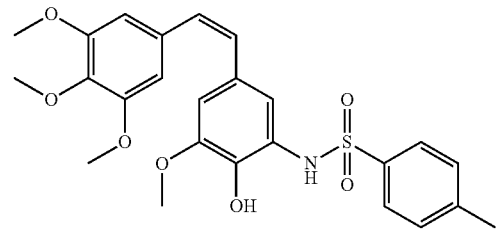
(16w)
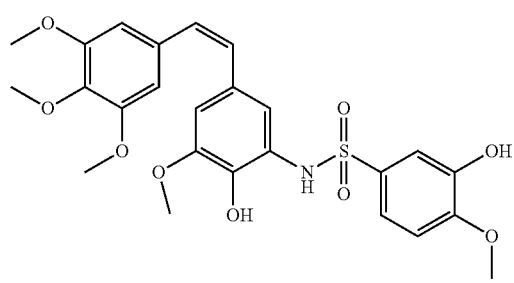
(16s)
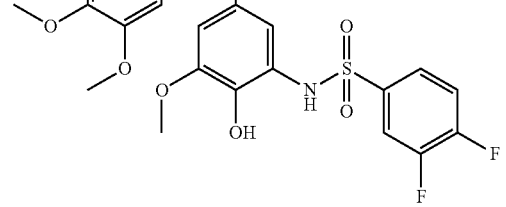
(16x)
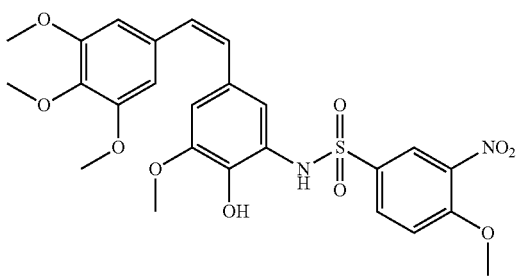
(16t)
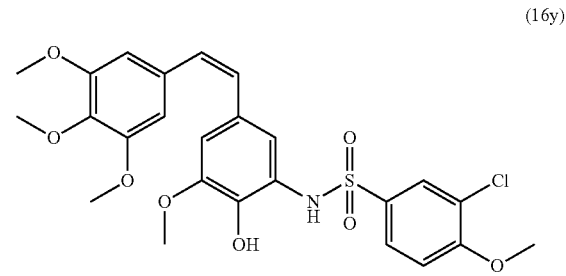
(16y)

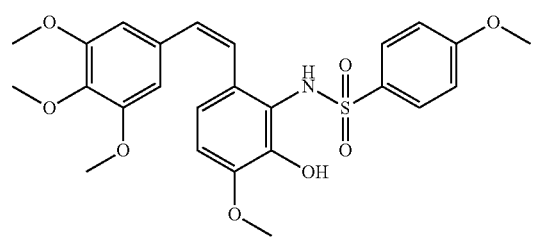 (17a)
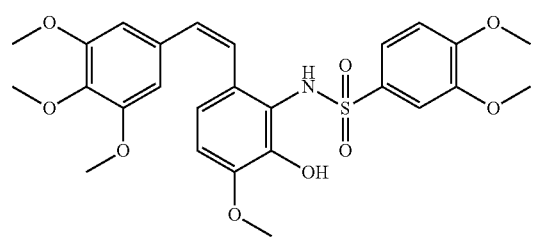 (17b)
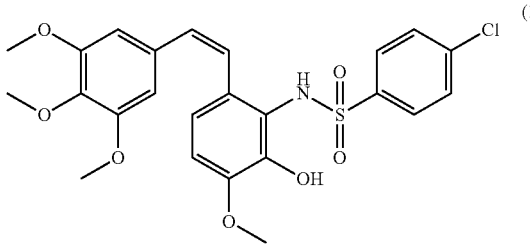 (17c)
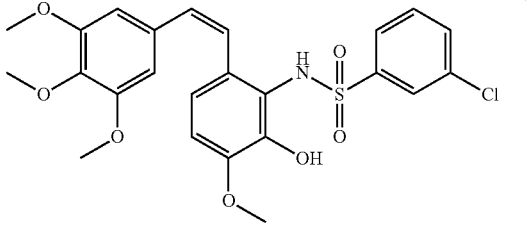 (17d)
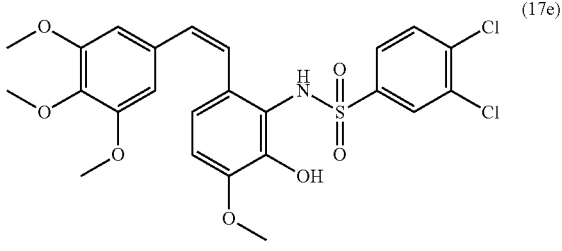 (17e)
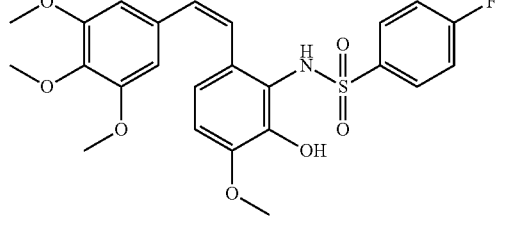 (17f)
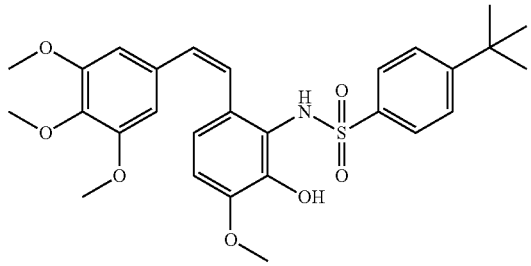 (17g)
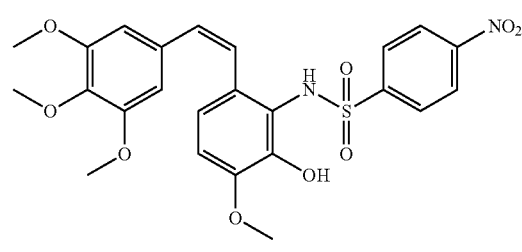 (17h)
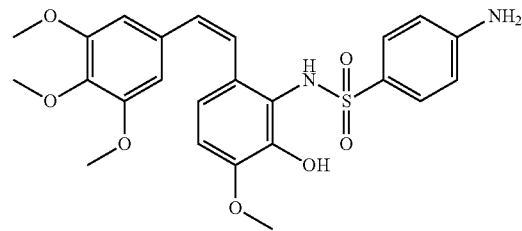 (17i)
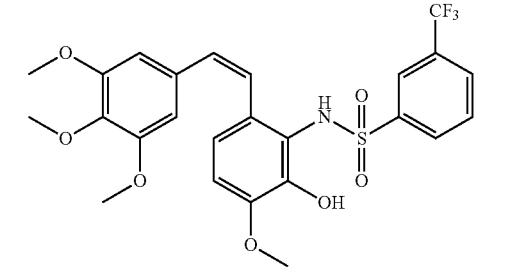 (17j)
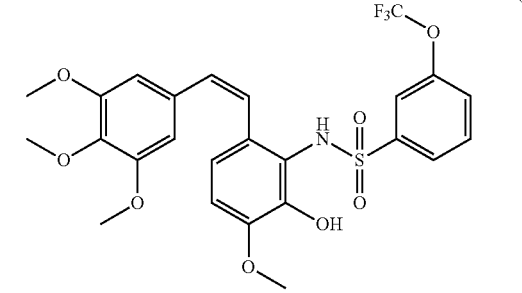 (17k)
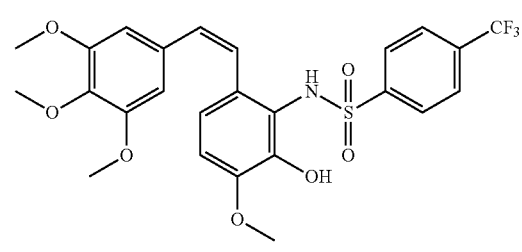 (17l)

(17m)
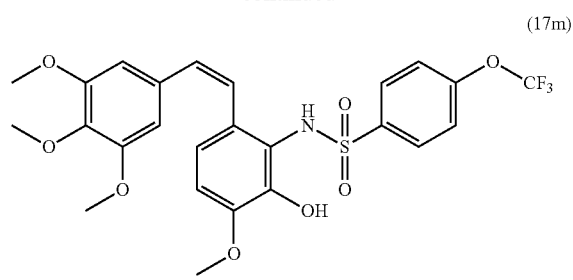
(17n)
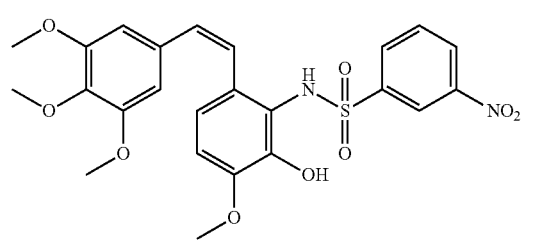
(17o)
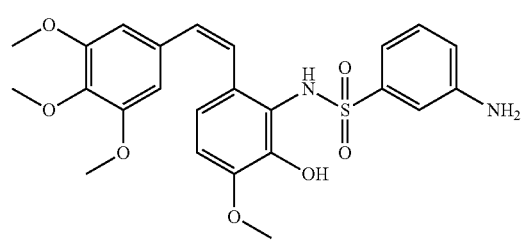
(17p)
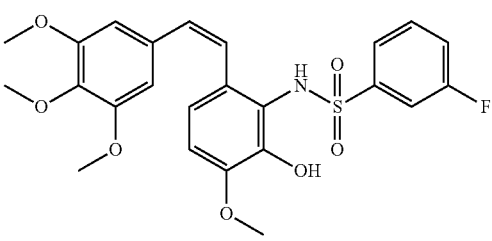
(17q)
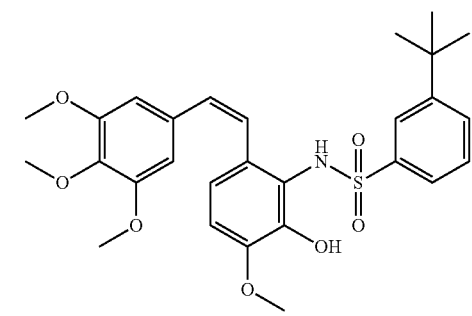
(17r)
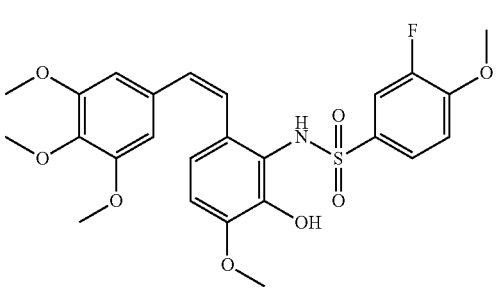
(17s)
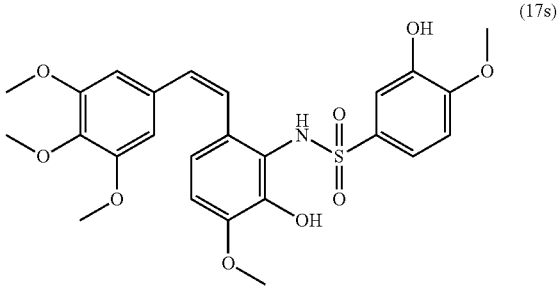
(17t)
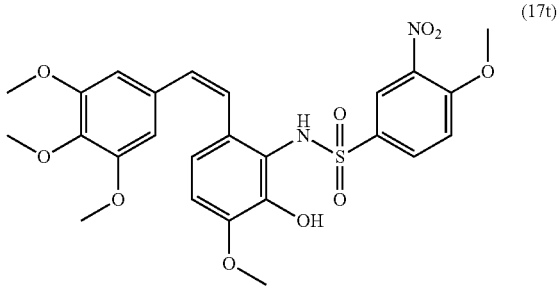
(17u)
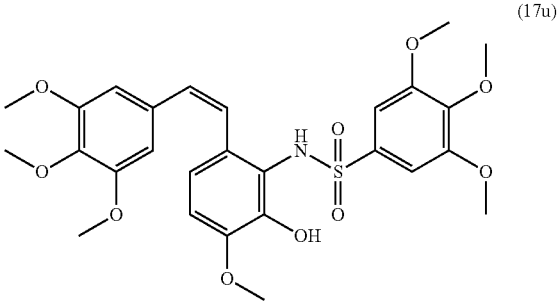
(17v)
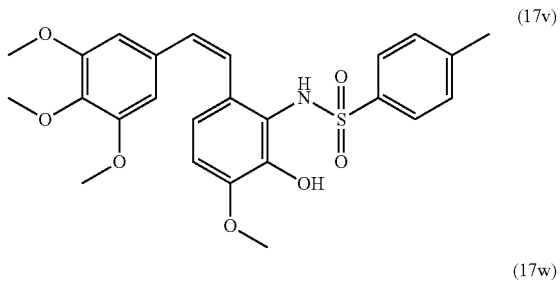
(17w)
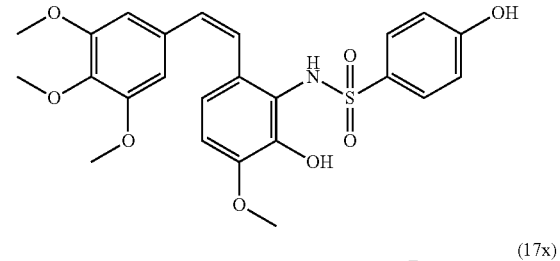
(17x)
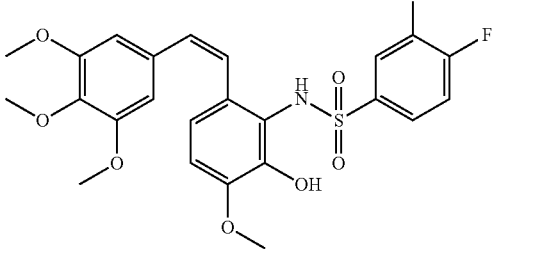

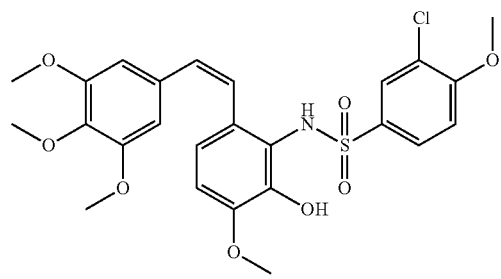
(17y)
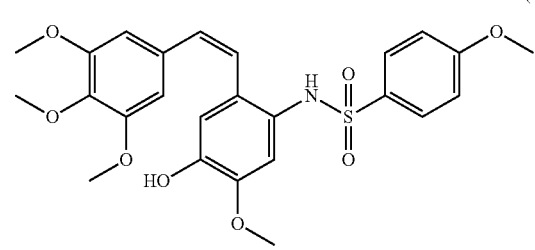
(18a)
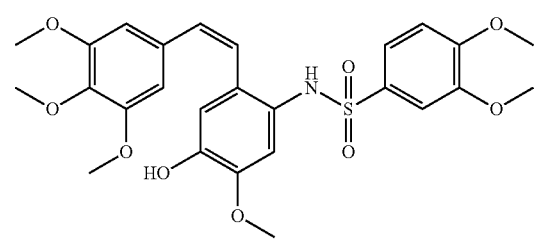
(18b)
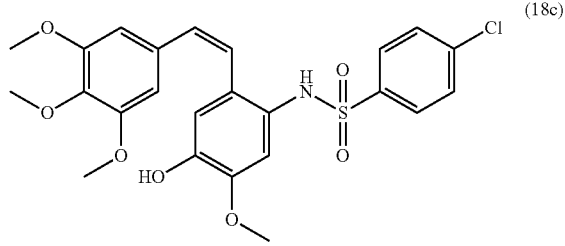
(18c)
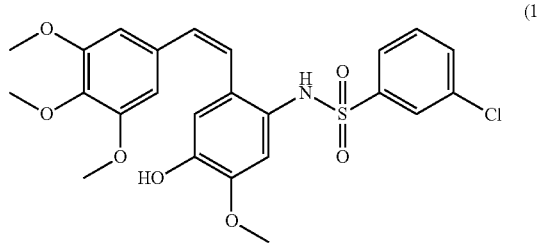
(18d)
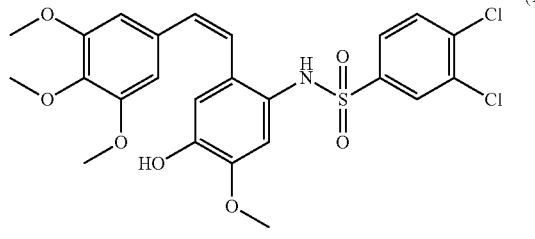
(18e)
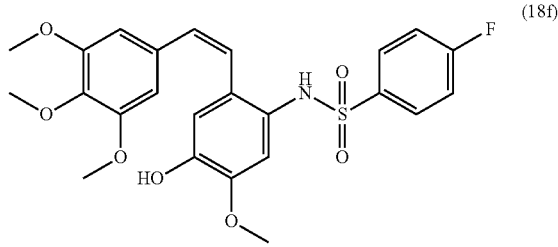
(18f)
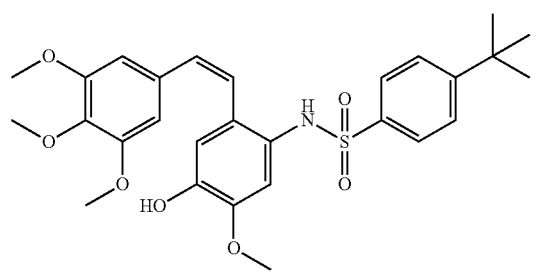
(18g)
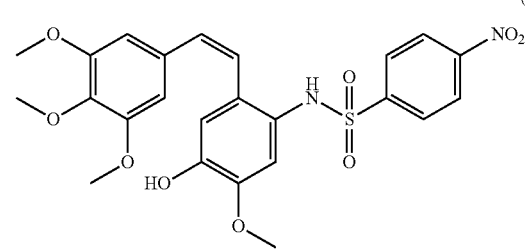
(18h)
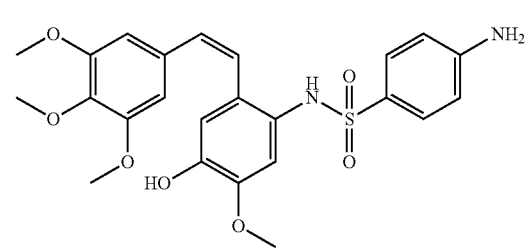
(18i)
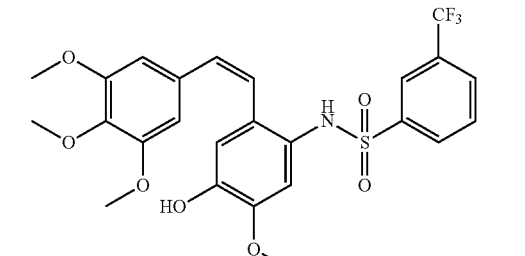
(18j)
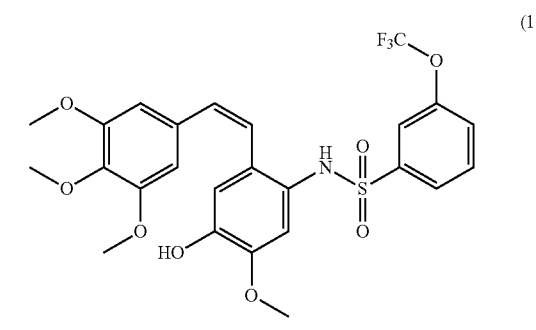
(18k)

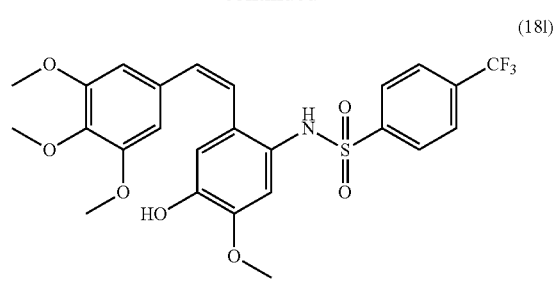
(18l)
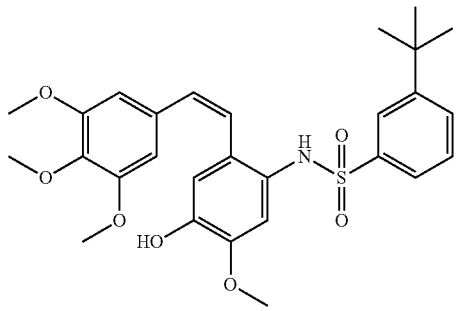
(18q)
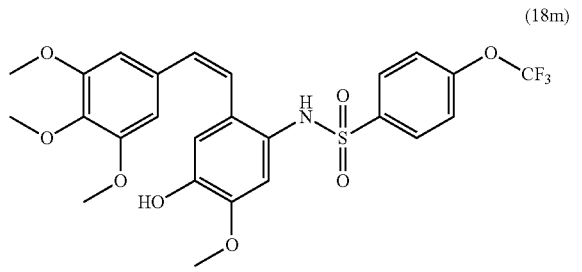
(18m)
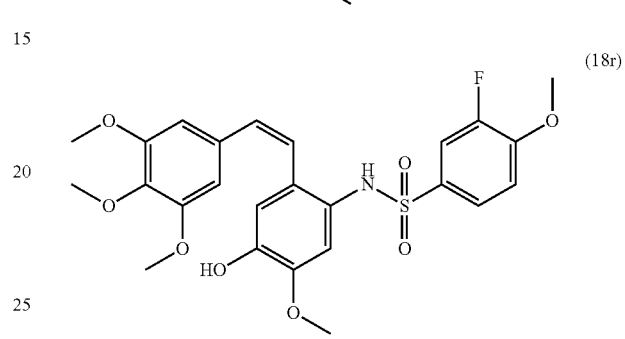
(18r)
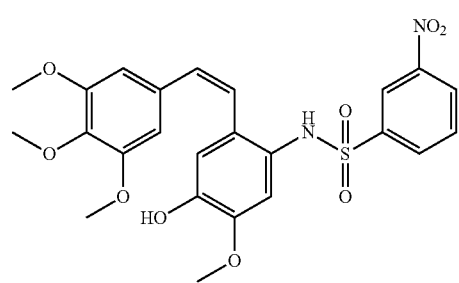
(18n)
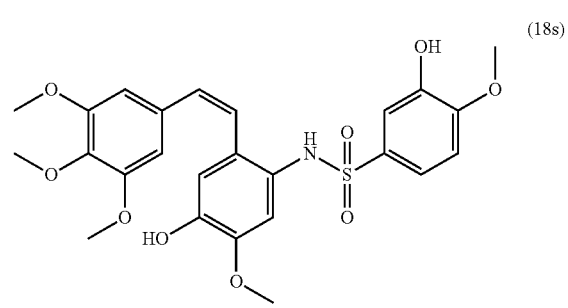
(18s)
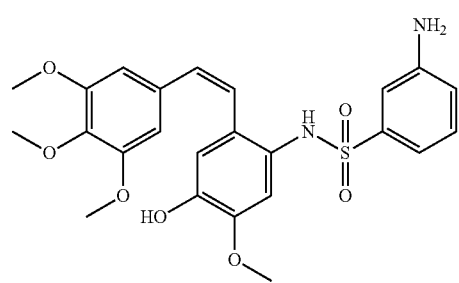
(18o)
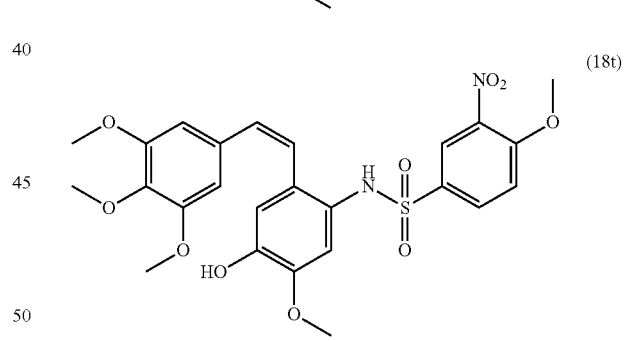
(18t)
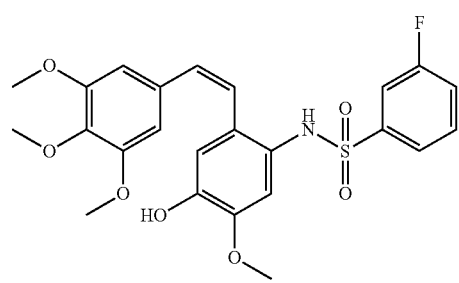
(18p)
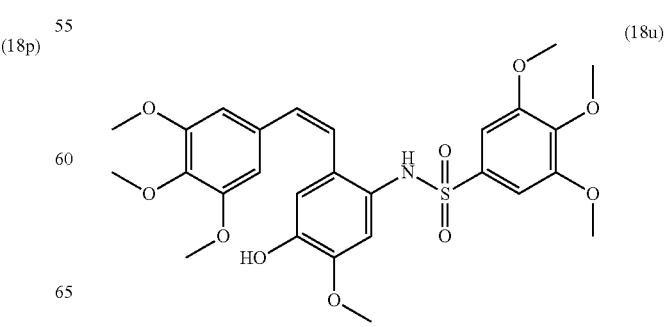
(18u)

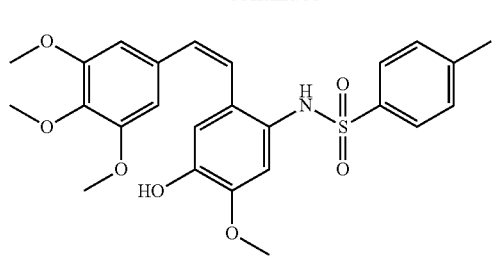
(18v)
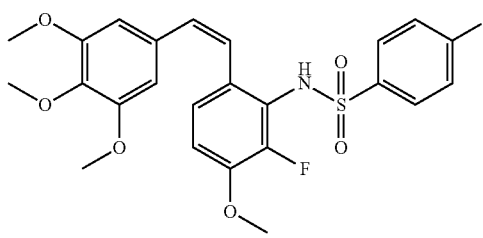
(19c)
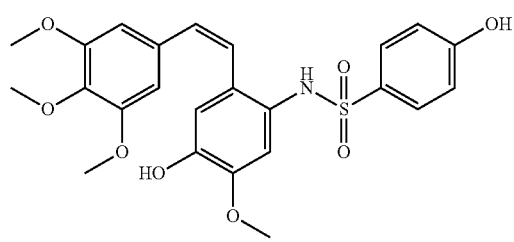
(18w)
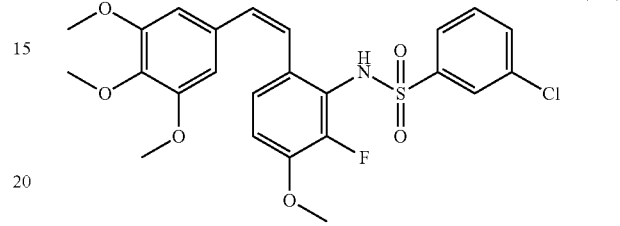
(19d)
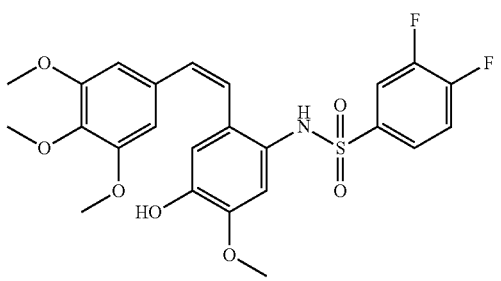
(18x)
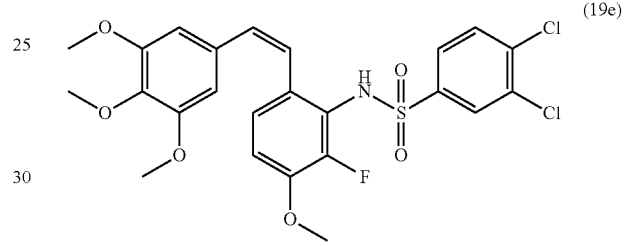
(19e)
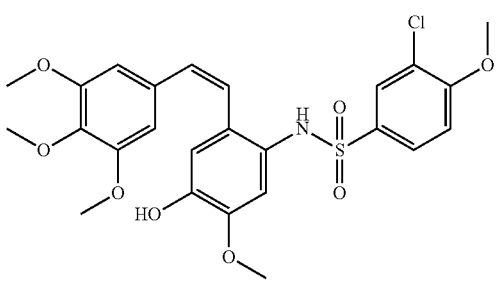
(18y)
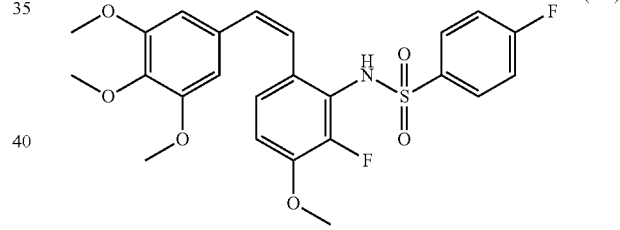
(19f)
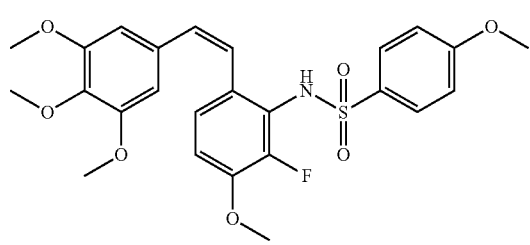
(19a)
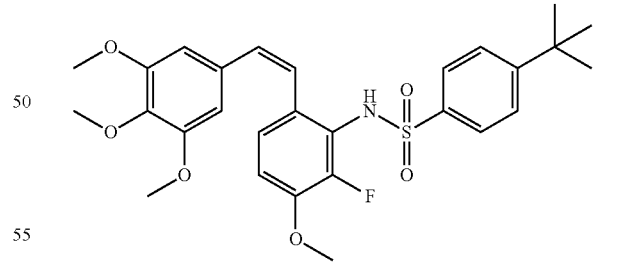
(19g)
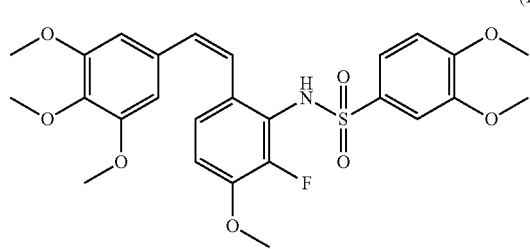
(19b)
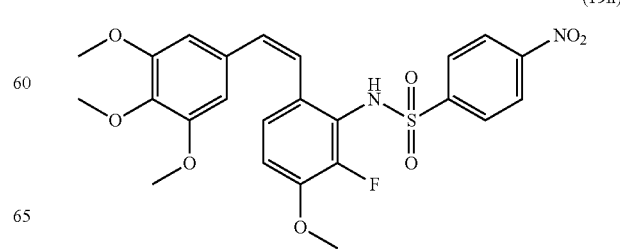
(19h)

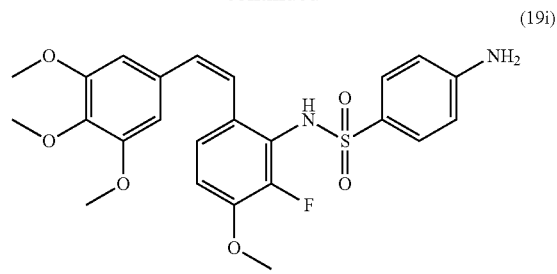
(19i)
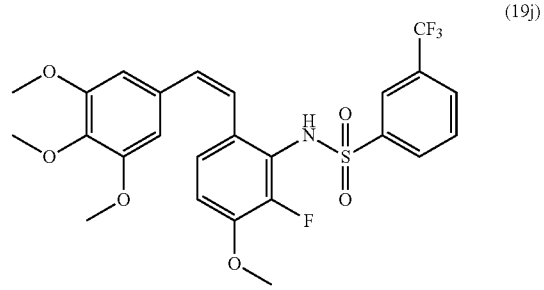
(19j)
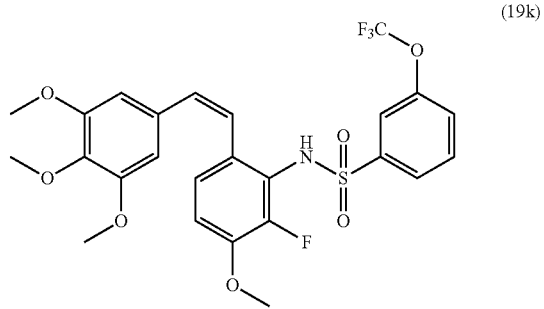
(19k)
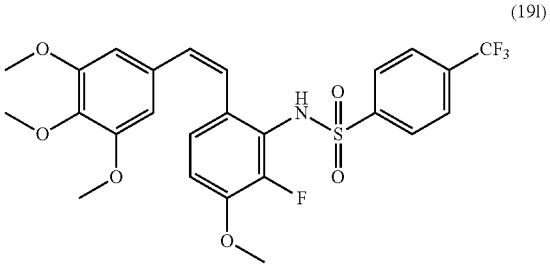
(19l)
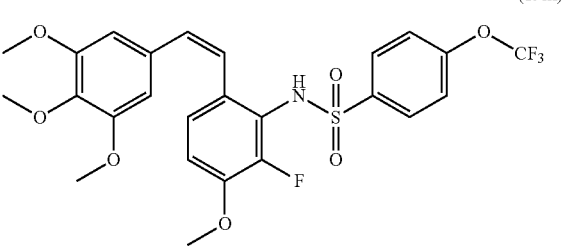
(19m)
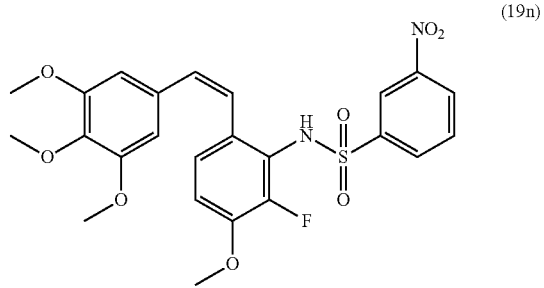
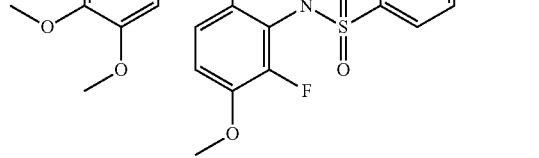
(19n)
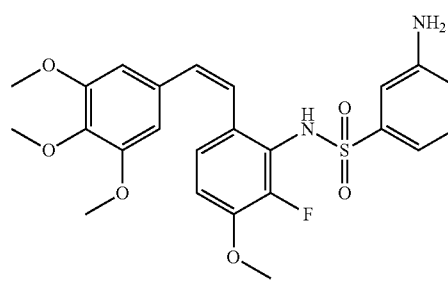
(19o)
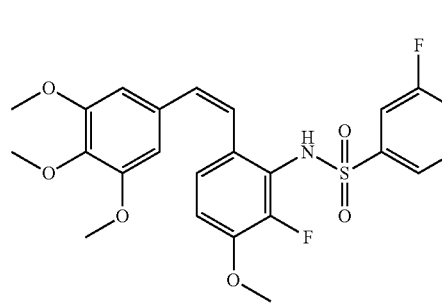
(19p)
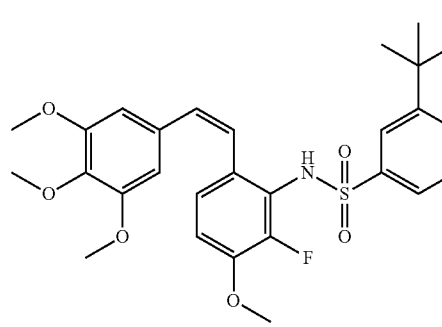
(19q)
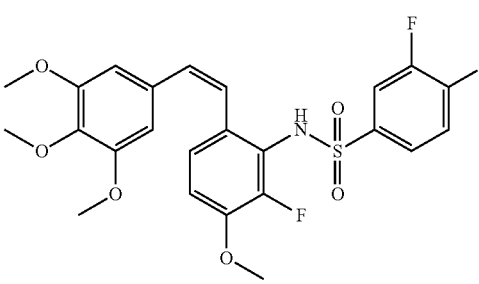
(19r)
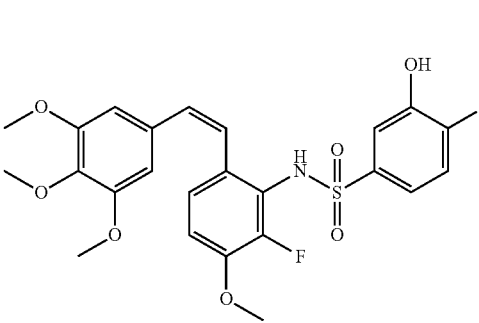
(19s)

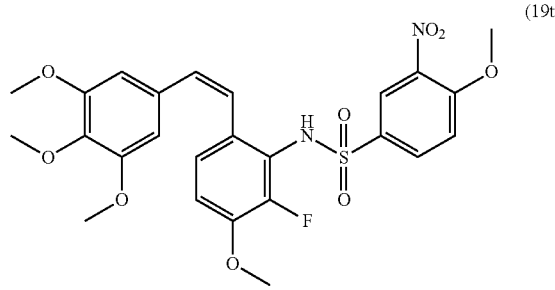 (19t)
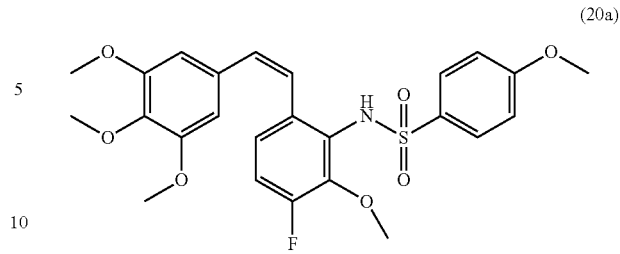 (20a)
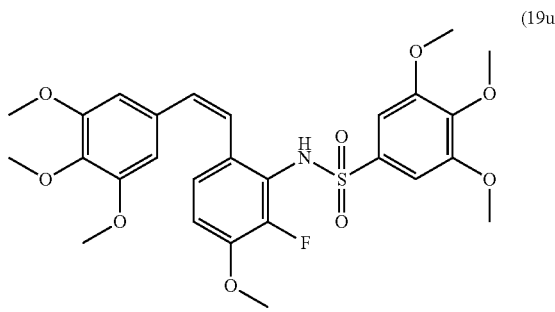 (19u)
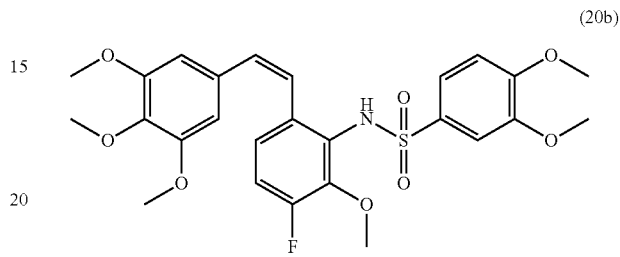 (20b)
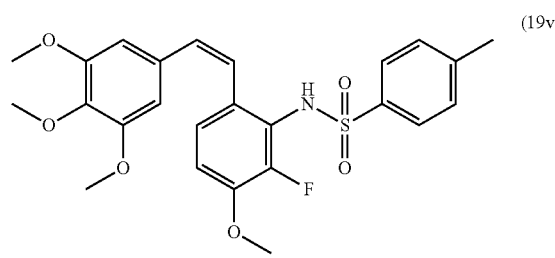 (19v)
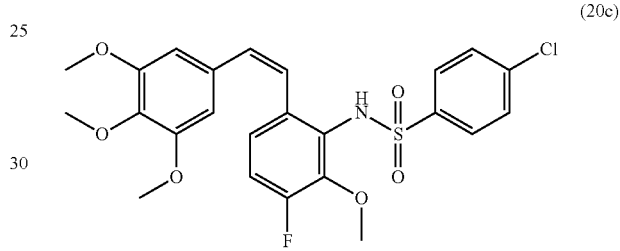 (20c)
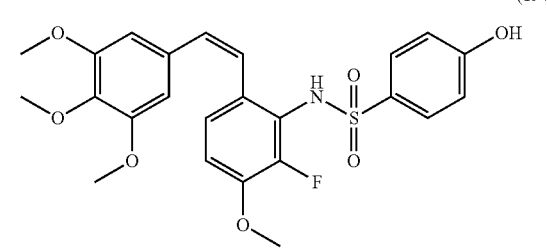 (19w)
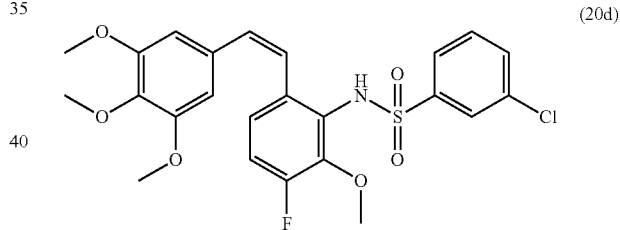 (20d)
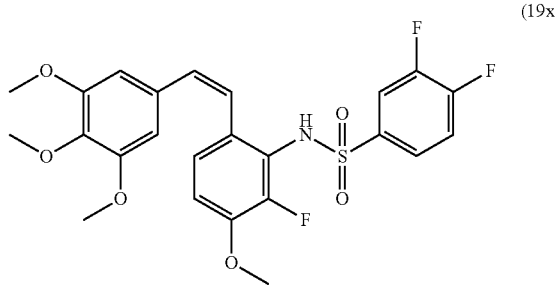 (19x)
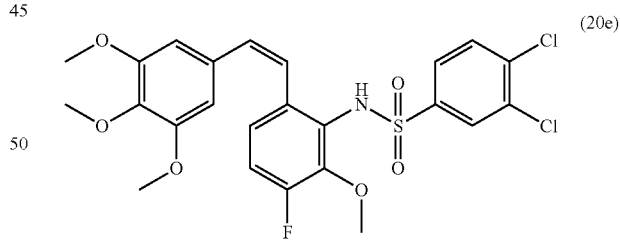 (20e)
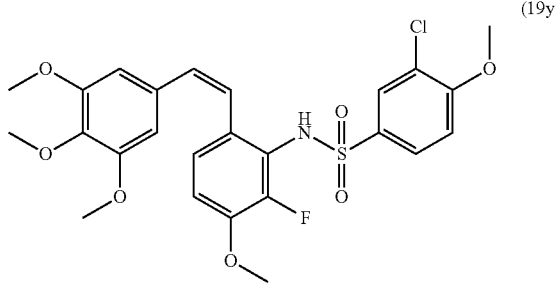 (19y)
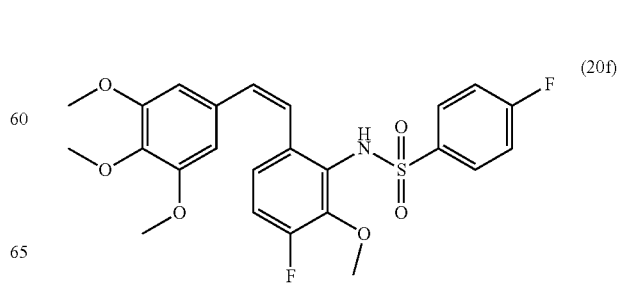 (20f)

(20g)
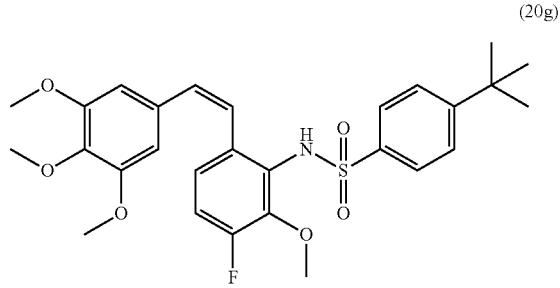
(20h)
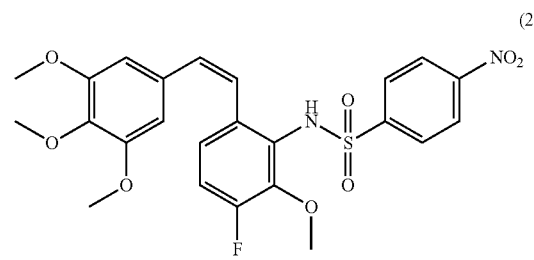
(20i)
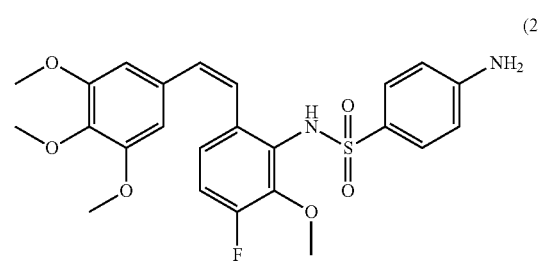
(20j)
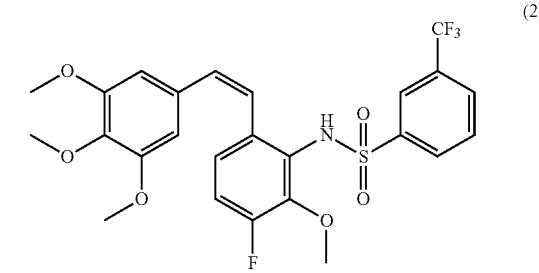
(20k)
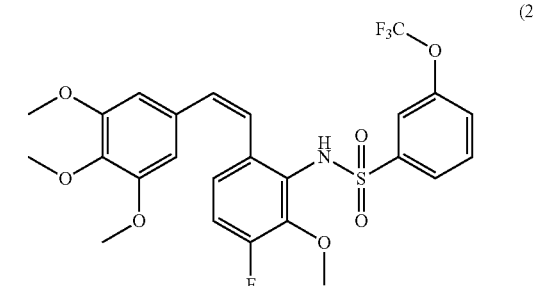
(20l)
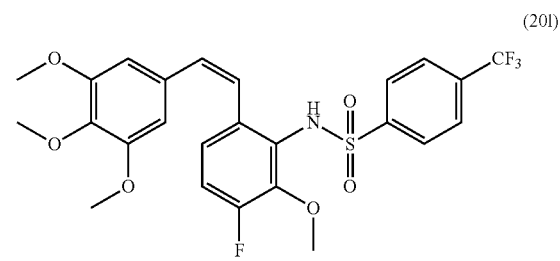
(20m)
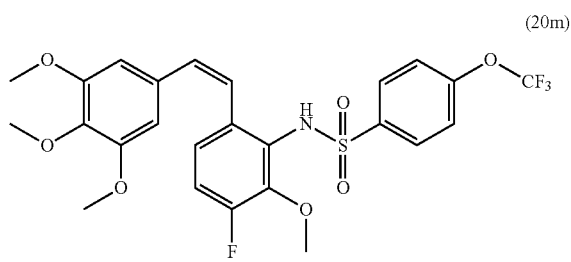
(20n)
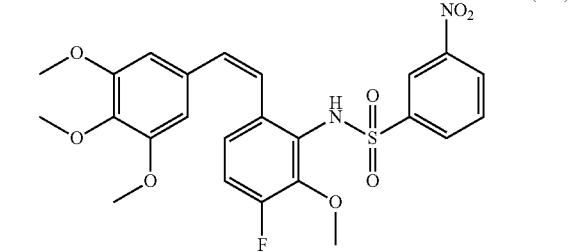
(20o)
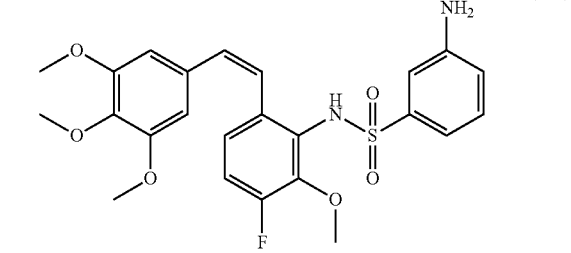
(20p)
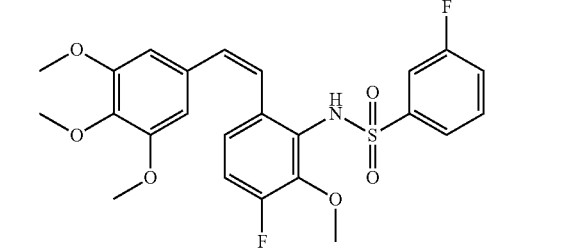
(20q)
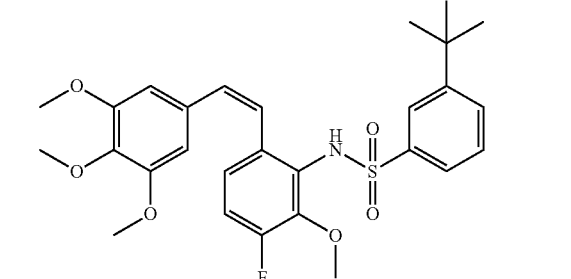
(20r)
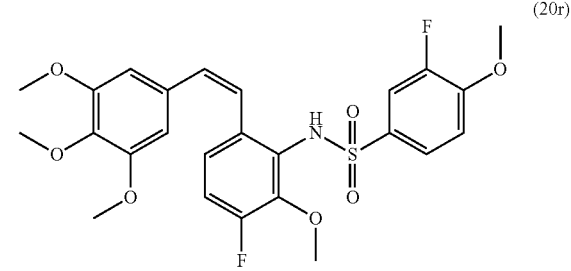

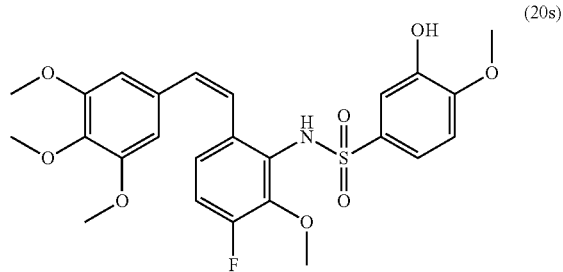
(20s)
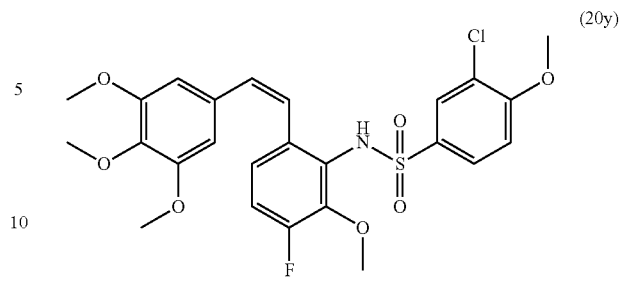
(20y)
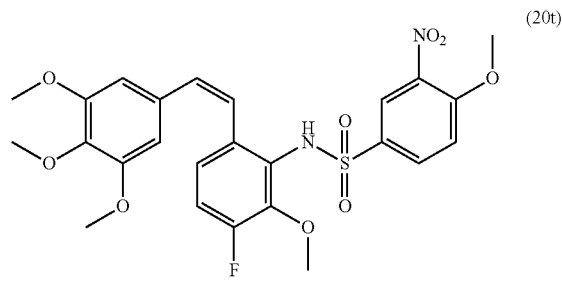
(20t)
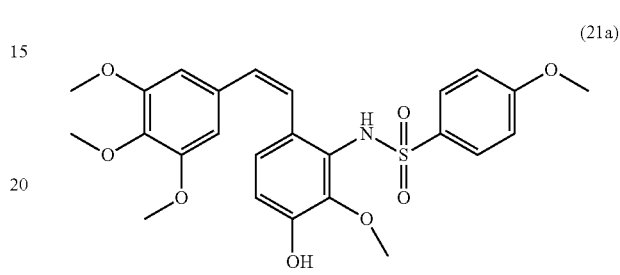
(21a)
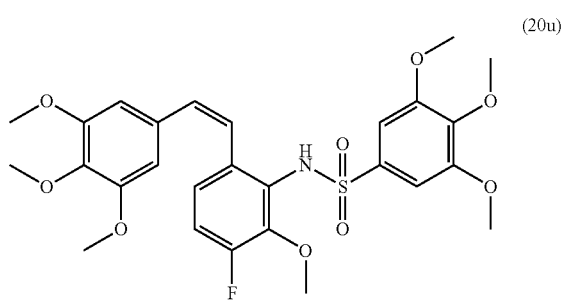
(20u)
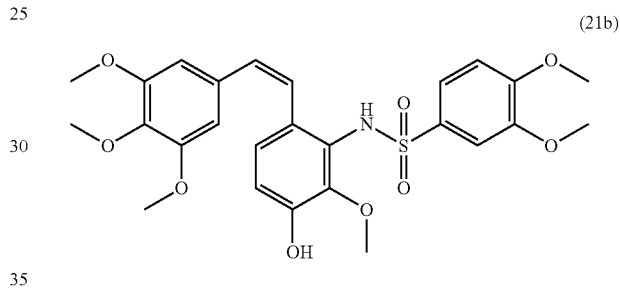
(21b)
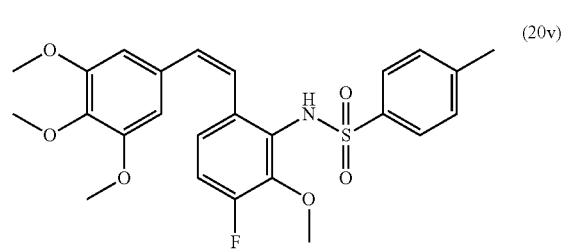
(20v)
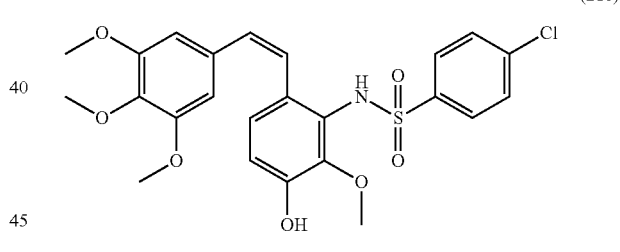
(21c)
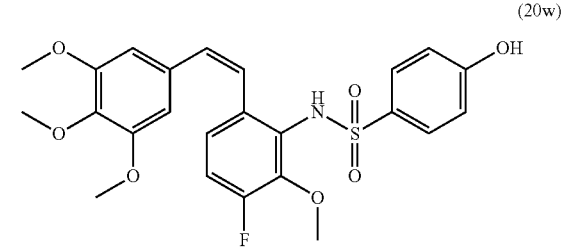
(20w)
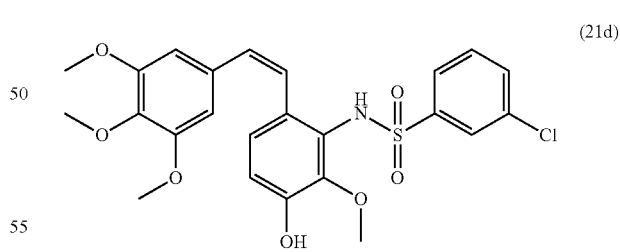
(21d)
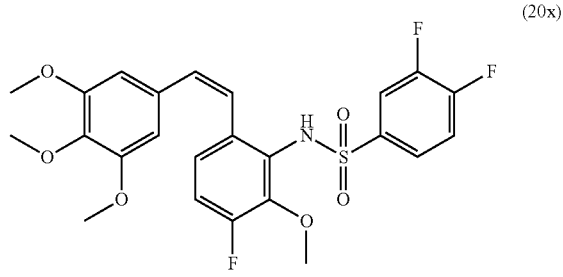
(20x)
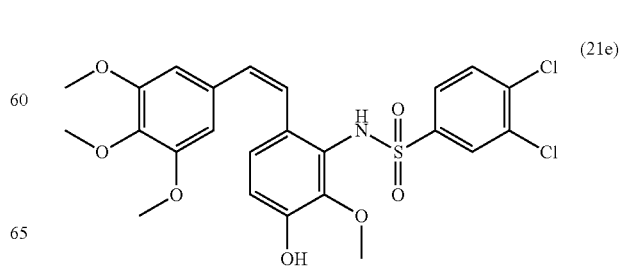
(21e)

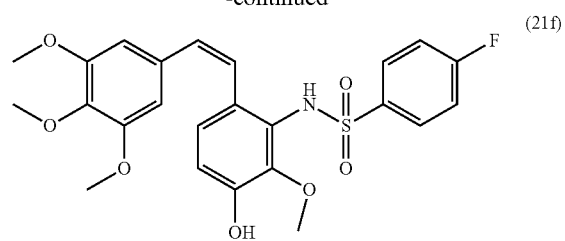
(21f)
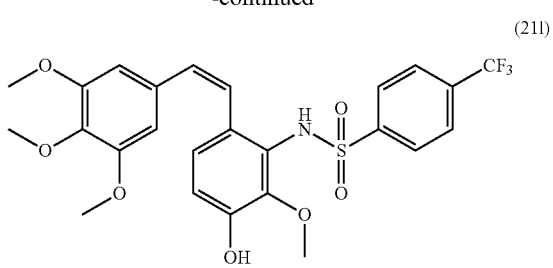
(21l)
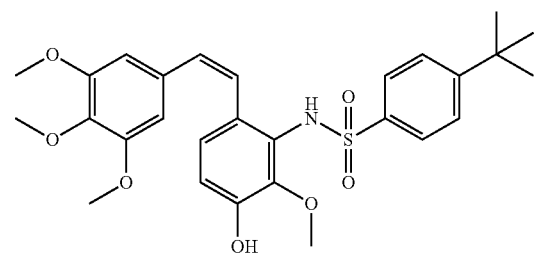
(21g)
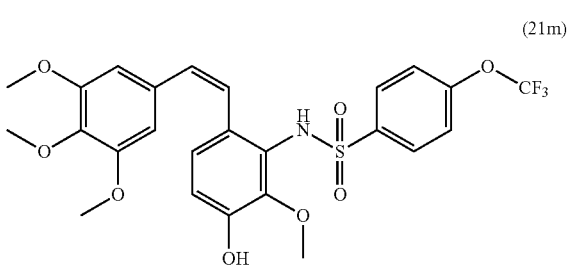
(21m)
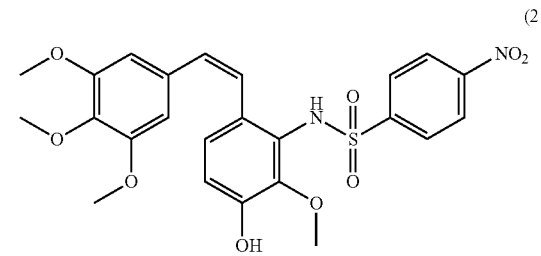
(21h)
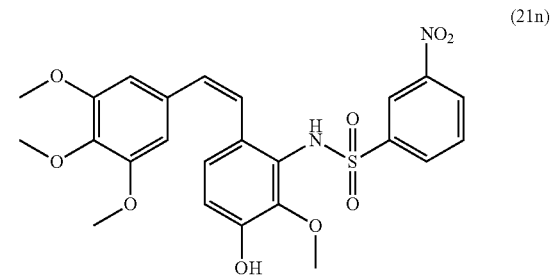
(21n)
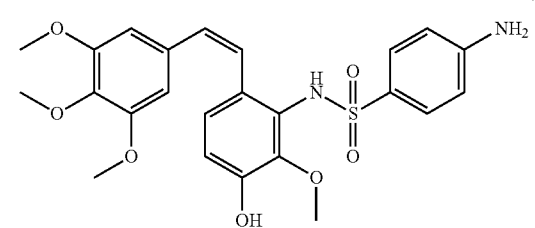
(21i)
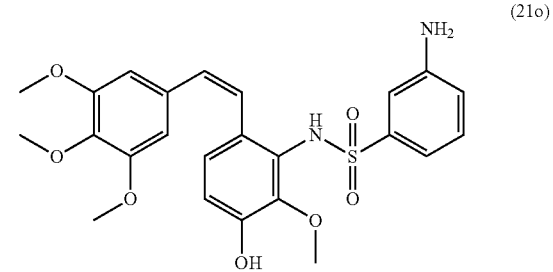
(21o)
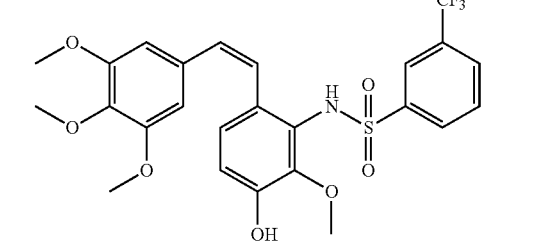
(21j)
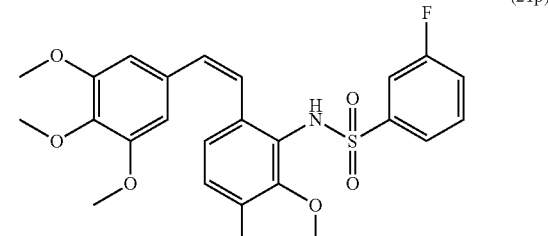
(21p)
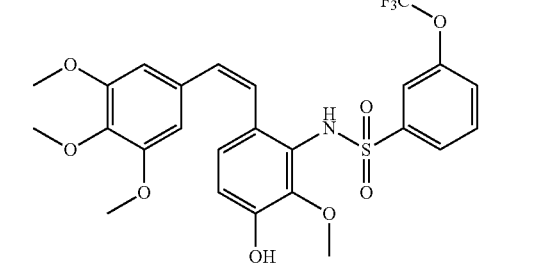
(21k)
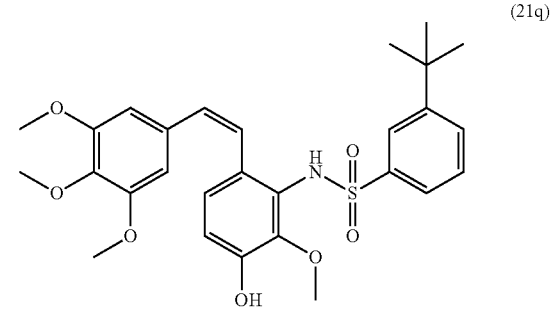
(21q)

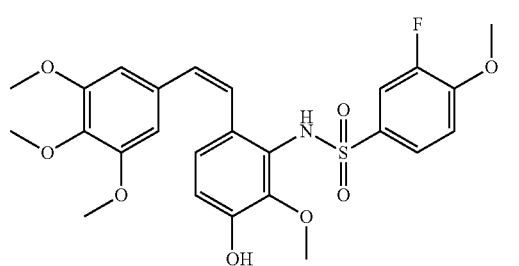
(21r)
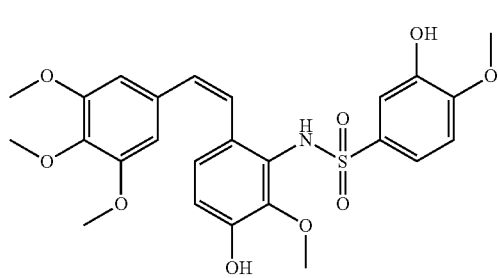
(21s)
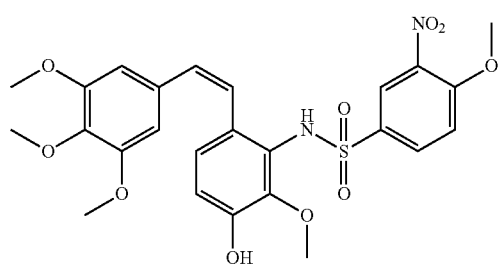
(21t)
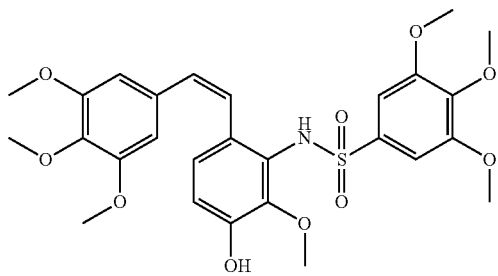
(21u)
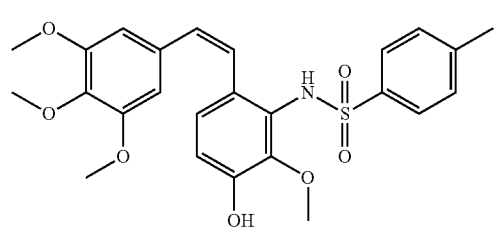
(21v)
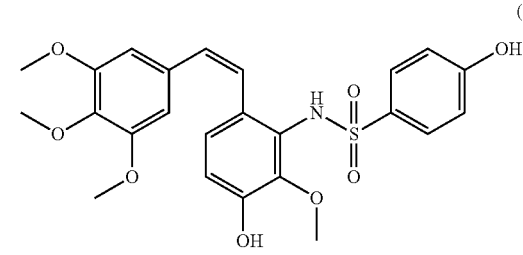
(21w)
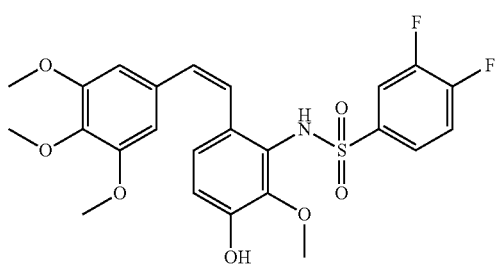
(21x)
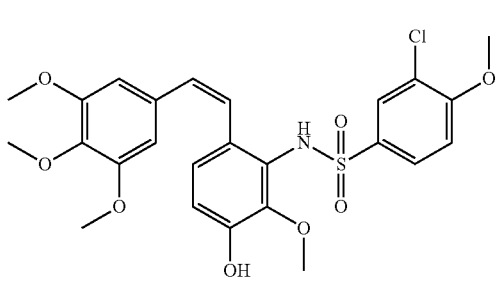
(21y)
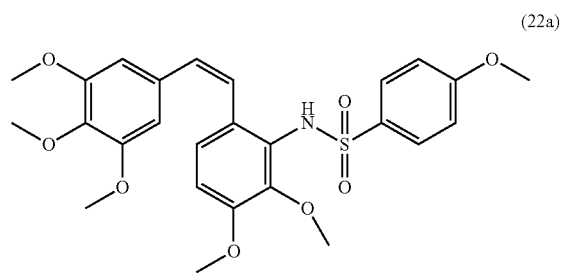
(22a)
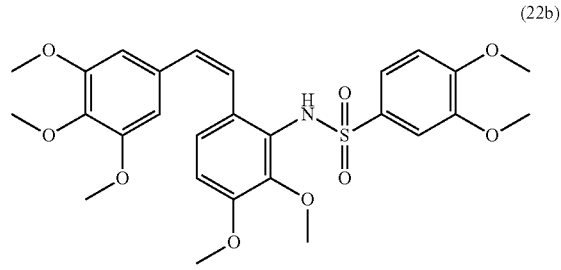
(22b)
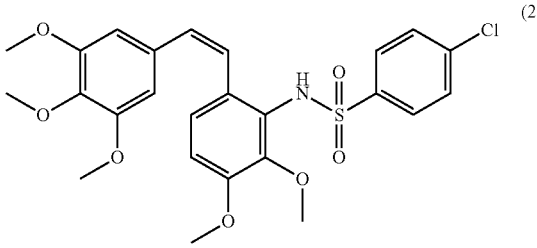
(22c)
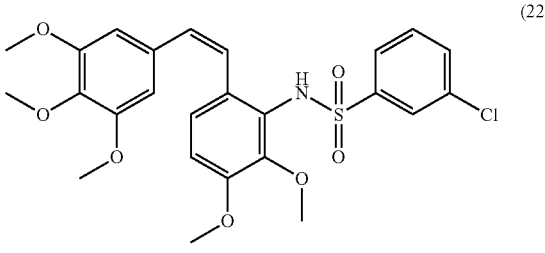
(22d)

101
-continued
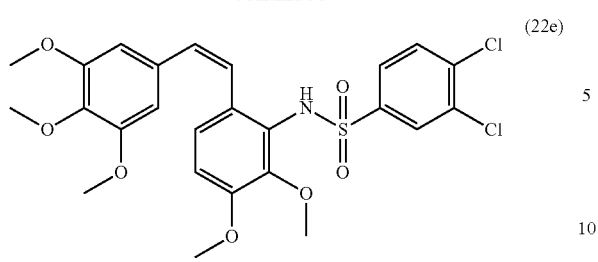
(22e)
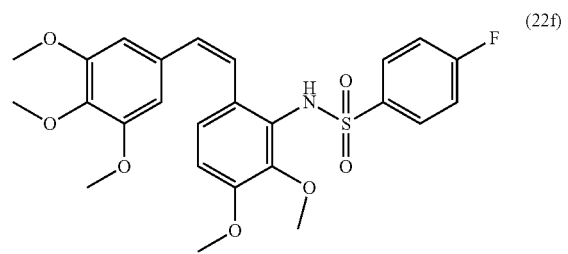
(22f)
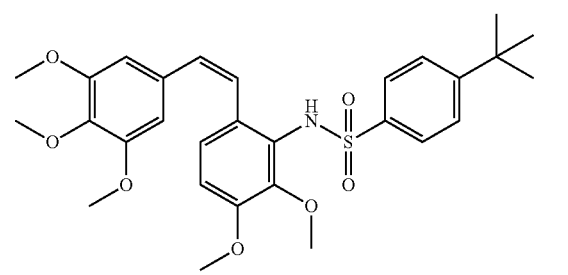
(22g)
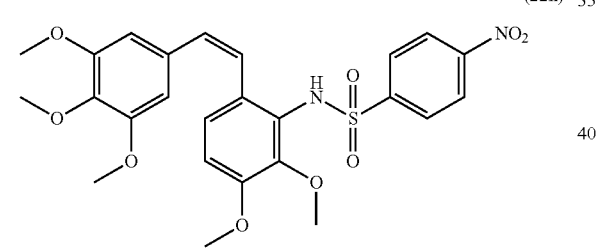
(22h)
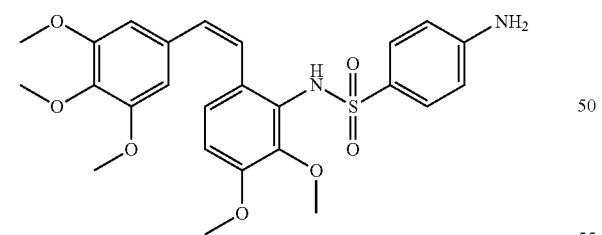
(22i)
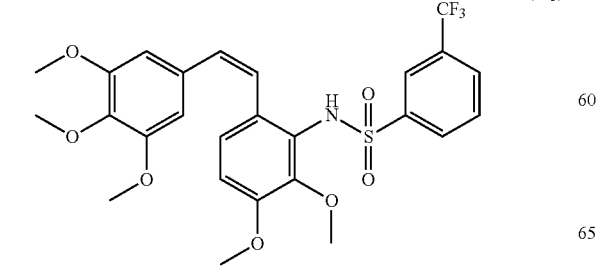
(22j)
102
-continued
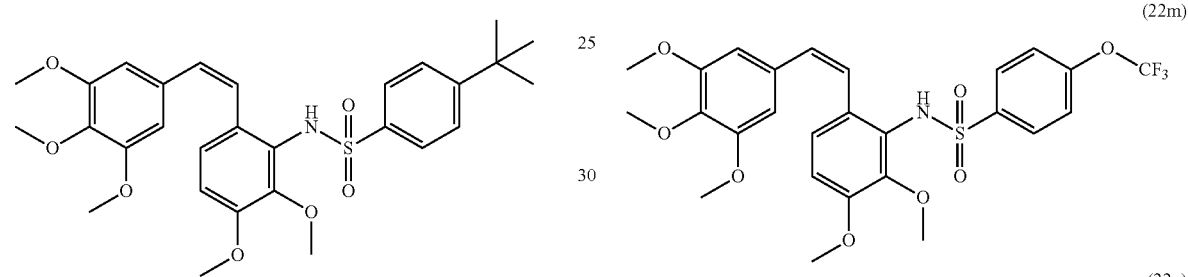
(22k)
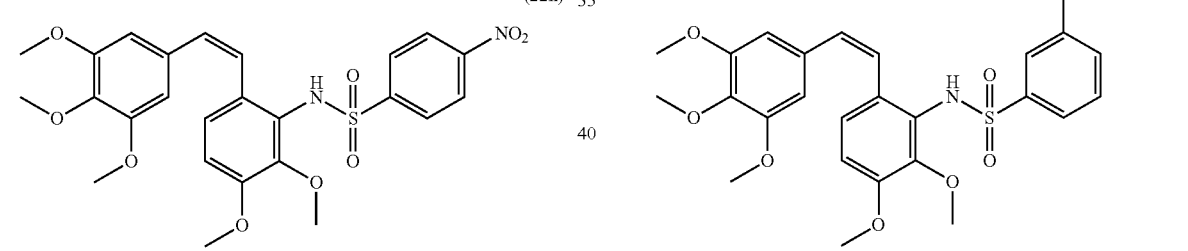
(22l)
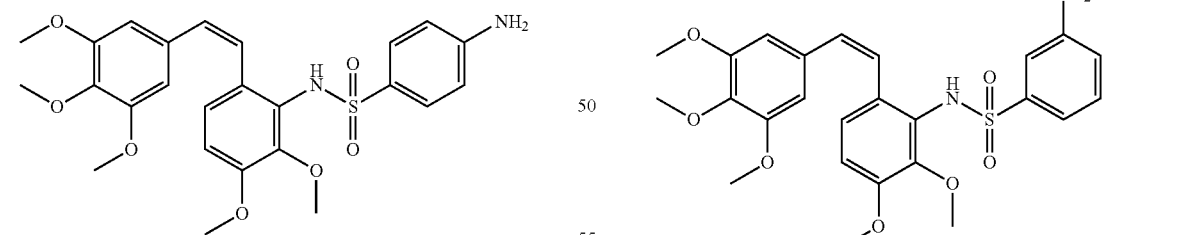
(22m)
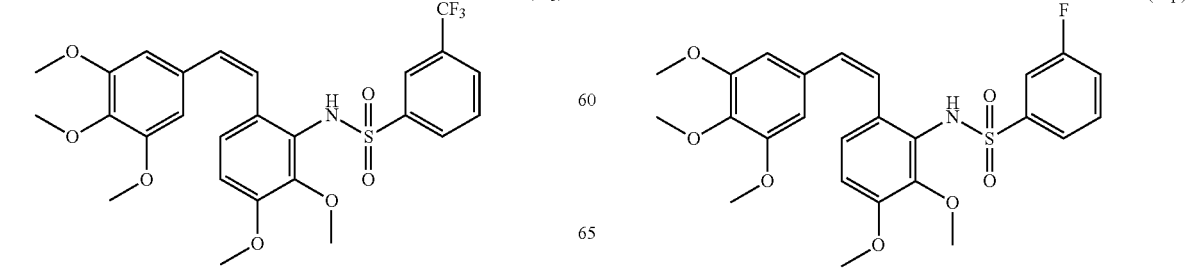
(22n)
(22o)
(22p)

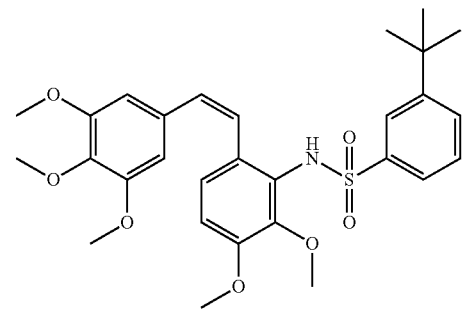
(22q)
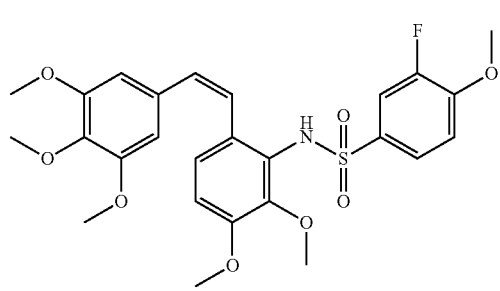
(22r)
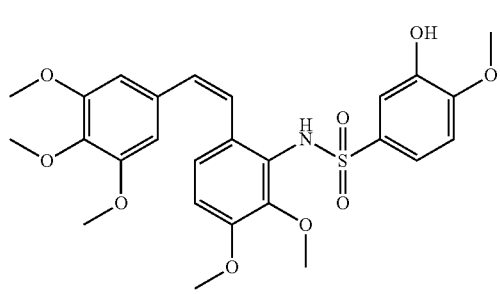
(22s)
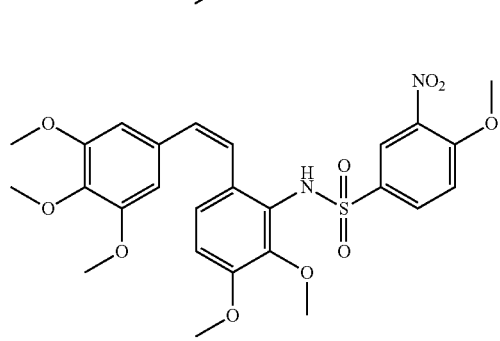
(22t)
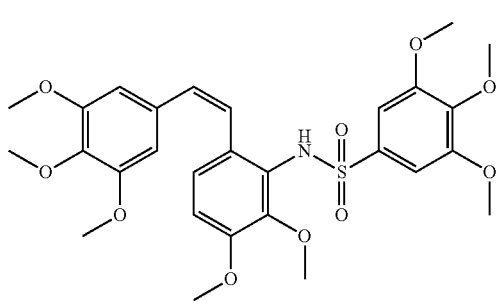
(22u)
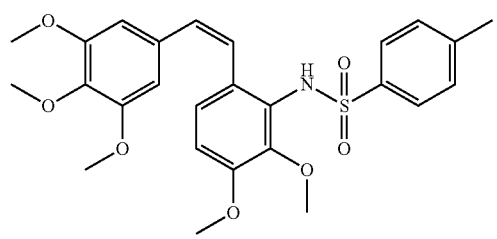
(22v)
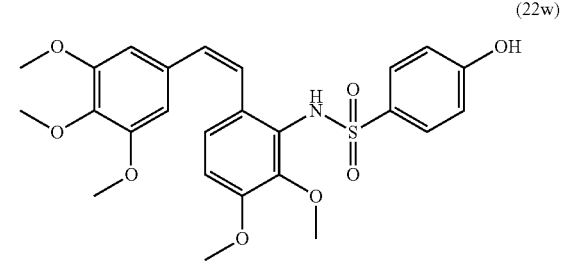
(22w)
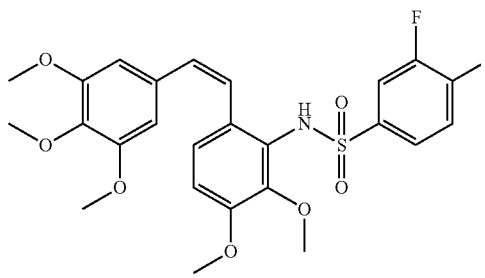
(22x)
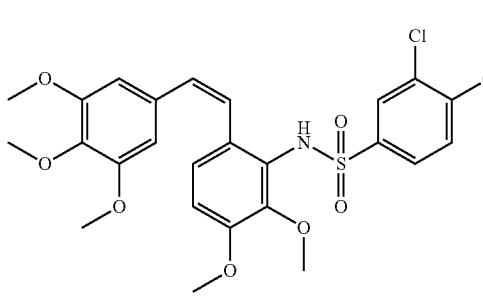
(22y)
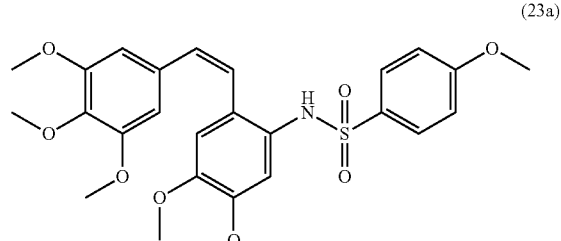
(23a)
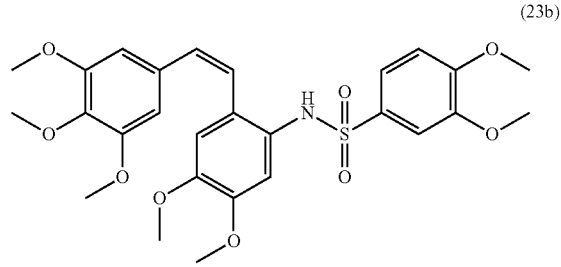
(23b)

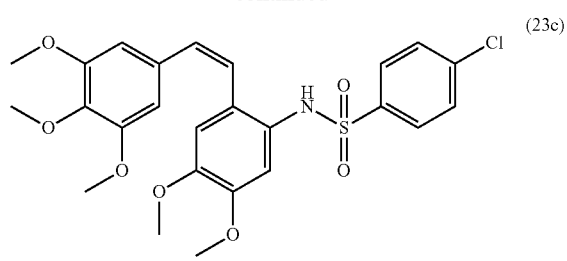
(23c)
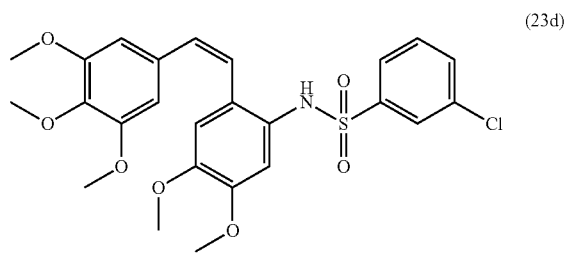
(23d)
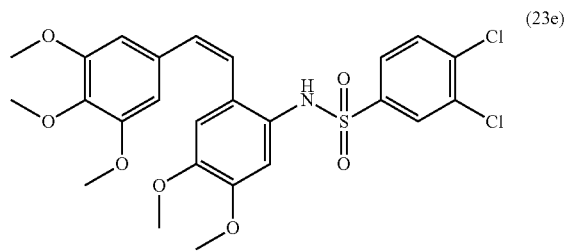
(23e)
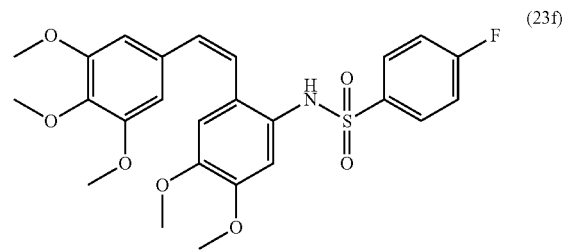
(23f)
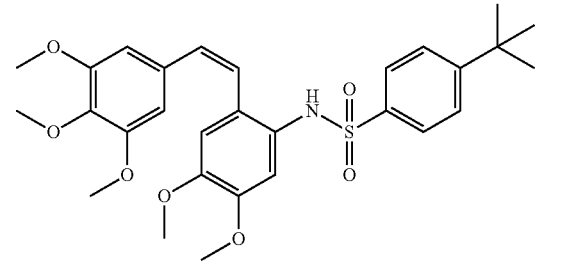
(23g)
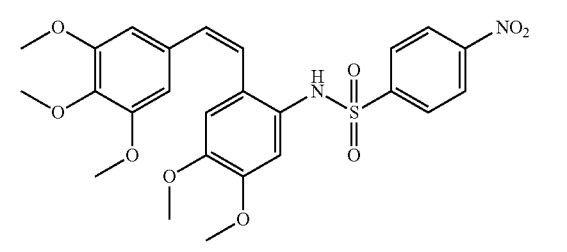
(23h)
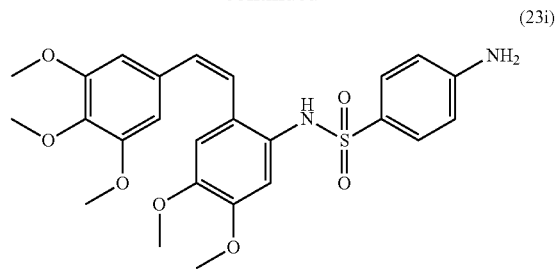
(23i)
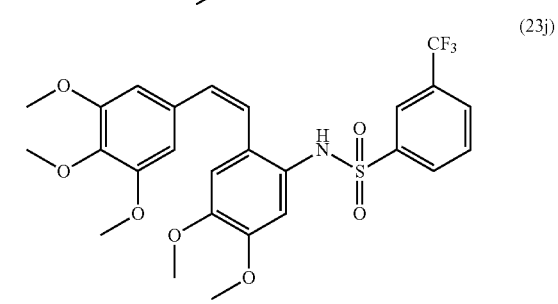
(23j)
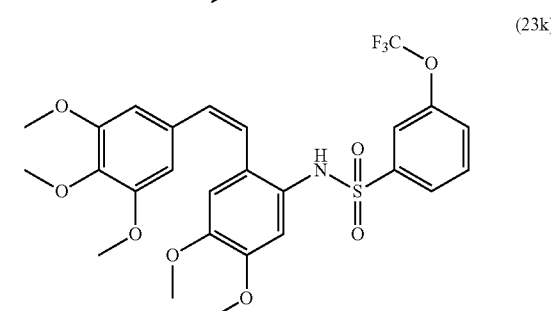
(23k)
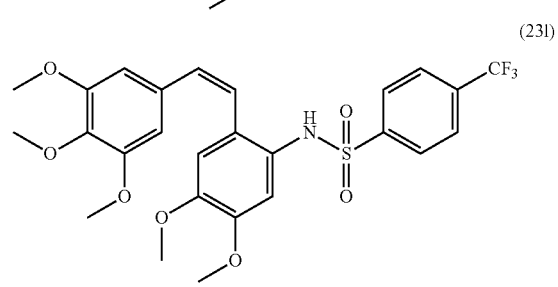
(23l)
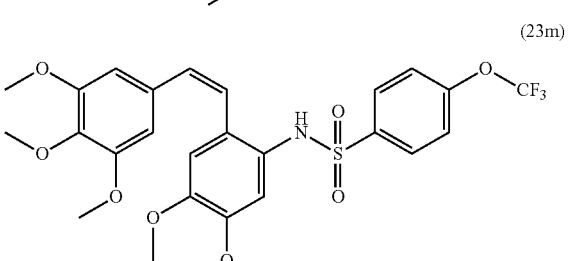
(23m)
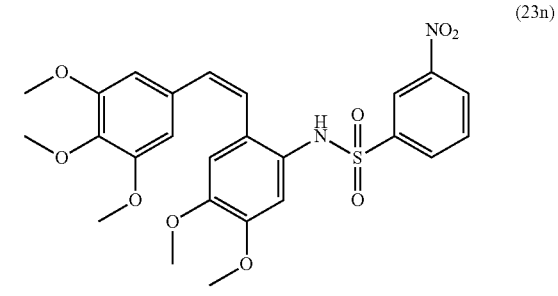
(23n)

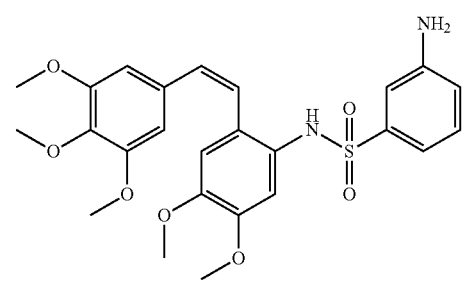
(23o)
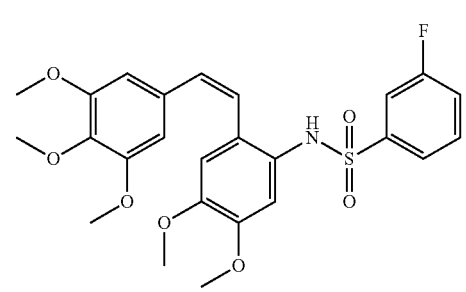
(23p)
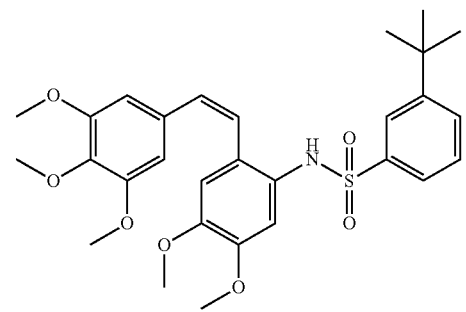
(23q)
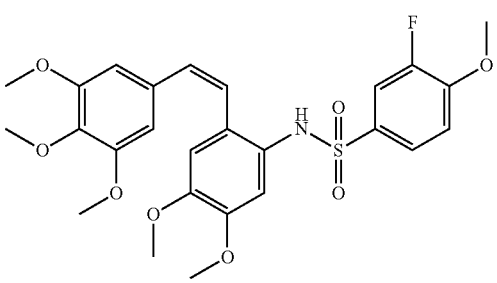
(23r)
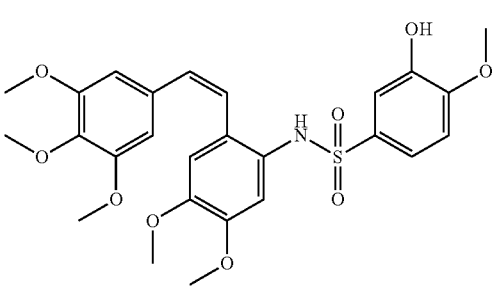
(23s)
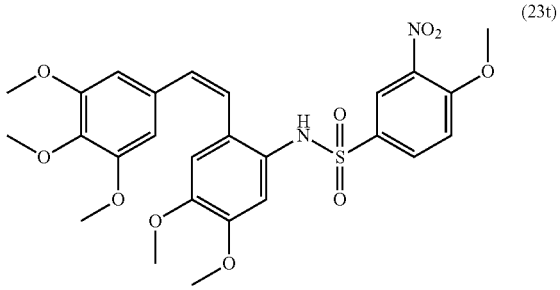
(23t)
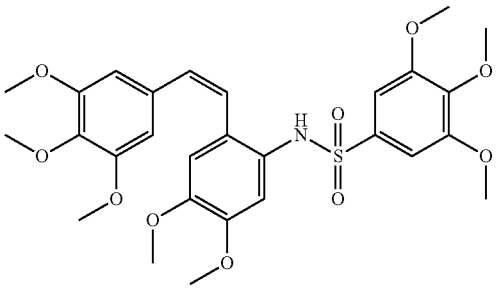
(23u)
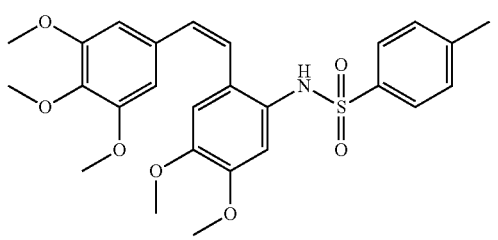
(23v)
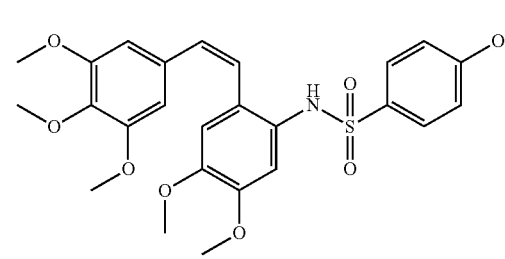
(23w)
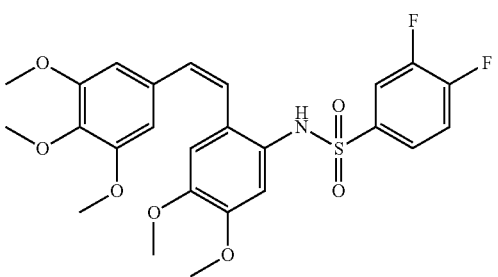
(23x)
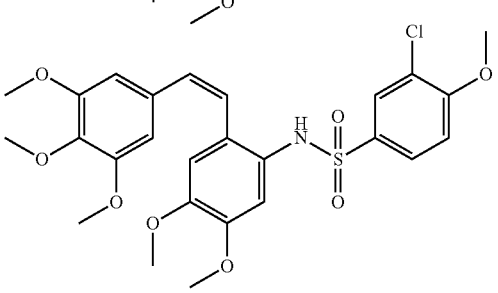
(23y)
wherein R=H, Cl, F, Br, OCH$_3$, NH$_2$, NO$_2$, OH The following examples are given by way of illustration and therefore should not be construed to limit the scope of the present invention.

EXAMPLES

Example 1

(Z)-4-methoxy-N-(2-methoxy-5-(3,4,5-trimethoxystyryl)phenyl)benzenesulfonamide (12a)

To a solution of (Z)-4-methoxy-N-(2-methoxy-5-(3,4,5-trimethoxystyryl) aniline (100 mg, 0.317 mmol) in a 1:4 mixture of pyridine and anhydrous $CH_2Cl_2$ (10 mL), benzenesulfonylchloride (79 mg, 0.380 mmol) was slowly added at 0° C. After 5 min stirring remove ice both and stirred at room temperature 3 h, then the reaction mixture was evaporated to dryness in vacuum and the residue was taken up with $CH_2Cl_2$ (10 mL). The organic solution was washed with water, 10% aqueous HCl, water and brine, dried over $MgSO_4$, and concentrated in vacuum to give 161 mg (90%) of analytically pure compound obtained from a 3:1 mixture of hexane and ethyl acetate.

$^1$H NMR (CDCl$_3$, 300 MHz) δ (ppm): 3.64 (s, 6H), 3.66 (s, 3H), 3.81 (s, 3H), 3.83 (s, 3H) 6.43 (s, 2H), 6.45 (s, 2H), 6.58 (s, 2H), 6.61 (d, J=8.5 Hz, 1H), 6.83 (d, J=9.1 Hz, 2H), 6.92-6.96 (m, 2H), 7.42 (d, J=1.8, NH), 7.61 (d, J=8.87 Hz, 2H); FABMAS: (M+H)=485.

Example 2

(Z)-3,4-dimethoxy-N-(2-methoxy-5-(3,4,5-trimethoxystyryl)phenyl)benzenesulfonamide (12b)

To a solution of (Z)-4-methoxy-N-(2-methoxy-5-(3,4,5-trimethoxystyryl) aniline (100 mg, 0.317 mmol) in a 1:4 mixture of pyridine and anhydrous $CH_2Cl_2$ (10 mL), 4-methoxy benzenesulfonyl chloride (91 mg 0.380 mmol) was slowly added at 0° C. After 5 min stirring remove ice both and stirred at room temperature 2-3 h, then the reaction mixture was evaporated to dryness in vacuum and the residue was taken up with $CH_2Cl_2$ (10 mL). The organic solution was washed with water, 10% aqueous HCl, water and brine, dried over $MgSO_4$, and concentrated in vacuum to give 170 mg (90%) of analytically pure compound obtained from a 3:1 mixture of hexane, ethyl acetate.

$^1$H NMR (CDCl$_3$, 300 MHz) ⌈⌈ (ppm): 3.64 (s, 6H), 3.66 (s, 3H), 3.81 (s, 3H), 3.83 (s, 3H), 3.89 (s, 3H) 6.43 (s, 2H), 6.45 (s, 2H), 6.61 (d, J=8.3 Hz, 1H), 6.79 (d, J=8.3 Hz, 1H), 6.98 (t, J=12.1, 8.98 Hz, 2H), 7.28 (t, J=12.1 Hz, 2H), 7.42 (d J=2.26 Hz, NH), 7.61 (d, J=8.87 Hz, 2H); FABMAS: (M+H)=515.

Example 3

(Z)-4-chloro-N-(2-methoxy-5-(3,4,5-trimethoxystyryl)phenyl)benzenesulfonamide (12c)

To a solution of (Z)-4-methoxy-N-(2-methoxy-5-(3,4,5-trimethoxystyryl) aniline (100 mg, 1 eqt, 0.317 mmol) in a 1:4 mixture of pyridine and anhydrous $CH_2Cl_2$ (10 mL), 4-chloro benzenesulfonylchloride (81 mg 0.380 mmol) was slowly added at 0° C. After 5 min stirring remove ice both and stirred at room temperature 2-3 h, then the reaction mixture was evaporated to dryness in vacuum and the residue was taken up with $CH_2Cl_2$ (10 mL). The organic solution was washed with water, 10% aqueous HCl, water and brine, dried over $MgSO_4$, and concentrated in vacuum to give 166 mg (93%) of analytically pure compound obtained from a 3:1 mixture of hexane, ethyl acetate.

$^1$H NMR (CDCl$_3$, 300 MHz) ⌉⌉ (ppm): 3.64 (s, 3H), 3.68 (s, 6H), 3.84 (s, 3H), 3.83 (s, 3H) 6.44 (s, 2H), 6.46 (s, 2H), 6.61 (d, J=8.3 Hz 1H), 6.93 (s, 1H), 6.98 (d, J=8.3 Hz, 1H), 7.02-7.03 (m, 2H), 7.40 (d, J=2.26 Hz, NH), 7.65-7.70 (d, J=12.1 Hz, 2H); FABMAS: (M+H)=489.

Example 4

(Z)—N-(2,3-dimethoxy-5-(3,4,5-trimethoxystyryl)phenyl)-4-methoxybenzene sulfonamide (13a)

To a solution of (Z)-2,3-dimethoxy-5-(3,4,5-trimethoxystyryl)benzenamine (100 mg, 1 eqt, 0.289 mmol) in a 1:4 mixture of pyridine and anhydrous $CH_2Cl_2$ (10 mL), 4-methoxy benzenesulfonyl chloride (71 mg, 0.347 mmol) was slowly added at 0° C. After 5 min stirring remove ice both and stirred at room temperature 2-3 h, then the reaction mixture was evaporated to dryness in vacuum and the residue was taken up with $CH_2Cl_2$ (10 mL). The organic solution was washed with water, 10% aqueous HCl, water and brine, dried over $MgSO_4$, and concentrated in vacuum to give 153 mg (90%) of analytically pure compound obtained from a 3:1 mixture of hexane, ethyl acetate.

$^1$H NMR (CDCl$_3$, 300 MHz) ⌉⌉ (ppm): 3.72 (s, 9H), 3.87 (s, 3H), 3.92 (s, 3H), 4.05 (s, 3H), 5.90 (d, J=7.55 Hz, 1H), 6.59 (d, J=12.1 Hz, 5H) 6.8 (s, 1H), 7.24-7.17 (m, 1H) 7.37 (s, 3H), 7.73 (s, 1H), 8.5 (s, 1H), 12.01 (d, J=12.1 Hz, NH); FABMAS: (M+H)=515.

Example 5

(Z)—N-(2,3-dimethoxy-5-(3,4,5-trimethoxystyryl)phenyl)-3,4-dimethoxybenzene sulfonamide (13b)

To a solution of (Z)-2,3-dimethoxy-5-(3,4,5-trimethoxystyryl)benzenamine (100 mg, 1 eqt, 0.289 mmol) in a 1:4 mixture of pyridine and anhydrous $CH_2Cl_2$ (10 mL), 3,4-dimethoxybenzene sulfonyl chloride (82 mg, 0.347 mmol) was slowly added at 0° C. After 5 min stirring remove ice both and stirred at room temperature 2-3 h, then the reaction mixture was evaporated to dryness in vacuum and the residue was taken up with $CH_2Cl_2$ (10 mL). The organic solution was washed with water, 10% aqueous HCl, water and brine, dried over $MgSO_4$, and concentrated in vacuum to give 165 mg (92%) of analytically pure compound obtained from a 3:1 mixture of hexane, ethyl acetate.

$^1$H NMR (CDCl$_3$, 300 MHz) ⌉⌈ (ppm): ⌉⌈ 3.72 (s, 6H), 3.82 (s, 3H), 3.84 (s, 3H), 3.90 (s, 3H), 3.94 (s, 3H), 3.96 (s, 3H), 5.93 (d, J=12.1 Hz, 1H), 6.58 (s, 2H) 6.79 (d, J=12.1 Hz, 1H), 7.19 (s, 1H) 7.23 (s, 1H), 6.70 (s, 1H), 6.73 (d, 1H), 6.82 (d, 1H); FABMAS: (M+H)=545.

Example 6

(Z)-4-chloro-N-(2,3-dimethoxy-5-(3,4,5-trimethoxystyryl)phenyl)benzenesulfonamide (13c)

To a solution of (Z)-2,3-dimethoxy-5-(3,4,5-trimethoxystyryl)benzenamine (100 mg, 0.289 mmol) in a 1:4 mixture of pyridine and anhydrous $CH_2Cl_2$ (10 mL), 4-chloro benzenesulfonyl chloride (73 mg, 0.347 mmol) was slowly added at 0° C. After 5 min stirring remove ice both and stirred at room temperature 2-3 h, then the reaction mixture was evaporated to dryness in vacuum and the residue was taken up with CH$_2$Cl$_2$(10 mL). The organic solution was washed with water, 10% aqueous HCl, water and brine, dried over MgSO$_4$, and concentrated in vacuum to give 157 mg (92%) of analytically pure compound obtained from a 3:1 mixture of hexane, ethyl acetate.

$^1$H NMR (CDCl$_3$, 300 MHz) ⎤⎡ (ppm): ⎤⎡ 3.72 (s, 6H), 3.83 (s, 3H), 3.90 (s, 3H), 3.95 (s, 3H), 5.96 (d, J=12.1 Hz, 1H), 6.75 (s, 2H) 6.81 (d, J=12.1 Hz, 1H), 7.06 (s, 1H), 7.23 (s, 1H), 7.34 (s, J=7.4 Hz, 2H), 7.43 (s, J=7.4 Hz, 2H); FABMAS: (M+H)=519.

Example 7

(Z)—N-(2-hydroxy-3-methoxy-6-(3,4,5-trimethoxystyryl)phenyl)-4-methoxybenzene sulfonamide (17a)

To a solution of (Z)-2-(tert-butyldimethylsilyloxy)-3-methoxy-6-(3,4,5-trimethoxystyryl)benzenamine (100 mg, 0.302 mmol) in a 1:4 mixture of pyridine and anhydrous CH$_2$Cl$_2$ (10 mL), 4-methoxybenzenesulfonyl chloride (74 mg 0.362 mmol) was slowly added at 0° C. After 5 min stirring remove ice both and stirred at room temperature 2-3 h, then the reaction mixture was evaporated to dryness in vacuum and the residue was taken up with CH$_2$Cl$_2$ (10 mL). The organic solution was washed with water, 10% aqueous HCl, water and brine, dried over MgSO$_4$, and concentrated in vacuum to give 158 mg (91%) of analytically pure compound obtained from a 3:1 mixture of hexane, ethyl acetate.

$^1$H NMR (CDCl$_3$, 300 MHz) ☐⊏ (ppm): 3.61 (s, 6H), 3.81 (s, 3H), 3.82 (s, 3H), 3.86 (s, 3H), 5.87 (d, J=12.1 Hz, 1H), 6.04 (s, 1H) 6.27 (s, 2H), 6.31 (d, J=12.1 Hz, 1H) 6.72 (m, 3H), 7.62 (d, J=8.4 Hz, 2H); FABMAS: (M+H)=501.55.

Example 8

(Z)—N-(2-hydroxy-3-methoxy-6-(3,45-trimethoxystyryl)phenyl)-3,4-dimethoxybenzene sulfonamide (17b)

To a solution of ((Z)-2-(tert-butyldimethylsilyloxy)-3-methoxy-6-(3,4,5-trimethoxystyryl)benzenamine (100 mg, 1 eqt, 0.302 mmol) in a 1:4 mixture of pyridine and anhydrous CH$_2$Cl$_2$ (10 mL), 3,4-dimethoxybenzene sulfonyl chloride (85 mg, 0.362 mmol) was slowly added at 0° C. After 5 min stirring remove ice both and stirred at room temperature 2-3 h, then the reaction mixture was evaporated to dryness in vacuum and the residue was taken up with CH$_2$Cl$_2$ (10 mL). The organic solution was washed with water, 10% aqueous HCl, water and brine, dried over MgSO$_4$, and concentrated in vacuum to give 164 mg (90%) of analytically pure compound obtained from a 3:1 mixture of hexane, ethyl acetate.

$^1$H NMR (CDCl$_3$, 300 MHz) ⎤⎡ (ppm): 3.61 (s, 6H), 3.76 (s, 3H), 3.81 (s, 3H), 3.86 (s, 3H), 3.91 (s, 3H), 5.86 (d, J=12.1 Hz 1H), 6.26 (d, J=12.1 Hz 1H), 6.27 (s, 2H), 6.63 (s, 1H), 6.70 (d, J=8.18 Hz1H), 6.73 (d, J=8.23 Hz 1H), 6.82 (d, J=8.45 Hz 1H), 7.12 (d, 1H), 7.63 (d, J=8.32 Hz1H); FABMAS: (M+H)=531.57.

Example 9

(Z)-4-chloro-N-(2-hydroxy-3-methoxy-6-(3,4,5-trimethoxystyryl)phenyl)benzenesulfonamide (17c)

To a solution of (Z)-2-(tert-butyldimethylsilyloxy)-3-methoxy-6-(3,4,5-trimethoxystyryl) benzenamine (100 mg, 0.302 mmol) in a 1:4 mixture of pyridine and anhydrous CH$_2$Cl$_2$ (10 mL), 4-chloro benzenesulfonylchloride (76 mg, 0.362 mmol) was slowly added at 0° C. After 5 min stirring remove ice both and stirred at room temperature 2-3 h, then the reaction mixture was evaporated to dryness in vacuum and the residue was taken up with CH$_2$Cl$_2$ (10 mL). The organic solution was washed with water, 10% aqueous HCl, water and brine, dried over MgSO$_4$, and concentrated in vacuum to give 160 mg (90%) of analytically pure compound obtained from a 3:1 mixture of hexane, ethyl acetate.

$^1$H NMR (CDCl$_3$, 300 MHz) |(ppm): 3.63 (s, 6H), 3.82 (s, 3H), 3.85 (s, 3H), 6.04 (d, J=12.1 Hz, 1H), 6.19 (s, H), 6.28 (d, J=12.1 Hz, 1H), 6.31 (s, 2H), 6.72 (s, 2H), 7.35 (d, J=8.42 Hz 2H), 7.65 (s, 2H), ppm. FABMAS: (M+H)=505

Example 10

(Z)-4-tert-butyl-N-(2-hydroxy-3-methoxy-6-(3,4,5-trimethoxystyryl)phenyl)benzenesulfonamide (17g)

To a solution of (Z)-2-(tert-butyldimethylsilyloxy)-3-methoxy-6-(3,4,5-trimethoxystyryl)benzenamine (100 mg, 0.302 mmol) in a 1:4 mixture of pyridine and anhydrous CH$_2$Cl$_2$ (10 mL), 4-tert-butylbenzenesulfonyl chloride (85.5 mg, 0.362 mmol) was slowly added at 0° C. After 5 min stirring remove ice both and stirred at room temperature 2-3 h, then the reaction mixture was evaporated to dryness in vacuum and the residue was taken up with CH2Cl2(10 mL). The organic solution was washed with water, 10% aqueous HCl, water and brine, dried over MgSO$_4$, and concentrated in vacuum to give 163 mg (90%) of analytically pure compound obtained from a 3:1 mixture of hexane, ethyl acetate.

$^1$H NMR (CDCl$_3$, 300 MHz) ⊓ (ppm): 1.30 (s, 9H) 3.62 (s, 6H), 3.81 (s, 3H), 3.87 (s, 3H), 5.76 (d, J=11.9 1H), 6.22 (d, J=11.897 1H), 6.26 (s, 2H), 6.68 (d, 1H), 6.72 (d, J=8.26 Hz 1H), 7.40 (d, J=8.49 Hz, 2H), 7.63 (d, J=8.498 Hz, 2H), ppm. FABMAS: (M+H)=527.

Anticancer activity: Some of in vitro biological activity studies were carried out at the National Cancer Institute, Maryland, USA.

In vitro cytotoxicity: The (Z)-3,4,5-trimethoxystyryl benzene sulfonamides (13a, 13c, 17a, 17c and 12a) have been tested against sixty human tumor cell lines derived from different type of nine cancer cell lines (leukemia, non-small cell lung cancer, colon cancer, CNS cancer, melanoma, ovarian cancer, renal cancer, prostate cancer and breast cancer) as per the NCI protocol. For each compound, dose response curves for individual cell lines have been measured at a minimum of five concentrations at 10 fold dilutions. A protocol of 48 h continuous drug exposure has been used, and a sulforhodamine B (SRB) protein assay was used to estimate cell viability or growth. The concentration for 50% cell growth inhibition (GI$_{50}$), total cell growth inhibition (TGI, 0% growth) and 50% cell death (LC$_{50}$, 50% growth) compared with the control has been calculated (Table-1). The compounds 13a, 13c, 17a, 17c and 12a has been evaluated for their in vitro cytotoxicity in sixty cell lines from nine human cancer types of leukemia (K-562, SR), lung (Hop-62, NCI-H226, NCI-H522), colon (HCT-116, HCT-15, HCC-2998), CNS (SF-539), melanoma (SK-MEL-5, UACC-62, M14), ovarian (IGROV1), renal (A498), prostate (PC3) breast (BT-549, MDA-MB-435, HS578T) origin. The results are expressed as percent of cell growth determined relative to that of untreated control cells (Table 2).

The representative compounds 13a, 13c, 17a, 17c and 12a showed significant cytotoxicity against almost 50 above cancer cell lines.

The compounds 17a, 17c, 13a, 13c and 12a exhibited a wide spectrum of activity against fifty six cell lines in nine different types of cancer cell lines, most of the compounds with $GI_{50}$ value range of 18-50 nM. Particularly, the compounds 13a, 17a, and 12a were more potent than the compounds 13c and 17c against all the tested cell lines. The $GI_{50}$ values for the compound 17a and 13a against almost all tumor cell lines below 50 nM, in that eight types of different tumor cell lines shows below 30 nM and below 40 nm shows by twenty five cell lines and around forty above cell lines shows with $GI_{50}$ values below 50 nM. 17c and 12a also shows good $GI_{50}$ values below 30 nm around eight tumor cell lines, with $GI_{50}$ values below 50 nm shows by thirty above cell lines. In detail, In the non-small cell lung cancer panel, the growth of NCI-H522 cell line were affected by compound 17a with $GI_{50}$ values as 20.2 nM. The $GI_{50}$ values for the compound 13a against non-small lung cancer cell line NCI-H522 19.7 nM. Whereas the colon cancer cell line colo-205 affected by compound 13a with $GI_{50}$ value of 21.4 nM. The $GI_{50}$ values for compounds 17a, 17c, 13a and 12a against renal A498 cell line were 18.8, 22.9, 21.7 and 35.3 nM respectively. In the leukemia cancer panel the cell lines CCRF-CEM, HL-60(TB), SR and K-562 were affected by 17a with $GI_{50}$ value 30.1, 23.5, 31.9 and 28.6 nM and 13a with $GI_{50}$ values 32.9, 23.4, 35.2 and 27.2 respectively, and The $GI_{50}$ values for compounds 17a, 17c and 13a against melanoma MDA-MB-435 cell line were 19.0, 22.2 and 21.1 nM, respectively. In the CNS cancer panel the cell lines SF-295, SF-539, U251 and SNB75 were affected by 17a with $GI_{50}$ values 33.9, 29.3, 37.4 and 25.5 nM and 13a with $GI_{50}$ values 31.1, 25.3, 35.7 and 26.5 respectively, the $GI_{50}$ values for the compound 12a against melanoma cancer cell line MDA-MB-435 is 27.4 nM. In the non-small cell lung cancer panel, the growth of HOP-62 and NCI-H522 cell lines were affected by compound 12a with $GI_{50}$ values as 41 and 20.4 nM, respectively. Whereas in the breast cancer cell line MCF-7, the growth was affected by 12a with $GI_{50}$ value 42.6 nM. The $GI_{50}$ values for the compounds 17a, 13a and 12a against Non-small cell lung cancer cell line NCI-H522 is 20.2, 19.7 and 20.4 nM respectively. The $GI_{50}$ values for compounds 17a, 17c, 13a and 12a against melanoma cell line MDA-MB-435 were 19.2, 22.2, 21.1 and 27.4 nM respectively. The $GI_{50}$ values for the compound 12a against renal cancer cell line A498 were 35.3 nM. Overall, the growth affected by the compounds 17a, 17c, 13a and 12a against all the cancer cell lines with $GI_{50}$ values range 18-50 nM.

Compounds 17a, 17c, 13a, 13c and 12a exhibited activity against fifty eight cell lines in nine cancer cell panels with $GI_{50}$ values of 20 nM to 50 nm. In vitro cytotoxicity of compounds 17a, 17c, 13a, 13c and 12a in the selected cancer cell lines has been illustrated in Table 1.

TABLE 1

In vitro cytotoxicity of compounds 17a, 17c, 13a, 13c and 12a in a panel of 60 human cancer cell lines.

| Cancer panel/ cell line | $GI_{50}$ (nM) | | | | |
|---|---|---|---|---|---|
| | 17a | 17c | 13a | 13c | 12a |
| Leukemia | | | | | |
| CCRF-CEM | 30.1 | 159 | 32.9 | 388 | 176 |
| HL-60(TB) | 23.5 | 33.1 | 23.4 | 249 | 195 |
| K-562 | 28.6 | 32.3 | 27.2 | 306 | 53 |
| MOLT-4 | 42.3 | 31.5 | 49.5 | 672 | 388 |
| RPMI-8226 | 46.9 | 207 | 45.9 | 387 | 319 |
| SR | 31.9 | 30.6 | 35.2 | 406 | 70.9 |
| Non-small cell lung | | | | | |
| A549/ATCC | 45.9 | 270 | 47.4 | 716 | 159 |
| HOP-62 | 39.7 | 671 | 40.5 | 414 | 41 |
| HOP92 | 1600 | 2360 | 1750 | 720 | 97.4 |
| NCI-H226 | 4130 | 24900 | 27300 | 13500 | 12800 |
| NCI-H23 | 52.0 | 288 | 59.3 | 710 | 480 |
| NCIH322M | 63.3 | 485 | 55.3 | 759 | 430 |
| NCI-H460 | 36.8 | 316 | 36.7 | 364 | 178 |
| NCI-H522 | 20.2 | 84.8 | 19.7 | 209 | 20.4 |
| Colon | | | | | |
| COLO-205 | 406 | 1740 | 21.4 | 252 | 38.3 |
| HCC-2998 | 31.6 | 429 | 39.1 | 1980 | 442 |
| HCT-116 | 32.0 | 114 | 35.0 | 469 | 79.7 |
| HCT-15 | 36.6 | 53.0 | 35.8 | 399 | 62.3 |
| HT29 | 1400 | 2760 | 33.1 | 348 | 81.0 |
| KM12 | 35.5 | 127 | 39.7 | 572 | 73.8 |
| SW-620 | 40.8 | 69.4 | 43.9 | 343 | 78.5 |
| CNS | | | | | |
| SF-268 | 83.9 | 380 | 57.5 | 1100 | 401 |
| SF-295 | 33.9 | 256 | 31.1 | 319 | 39.3 |
| SF-539 | 29.3 | 37.0 | 25.3 | 303 | 126 |
| SNB -19 | 60.2 | 807 | 60.1 | 745 | 352 |
| SNB -75 | 25.5 | 33.1 | 26.5 | 227 | 70.8 |
| U251 | 37.4 | 287 | 35.7 | 461 | 108 |
| Melanoma | | | | | |
| LOX IMVI | 45.5 | 153 | 50.0 | 566 | 272 |
| MALME-3M | 1510 | NT | 12600 | NT | 52.7 |
| M14 | 31.3 | 91.3 | 30.1 | 391 | 103 |
| MDA-MB-435 | 19.0 | 22.2 | 21.1 | 188 | 27.4 |
| SK-MEL-2 | 43.7 | 65.9 | 37.4 | 613 | 80.3 |
| SK-MEL-28 | NT | 84.1 | 76.5 | 1140 | 143 |
| SK-MEL-5 | 36.3 | 51.0 | 35.9 | 297 | 48.8 |
| UACC-257 | NT | 14200 | 4100 | 12500 | 2980 |
| UACC-62 | 38.9 | 63.5 | 46.1 | 435 | 49.0 |
| Ovarian | | | | | |
| IGROV1 | 54.0 | 379 | 57.7 | 914 | 166 |
| OVCAR-3 | 33.9 | 60.2 | 34.5 | 364 | 52.8 |
| OVCAR-4 | 76.3 | 97.2 | 84.2 | 1530 | 581 |
| OVCAR-5 | 1020 | 2860 | 49.9 | 726 | 323 |
| OVCAR-8 | 46.6 | 294 | 45.9 | 600 | 276 |
| NCI/ADR-RES | 155 | 263 | 35.3 | 364 | 71.1 |
| SK-OV-3 | 29.6 | 229 | 37.8 | 449 | 96.3 |
| Renal | | | | | |
| 786-0 | 375 | 572 | 57.9 | 666 | 361 |
| A498 | 18.8 | 22.9 | 21.7 | 179 | 35.3 |
| ACHN | 61.3 | 83.8 | 57.0 | 586 | 58.7 |
| CAKI-1 | 51.6 | 54.2 | 53.1 | 374 | 51.5 |
| RXF 393 | 31.8 | 35.5 | 40.1 | 272 | 81.4 |
| SN12C | 86.9 | 708 | 69.8 | 750 | 682 |
| TK-10 | 73.2 | 998 | 65.0 | 779 | 76.8 |
| UO-31 | 61.9 | 73.9 | 63.6 | 696 | 131 |
| Prostate | | | | | |
| PC-3 | 40.8 | 153 | 38.0 | 395 | 124 |
| DU-145 | 42.5 | 200 | 41.6 | 507 | 341 |
| Breast | | | | | |
| MCF7 | 38.0 | 38.4 | 36.0 | 375 | 42.6 |
| MDA-MB-231/ATCC | 50.3 | 206 | 47.9 | 1160 | 399 |

TABLE 1-continued

In vitro cytotoxicity of compounds 17a, 17c, 13a, 13c and 12a in a panel of 60 human cancer cell lines.

| Cancer panel/ | $GI_{50}$ (nM) | | | | |
|---|---|---|---|---|---|
| cell line | 17a | 17c | 13a | 13c | 12a |
| HS 578T | 47.0 | 292 | 45.2 | 351 | 226 |
| BT-549 | 50.1 | 353 | 42.5 | 966 | 197 |
| T-47D | NT | NT | 5210 | 381 | NT |
| MDA-MB-435 | 43.9 | 36.7 | 42.0 | 271 | 168 |

NT = NotTested.

The mean graph midpoint values of $Log_{10}$ TGI and $Log_{10}$ $LC_{50}$ as well as $Log_{10}$ $GI_{50}$ for compounds 17a, 17c, 13a, 13c and 12a is listed in Table-2. As demonstrated by mean graph pattern, compounds 17a, 17c, 13a, 13c and 12a exhibited an interesting profile of activity and selectivity for various cell lines. The mean graph midpoints of $Log_{10}$ TGI and $Log_{10}$ $LC_{50}$ have shown similar pattern to the $log_{10}$ $GI_{50}$ mean graph mid points.

TABLE 2

$Log_{10}GI_{50}$, $Log_{10}TGI$ and $Log_{10}LC_{50}$ mean graphs mid points(MG_MID) of in vitro cytotoxicity data for the compound 17a, 17c, 13a, 13c and 12a against human tumor cell lines.

| Compound | $Log_{10}GI_{50}$ | $Log_{10}TGI$ | $Log_{10}LC_{50}$ |
|---|---|---|---|
| 17a | −7.17 | −4.55 | −4.05 |
| 17c | −6.71 | −4.66 | −4.07 |
| 13a | −7.2 | −4.55 | −4.07 |
| 13c | −6.27 | −4.42 | −4.03 |
| 12a | −6.86 | −4.49 | −4.06 |

Advantages of the Present Invention

1. The present invention provides new (Z)-3,4,5-trimethoxystyrylbenzenesulfonamides that may be useful as antitumor agents.
2. It also provides a process for the preparation of (Z)-3,4,5-trimethoxystyrylbenzenesulfonamides.
3. Some new (Z)-3,4,5-trimethoxystyrylbenzenesulfonamides that have been synthesized exhibited significant cytotoxic activity against sixty human cancer cell lines.

We claim:

1. A (Z)-3,4,5-trimethoxystyryl benzenesulfonamide of general formula A

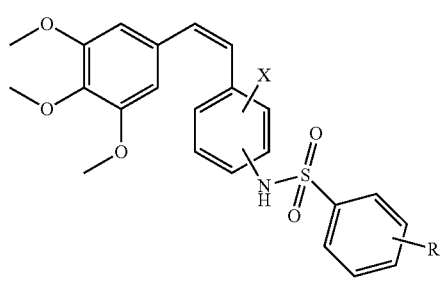

A wherein, X=H, F, $OCH_3$, $NH_2$, or OH; and R=H, Cl, F, $OCH_3$, $NH_2$, $NO_2$, OH, trifluoromethyl, trifluoromethoxy, methyl, or tert-butyl.

2. A (Z)-3,4,5-trimethoxystyryl benzenesulfonamide having one of the following formulae, 9, 10, 11, 12, 13, 14, 15, 16, 17, 18, 19, 20, 21, 22, or 23,

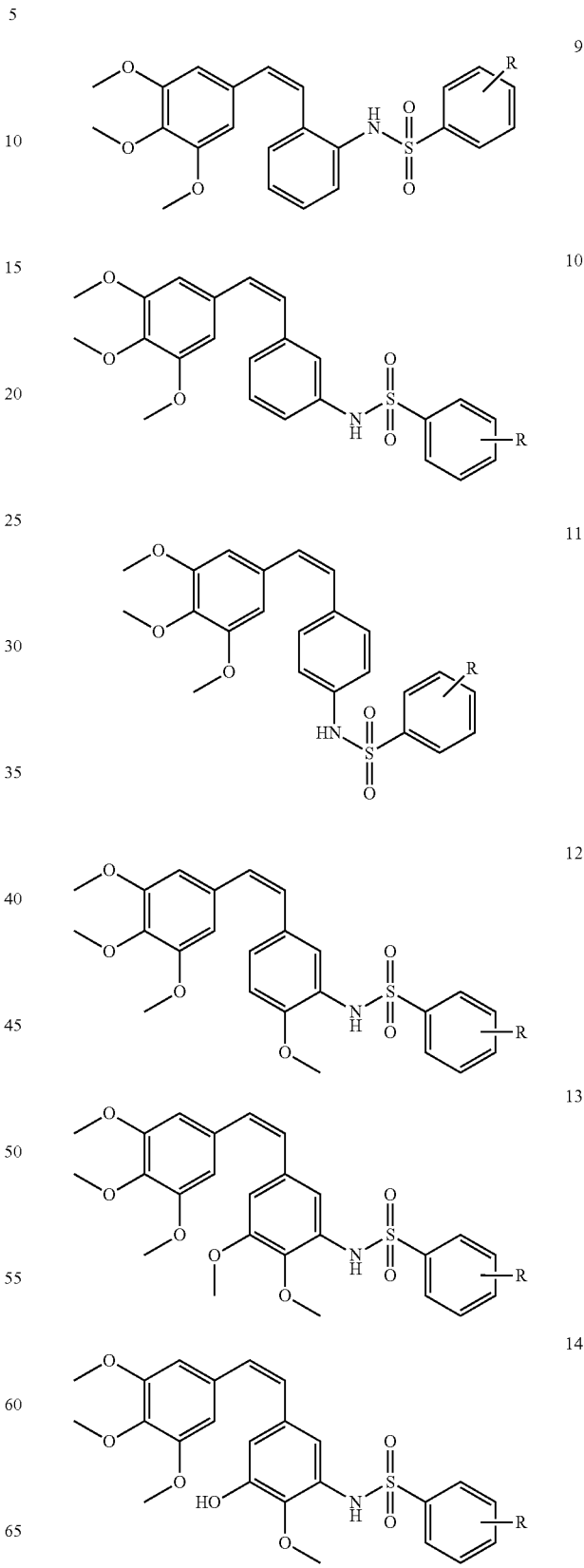

15

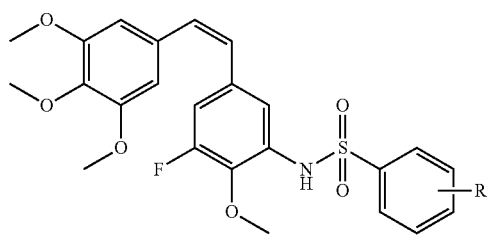

16

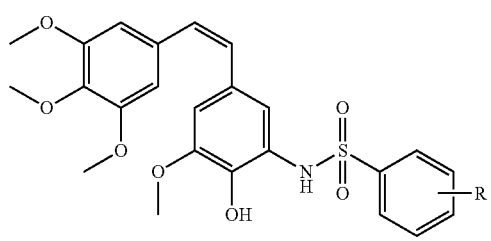

17

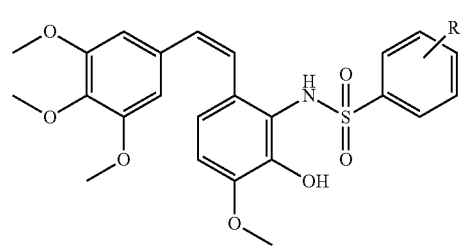

18

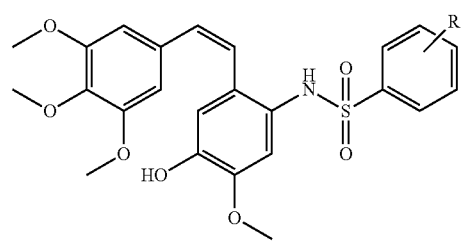

19

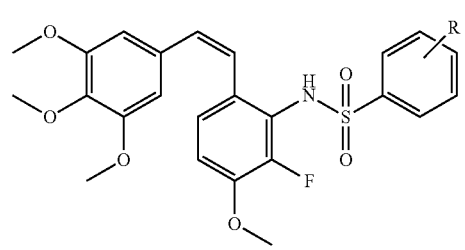

20

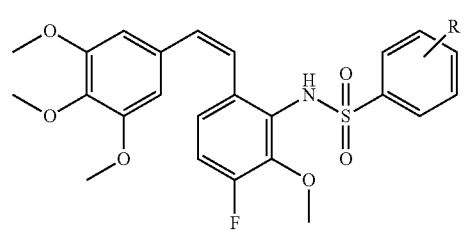

21

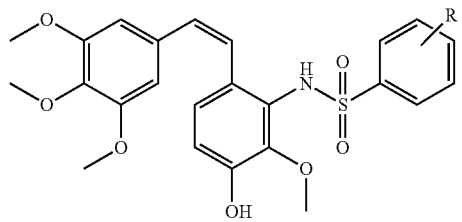

22

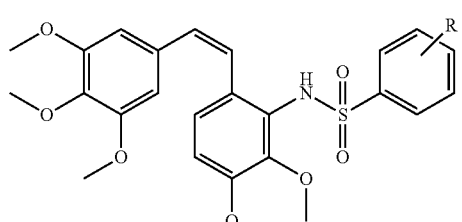

23

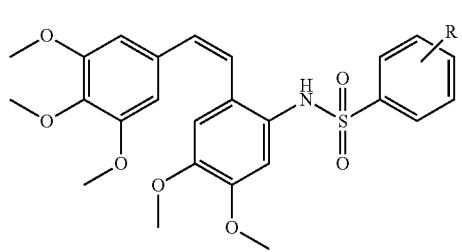

wherein R=H, Cl, F, OCH₃, NH₂, NO₂, or OH.

3. A (Z)-3,4,5-trimethoxystyryl benzenesulfonamide selected from the group consisting of:

(Z)-4-methoxy-N-(2-(3,4,5-trimethoxystyryl)phenyl)benzenesulfonamide (9a)

(Z)-3,4-dimethoxy-N-(2-(3,4,5-trimethoxystyryl)phenyl)benzenesulfonamide (9b)

(Z)-4-chloro-N-(2-(3,4,5-trimethoxystyryl)phenyl)benzenesulfonamide (9c)

(Z)-3-chloro-N-(2-(3,4,5-trimethoxystyryl)phenyl)benzenesulfonamide (9d)

(Z)-3,4-dichloro-N-(2-(3,4,5-trimethoxystyryl)phenyl)benzenesulfonamide (9e)

(Z)-4-fluoro-N-(2-(3,4,5-trimethoxystyryl)phenyl)benzenesulfonamide (9f)

(Z)-4-tert-butyl-N-(2-(3,4,5-trimethoxystyryl)phenyl)benzenesulfonamide (9g)

(Z)-4-nitro-N-(2-(3,4,5-trimethoxystyryl)phenyl)benzenesulfonamide (9h)

(Z)-4-amino-N-(2-(3,4,5-trimethoxystyryl)phenyl)benzenesulfonamide (9i)

(Z)-3-(trifluoromethyl)-N-(2-(3,4,5-trimethoxystyryl)phenyl)benzenesulfonamide (9J)

(Z)-3-(trifluoromethoxy)-N-(2-(3,4,5-trimethoxystyryl)phenyl)benzenesulfonamide (9k)

(Z)-4-(trifluoromethyl)-N-(2-(3,4,5-trimethoxystyryl)phenyl)benzenesulfonamide (9l)

(Z)-4-(trifluoromethoxy)-N-(2-(3,4,5-trimethoxystyryl)phenyl)benzenesulfonamide (9m)

(Z)-3-nitro-N-(2-(3,4,5-trimethoxystyryl)phenyl)benzenesulfonamide (9n)

(Z)-3-amino-N-(2-(3,4,5-trimethoxystyryl)phenyl)benzenesulfonamide (9o)

(Z)-3-fluoro-N-(2-(3,4,5-trimethoxystyryl)phenyl)benzenesulfonamide (9p)

(Z)-3-tert-butyl-N-(2-(3,4,5-trimethoxystyryl)phenyl)benzenesulfonamide (9q)
(Z)-3-fluoro-4-methoxy-N-(2-(3,4,5-trimethoxystyryl)phenyl)benzenesulfonamide (9r)
(Z)-3-hydroxy-4-methoxy-N-(2-(3,4,5-trimethoxystyryl)phenyl)benzenesulfonamide (9s)
(Z)-4-methoxy-3-nitro-N-(2-(3,4,5-trimethoxystyryl)phenyl)benzenesulfonamide (9t)
(Z)-3,4,5-trimethoxy-N-(2-(3,4,5-trimethoxystyryl)phenyl)benzenesulfonamide (9u)
(Z)-4-methyl-N-(2-(3,4,5-trimethoxystyryl)phenyl)benzenesulfonamide (9v)
(Z)-4-hydroxy-N-(2-(3,4,5-trimethoxystyryl)phenyl)benzenesulfonamide (9w)
(Z)-3,4-difluoro-N-(2-(3,4,5-trimethoxystyryl)phenyl)benzenesulfonamide (9x)
(Z)-3-chloro-4-methoxy-N-(2-(3,4,5-trimethoxystyryl)phenyl)benzenesulfonamide (9y)
(Z)-4-methoxy-N-(3-(3,4,5-trimethoxystyryl)phenyl)benzenesulfonamide (10a)
(Z)-3,4-dimethoxy-N-(3-(3,4,5-trimethoxystyryl)phenyl)benzenesulfonamide (10b)
(Z)-4-chloro-N-(3-(3,4,5-trimethoxystyryl)phenyl)benzenesulfonamide (10c)
(Z)-3-chloro-N-(3-(3,4,5-trimethoxystyryl)phenyl)benzenesulfonamide (10d)
(Z)-3,4-dichloro-N-(3-(3,4,5-trimethoxystyryl)phenyl)benzenesulfonamide (10e)
(Z)-4-fluoro-N-(3-(3,4,5-trimethoxystyryl)phenyl)benzenesulfonamide (10f)
(Z)-4-tert-butyl-N-(3-(3,4,5-trimethoxystyryl)phenyl)benzenesulfonamide (10g)
(Z)-4-nitro-N-(3-(3,4,5-trimethoxystyryl)phenyl)benzenesulfonamide (10h)
(Z)-4-amino-N-(3-(3,4,5-trimethoxystyryl)phenyl)benzenesulfonamide (10i)
(Z)-3-(trifluoromethyl)-N-(3-(3,4,5-trimethoxystyryl)phenyl)benzenesulfonamide (10j)
(Z)-3-(trifluoromethoxy)-N-(3-(3,4,5-trimethoxystyryl)phenyl)benzenesulfonamide (10k)
(Z)-4-(trifluoromethyl)-N-(3-(3,4,5-trimethoxystyryl)phenyl)benzenesulfonamide (10l)
(Z)-4-(trifluoromethoxy)-N-(3-(3,4,5-trimethoxystyryl)phenyl)benzenesulfonamide (10m)
(Z)-3-nitro-N-(3-(3,4,5-trimethoxystyryl)phenyl)benzenesulfonamide (10n)
(Z)-3-amino-N-(3-(3,4,5-trimethoxystyryl)phenyl)benzenesulfonamide (10o)
(Z)-3-fluoro-N-(3-(3,4,5-trimethoxystyryl)phenyl)benzenesulfonamide (10p)
(Z)-3-tert-butyl-N-(3-(3,4,5-trimethoxystyryl)phenyl)benzenesulfonamide (10q)
(Z)-3-fluoro-4-methoxy-N-(3-(3,4,5-trimethoxystyryl)phenyl)benzenesulfonamide (10r)
(Z)-3-hydroxy-4-methoxy-N-(3-(3,4,5-trimethoxystyryl)phenyl)benzenesulfonamide (10s)
(Z)-4-methoxy-3-nitro-N-(3-(3,4,5-trimethoxystyryl)phenyl)benzenesulfonamide (10t)
(Z)-3-amino-4-methoxy-N-(3-(3,4,5-trimethoxystyryl)phenyl)benzenesulfonamide (10u)
(Z)-3,4,5-trimethoxy-N-(3-(3,4,5-trimethoxystyryl)phenyl)benzenesulfonamide (10v)
(Z)-4-methyl-N-(3-(3,4,5-trimethoxystyryl)phenyl)benzenesulfonamide (10w)
(Z)-3,4-difluoro-N-(3-(3,4,5-trimethoxystyryl)phenyl)benzenesulfonamide (10x)
(Z)-3-chloro-4-methoxy-N-(3-(3,4,5-trimethoxystyryl)phenyl)benzenesulfonamide (10y)
(Z)-4-methoxy-N-(4-(3,4,5-trimethoxystyryl)phenyl)benzenesulfonamide (11a)
(Z)-3,4-dimethoxy-N-(4-(3,4,5-trimethoxystyryl)phenyl)benzenesulfonamide (11b)
(Z)-4-chloro-N-(4-(3,4,5-trimethoxystyryl)phenyl)benzenesulfonamide (11c)
(Z)-3-chloro-N-(4-(3,4,5-trimethoxystyryl)phenyl)benzenesulfonamide (11d)
(Z)-3,4-dichloro-N-(4-(3,4,5-trimethoxystyryl)phenyl)benzenesulfonamide (11e)
(Z)-4-fluoro-N-(4-(3,4,5-trimethoxystyryl)phenyl)benzenesulfonamide (11f)
(Z)-4-tert-butyl-N-(4-(3,4,5-trimethoxystyryl)phenyl)benzenesulfonamide (11g)
(Z)-4-nitro-N-(4-(3,4,5-trimethoxystyryl)phenyl)benzenesulfonamide (11h)
(Z)-4-amino-N-(4-(3,4,5-trimethoxystyryl)phenyl)benzenesulfonamide (11i)
(Z)-3-(trifluoromethyl)-N-(4-(3,4,5-trimethoxystyryl)phenyl)benzenesulfonamide (11j)
(Z)-3-(trifluoromethoxy)-N-(4-(3,4,5-trimethoxystyryl)phenyl)benzenesulfonamide (11k)
(Z)-4-(trifluoromethyl)-N-(4-(3,4,5-trimethoxystyryl)phenyl)benzenesulfonamide (11l)
(Z)-4-(trifluoromethoxy)-N-(4-(3,4,5-trimethoxystyryl)phenyl)benzenesulfonamide (11m)
(Z)-3-nitro-N-(4-(3,4,5-trimethoxystyryl)phenyl)benzenesulfonamide (11n)
(Z)-3-amino-N-(4-(3,4,5-trimethoxystyryl)phenyl)benzenesulfonamide (11o)
(Z)-3-fluoro-N-(4-(3,4,5-trimethoxystyryl)phenyl)benzenesulfonamide (11p)
(Z)-3-tert-butyl-N-(4-(3,4,5-trimethoxystyryl)phenyl)benzenesulfonamide (11q)
(Z)-3-fluoro-4-methoxy-N-(4-(3,4,5-trimethoxystyryl)phenyl)benzenesulfonamide (11r)
(Z)-3-hydroxy-4-methoxy-N-(4-(3,4,5-trimethoxystyryl)phenyl)benzenesulfonamide (11s)
(Z)-4-methoxy-3-nitro-N-(4-(3,4,5-trimethoxystyryl)phenyl)benzenesulfonamide (11t)
(Z)-3-amino-4-methoxy-N-(4-(3,4,5-trimethoxystyryl)phenyl)benzenesulfonamide (11u)
(Z)-3,4,5-trimethoxy-N-(4-(3,4,5-trimethoxystyryl)phenyl)benzenesulfonamide (11v)
(Z)-4-methyl-N-(4-(3,4,5-trimethoxystyryl)phenyl)benzenesulfonamide (11w)
(Z)-3,4-difluoro-N-(4-(3,4,5-trimethoxystyryl)phenyl)benzenesulfonamide (11x)
(Z)-3-chloro-4-methoxy-N-(4-(3,4,5-trimethoxystyryl)phenyl)benzenesulfonamide (11y)
(Z)-4-methoxy-N-(2-methoxy-5-(3,4,5-trimethoxystyryl)phenyl)benzenesulfonamide (12a)
(Z)-3,4-dimethoxy-N-(2-methoxy-5-(3,4,5-trimethoxystyryl)phenyl)benzenesulfonamide (12b)
(Z)-4-chloro-N-(2-methoxy-5-(3,4,5-trimethoxystyryl)phenyl)benzenesulfonamide (12c)
(Z)-3-chloro-N-(2-methoxy-5-(3,4,5-trimethoxystyryl)phenyl)benzenesulfonamide (12d)
(Z)-3,4-dichloro-N-(2-methoxy-5-(3,4,5-trimethoxystyryl)phenyl)benzenesulfonamide (12e)
(Z)-4-fluoro-N-(2-methoxy-5-(3,4,5-trimethoxystyryl)phenyl)benzenesulfonamide (12f)
(Z)-4-tert-butyl-N-(2-methoxy-5-(3,4,5-trimethoxystyryl)phenyl)benzenesulfonamide (12g)

(Z)—N-(2-methoxy-5-(3,4,5-trimethoxystyryl)phenyl)-4-nitrobenzenesulfonamide (12h)
(Z)-4-amino-N-(2-methoxy-5-(3,4,5-trimethoxystyryl)phenyl)benzenesulfonamide (12i)
(Z)—N-(2-methoxy-5-(3,4,5-trimethoxystyryl)phenyl)-3-(trifluoromethyl)benzenesulfonamide (12j)
(Z)—N-(2-methoxy-5-(3,4,5-trimethoxystyryl)phenyl)-3-(trifluoromethoxy) benzenesulfonamide (12k)
(Z)—N-(2-methoxy-5-(3,4,5-trimethoxystyryl)phenyl)-4-(trifluoromethyl)benzenesulfonamide (12l)
(Z)—N-(2-methoxy-5-(3,4,5-trimethoxystyryl)phenyl)-4-(trifluoromethoxy)benzenesulfonamide (12m)
(Z)—N-(2-methoxy-5-(3,4,5-trimethoxystyryl)phenyl)-3-nitrobenzenesulfonamide (12n)
(Z)-3-amino-N-(2-methoxy-5-(3,4,5-trimethoxystyryl)phenyl)benzenesulfonamide (12o)
(Z)-3-fluoro-N-(2-methoxy-5-(3,4,5-trimethoxystyryl)phenyl)benzenesulfonamide (12p)
(Z)-3-tert-butyl-N-(2-methoxy-5-(3,4,5-trimethoxystyryl)phenyl)benzenesulfonamide (12q)
(Z)-3-fluoro-4-methoxy-N-(2-methoxy-5-(3,4,5-trimethoxystyryl)phenyl)benzenesulfonamide (12r)
(Z)-3-hydroxy-4-methoxy-N-(2-methoxy-5-(3,4,5-trimethoxystyryl)phenyl)benzenesulfonamide (12s)
(Z)-4-methoxy-N-(2-methoxy-5-(3,4,5-trimethoxystyryl)phenyl)-3-nitrobenzenesulfonamide (12t)
(Z)-3-amino-4-methoxy-N-(2-methoxy-5-(3,4,5-trimethoxystyryl)phenyl)benzenesulfonamide (12u)
(Z)-3,4,5-trimethoxy-N-(2-methoxy-5-(3,4,5-trimethoxystyryl)phenyl)benzenesulfonamide (12v)
(Z)—N-(2-methoxy-5-(3,4,5-trimethoxystyryl)phenyl)-4-methylbenzenesulfonamide (12w)
(Z)-3,4-difluoro-N-(2-methoxy-5-(3,4,5-trimethoxystyryl)phenyl)benzenesulfonamide (12x)
(Z)-3-chloro-4-methoxy-N-(2-methoxy-5-(3,4,5-trimethoxystyryl)phenyl)benzenesulfonamide (12y)
(Z)—N-(2,3-dimethoxy-5-(3,4,5-trimethoxystyryl)phenyl)-4-methoxybenzenesulfonamide (13a)
(Z)—N-(2,3-dimethoxy-5-(3,4,5-trimethoxystyryl)phenyl)-3,4-dimethoxybenzenesulfonamide (13b)
(Z)-4-chloro-N-(2,3-dimethoxy-5-(3,4,5-trimethoxystyryl)phenyl)benzenesulfonamide (13c)
(Z)-3-chloro-N-(2,3-dimethoxy-5-(3,4,5-trimethoxystyryl)phenyl)benzenesulfonamide (13d)
(Z)-3,4-dichloro-N-(2,3-dimethoxy-5-(3,4,5-trimethoxystyryl)phenyl)benzenesulfonamide (13e)
(Z)—N-(2,3-dimethoxy-5-(3,4,5-trimethoxystyryl)phenyl)-4-fluorobenzenesulfonamide (13f)
(Z)-4-tert-butyl-N-(2,3-dimethoxy-5-(3,4,5-trimethoxystyryl)phenyl)benzenesulfonamide (13g)
(Z)—N-(2,3-dimethoxy-5-(3,4,5-trimethoxystyryl)phenyl)-4-nitrobenzenesulfonamide (13h)
(Z)-4-amino-N-(2,3-dimethoxy-5-(3,4,5-trimethoxystyryl)phenyl)benzenesulfonamide (13i)
(Z)—N-(2,3-dimethoxy-5-(3,4,5-trimethoxystyryl)phenyl)-3-(trifluoromethyl)benzenesulfonamide (13j)
(Z)—N-(2,3-dimethoxy-5-(3,4,5-trimethoxystyryl)phenyl)-3(trifluoromethoxy) benzenesulfonamide (13k)
(Z)—N-(2,3-dimethoxy-5-(3,4,5-trimethoxystyryl)phenyl)-4-(trifluoromethyl) benzenesulfonamide (13l)
(Z)—N-(2,3-dimethoxy-5-(3,4,5-trimethoxystyryl)phenyl)-4-(trifluoromethoxy)Benzenesulfonamide (13m)
(Z)—N-(2,3-dimethoxy-5-(3,4,5-trimethoxystyryl)phenyl)-3-nitrobenzenesulfonamide (13n)
(Z)-3-amino-N-(2,3-dimethoxy-5-(3,4,5-trimethoxystyryl)phenyl)benzenesulfonamide (13o)
(Z)—N-(2,3-dimethoxy-5-(3,4,5-trimethoxystyryl)phenyl)-3-fluorobenzenesulfonamide (13p)
(Z)-3-tert-butyl-N-(2,3-dimethoxy-5-(3,4,5-trimethoxystyryl)phenyl)benzenesulfonamide (13q)
(Z)—N-(2,3-dimethoxy-5-(3,4,5-trimethoxystyryl)phenyl)-3-fluoro-4-methoxyBenzenesulfonamide (13r)
(Z)—N-(2,3-dimethoxy-5-(3,4,5-trimethoxystyryl)phenyl)-3-hydroxy-4-methoxy Benzenesulfonamide (13s)
(Z)—N-(2,3-dimethoxy-5-(3,4,5-trimethoxystyryl)phenyl)-4-methoxy-3-nitro Benzenesulfonamide (13t)
(Z)-3-amino-N-(2,3-dimethoxy-5-(3,4,5-trimethoxystyryl)phenyl)-4-methoxyBenzenesulfonamide (13u)
(Z)—N-(2,3-dimethoxy-5-(3,4,5-trimethoxystyryl)phenyl)-3,4,5-trimethoxyBenzenesulfonamide (13v)
(Z)—N-(2,3-dimethoxy-5-(3,4,5-trimethoxystyryl)phenyl)-4-methyl benzene sulfonamide (13w)
(Z)—N-(2,3-dimethoxy-5-(3,4,5-trimethoxystyryl)phenyl)-3,4-difluoro Benzenesulfonamide (13x)
(Z)-3-chloro-N-(2,3-dimethoxy-5-(3,4,5-trimethoxystyryl)phenyl)-4-methoxybenzene sulfonamide (13y)
(Z)—N-(3-hydroxy-2-methoxy-5-(3,4,5-trimethoxystyryl)phenyl)-4-methoxy benzene sulfonamide (14a)
(Z)—N-(3-hydroxy-2-methoxy-5-(3,4,5-trimethoxystyryl)phenyl)-3,4-dimethoxybenzenesulfonamide (14b)
(Z)-4-chloro-N-(3-hydroxy-2-methoxy-5-(3,4,5-trimethoxystyryl)phenyl)benzenesulfonamide (14c)
(Z)-3-chloro-N-(3-hydroxy-2-methoxy-5-(3,4,5-trimethoxystyryl) phenyl)benzenesulfonamide (14d)
(Z)-3,4-dichloro-N-(3-hydroxy-2-methoxy-5-(3,4,5-trimethoxystyryl)phenyl)benzenesulfonamide (14e)
(Z)-4-fluoro-N-(3-hydroxy-2-methoxy-5-(3,4,5-trimethoxystyryl)phenyl)benzenesulfonamide (14f)
(Z)-4-tert-butyl-N-(3-hydroxy-2-methoxy-5-(3,4,5-trimethoxystyryl)phenyl)benzenesulfonamide (14g)
(Z)—N-(3-hydroxy-2-methoxy-5-(3,4,5-trimethoxystyryl)phenyl)-4-nitrobenzenesulfonamide (14h)
(Z)-4-amino-N-(3-hydroxy-2-methoxy-5-(3,4,5-trimethoxystyryl)phenyl)benzenesulfonamide (14i)
(Z)—N-(3-hydroxy-2-methoxy-5-(3,4,5-trimethoxystyryl)phenyl)-3-(trifluoromethyl)benzenesulfonamide (14j)
(Z)—N-(3-hydroxy-2-methoxy-5-(3,4,5-trimethoxystyryl)phenyl)-3-(trifluoromethoxy)benzenesulfonamide (14k)
(Z)—N-(3-hydroxy-2-methoxy-5-(3,4,5-trimethoxystyryl)phenyl)-4-(trifluoromethyl)benzenesulfonamide (14l)
(Z)—N-(3-hydroxy-2-methoxy-5-(3,4,5-trimethoxystyryl)phenyl)-4-(trifluoromethoxy)benzenesulfonamide (14m)
(Z)—N-(3-hydroxy-2-methoxy-5-(3,4,5-trimethoxystyryl)phenyl)-3-nitrobenzenesulfonamide (14n)
(Z)-3-amino-N-(3-hydroxy-2-methoxy-5-(3,4,5-trimethoxystyryl)phenyl)benzenesulfonamide (14o)
(Z)-3-fluoro-N-(3-hydroxy-2-methoxy-5-(3,4,5-trimethoxystyryl)phenyl)benzenesulfonamide (14p)
(Z)-3-tert-butyl-N-(3-hydroxy-2-methoxy-5-(3,4,5-trimethoxystyryl)phenyl)benzenesulfonamide (14q)
(Z)-3-fluoro-N-(3-hydroxy-2-methoxy-5-(3,4,5-trimethoxystyryl)phenyl)-4-methoxybenzenesulfonamide (14r)
(Z)-3-hydroxy-N-(3-hydroxy-2-methoxy-5-(3,4,5-trimethoxystyryl)phenyl)-4-ethoxybenzenesulfonamide (14s)

(Z)—N-(3-hydroxy-2-methoxy-5-(3,4,5-trimethoxystyryl)phenyl)-4-methoxy-3-nitrobenzenesulfonamide (14t)
(Z)-3-amino-N-(3-hydroxy-2-methoxy-5-(3,4,5-trimethoxystyryl)phenyl)-4-ethoxybenzenesulfonamide (14u)
(Z)—N-(3-hydroxy-2-methoxy-5-(3,4,5-trimethoxystyryl)phenyl)-3,4,5-trimethoxybenzenesulfonamide (14v)
(Z)—N-(3-hydroxy-2-methoxy-5-(3,4,5-trimethoxystyryl)phenyl)-4-methylbenzenesulfonamide (14w)
(Z)-3,4-difluoro-N-(3-hydroxy-2-methoxy-5-(3,4,5-trimethoxystyryl)phenyl)benzenesulfonamide (14x)
(Z)-3-chloro-N-(3-hydroxy-2-methoxy-5-(3,4,5-trimethoxystyryl)phenyl)-4-methoxybenzenesulfonamide (14y)
(Z)—N-(3-fluoro-2-methoxy-5-(3,4,5-trimethoxystyryl)phenyl)-4-methoxybenzenesulfonamide (15a)
(Z)—N-(3-fluoro-2-methoxy-5-(3,4,5-trimethoxystyryl)phenyl)-3,4-dimethoxybenzenesulfonamide (15b)
(Z)-4-chloro-N-(3-fluoro-2-methoxy-5-(3,4,5-trimethoxystyryl)phenyl)benzenesulfonamide (15c)
(Z)-3-chloro-N-(3-fluoro-2-methoxy-5-(3,4,5-trimethoxystyryl)phenyl)benzenesulfonamide (15d)
(Z)-3,4-dichloro-N-(3-fluoro-2-methoxy-5-(3,4,5-trimethoxystyryl)phenyl)benzenesulfonamide (15e)
(Z)-4-fluoro-N-(3-fluoro-2-methoxy-5-(3,4,5-trimethoxystyryl)phenyl)benzenesulfonamide (15f)
(Z)-4-tert-butyl-N-(3-fluoro-2-methoxy-5-(3,4,5-trimethoxystyryl)phenyl)benzenesulfonamide (15g)
(Z)—N-(3-fluoro-2-methoxy-5-(3,4,5-trimethoxystyryl)phenyl)-4-nitrobenzenesulfonamide (15h)
(Z)-4-amino-N-(3-fluoro-2-methoxy-5-(3,4,5-trimethoxystyryl)phenyl)benzenesulfonamide (15i)
(Z)—N-(3-fluoro-2-methoxy-5-(3,4,5-trimethoxystyryl)phenyl)-3-(trifluoromethyl)benzenesulfonamide (15j)
(Z)—N-(3-fluoro-2-methoxy-5-(3,4,5-trimethoxystyryl)phenyl)-3-(trifluoromethoxy)benzenesulfonamide (15k)
(Z)—N-(3-fluoro-2-methoxy-5-(3,4,5-trimethoxystyryl)phenyl)-4-(trifluoromethyl)benzenesulfonamide (15l)
(Z)—N-(3-fluom-2-methoxy-5-(3,4,5-trimethoxystyryl)phenyl)-4-(trifluoromethoxy)benzenesulfonamide (15m)
(Z)—N-(3-fluoro-2-methoxy-5-(3,4,5-trimethoxystyryl)phenyl)-3-nitrobenzenesulfonamide (15n)
(Z)-3-amino-N-(3-fluoro-2-methoxy-5-(3,4,5-trimethoxystyryl)phenyl)benzenesulfonamide (15o)
(Z)-3-fluoro-N-(3-fluoro-2-methoxy-5-(3,4,5-trimethoxystyryl)phenyl)benzenesulfonamide (15p)
(Z)-3-tert-butyl-N-(3-fluoro-2-methoxy-5-(3,4,5-trimethoxystyryl)phenyl)benzenesulfonamide (15q)
(Z)-3-fluoro-N-(3-fluoro-2-methoxy-5-(3,4,5-trimethoxystyryl)phenyl)-4-methoxybenzenesulfonamide (15r)
(Z)—N-(3-fluoro-2-methoxy-5-(3,4,5-trimethoxystyryl)phenyl)-3-hydroxy-4-methoxybenzenesulfonamide (15s)
(Z)—N-(3-fluoro-2-methoxy-5-(3,4,5-trimethoxystyryl)phenyl)-4-methoxy-3-nitrobenzenesulfonamide (15t)
(Z)-3-amino-N-(3-fluoro-2-methoxy-5-(3,4,5-trimethoxystyryl)phenyl)-4-methoxybenzenesulfonamide (15u)
(Z)—N-(3-fluoro-2-methoxy-5-(3,4,5-trimethoxystyryl)phenyl)-3,4,5-trimethoxybenzenesulfonamide (15v)
(Z)—N-(3-fluoro-2-methoxy-5-(3,4,5-trimethoxystyryl)phenyl)-4-methyl benzenesulfonamide (15w)
(Z)-3,4-difluoro-N-(3-fluoro-2-methoxy-5-(3,4,5-trimethoxystyryl)phenyl)benzenesulfonamide (15x)
(Z)-3-chloro-N-(3-fluoro-2-methoxy-5-(3,4,5-trimethoxystyryl)phenyl)-4-methoxybenzenesulfonamide (15y)
(Z)—N-(2-hydroxy-3-methoxy-5-(3,4,5-trimethoxystyryl)phenyl)-4-methoxybenzenesulfonamide (16a)
(Z)—N-(2-hydroxy-3-methoxy-5-(3,4,5-trimethoxystyryl)phenyl)-3,4-dimethoxybenzenesulfonamide (16b)
(Z)-4-chloro-N-(2-hydroxy-3-methoxy-5-(3,4,5-trimethoxystyryl)phenyl)benzenesulfonamide (16c)
(Z)-3-chloro-N-(2-hydroxy-3-methoxy-5-(3,4,5-trimethoxystyryl)phenyl)Benzenesulfonamide (16d)
(Z)-3,4-dichloro-N-(2-hydroxy-3-methoxy-5-(3,4,5-trimethoxystyryl)phenyl)benzenesulfonamide (16e)
(Z)-4-fluoro-N-(2-hydroxy-3-methoxy-5-(3,4,5-trimethoxystyryl)phenyl)benzenesulfonamide (16f)
(Z)-4-tert-butyl-N-(2-hydroxy-3-methoxy-5-(3,4,5-trimethoxystyryl)phenyl)benzenesulfonamide (16g)
(Z)—N-(2-hydroxy-3-methoxy-5-(3,4,5-trimethoxystyryl)phenyl)-4-nitrobenzenesulfonamide (16h)
(Z)-4-amino-N-(2-hydroxy-3-methoxy-5-(3,4,5-trimethoxystyryl)phenyl)benzenesulfonamide (16i)
(Z)—N-(2-hydroxy-3-methoxy-5-(3,4,5-trimethoxystyryl)phenyl)-3-(trifluoromethyl)benzenesulfonamide (16j)
(Z)—N-(2-hydroxy-3-methoxy-5-(3,4,5-trimethoxystyryl)phenyl)-3-(trifluoromethoxy)benzenesulfonamide (16k)
(Z)—N-(2-hydroxy-3-methoxy-5-(3,4,5-trimethoxystyryl)phenyl)-4-(trifluoromethyl)benzenesulfonamide (16l)
(Z)—N-(2-hydroxy-3-methoxy-5-(3,4,5-trimethoxystyryl)phenyl)-4-(trifluoromethoxy) benzenesulfonamide (16m)
(Z)—N-(2-hydroxy-3-methoxy-5-(3,4,5-trimethoxystyryl)phenyl)-3-nitrobenzenesulfonamide (16n)
(Z)-3-amino-N-(2-hydroxy-3-methoxy-5-(3,4,5-trimethoxystyryl)phenyl) benzenesulfonamide (16o)
(Z)-3-fluoro-N-(2-hydroxy-3-methoxy-5-(3,4,5-trimethoxystyryl)phenyl)benzenesulfonamide (16p)
(Z)-3-tert-butyl-N-(2-hydroxy-3-methoxy-5-(3,4,5-trimethoxystyryl)phenyl)benzenesulfonamide (16q)
(Z)-3-fluoro-N-(2-hydroxy-3-methoxy-5-(3,4,5-trimethoxystyryl)phenyl)-4-methoxybenzenesulfonamide (16r)
(Z)-3-hydroxy-N-(2-hydroxy-3-methoxy-5-(3,4,5-trimethoxystyryl)phenyl)-4-methoxybenzenesulfonamide (16s)
(Z)—N-(2-hydroxy-3-methoxy-5-(3,4,5-trimethoxystyryl)phenyl)-4-methoxy-3-nitrobenzenesulfonamide (16t)
(Z)-3-amino-N-(2-hydroxy-3-methoxy-5-(3,4,5-trimethoxystyryl)phenyl)-4-methoxybenzenesulfonamide (16u)
(Z)—N-(2-hydroxy-3-methoxy-5-(3,4,5-trimethoxystyryl)phenyl)-3,4,5-trimethoxybenzenesulfonamide (16v)
(Z)—N-(2-hydroxy-3-methoxy-5-(3,4,5-trimethoxystyryl)phenyl)-4-methylbenzenesulfonamide (16w)
(Z)-3,4-difluoro-N-(2-hydroxy-3-methoxy-5-(3,4,5-trimethoxystyryl)phenyl)benzenesulfonamide (16x)
(Z)-3-chloro-N-(2-hydroxy-3-methoxy-5-(3,4,5-trimethoxystyryl)phenyl)-4-methoxybenzenesulfonamide (16y)
(Z)—N-(2-hydroxy-3-methoxy-6-(3,4,5-trimethoxystyryl)phenyl)-4-methoxybenzenesulfonamide (17a)

(Z)—N-(2-hydroxy-3-methoxy-6-(3,4,5-trimethoxystyryl)phenyl)-3,4-dimethoxybenzenesulfonamide (17b)
(Z)-4-chloro-N-(2-hydroxy-3-methoxy-6-(3,4,5-trimethoxystyryl)phenyl)benzenesulfonamide (17c)
(Z)-3-chloro-N-(2-hydroxy-3-methoxy-6-(3,4,5-trimethoxystyryl)phenyl)benzenesulfonamide (17d)
(Z)-3,4-dichloro-N-(2-hydroxy-3-methoxy-6-(3,4,5-trimethoxystyryl)phenyl)benzenesulfonamide (17e)
(Z)-4-fluoro-N-(2-hydroxy-3-methoxy-6-(3,4,5-trimethoxystyryl)phenyl)benzenesulfonamide (17f)
(Z)-4-tert-butyl-N-(2-hydroxy-3-methoxy-6-(3,4,5-trimethoxystyryl)phenyl)benzenesulfonamide (17g)
(Z)—N-(2-hydroxy-3-methoxy-6-(3,4,5-trimethoxystyryl)phenyl)-4-nitrobenzenesulfonamide (17h)
(Z)—N-(2-hydroxy-3-methoxy-6-(3,4,5-trimethoxystyryl)phenyl)-3-(trifluoromethyl)benzenesulfonamide (17i)
(Z)—N-(2-hydroxy-3-methoxy-6-(3,4,5-trimethoxystyryl)phenyl)-3-(trifluoromethoxy)benzenesulfonamide (17j)
(Z)—N-(2-hydroxy-3-methoxy-6-(3,4,5-trimethoxystyryl)phenyl)-3-(trifluoromethoxy)benzenesulfonamide (17k)
(Z)—N-(2-hydroxy-3-methoxy-6-(3,4,5-trimethoxystyryl)phenyl)-4-(trifluoromethyl)benzenesulfonamide (17l)
(Z)—N-(2-hydroxy-3-methoxy-6-(3,4,5-trimethoxystyryl)phenyl)-4-(trifluoromethoxy)benzenesulfonamide (17m)
(Z)—N-(2-hydroxy-3-methoxy-6-(3,4,5-trimethoxystyryl)phenyl)-3-nitrobenzenesulfonamide (17n)
(Z)-3-amino-N-(2-hydroxy-3-methoxy-6-(3,4,5-trimethoxystyryl)phenyl)benzenesulfonamide (17o)
(Z)-3-fluoro-N-(2-hydroxy-3-methoxy-6-(3,4,5-trimethoxystyryl)phenyl)benzenesulfonamide (17p)
(Z)-3-tert-butyl-N-(2-hydroxy-3-methoxy-6-(3,4,5-trimethoxystyryl)phenyl)benzenesulfonamide (17q)
(Z)-3-fluoro-N-(2-hydroxy-3-methoxy-6-(3,4,5-trimethoxystyryl)phenyl)-4-methoxybenzenesulfonamide (17r)
(Z)-3-hydroxy-N-(2-hydroxy-3-methoxy-6-(3,4,5-trimethoxystyryl)phenyl)-4-methoxybenzenesulfonamide (17s)
(Z)—N-(2-hydroxy-3-methoxy-6-(3,4,5-trimethoxystyryl)phenyl)-4-methoxy-3-nitrobenzenesulfonamide (17t)
(Z)—N-(2-hydroxy-3-methoxy-6-(3,4,5-trimethoxystyryl)phenyl)-3,4,5-trimethoxybenzenesulfonamide (17u)
(Z)—N-(2-hydroxy-3-methoxy-6-(3,4,5-trimethoxystyryl)phenyl)-4-methylbenzenesulfonamide (17v)
(Z)-4-hydroxy-N-(2-hydroxy-3-methoxy-6-(3,4,5-trimethoxystyryl)phenyl)benzenesulfonamide (17w)
(Z)-3,4-difluoro-N-(2-hydroxy-3-methoxy-6-(3,4,5-trimethoxystyryl)phenyl)benzenesulfonamide (17x)
(Z)-3-chloro-N-(2-hydroxy-3-methoxy-6-(3,4,5-trimethoxystyryl)phenyl)-4-methoxybenzenesulfonamide (17y)
(Z)—N-(4-hydroxy-5-methoxy-2-(3,4,5-trimethoxystyryl)phenyl)-4-methoxybenzenesulfonamide (18a)
(Z)—N-(4-hydroxy-5-methoxy-2-(3,4,5-trimethoxystyryl)phenyl)-3,4-dimethoxybenzenesulfonamide (18b)
(Z)-4-chloro-N-(4-hydroxy-5-methoxy-2-(3,4,5-trimethoxystyryl)phenyl)benzenesulfonamide (18c)
(Z)-3-chloro-N-(4-hydroxy-5-methoxy-2-(3,4,5-trimethoxystyryl)phenyl)benzenesulfonamide (18d)
(Z)-3,4-dichloro-N-(4-hydroxy-5-methoxy-2-(3,4,5-trimethoxystyryl)phenyl)benzenesulfonamide (18e)
(Z)-4-fluoro-N-(4-hydroxy-5-methoxy-2-(3,4,5-trimethoxystyryl)phenyl)benzenesulfonamide (18f)
(Z)-4-tert-butyl-N-(4-hydroxy-5-methoxy-2-(3,4,5-trimethoxystyryl)phenyl)benzenesulfonamide (18g)
(Z)—N-(4-hydroxy-5-methoxy-2-(3,4,5-trimethoxystyryl)phenyl)-4-nitrobenzenesulfonamide (18h)
(Z)-4-amino-N-(4-hydroxy-5-methoxy-2-(3,4,5-trimethoxystyryl)phenyl)benzenesulfonamide (18i)
(Z)—N-(4-hydroxy-5-methoxy-2-(3,4,5-trimethoxystyryl)phenyl)-3-(trifluoromethyl)benzenesulfonamide (18j)
(Z)—N-(4-hydroxy-5-methoxy-2-(3,4,5-trimethoxystyryl)phenyl)-4-(trifluoromethyl)benzenesulfonamide (18k)
(Z)—N-(4-hydroxy-5-methoxy-2-(3,4,5-trimethoxystyryl)phenyl)-4-(trifluoromethyl)benzenesulfonamide (18l)
(Z)—N-(4-hydroxy-5-methoxy-2-(3,4,5-trimethoxystyryl)phenyl)-4-(trifluoromethoxy)benzenesulfonamide (18m)
(Z)—N-(4-hydroxy-5-methoxy-2-(3,4,5-trimethoxystyryl)phenyl)-3-nitrobenzenesulfonamide (18n)
(Z)-3-amino-N-(4-hydroxy-5-methoxy-2-(3,4,5-trimethoxystyryl)phenyl)benzenesulfonamide (18o)
(Z)-3-fluoro-N-(4-hydroxy-5-methoxy-2-(3,4,5-trimethoxystyryl)phenyl)benzenesulfonamide (18p)
(Z)-3-tert-butyl-N-(4-hydroxy-5-methoxy-2-(3,4,5-trimethoxystyryl)phenyl)benzenesulfonamide (18q)
(Z)-3-fluoro-N-(4-hydroxy-5-methoxy-2-(3,4,5-trimethoxystyryl)phenyl)-4-methoxybenzenesulfonamide (18r)
(Z)-3-hydroxy-N-(4-hydroxy-5-methoxy-2-(3,4,5-trimethoxystyryl)phenyl)-4-methoxybenzenesulfonamide (18s)
(Z)—N-(4-hydroxy-5-methoxy-2-(3,4,5-trimethoxystyryl)phenyl)-4-methoxy-3-nitrobenzenesulfonamide (18t)
(Z)—N-(4-hydroxy-5-methoxy-2-(3,4,5-trimethoxystyryl)phenyl)-3,4,5-trimethoxybenzenesulfonamide (18u)
(Z)—N-(4-hydroxy-5-methoxy-2-(3,4,5-trimethoxystyryl)phenyl)-4-methylbenzenesulfonamide (18v)
(Z)-4-hydroxy-N-(4-hydroxy-5-methoxy-2-(3,4,5-trimethoxystyryl)phenyl)benzenesulfonamide (18w)
(Z)-3,4-difluoro-N-(4-hydroxy-5-methoxy-2-(3,4,5-trimethoxystyryl)phenyl)benzenesulfonamide (18x)
(Z)-3-chloro-N-(4-hydroxy-5-methoxy-2-(3,4,5-trimethoxystyryl)phenyl)-4-methoxybenzenesulfonamide (18y)
(Z)—N-(2-fluoro-3-methoxy-6-(3,4,5-trimethoxystyryl)phenyl)-4-methoxybenzenesulfonamide (19a)
(Z)—N-(2-fluoro-3-methoxy-6-(3,4,5-trimethoxystyryl)phenyl)-3,4-dimethoxybenzenesulfonamide (19b)
(Z)-4-chloro-N-(2-fluoro-3-methoxy-6-(3,4,5-trimethoxystyryl)phenyl)benzenesulfonamide (19c)
(Z)-3-chloro-N-(2-fluoro-3-methoxy-6-(3,4,5-trimethoxystyryl)phenyl)benzenesulfonamide (19d)
(Z)-3,4-dichloro-N-(2-fluoro-3-methoxy-6-(3,4,5-trimethoxystyryl)phenyl)benzenesulfonamide (19e)
(Z)-4-fluoro-N-(2-fluoro-3-methoxy-6-(3,4,5-trimethoxystyryl)phenyl)benzenesulfonamide (19f)
(Z)-4-tert-butyl-N-(2-fluoro-3-methoxy-6-(3,4,5-trimethoxystyryl)phenyl)benzenesulfonamide (19g)

(Z)—N-(2-fluoro-3-methoxy-6-(3,4,5-trimethoxystyryl)phenyl)-4-nitrobenzenesulfonamide (19h)
(Z)-4-amino-N-(2-fluoro-3-methoxy-6-(3,4,5-trimethoxystyryl)phenyl)benzenesulfonamide (19i)
(Z)—N-(2-fluoro-3-methoxy-6-(3,4,5-trimethoxystyryl)phenyl)-3-(trifluoromethyl)benzenesulfonamide (19j)
(Z)—N-(2-fluoro-3-methoxy-6-(3,4,5-trimethoxystyryl)phenyl)-3-(trifluoromethoxy) benzenesulfonamide (19k)
(Z)—N-(2-fluoro-3-methoxy-6-(3,4,5-trimethoxystyryl)phenyl)-4-(trifluoromethyl)benzenesulfonamide (19l)
(Z)—N-(2-fluoro-3-methoxy-6-(3,4,5-trimethoxystyryl)phenyl)-4-(trifluoromethoxy)benzenesulfonamide (19m)
(Z)—N-(2-fluoro-3-methoxy-6-(3,4,5-trimethoxystyryl)phenyl)-3-nitrobenzenesulfonamide (19n)
(Z)-3-amino-N-(2-fluoro-3-methoxy-6-(3,4,5-trimethoxystyryl)phenyl)benzenesulfonamide (19o)
(Z)-3-fluoro-N-(2-fluoro-3-methoxy-6-(3,4,5-trimethoxystyryl)phenyl)benzenesulfonamide (19p)
(Z)-3-tert-butyl-N-(2-fluoro-3-methoxy-6-(3,4,5-trimethoxystyryl)phenyl)benzenesulfonamide (19q)
(Z)-3-fluoro-N-(2-fluoro-3-methoxy-6-(3,4,5-trimethoxystyryl)phenyl)-4-methoxybenzenesulfonamide (19r)
(Z)—N-(2-fluoro-3-methoxy-6-(3,4,5-trimethoxystyryl)phenyl)-3-hydroxy-4-methoxybenzenesulfonamide (19s)
(Z)—N-(2-fluoro-3-methoxy-6-(3,4,5-trimethoxystyryl)phenyl)-4-methoxy-3-nitrobenzenesulfonamide (19t)
(Z)—N-(2-fluoro-3-methoxy-6-(3,4,5-trimethoxystyryl)phenyl)-3,4,5-trimethoxybenzenesulfonamide (19u)
(Z)—N-(2-fluoro-3-methoxy-6-(3,4,5-trimethoxystyryl)phenyl)-4-methylbenzenesulfonamide (19v)
(Z)—N-(2-fluoro-3-methoxy-6-(3,4,5-trimethoxystyryl)phenyl)-4-hydroxybenzenesulfonamide (19w)
(Z)-3,4-difluoro-N-(2-fluoro-3-methoxy-6-(3,4,5-trimethoxystyryl)phenyl)benzenesulfonamide (19x)
(Z)-3-chloro-N-(2-fluoro-3-methoxy-6-(3,4,5-trimethoxystyryl)phenyl)-4-methoxybenzenesulfonamide (19y)
(Z)—N-(3-fluoro-2-methoxy-6-(3,4,5-trimethoxystyryl)phenyl)-4-methoxybenzenesulfonamide (20a)
(Z)—N-(3-fluoro-2-methoxy-6-(3,4,5-trimethoxystyryl)phenyl)-3,4-dimethoxybenzenesulfonamide (20b)
(Z)-4-chloro-N-(3-fluoro-2-methoxy-6-(3,4,5-trimethoxystyryl)phenyl)benzenesulfonamide (20c)
(Z)-3-chloro-N-(3-fluoro-2-methoxy-6-(3,4,5-trimethoxystyryl)phenyl)benzenesulfonamide (20d)
(Z)-3,4-dichloro-N-(3-fluoro-2-methoxy-6-(3,4,5-trimethoxystyryl)phenyl) benzenesulfonamide (20e)
(Z)-4-fluoro-N-(3-fluoro-2-methoxy-6-(3,4,5-trimethoxystyryl)phenyl)benzenesulfonamide (20f)
(Z)-4-tert-butyl-N-(3-fluoro-2-methoxy-6-(3,4,5-trimethoxystyryl)phenyl)benzenesulfonamide (20g)
(Z)—N-(3-fluoro-2-methoxy-6-(3,4,5-trimethoxystyryl)phenyl)-4-nitrobenzenesulfonamide (20h)
(Z)-4-amino-N-(3-fluoro-2-methoxy-6-(3,4,5-trimethoxystyryl)phenyl)benzenesulfonamide (20i)
(Z)—N-(3-fluoro-2-methoxy-6-(3,4,5-trimethoxystyryl)phenyl)-3-(trifluoromethyl)benzenesulfonamide (20j)
(Z)—N-(3-fluoro-2-methoxy-6-(3,4,5-trimethoxystyryl)phenyl)-3-(trifluoromethoxy)benzenesulfonamide (20k)
(Z)—N-(3-fluoro-2-methoxy-6-(3,4,5-trimethoxystyryl)phenyl)-4-(trifluoromethyl)benzenesulfonamide (20l)
(Z)—N-(3-fluoro-2-methoxy-6-(3,4,5-trimethoxystyryl)phenyl)-4-(trifluoromethoxy)benzenesulfonamide (20m)
(Z)—N-(3-fluoro-2-methoxy-6-(3,4,5-trimethoxystyryl)phenyl)-3-nitrobenzenesulfonamide (20n)
(Z)-3-amino-N-(3-fluoro-2-methoxy-6-(3,4,5-trimethoxystyryl)phenyl)benzenesulfonamide (20o)
(Z)-3-fluoro-N-(3-fluoro-2-methoxy-6-(3,4,5-trimethoxystyryl)phenyl)benzenesulfonamide (20p)
(Z)-3-tert-butyl-N-(3-fluoro-2-methoxy-6-(3,4,5-trimethoxystyryl)phenyl)benzenesulfonamide (20q)
(Z)-3-fluoro-N-(3-fluoro-2-methoxy-6-(3,4,5-trimethoxystyryl)phenyl)-4-methoxybenzenesulfonamide (20r)
(Z)—N-(3-fluoro-2-methoxy-6-(3,4,5-trimethoxystyryl)phenyl)-3-hydroxy-4-methoxybenzenesulfonamide (20s)
(Z)—N-(3-fluoro-2-methoxy-6-(3,4,5-trimethoxystyryl)phenyl)-4-methoxy-3-nitrobenzenesulfonamide (20t)
(Z)—N-(3-fluoro-2-methoxy-6-(3,4,5-trimethoxystyryl)phenyl)-3,4,5-trimethoxybenzenesulfonamide (20u)
(Z)—N-(3-fluoro-2-methoxy-6-(3,4,5-trimethoxystyryl)phenyl)-4-methylbenzenesulfonamide (20v)
(Z)—N-(3-fluoro-2-methoxy-6-(3,4,5-trimethoxystyryl)phenyl)-4-hydroxybenzenesulfonamide (20w)
(Z)-3,4-difluoro-N-(3-fluoro-2-methoxy-6-(3,4,5-trimethoxystyryl)phenyl)benzenesulfonamide (20x)
(Z)-3-chloro-N-(3-fluoro-2-methoxy-6-(3,4,5-trimethoxystyryl)phenyl)-4-methoxybenzenesulfonamide (20y)
(Z)—N-(3-hydroxy-2-methoxy-6-(3,4,5-trimethoxystyryl)phenyl)-4-methoxybenzenesulfonamide (21a)
(Z)—N-(3-hydroxy-2-methoxy-6-(3,4,5-trimethoxystyryl)phenyl)-3,4-dimethoxybenzenesulfonamide (21b)
(Z)-4-chloro-N-(3-hydroxy-2-methoxy-6-(3,4,5-trimethoxystyryl)phenyl)benzenesulfonamide (21c)
(Z)-3-chloro-N-(3-hydroxy-2-methoxy-6-(3,4,5-trimethoxystyryl)phenyl)benzenesulfonamide (21d)
(Z)-3,4-dichloro-N-(3-hydroxy-2-methoxy-6-(3,4,5-trimethoxystyryl)phenyl)benzenesulfonamide (21e)
(Z)-4-fluoro-N-(3-hydroxy-2-methoxy-6-(3,4,5-trimethoxystyryl)phenyl)benzenesulfonamide (21f)
(Z)-4-tert-butyl-N-(3-hydroxy-2-methoxy-6-(3,4,5-trimethoxystyryl)phenyl)benzenesulfonamide (21g)
(Z)—N-(3-hydroxy-2-methoxy-6-(3,4,5-trimethoxystyryl)phenyl)-4-nitrobenzenesulfonamide (21h)
(Z)-4-amino-N-(3-hydroxy-2-methoxy-6-(3,4,5-trimethoxystyryl)phenyl)benzenesulfonamide (21i)
(Z)—N-(3-hydroxy-2-methoxy-6-(3,4,5-trimethoxystyryl)phenyl)-3-(trifluoromethyl)benzenesulfonamide (21j)
(Z)—N-(3-hydroxy-2-methoxy-6-(3,4,5-trimethoxystyryl)phenyl)-3-(trifluoromethoxy)benzenesulfonamide (21k)
(Z)—N-(3-hydroxy-2-methoxy-6-(3,4,5-trimethoxystyryl)phenyl)-4-(trifluoromethyl)benzenesulfonamide (21l)
(Z)—N-(3-hydroxy-2-methoxy-6-(3,4,5-trimethoxystyryl)phenyl)-4-(trifluoromethoxy)benzenesulfonamide (21m)
(Z)—N-(3-hydroxy-2-methoxy-6-(3,4,5-trimethoxystyryl)phenyl)-3-nitrobenzenesulfonamide (21n)
(Z)-3-amino-N-(3-hydroxy-2-methoxy-6-(3,4,5-trimethoxystyryl)phenyl)benzenesulfonamide (21o)
(Z)-3-fluoro-N-(3-hydroxy-2-methoxy-6-(3,4,5-trimethoxystyryl)phenyl)benzenesulfonamide (21p)
(Z)-3-tert-butyl-N-(3-hydroxy-2-methoxy-6-(3,4,5-trimethoxystyryl)phenyl)benzenesulfonamide (21q)
(Z)-3-fluoro-N-(3-hydroxy-2-methoxy-6-(3,4,5-trimethoxystyryl)phenyl)-4-methoxybenzenesulfonamide (21r)

(Z)-3-hydroxy-N-(3-hydroxy-2-methoxy-6-(3,4,5-trimethoxystyryl)phenyl)-4-methoxybenzenesulfonamide (21s)

(Z)—N-(3-hydroxy-2-methoxy-6-(3,4,5-trimethoxystyryl)phenyl)-4-methoxy-3-nitrobenzenesulfonamide (21t)

(Z)—N-(3-hydroxy-2-methoxy-6-(3,4,5-trimethoxystyryl)phenyl)-3,4,5-trimethoxybenzenesulfonamide (21u)

(Z)—N-(3-hydroxy-2-methoxy-6-(3,4,5-trimethoxystyryl)phenyl)-4-methylbenzenesulfonamide (21v)

(Z)-4-hydroxy-N-(3-hydroxy-2-methoxy-6-(3,4,5-trimethoxystyryl)phenyl)benzenesulfonamide (21w)

(Z)-3,4-difluoro-N-(3-hydroxy-2-methoxy-6-(3,4,5-trimethoxystyryl)phenyl)benzenesulfonamide (21x)

(Z)-3-chloro-N-(3-hydroxy-2-methoxy-6-(3,4,5-trimethoxystyryl)phenyl)-4-methoxybenzenesulfonamide (21y)

(Z)—N-(2,3-dimethoxy-6-(3,4,5-trimethoxystyryl)phenyl)-4-methoxybenzenesulfonamide (22a)

(Z)—N-(2,3-dimethoxy-6-(3,4,5-trimethoxystyryl)phenyl)-3,4-dimethoxybenzenesulfonamide (22b)

(Z)-4-chloro-N-(2,3-dimethoxy-6-(3,4,5-trimethoxystyryl)phenyl)benzenesulfonamide (22c)

(Z)-3-chloro-N-(2,3-dimethoxy-6-(3,4,5-trimethoxystyryl)phenyl)benzenesulfonamide (22d)

(Z)-3,4-dichloro-N-(2,3-dimethoxy-6-(3,4,5-trimethoxystyryl)phenyl)benzenesulfonamide (22e)

(Z)—N-(2,3-dimethoxy-6-(3,4,5-trimethoxystyryl)phenyl)-4-fluorobenzenesulfonamide (22f)

(Z)-4-tert-butyl-N-(2,3-dimethoxy-6-(3,4,5-trimethoxystyryl)phenyl)benzenesulfonamide (22g)

(Z)—N-(2,3-dimethoxy-6-(3,4,5-trimethoxystyryl)phenyl)-4-nitrobenzenesulfonamide (22h)

(Z)-4-amino-N-(2,3-dimethoxy-6-(3,4,5-trimethoxystyryl)phenyl)benzenesulfonamide (22i)

(Z)—N-(2,3-dimethoxy-6-(3,4,5-trimethoxystyryl)phenyl)-3-(trifluoromethyl)benzenesulfonamide (22j)

(Z)—N-(2,3-dimethoxy-6-(3,4,5-trimethoxystyryl)phenyl)-3-(trifluoromethoxy)benzenesulfonamide (22k)

(Z)—N-(2,3-dimethoxy-6-(3,4,5-trimethoxystyryl)phenyl)-4-(trifluoromethyl)benzenesulfonamide (22l)

(Z)—N-(2,3-dimethoxy-6-(3,4,5-trimethoxystyryl)phenyl)-4-(trifluoromethoxy)benzenesulfonamide (22m)

(Z)—N-(2,3-dimethoxy-6-(3,4,5-trimethoxystyryl)phenyl)-3-nitrobenzenesulfonamide (22n)

(Z)-3-amino-N-(2,3-dimethoxy-6-(3,4,5-trimethoxystyryl)phenyl)benzenesulfonamide (22o)

(Z)—N-(2,3-dimethoxy-6-(3,4,5-trimethoxystyryl)phenyl)-3-fluorobenzenesulfonamide (22p)

(Z)-3-tert-butyl-N-(2,3-dimethoxy-6-(3,4,5-trimethoxystyryl)phenyl)benzenesulfonamide (22q)

(Z)—N-(2,3-dimethoxy-6-(3,4,5-trimethoxystyryl)phenyl)-3-fluoro-4-methoxybenzenesulfonamide (22r)

(Z)—N-(2,3-dimethoxy-6-(3,4,5-trimethoxystyryl)phenyl)-3-hydroxy-4-methoxybenzenesulfonamide (22s)

(Z)—N-(2,3-dimethoxy-6-(3,4,5-trimethoxystyryl)phenyl)-4-methoxy-3-nitrobenzenesulfonamide (22t)

(Z)—N-(2,3-dimethoxy-6-(3,4,5-trimethoxystyryl)phenyl)-3,4,5-trimethoxybenzenesulfonamide (22u)

(Z)—N-(2,3-dimethoxy-6-(3,4,5-trimethoxystyryl)phenyl)-4-methylbenzenesulfonamide (22v)

(Z)—N-(2,3-dimethoxy-6-(3,4,5-trimethoxystyryl)phenyl)-4-hydroxybenzenesulfonamide (22w)

(Z)—N-(2,3-dimethoxy-6-(3,4,5-trimethoxystyryl)phenyl)-3,4-difluorobenzenesulfonamide (22x)

(Z)-3-chloro-N-(2,3-dimethoxy-6-(3,4,5-trimethoxystyryl)phenyl)-4-methoxybenzenesulfonamide (22y)

(Z)—N-(4,5-dimethoxy-2-(3,4,5-trimethoxystyryl)phenyl)-4-methoxybenzenesulfonamide (23a)

(Z)—N-(4,5-dimethoxy-2-(3,4,5-trimethoxystyryl)phenyl)-3,4-dimethoxybenzenesulfonamide (23b)

(Z)-4-chloro-N-(4,5-dimethoxy-2-(3,4,5-trimethoxystyryl)phenyl)benzenesulfonamide (23c)

(Z)-3-chloro-N-(4,5-dimethoxy-2-(3,4,5-trimethoxystyryl)phenyl)benzenesulfonamide (23d)

(Z)-3,4-dichloro-N-(4,5-dimethoxy-2-(3,4,5-trimethoxystyryl)phenyl)benzenesulfonamide (23e)

(Z)—N-(4,5-dimethoxy-2-(3,4,5-trimethoxystyryl)phenyl)-4-fluorobenzenesulfonamide (23f)

(Z)-4-tert-butyl-N-(4,5-dimethoxy-2-(3,4,5-trimethoxystyryl)phenyl)benzenesulfonamide (23g)

(Z)—N-(4,5-dimethoxy-2-(3,4,5-trimethoxystyryl)phenyl)-4-nitrobenzenesulfonamide (23h)

(Z)-4-amino-N-(4,5-dimethoxy-2-(3,4,5-trimethoxystyryl)phenyl)benzenesulfonamide (23i)

(Z)—N-(4,5-dimethoxy-2-(3,4,5-trimethoxystyryl)phenyl)-3-(trifluoromethyl)benzenesulfonamide (23j)

(Z)—N-(4,5-dimethoxy-2-(3,4,5-trimethoxystyryl)phenyl)-3-(trifluoromethoxy)benzenesulfonamide (23k)

(Z)—N-(4,5-dimethoxy-2-(3,4,5-trimethoxystyryl)phenyl)-4-(trifluoromethyl)benzenesulfonamide (23l)

(Z)—N-(4,5-dimethoxy-2-(3,4,5-trimethoxystyryl)phenyl)-4-(trifluoromethoxy)benzenesulfonamide (23m)

(Z)—N-(4,5-dimethoxy-2-(3,4,5-trimethoxystyryl)phenyl)-3-nitrobenzenesulfonamide (23n)

(Z)-3-amino-N-(4,5-dimethoxy-2-(3,4,5-trimethoxystyryl)phenyl)benzenesulfonamide (23o)

(Z)—N-(4,5-dimethoxy-2-(3,4,5-trimethoxystyryl)phenyl)-3-fluorobenzenesulfonamide (23p)

(Z)-3-tert-butyl-N-(4,5-dimethoxy-2-(3,4,5-trimethoxystyryl)phenyl)benzenesulfonamide (23q)

(Z)—N-(4,5-dimethoxy-2-(3,4,5-trimethoxystyryl)phenyl)-3-fluoro-4-methoxybenzenesulfonamide (23r)

(Z)—N-(4,5-dimethoxy-2-(3,4,5-trimethoxystyryl)phenyl)-3-hydroxy-4-methoxybenzenesulfonamide (23s)

(Z)—N-(4,5-dimethoxy-2-(3,4,5-trimethoxystyryl)phenyl)-4-methoxy-3-nitrobenzenesulfonamide (23t)

(Z)—N-(4,5-dimethoxy-2-(3,4,5-trimethoxystyryl)phenyl)-3,4,5-trimethoxybenzenesulfonamide (23u)

(Z)—N-(4,5-dimethoxy-2-(3,4,5-trimethoxystyryl)phenyl)-4-methylbenzenesulfonamide (23v)

(Z)—N-(4,5-dimethoxy-2-(3,4,5-trimethoxystyryl)phenyl)-4-hydroxybenzenesulfonamide (23w)

(Z)—N-(4,5-dimethoxy-2-(3,4,5-trimethoxystyryl)phenyl)-3,4-difluorobenzenesulfonamide (23x) and (Z)-3-chloro-N-(4,5-dimethoxy-2-(3,4,5-trimethoxystyryl)phenyl)-4-methoxybenzenesulfonamide (23y).

4. A method of treatment comprising,
   treating a cell line selected from the group consisting of non-small cell lung cancer, colon cancer, and breast cancer with a (Z)-3,4,5-trimethoxystyryl benzene sulfonamide compound of general formula A

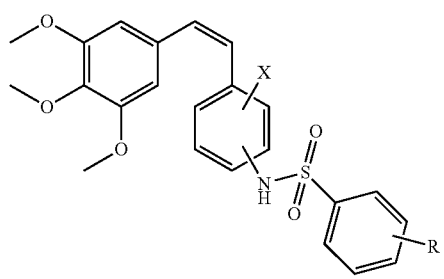

wherein, X=H, F, OCH$_3$ NH$_2$, or OH; and R=H, Cl, F, OCH$_3$ NH$_2$ NO$_2$ OH, trifluoromethyl, trifluoromethoxy, methyl, or tert-butyl.

5. A method of treating a tumor, the method comprising administering a compound of general formula A

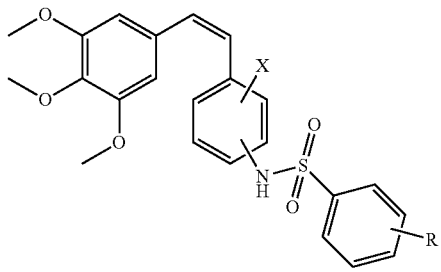

wherein, X=H, F, OCH$_3$ NH$_2$, or OH; and R=H, Cl, F, OCH$_3$, NH$_2$, NO$_2$, OH, trifluoromethyl, trifluoromethoxy, methyl, or tert-butyl,
to a tumor, wherein the tumor is from leukemia, non-small cell lung cancer, colon cancer, CNS cancer, melanoma, ovarian cancer, renal cancer, prostate cancer, or breast cancer.

* * * * *